United States Patent
Wolleb et al.

(10) Patent No.: US 10,217,946 B2
(45) Date of Patent: Feb. 26, 2019

(54) DIBENZOFURANS AND DIBENZOTHIOPHENES

(71) Applicant: IDEMITSU KOSAN CO., LTD., Chiyoda-ku (JP)

(72) Inventors: Heinz Wolleb, Fehren (CH); Yuki Nakano, Basel (CH); Thomas Raimann, Sisseln (CH); Ute Heinemeyer, Neustadt (DE); Hideaki Nagashima, Basel (CH); Yuichi Nishimae, Basel (CH)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 90 days.

(21) Appl. No.: 15/126,906

(22) PCT Filed: Mar. 13, 2015

(86) PCT No.: PCT/EP2015/055319
§ 371 (c)(1),
(2) Date: Sep. 16, 2016

(87) PCT Pub. No.: WO2015/140073
PCT Pub. Date: Sep. 24, 2015

(65) Prior Publication Data
US 2017/0098781 A1    Apr. 6, 2017

(30) Foreign Application Priority Data
Mar. 17, 2014  (EP) .................................. 14160197

(51) Int. Cl.
| H01L 51/50 | (2006.01) |
| H01L 51/00 | (2006.01) |
| C07D 405/14 | (2006.01) |
| C09K 11/06 | (2006.01) |
| C07D 403/04 | (2006.01) |
| C07D 409/14 | (2006.01) |
| C09K 11/02 | (2006.01) |

(52) U.S. Cl.
CPC ........ *H01L 51/0072* (2013.01); *C07D 403/04* (2013.01); *C07D 405/14* (2013.01); *C07D 409/14* (2013.01); *C09K 11/025* (2013.01); *C09K 11/06* (2013.01); *H01L 51/0073* (2013.01); *H01L 51/0074* (2013.01); *H01L 51/0085* (2013.01); *C09K 2211/1007* (2013.01); *C09K 2211/1074* (2013.01); *C09K 2211/185* (2013.01); *H01L 51/5016* (2013.01); *H01L 51/5072* (2013.01); *H01L 51/5096* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| 2009/0039765 | A1 | 2/2009 | Uetani et al. |
| 2010/0295027 | A1 | 11/2010 | Kawamura et al. |
| 2011/0278552 | A1 | 11/2011 | Numata et al. |
| 2013/0092905 | A1 | 4/2013 | Numata et al. |
| 2013/0234119 | A1 | 9/2013 | Mizuki et al. |
| 2013/0285035 | A1 | 10/2013 | Taka et al. |
| 2014/0073784 | A1 † | 3/2014 | Mizutani |
| 2014/0339529 | A1 | 11/2014 | Tani et al. |
| 2015/0098015 | A1 | 4/2015 | Ueda et al. |
| 2015/0243903 | A1* | 8/2015 | Zeng ................... H01L 51/0067 257/40 |

FOREIGN PATENT DOCUMENTS

| CN | 102850334 A † | 1/2013 | |
| JP | 2004-171808 A | 6/2004 | |
| JP | 2008-252094 | * 10/2008 | ............. H01L 51/50 |
| JP | WO 2013/058098 A1 | 4/2013 | |
| KR | 10-2014-0132244 A | 11/2014 | |
| WO | WO 2013/145923 A1 | 10/2013 | |

OTHER PUBLICATIONS

International Search Report dated May 26, 2015 in PCT/EP2015/055319.

* cited by examiner
† cited by third party

*Primary Examiner* — Gregory D Clark
(74) *Attorney, Agent, or Firm* — Oblon, McClelland, Maier & Neustadt, L.L.P.

(57) ABSTRACT

The present invention relates to compounds of formula (I) which are characterized in that they are substituted by at least one nitrile substituted carbazolyl group and their use in electronic devices, especially electroluminescent devices. When used as electron transport material, hole blocking material and/or host material for phosphorescent emitters in electroluminescent devices, the compounds of formula I may provide improved efficiency, stability, manufacturability, or spectral characteristics of electroluminescent devices.

(I)

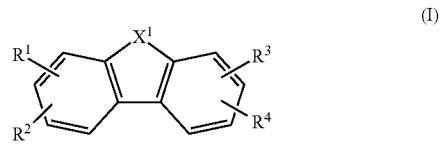

28 Claims, No Drawings

DIBENZOFURANS AND DIBENZOTHIOPHENES

CROSS-REFERENCE TO RELATED APPLICATIONS

This application is a National Stage of PCT/EP2015/055319, which was filed on Mar. 13, 2015. This application is based upon and claims the benefit of priority to European Application No. 14160197.1, which was filed on Mar. 17, 2014.

The present invention relates to compounds of formula (I) and their use in electronic devices, especially electroluminescent devices. When used as electron transport material, hole blocking material and/or host material for phosphorescent emitters in electroluminescent devices, the compounds of formula I may provide improved efficiency, stability, manufacturability, or spectral characteristics of electroluminescent devices.

JP2004171808 relates to a phosphorescent electroluminescence device, comprising a carbazole derivative represented by formula

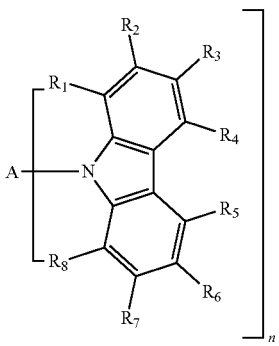

[A=aromatic ring residue; $R_{1-8}$=H, or a substituted group (at least one of $R_{1-8}$ is a substituted group other than H); n≥1]. Among others a compound of formula

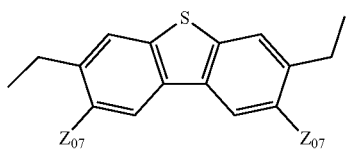

is disclosed, wherein Z07 is a group of formula

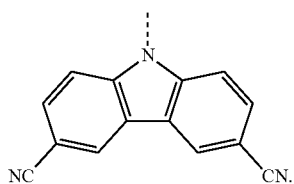

US2009039765 relates to a light emitting polymer composition comprising a light emitting polymer and among others a compound of formulae (1a):

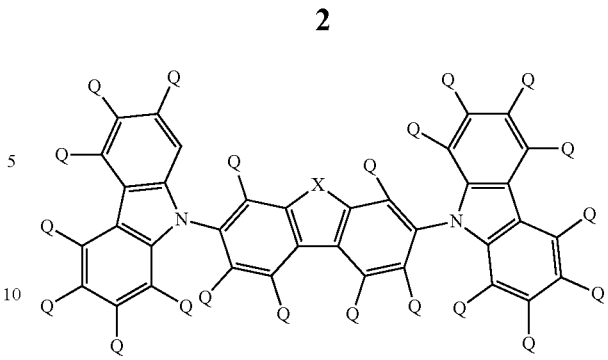

(wherein, X represents an atom or atomic group forming a 5-membered or 6-membered ring together with four carbon atoms on two benzene rings in the formula, Q represents each independently a hydrogen atom, halogen atom, alkyl group, alkyloxy group, alkylthio group, aryl group, aryloxy group, arylthio group, arylalkyl group, arylalkyloxy group, arylalkylthio group, alkenyl group, alkynyl group, arylalkenyl group, arylalkynyl group, substituted silyloxy group, substituted silylthio group, substituted silylamino group, substituted amino group, amide group, acid imide group, acyloxy group, mono-valent heterocyclic group, heteroaryloxy group, heteroarylthio group, cyano group or nitro group).

US20130092905 relates to a material for an organic electroluminescence device of formula

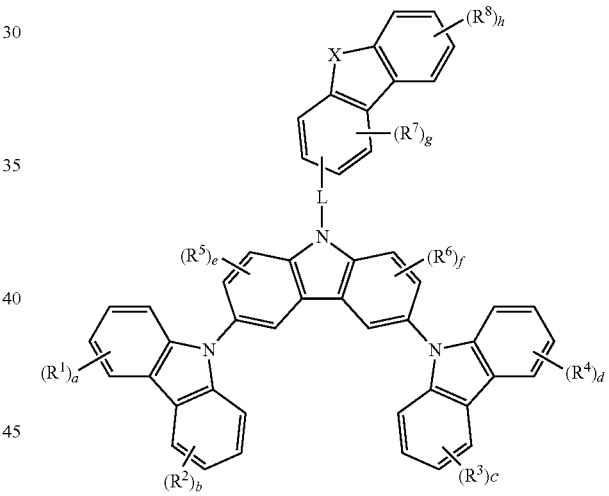

wherein X is an oxygen atom or a sulfur atom; $R^1$ to $R^8$ are each independently an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group, or a cyano group, and each of $R^1$ to $R^8$ is independently optionally substituted, each of a to d and h is independently an integer of from 0 to 4;

each of e to g is independently an integer of from 0 to 3;

a total of a to h is 6 or less; and

L is a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms;

is optionally substituted with an optionally substituted alkyl group having 1 to 20 carbon atoms, an optionally substituted cycloalkyl group having 3 to 20 ring carbon atoms, an optionally substituted alkoxy group having 1 to 20 carbon atoms, an optionally substituted cycloalkoxy group having 3 to 20 ring carbon atoms, an optionally substituted aryl group having 6 to 18 ring carbon atoms, an optionally substituted aryloxy group having 6 to 18 ring carbon atoms, an optionally substituted heteroaryl group having 5 to 18 ring atoms, an optionally substituted amino group, an optionally substituted silyl group, an optionally substituted fluoro group, or an optionally substituted cyano group, and the material is suitable for an organic electroluminescence device. The material is preferably a host material to be incorporated into the light emitting layer of an organic EL device.

US20110278552 relates to a material for an organic electroluminescence device represented by formula

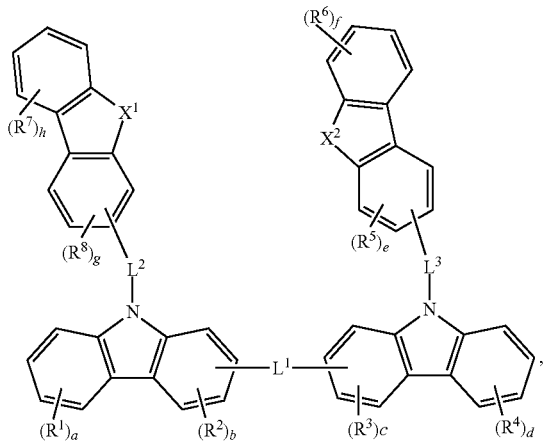

wherein
$X^1$ and $X^2$ each are independently an oxygen atom or a sulfur atom, and they are not a sulfur atom at the same time; $R^1$ to $R^8$ each represent independently an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group or a cyano group, and the above substituents $R^1$ to $R^8$ may be further substituted with the above substituents; when $R^1$ to $R^8$ each are present in a plural number, they may be the same as or different from each other;

a, d, f and h each represent independently an integer of any of 0 to 4, and b, c, e and g each represent independently an integer of any of 0 to 3; a sum of a to h is 6 or less;

$L^1$ represents a single bond, a divalent linkage group containing N, a divalent linkage group containing O, a divalent linkage group containing Si, a divalent linkage group containing P, a divalent linkage group containing S, an alkylene group having 1 to 20 carbon atoms, a cycloalkylene group having 3 to 20 ring carbon atoms, an arylene group having 6 to 18 ring carbon atoms, a heteroarylene group having 5 to 18 ring atoms, a divalent amino group or a divalent silyl group;

$L^2$ and $L^3$ each represent independently a single bond, an alkylene group having 1 to 20 carbon atoms, a cycloalkylene group having 3 to 20 ring carbon atoms, an arylene group having 6 to 18 ring carbon atoms or a heteroarylene group having 5 to 18 ring atoms; $L^1$ to $L^3$ may be further substituted with any of the substituents $R^1$ to $R^8$ described above; provided that when $L^1$ is an arylene group having 6 to 18 ring carbon atoms or a heteroarylene group having 5 to 18 ring atoms, a and d each represent independently an integer of any of 1 to 4.

US2013285035 discloses an organic electroluminescent element comprising an anode, a cathode, and an organic compound layer sandwiched by the anode and the cathode, wherein the organic compound layer at least comprises a light-emitting layer and a charge-generating layer; (1) the charge-generating layer is composed of at least one layer and provided between the anode and the light-emitting layer; and (2) at least one layer of the charge-generating layer comprises an organic metal complex. The compound of formula

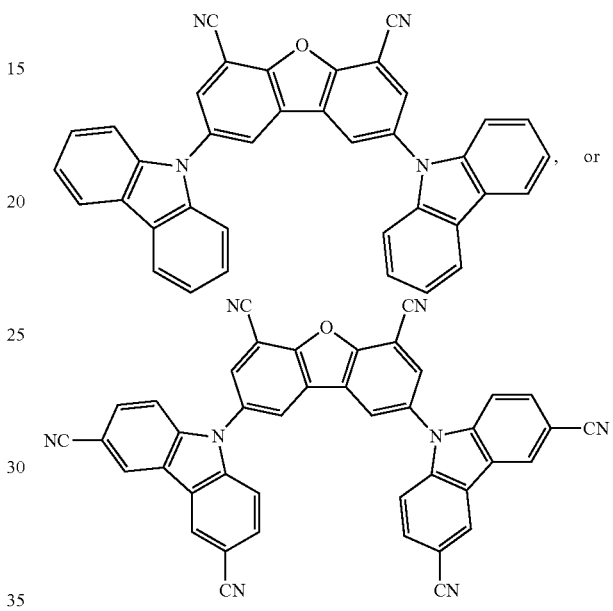

is used as an electron extracting material in the charge generating layer.

WO2013058098 relates to an organic electroluminescent element wherein a hole injection layer (HI), a hole transport layer (HT1), a second hole transport layer (HT2) and a light emitting layer that contains a host compound (H) and a phosphorescent dopant compound (D) are sequentially laminated in this order between a positive electrode and a negative electrode. The compound of formula

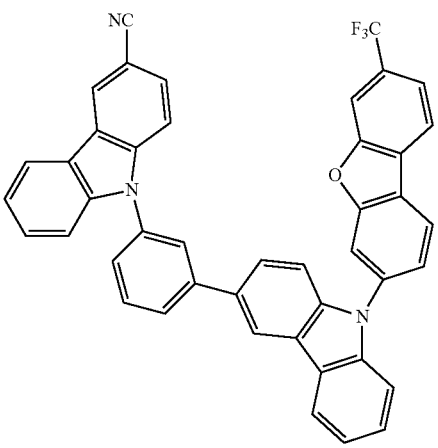 [SMILES: N#Cc1ccc2c(c1)c1ccccc1n2-c1cccc(-c2ccc3c(c2)c2ccccc2n3-c2ccc3c(c2)oc2cc(C(F)(F)F)ccc23)c1]

is mentioned as an example of a host.

US20130234119 relates to an organic electroluminescence device employing a specific biscarbazole derivative having a cyano group as a first host and a compound having both a carbazole structure and a nitrogen-containing aromatic heteroring as a second host.

WO2013145923 relates to an organic electroluminescent element which is characterized by: using, as a first host, a biscarbazole derivative that has a specific structure having a cyano group; and using, as a second host, a compound that has both a carbazole derivative structure and a nitrogen-containing heteroaromatic ring. This organic electroluminescent element has a long service life.

KR20140132244 relates to an organic electronic device containing a heterocyclic compound of formula

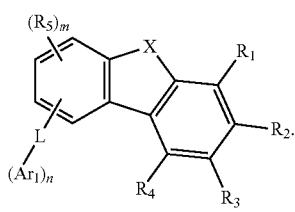

The substituent $R_3$ represents CN. The substituents $R_1$, $R_2$, $R_4$ and $R_5$ may represent CN.

Notwithstanding these developments, there remains a need for organic light emitting devices comprising new electron transport materials to provide improved efficiency, stability, manufacturability, and/or spectral characteristics of electroluminescent devices.

Accordingly, it is an object of the present invention, with respect to the aforementioned prior art, to provide further materials suitable for use in OLEDs and further applications in organic electronics. More particularly, it should be possible to provide electron transport materials, hole/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Certain dibenzofurans and dibenzothiophenes, which are substituted by nitrile substituted carbazolyl groups, are found to be suitable for use in organo-electroluminescent devices. In particular, said derivatives are suitable electron transporting materials, hole blocking materials or host materials for phosphorescent emitters with good efficiency and durability.

Accordingly the present invention relates to compounds of formula

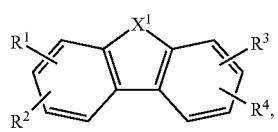

wherein
$R^1$, $R^2$ and $R^3$ are independently of each other H, F, a $C_3$-$C_{18}$cycloalkyl group, which can optionally be substituted by G; a $C_6$-$C_{24}$aryl group, which can optionally be substituted by G, a $C_2$-$C_{30}$heteroaryl group, which can optionally be substituted by G; a group of formula Si($R^{91}$)($R^{92}$)($R^{93}$),

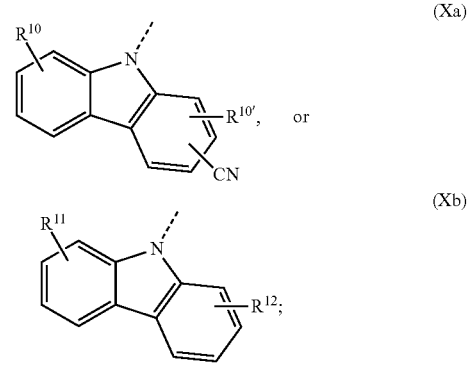

$R^4$ is H, F, a $C_3$-$C_{18}$cycloalkyl group, which can optionally be substituted by G; a $C_6$-$C_{24}$aryl group, which can optionally be substituted by G, a $C_2$-$C_{30}$heteroaryl group, which can optionally be substituted by G; a group of formula —Si($R^{91}$)($R^{92}$)($R^{93}$),

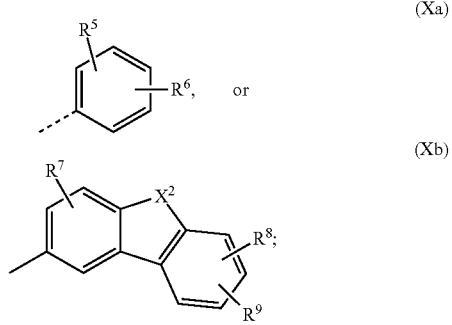

$R^{91}$, $R^{92}$ and $R^{93}$ are independently of each other a $C_1$-$C_{25}$alkyl group, or a $C_6$-$C_{24}$aryl group, which can optionally be substituted by G;
$X^1$ and $X^2$ are independently of each other O, or S;
$R^5$, $R^7$, $R^9$ and $R^{11}$ are independently of each other H, F, a $C_1$-$C_{25}$alkyl group, which can optionally be substituted by E and or interrupted by D; a $C_1$-$C_{25}$alkoxy group; a $C_3$-$C_{18}$cycloalkyl group, which can optionally be substituted by G; a $C_6$-$C_{10}$aryl group, which can optionally be substituted by G, a $C_2$-$C_9$heteroaryl group, which can optionally be substituted by G;
$R^6$ and $R^8$ are independently of each other H, a $C_1$-$C_{25}$alkyl group, a group of formula (Xa), or (Xb);
$R^{10}$ is H, or a $C_1$-$C_{25}$alkyl group and $R^{10'}$ is H, or a $C_1$-$C_{25}$alkyl group; or $R^{10}$ is H, or a $C_1$-$C_{25}$alkyl group and $R^{10'}$ is CN; or $R^{10}$ is CN and $R^{10'}$ is H, or a $C_1$-$C_{25}$alkyl group;
$R^{12}$ is a group of formula (Xa); D is —CO—, —COO—, —S—, —SO—, —SO$_2$—, —O—, —NR$^{65}$—, —SiR$^{70}$R$^{71}$—, —POR$^{72}$—, —CR$^{63}$═CR$^{64}$—, or —C≡C—;
E is —OR$^{69}$, —SR$^{69}$, —NR$^{65}$R$^{66}$, —COR$^{68}$, —COOR$^{67}$, —CONR$^{65}$R$^{66}$, —CN, or F,
G is E, or a $C_1$-$C_{18}$alkyl group, a $C_3$-$C_{18}$cycloalkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl, with the proviso that at least one of the substituents $R^1$, $R^2$, $R^3$, $R^4$, $R^6$, $R^8$ and $R^{12}$ is a group of formula (Xa).

Certain compounds of the present invention show, when used as host and/or hole blocker in combination with phosphorescent emitters, excellent power efficiencies, in particular electroluminescent (EL) devices comprising the compounds of the present invention exhibit reduced drive voltage while maintaining excellent luminance properties. Furthermore, the colour and external quantum efficiency (EQE) can be improved and the roll-off may be reduced by use of the inventive compounds.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, electron transport and/or hole blocking material.

Hence, a further subject of the present invention is directed to an electron transport layer and/or a hole blocking layer comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

D is preferably —CO—, —COO—, —S—, —SO—, —$SO_2$—, —O—, —$NR^{65}$—, wherein $R^{65}$ is $C_1$-$C_{18}$alkyl, such as methyl, ethyl, n-propyl, iso-propyl, n-butyl, isobutyl, tert-butyl, or sec-butyl, or $C_6$-$C_{14}$aryl, such as phenyl, tolyl, naphthyl, or biphenylyl.

E is preferably —$OR^{69}$; —$SR^{69}$; —$NR^{65}R^{65}$; —$COR^{68}$; —$COOR^{67}$; —$CONR^{65}R^{65}$; or —CN; wherein $R^{65}$, $R^{67}$, $R^{68}$ and $R^{69}$ are independently of each other $C_1$-$C_{18}$alkyl, such as methyl, ethyl, n-propyl, iso-propyl, n-butyl, isobutyl, tert-butyl, sec-butyl, hexyl, octyl, or 2-ethyl-hexyl, or $C_6$-$C_{14}$aryl, such as phenyl, tolyl, naphthyl, or biphenylyl.

G has the same preferences as E, or is $C_1$-$C_{18}$alkyl, especially $C_1$-$C_8$alkyl, such as methyl, ethyl, n-propyl, iso-propyl, n-butyl, isobutyl, tert-butyl, sec-butyl, hexyl, octyl, or 2-ethyl-hexyl.

$R^1$, $R^2$, $R^3$ and $R^4$ may be a $C_6$-$C_{24}$aryl group, which can optionally be substituted by G, or a $C_2$-$C_{30}$heteroaryl group, which can optionally be substituted by G.

The $C_6$-$C_{24}$aryl groups $R^1$, $R^2$, $R^3$ and $R^4$, which optionally can be substituted by G, are typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted by G.

The $C_2$-$C_{30}$heteroaryl group groups $R^1$, $R^2$, $R^3$ and $R^4$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated m-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, benzimidazo[1,2-a]benzimidazo-5-yl, carbazolyl, or phenoxazinyl, which can be unsubstituted or substituted by G.

Preferred $C_2$-$C_{30}$heteroaryl groups are pyridyl, benzimidazo[1,2-a]benzimidazo-5-yl

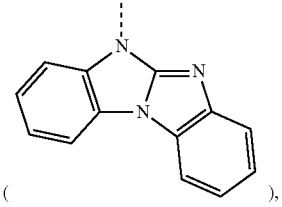

( ), carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{14}$heteroaryl, especially

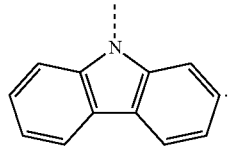

In a preferred embodiment of the present invention the compounds of formula (I) comprise 1, or 2 groups of formula (Xa).

Preferred embodiments of the present invention are directed to compounds of formula

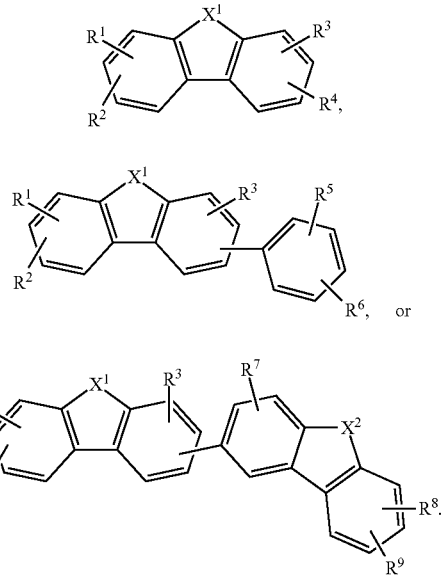

(I)

(II)

(III)

$R^4$ is H, F, a $C_3$-$C_{18}$cycloalkyl group, which can optionally be substituted by G; a $C_6$-$C_{24}$aryl group, which can optionally be substituted by G, a $C_2$-$C_{30}$heteroaryl group, which can optionally be substituted by G; a group of formula —Si($R^{91}$)($R^{92}$)($R^{93}$), (Xa), or (Xb).

(Xa), (Xb), G, $X^1$, $X^2$, $R^{91}$, $R^{92}$, $R^{93}$, $R^1$, $R^2$, $R^3$, $R^5$, $R^6$, $R^7$, $R^8$ and $R^9$ are as defined above.

In a preferred embodiment the present invention is directed to compounds of formula

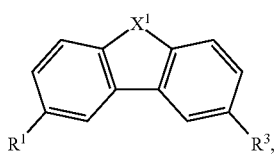

(Ia)

wherein
$X^1$ is O, or S;
$R^1$ is a group of formula

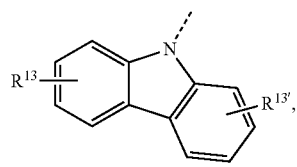

and $R^3$ is a group of formula (Xa); or $R^1$ is a group of formula

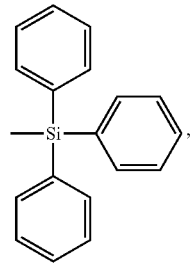 [SMILES: C[Si](c1ccccc1)(c1ccccc1)c1ccccc1]

and $R^3$ is a group of formula (Xa); or
$R^1$ and $R^3$ are independently of each other a group of formula (Xa); or
$R^1$ is a group of formula (Xa), or (Xb) and $R^3$ is H; or
compounds of formula

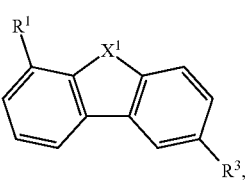

(Ib)

wherein
$X^1$ is O, or S;
$R^1$ is a group of formula

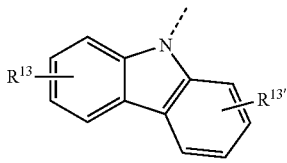

and $R^3$ is a group of formula (Xa); or
$R^1$ is a group of formula (Xa) and $R^3$ is a group of formula

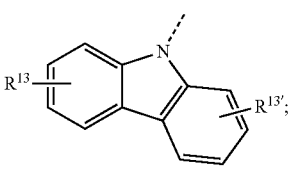

or
$R^1$ is a group of formula

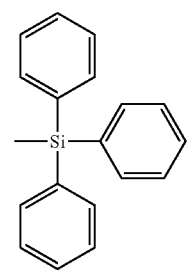 [SMILES: C[Si](c1ccccc1)(c1ccccc1)c1ccccc1]

and $R^3$ is a group of formula (Xa); or $R^1$ is a group of formula (Xa) and $R^3$ is a group of formula

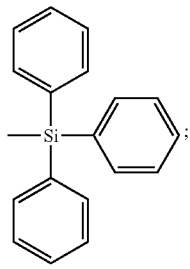 [SMILES: C[Si](c1ccccc1)(c1ccccc1)c1ccccc1]

or $R^1$ and $R^3$ are independently of each other a group of formula (Xa); or $R^1$ is a group of formula (Xa), or (Xb) and $R^3$ is H, or $R^1$ is H and $R^3$ is a group of formula (Xa), or (Xb) and $R^{13}$ and $R^{13'}$ are independently of each other H, or a $C_1$-$C_{25}$alkyl group.

In another preferred embodiment the present invention is directed to compounds of formula

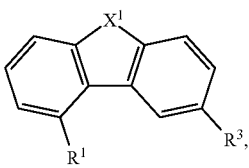 (Ic)

wherein $X^1$ is O, or S;

$R^1$ is a group of formula

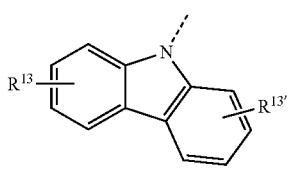

and $R^3$ is a group of formula (Xa); or $R^1$ is a group of formula (Xa) and $R^3$ is a group of formula or $R^1$ is a group of formula

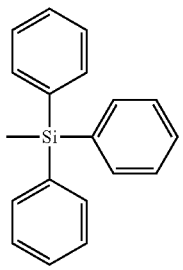

and $R^3$ is a group of formula (Xa); or $R^1$ is a group of formula (Xa) and $R^3$ is a group of formula

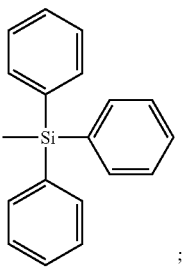

or $R^1$ and $R^3$ are independently of each other a group of formula (Xa); or $R^1$ is H and $R^3$ is a group of formula (Xa), or (Xb) and $R^{13}$ and $R^{13'}$ are independently of each other H, or a $C_1$-$C_{25}$alkyl group; or compounds of formula

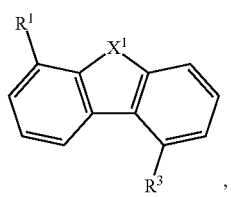 (Id)

wherein $X^1$ is O, or S;

$R^1$ is a group of formula

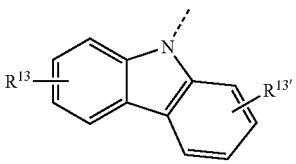

and $R^3$ is a group of formula (Xa); or $R^1$ is a group of formula (Xa) and $R^3$ is a group of formula

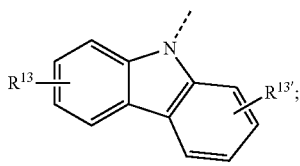

or $R^1$ is a group of formula

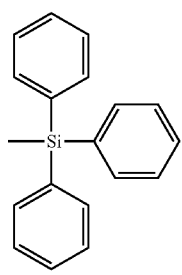 [SMILES: C[Si](c1ccccc1)(c1ccccc1)c1ccccc1]

and $R^3$ is a group of formula (Xa); or
$R^1$ is a group of formula (Xa) and $R^3$ is a group of formula

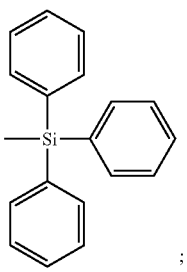 [SMILES: C[Si](c1ccccc1)(c1ccccc1)c1ccccc1]

10 or $R^1$ and $R^3$ are independently of each other a group of formula (Xa); or $R^3$ is H and $R^1$ is a group of formula (Xa), or (Xb) and $R^{13}$ and $R^{13'}$ are independently of each other H, or a $C_1$-$C_{25}$alkyl group.

The compound of formula (II) is preferably a compound of formula

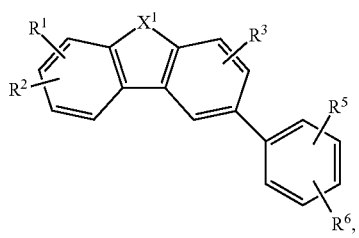

(II')

wherein (Xa), (Xb), $X^1$, $R^1$, $R^2$, $R^3$, $R^5$ and $R^6$ are as defined above; more preferably a compound of formula

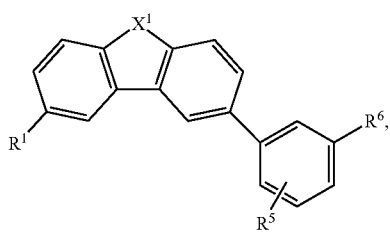

(IIa)

wherein $X^1$ is O, or S;

$R^1$ is a group of formula

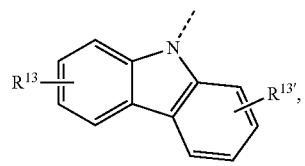

and $R^6$ is a group of formula (Xa), or (Xb); or $R^1$ is a group of formula (Xa), or (Xb) and $R^6$ is a group of formula

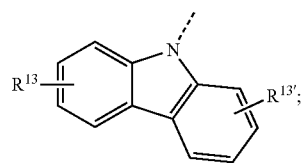

or $R^1$ and $R^6$ are independently of each other a group of formula (Xa); $R^5$ is H, or a $C_1$-$C_{25}$alkyl group and $R^{13}$ and $R^{13'}$ are independently of each other H, or a $C_1$-$C_{25}$alkyl group.

The compound of formula (III) is preferably a compound of formula

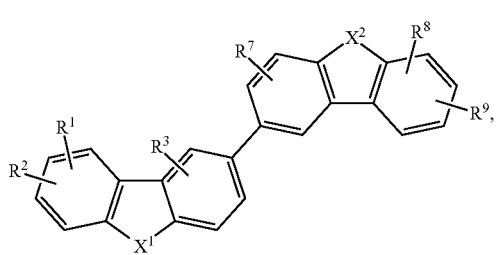

(III')

wherein (Xa), (Xb), $X^1$, $X^2$, $R^1$, $R^2$, $R^3$, $R^7$, $R^8$ and $R^9$ are as defined above; more preferably a compound of formula (IIIa)

wherein
X¹ and X² are independently of each other O, or S;
R¹ is a group of formula and R⁸ is a group of formula (Xa); or
R¹ is a group of formula (Xa) and R⁸ is a group of formula or R¹ and R⁸ are independently of each other a group of formula (Xa) and R¹³ and R¹³' are independently of each other H, or a $C_1$-$C_{25}$alkyl group.

The group of formula (Xa) is preferably a group of formula (XIIa)

(XIIb)

(XIIc)

(XIId)

(XIIe)

(XIIf)

(XIIg)

(XIIh)

(XIIi)

(XIIj)

(XIIk)

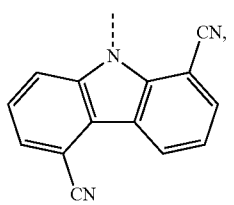 (XIIi)

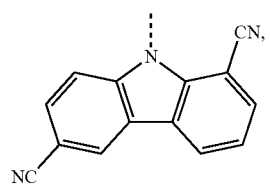 (XIIk)

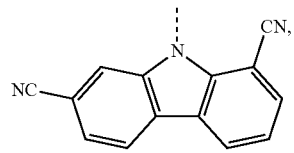 (XIIl)

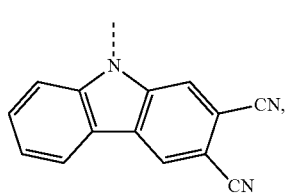 (XIIm)

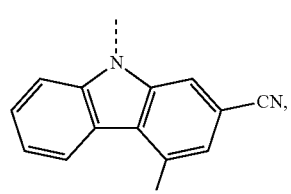 (XIIn)

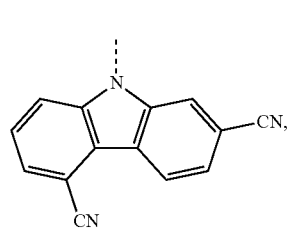 (XIIo)

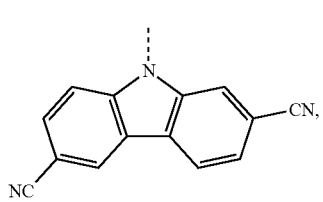 (XIIp)

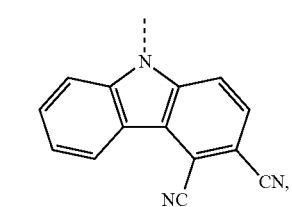 (XIIq)

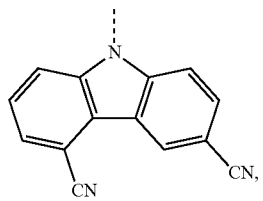 (XIIr)

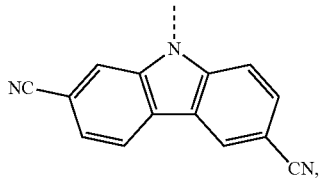 (XIIs)

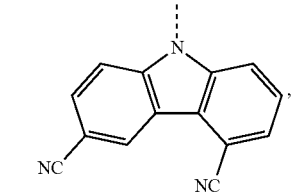 (XIIt)

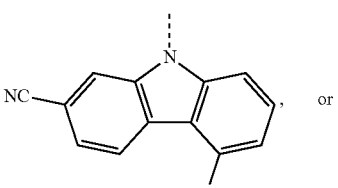 (XIIu)

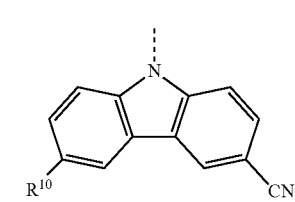

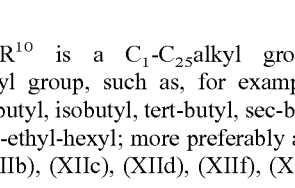 (XIIv)

wherein $R^{10}$ is a $C_1$-$C_{25}$alkyl group, especially a $C_3$-$C_{12}$alkyl group, such as, for example, n-propyl, iso-propyl, n-butyl, isobutyl, tert-butyl, sec-butyl, hexyl, heptyl, octyl, or 2-ethyl-hexyl; more preferably a group of formula (XIIa), (XIIb), (XIIc), (XIId), (XIIf), (XIIg), or (XIIv).

The group of formula (Xb) is preferably a group of formula

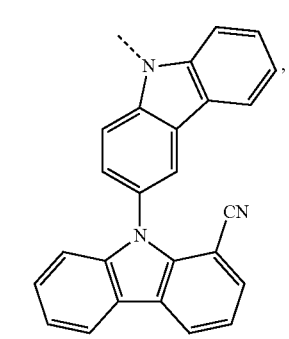 (XIIIa)

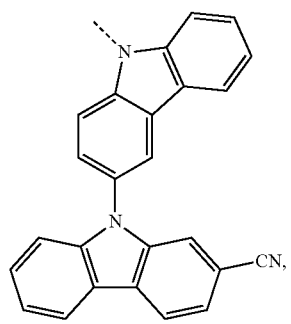
(XIIIb)
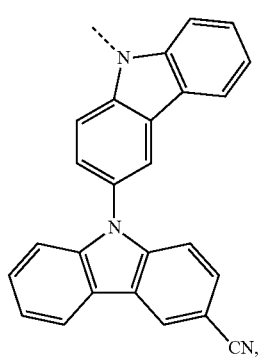
(XIIIc)
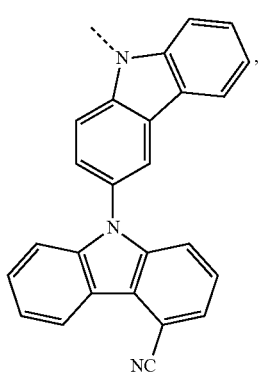
(XIIId)
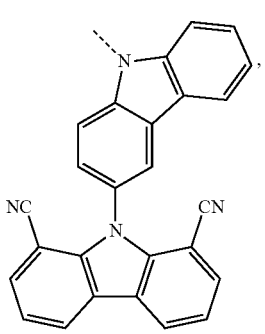
(XIIIe)
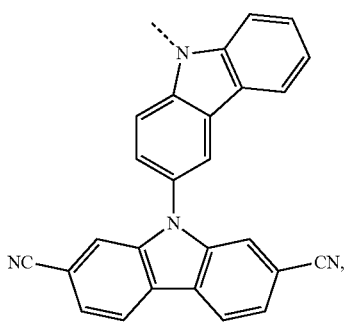
(XIIIf)
(XIIIg)
(XIIIh)
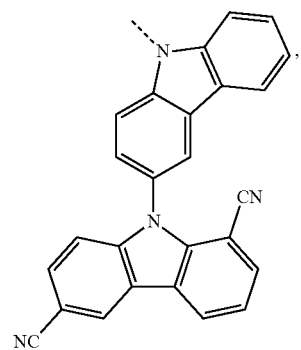
(XIIIi)

-continued
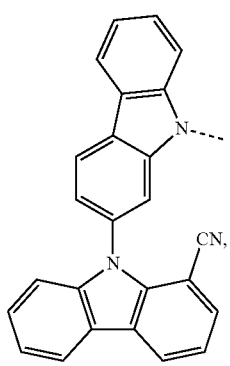
(XIIIj)
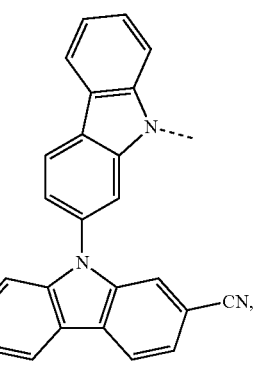
(XIIIk)
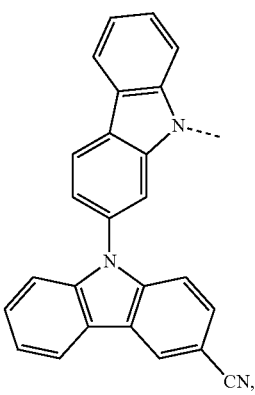
(XIIIl)
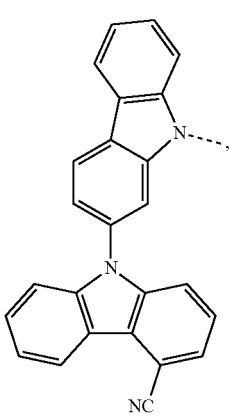
(XIIIm)
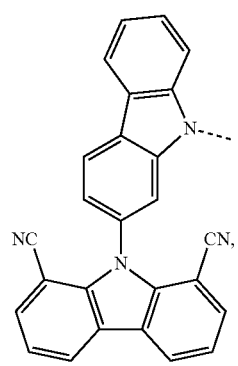
(XIIIn)
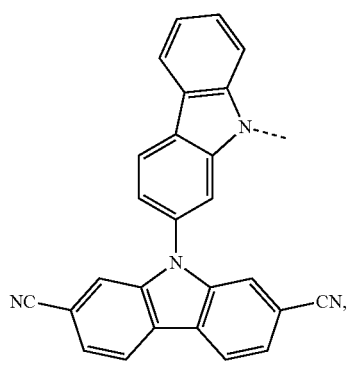
(XIIIo)
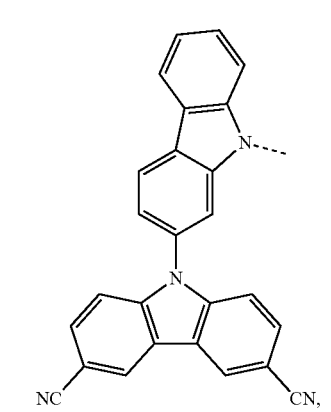
(XIIIp)
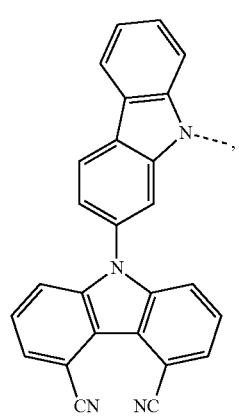
(XIIIq)

-continued

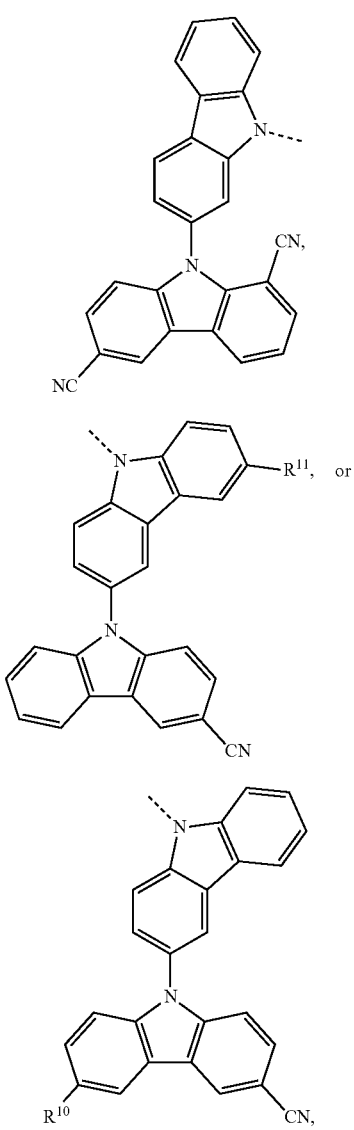

wherein R[10] is a C$_1$-C$_{25}$alkyl group, especially a C$_3$-C$_{12}$alkyl group, such as, for example, n-propyl, iso-propyl, n-butyl, isobutyl, tert-butyl, sec-butyl, hexyl, heptyl, octyl, or 2-ethyl-hexyl; and R[11] is a C$_1$-C$_{25}$alkyl group, especially a C$_3$-C$_{12}$alkyl group, such as, for example, n-propyl, iso-propyl, n-butyl, isobutyl, tert-butyl, sec-butyl, hexyl, heptyl, octyl, or 2-ethyl-hexyl; more preferably a group of formula (XIIIa), (XIIIb), (XIIIc), (XIIId), (XIIIe), (XIIIf), (XIIIg), (XIIIs), or (XIIIt).

In a particularly preferred embodiment the present invention is directed to compounds of formula

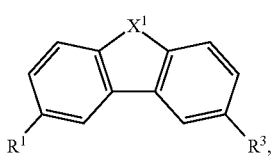
(Ia)

wherein
X$^1$ is O, or S;
R$^1$ is a group of formula

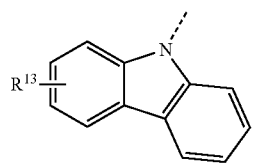

and R$^3$ is a group of formula (XIIa), (XIIb), (XIIc), (XIId), (XIIf), (XIIg), or (XIIv); or
R$^1$ is a group of formula

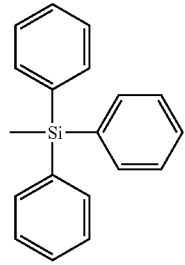

and R$^3$ is a group of formula (XIIa), (XIIb), (XIIc), (XIId), (XIIf), (XIIg), or (XIIv); or
R$^1$ and R$^3$ are independently of each other a group of formula (XIIa), (XIIb), (XIIc), (XIId), (XIIf), (XIIg), or (XIIv); or
R$^1$ is a group of formula (XIIIa), (XIIIb), (XIIIc), (XIIId), (XIIIf), (XIIIg), (XIIIs), or (XIIIt) and R$^3$ is H. R$^{13}$ is a C$_1$-C$_{25}$alkyl group, especially a C$_3$-C$_{12}$alkyl group, such as, for example, n-propyl, iso-propyl, n-butyl, isobutyl, tert-butyl, sec-butyl, hexyl, heptyl, octyl, or 2-ethyl-hexyl.

In another particularly preferred embodiment the present invention is directed to compounds of formula

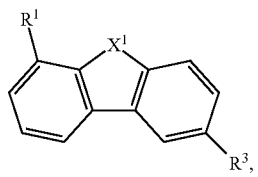
(Ib)

wherein
X$^1$ is O, or S;
R$^1$ is a group of formula

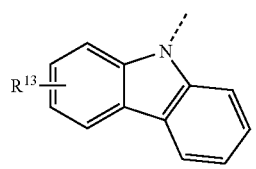

and R$^3$ is a group of formula (XIIa), (XIIb), (XIIc), (XIId), (XIIf), (XIIg), or (XIIv); or R¹ is a group of formula (XIIa), (XIIb), (XIIc), (XIId), (XIIf), (XIIg), or (XIIv) and R³ is a group of formula

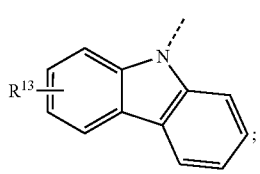

or R¹ is a group of formula

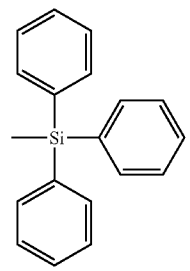 [SMILES: C[Si](c1ccccc1)(c1ccccc1)c1ccccc1]

and R³ is a group of formula (XIIa), (XIIb), (XIIc), (XIId), (XIIf), (XIIg), or (XIIv); or R¹ is a group of formula (XIIa), (XIIb), (XIIc), (XIId), (XIIf), (XIIg), or (XIIv) and R³ is a group of formula

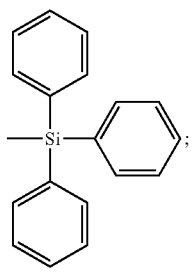

or

R¹ and R³ are independently of each other a group of formula (XIIa), (XIIb), (XIIc), (XIId), (XIIf), (XIIg), or (XIIv); or R¹ is a group of formula (XIIIa), (XIIIb), (XIIIc), (XIIId), (XIIIf), (XIIIg), (XIIIs), or (XIIIt) and R³ is H; or R¹ is H and R³ is a group of formula (XIIIa), (XIIIb), (XIIIc), (XIIId), (XIIIf), (XIIIg), (XIIIs), or (XIIIt). R¹³ is a $C_1$-$C_{25}$alkyl group, especially a $C_3$-$C_{12}$alkyl group, such as, for example, n-propyl, iso-propyl, n-butyl, isobutyl, tert-butyl, sec-butyl, hexyl, heptyl, octyl, or 2-ethylhexyl.

Examples of particularly preferred compounds of formula (Ia) and (Ib) are shown below:

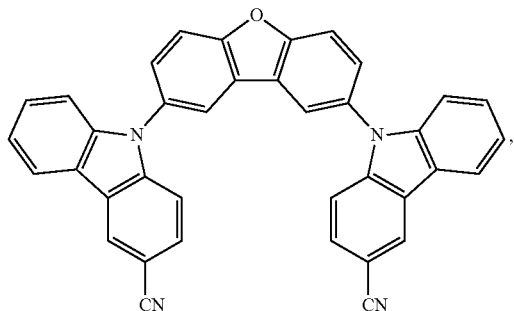
(A-1)

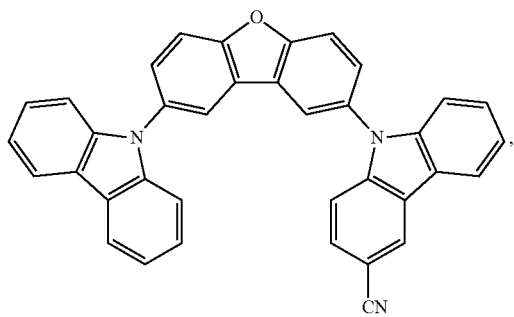
(A-2)

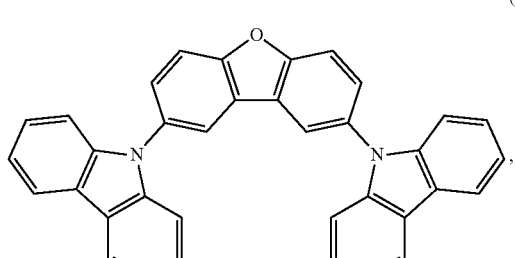
(A-3)

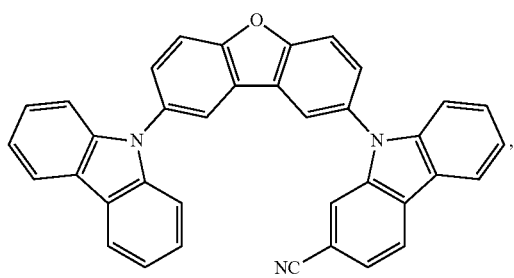
(A-4)

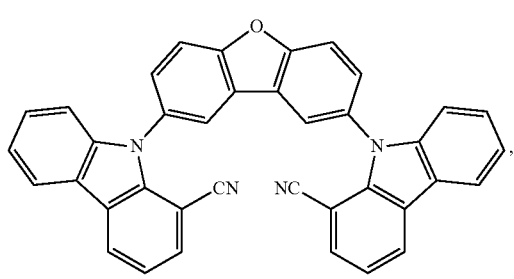
(A-5)

-continued
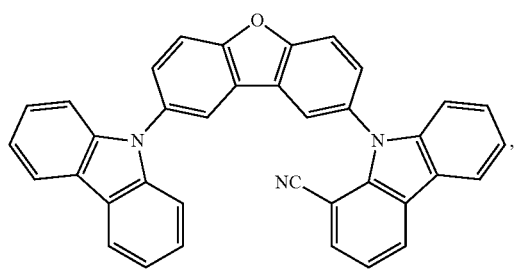
(A-6)
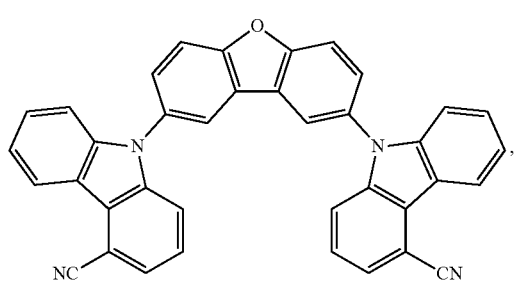
(A-7)
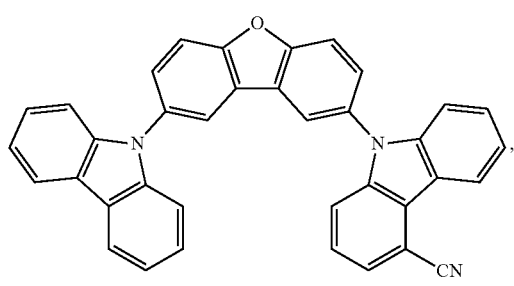
(A-8)
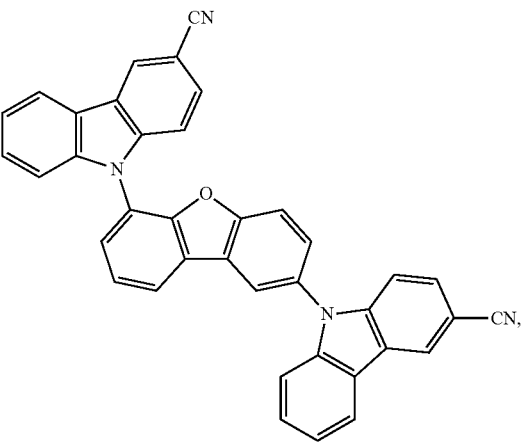
(A-9)
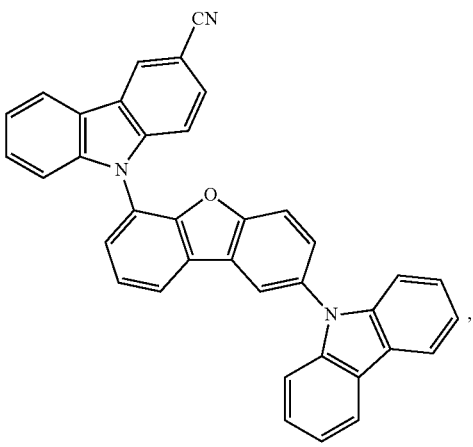
(A-10)
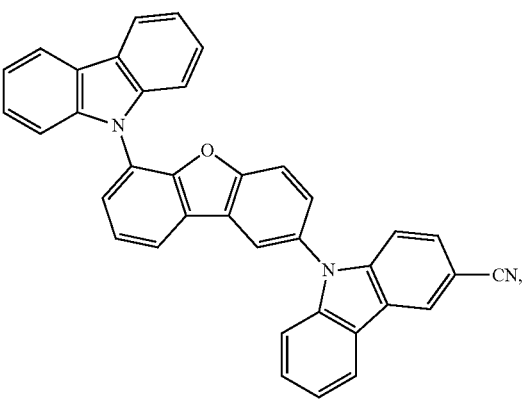
(A-11)
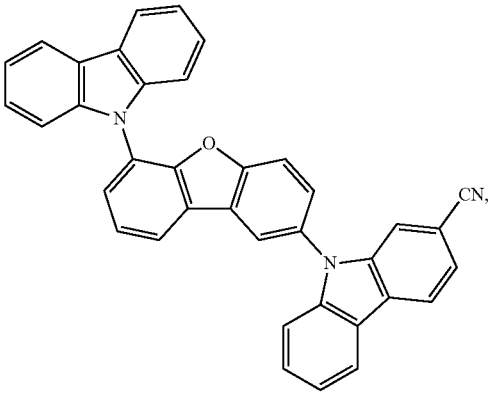
(A-12)
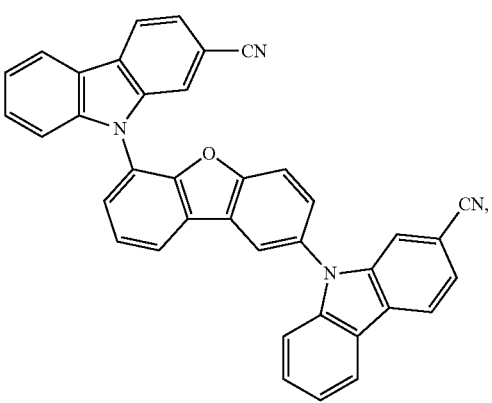
(A-13)

(A-14)
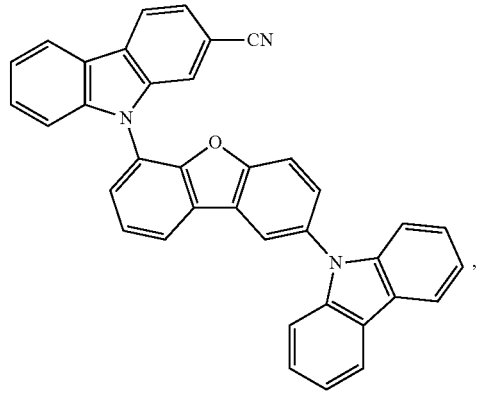
(A-15)
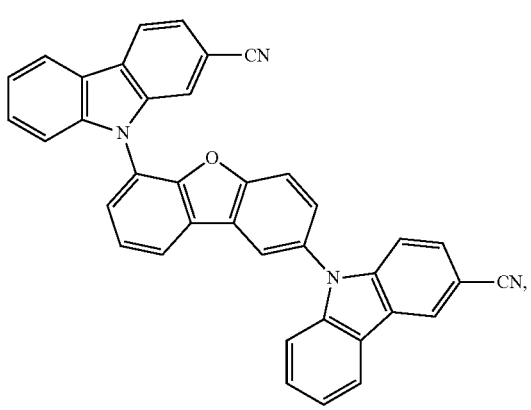
(A-16)
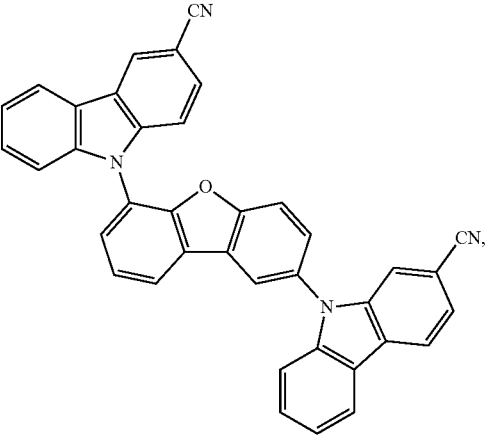
(A-17)
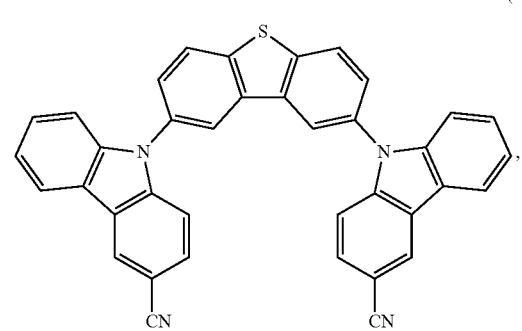
(A-18)
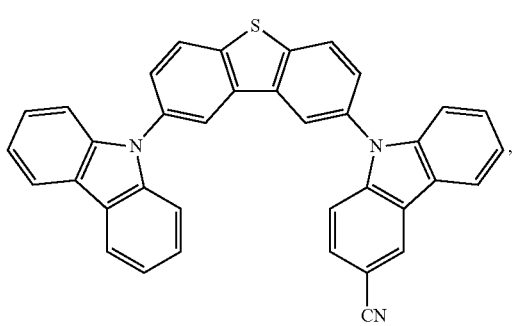
(A-19)
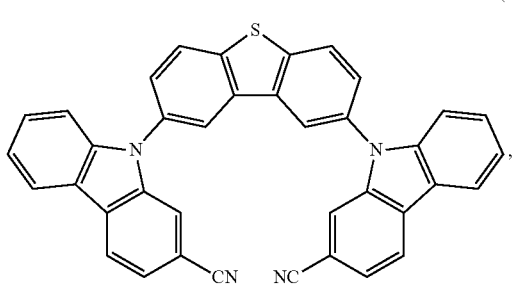
(A-20)
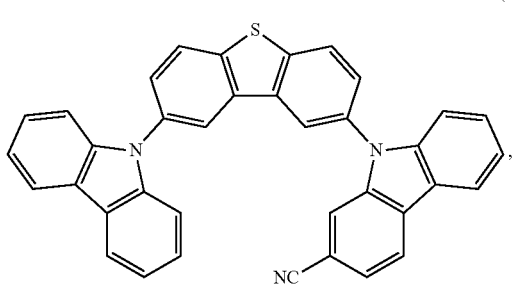
(A-21)
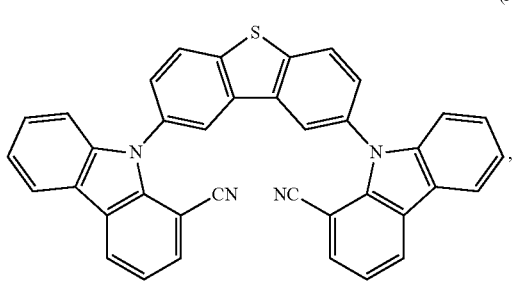
(A-22)
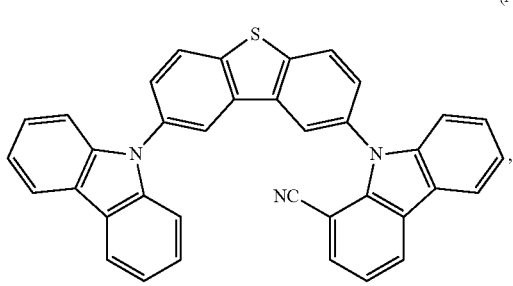

(A-23)
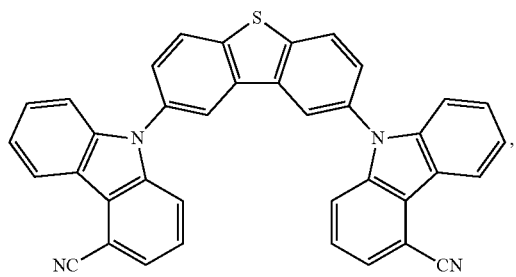
(A-24)
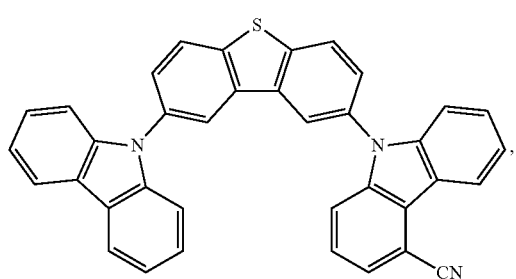
(A-25)
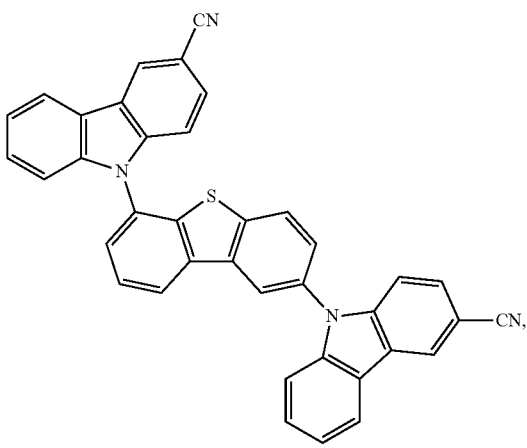
(A-26)
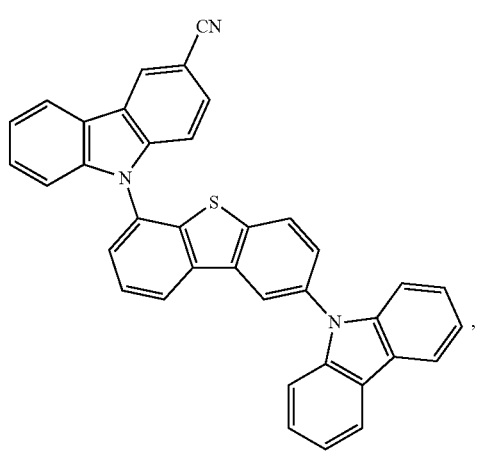
(A-27)
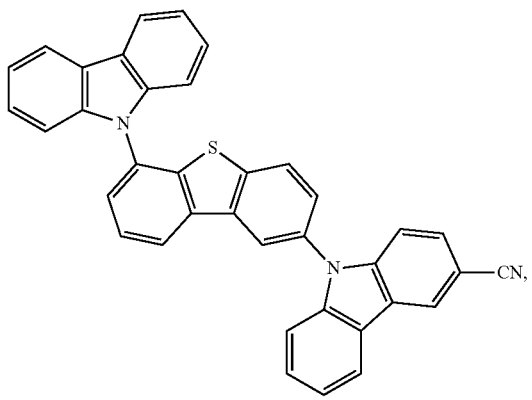
(A-28)
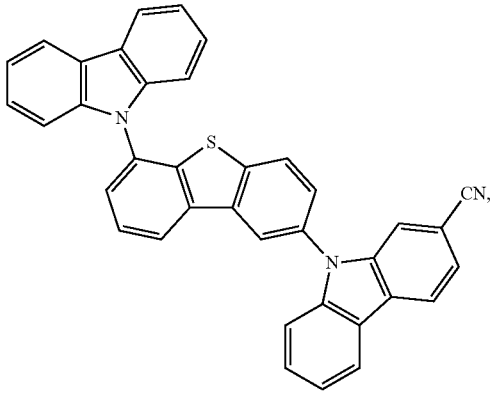
(A-29)
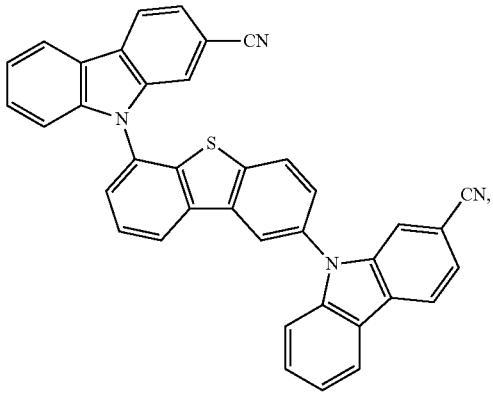
(A-30)
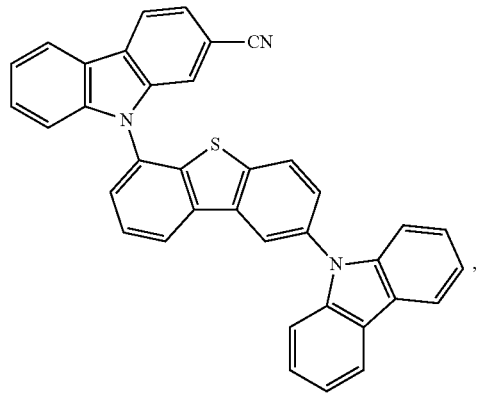

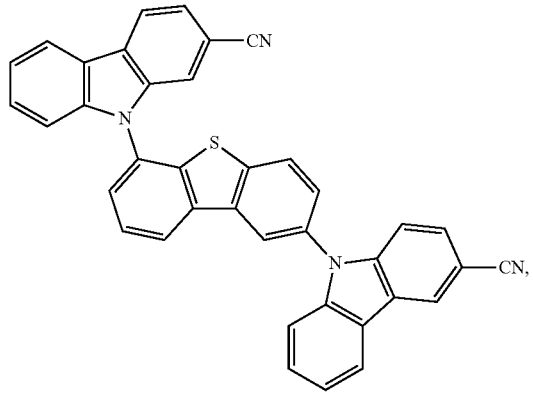
(A-31)
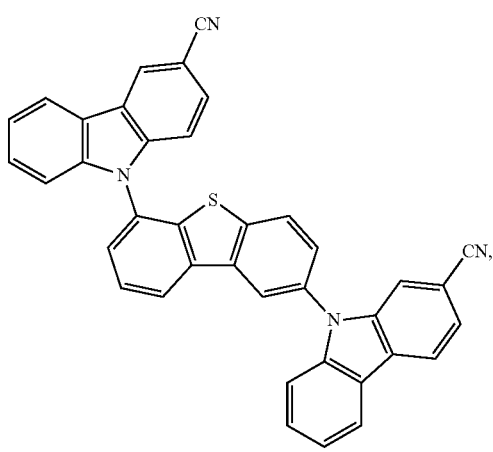
(A-32)
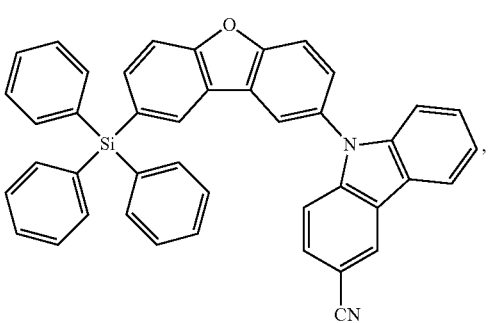
(A-33)
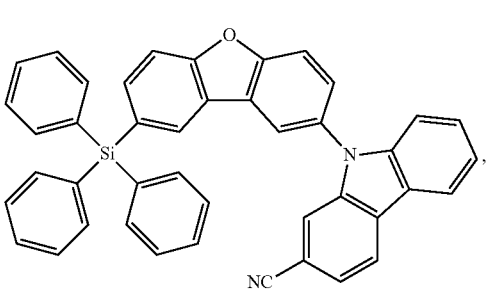
(A-34)
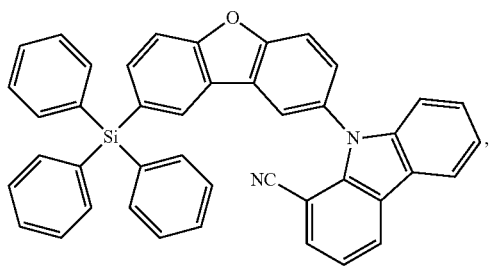
(A-35)
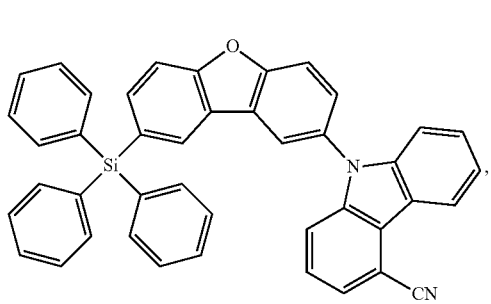
(A-36)
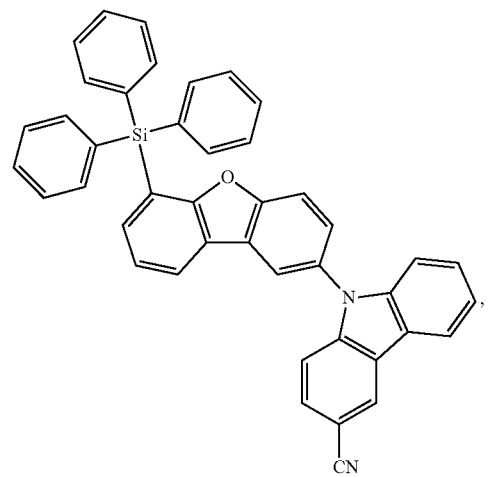
(A-37)
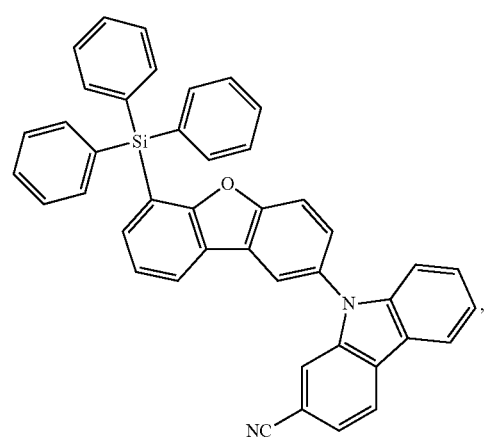
(A-38)

(A-39)
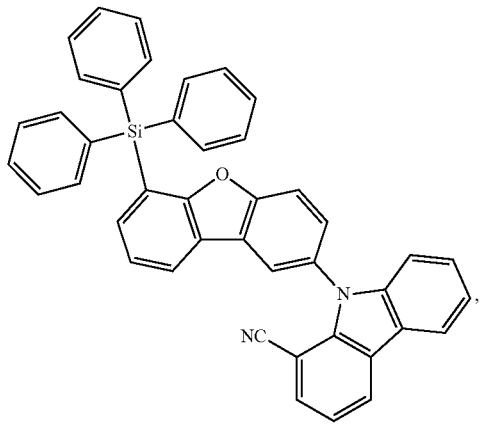
(A-43)
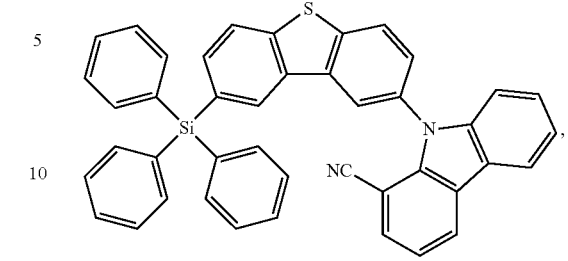
(A-40)
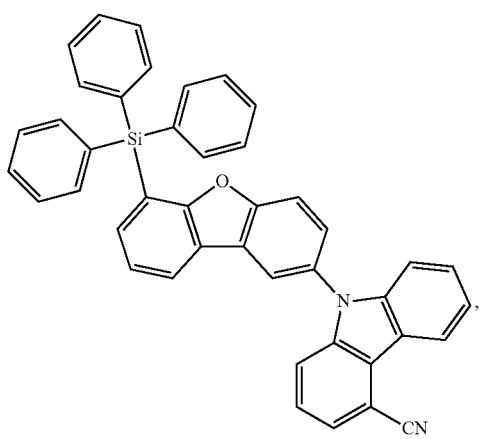
(A-44)
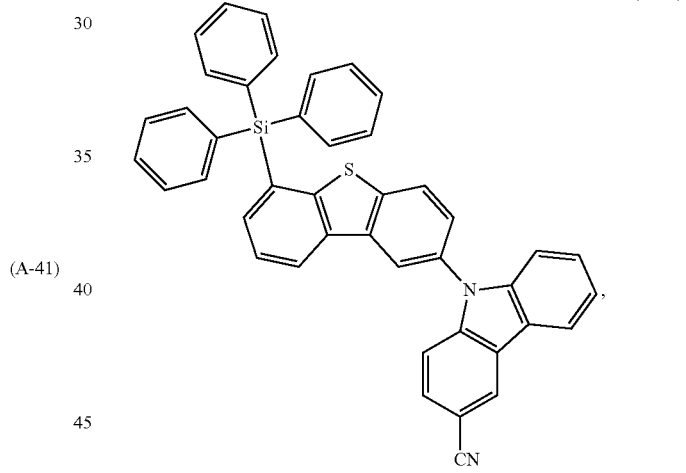
(A-41)
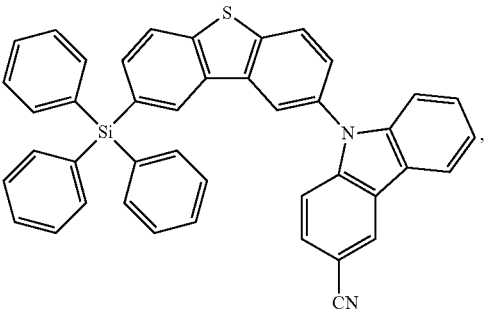
(A-45)
(A-42)
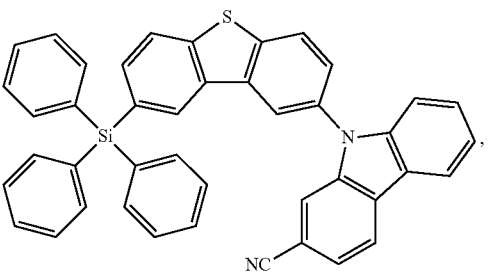
(A-46)
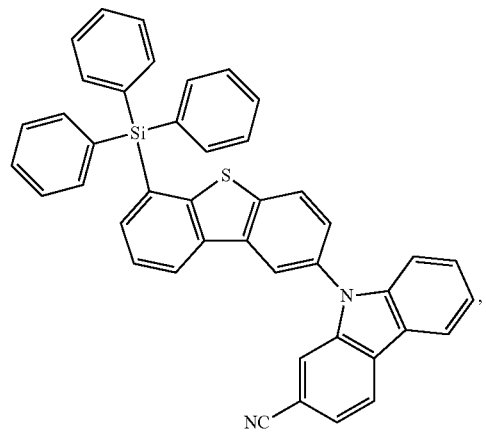

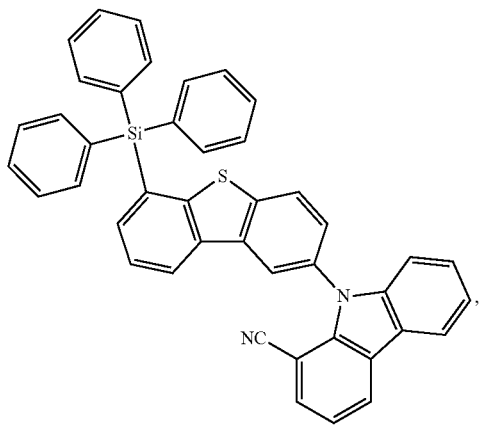
(A-47)
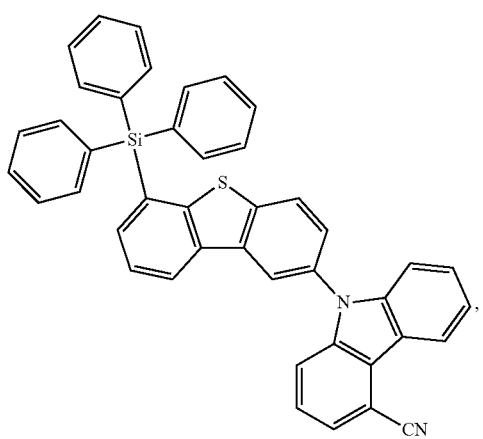
(A-48)
(A-49)
(A-50)
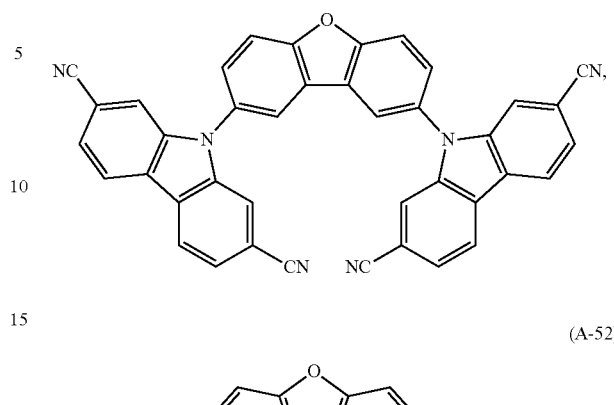
(A-51)
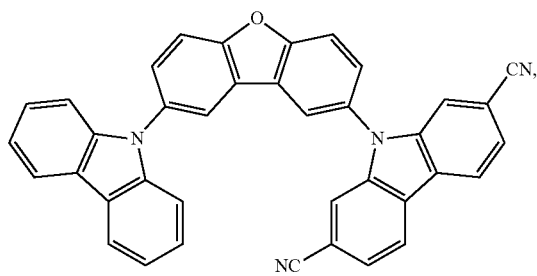
(A-52)
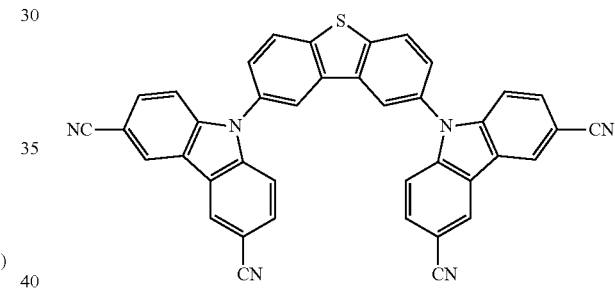
(A-53)
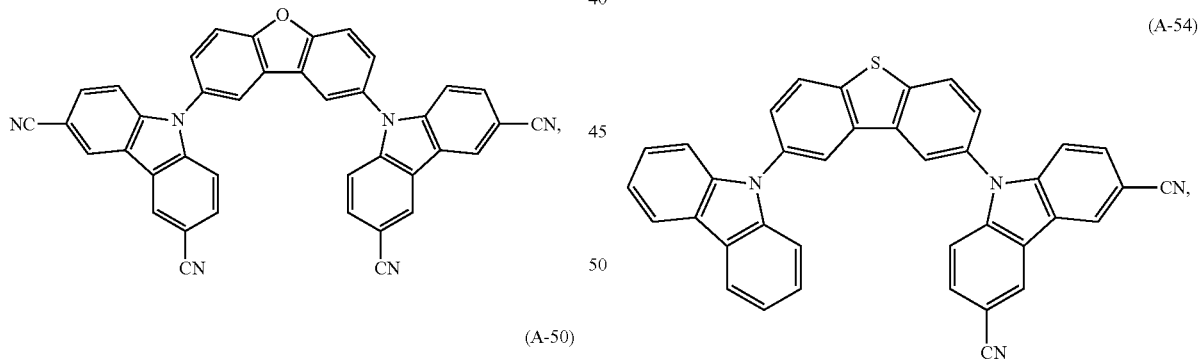
(A-54)
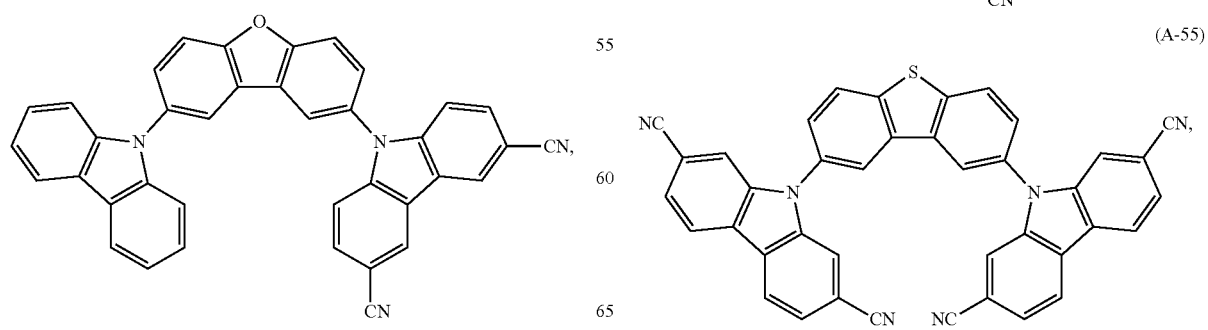
(A-55)

(A-56)
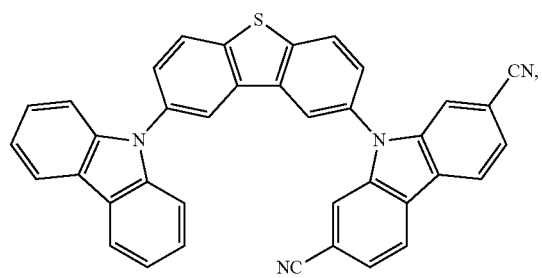
(A-57)
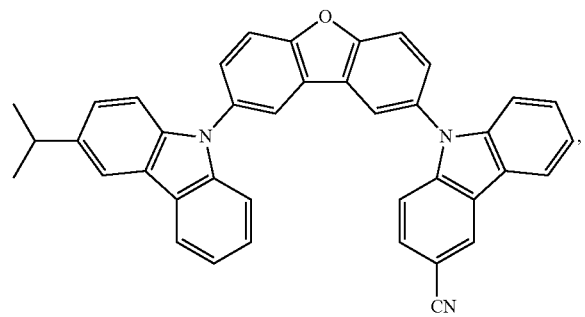
(A-58)
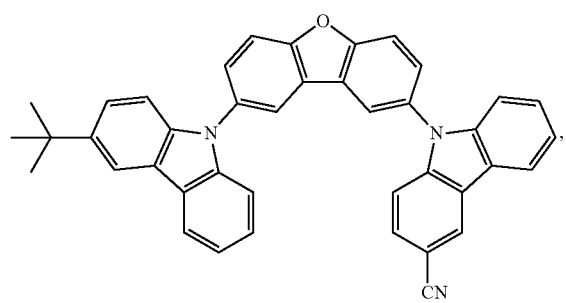
(A-59)
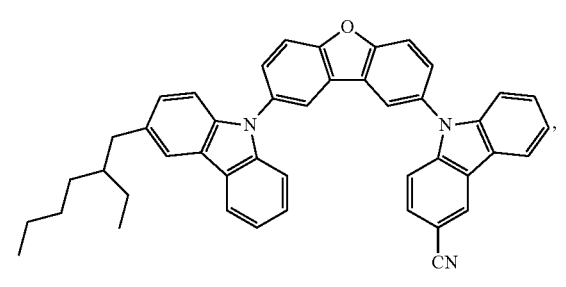
(A-60)
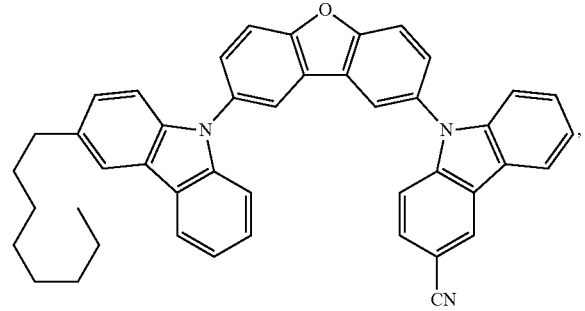
(A-61)
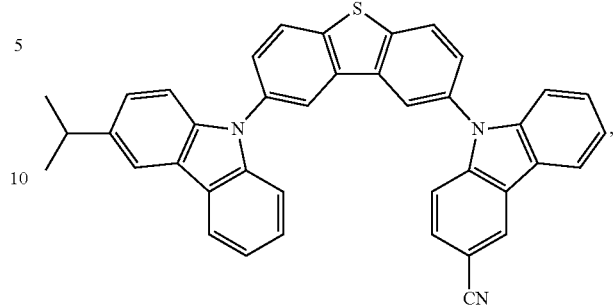
(A-62)
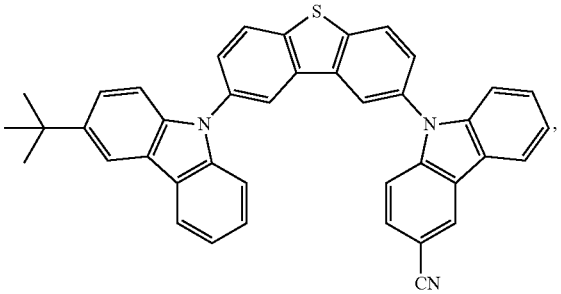
(A-63)
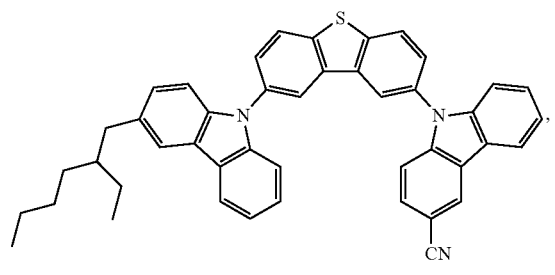
(A-64)
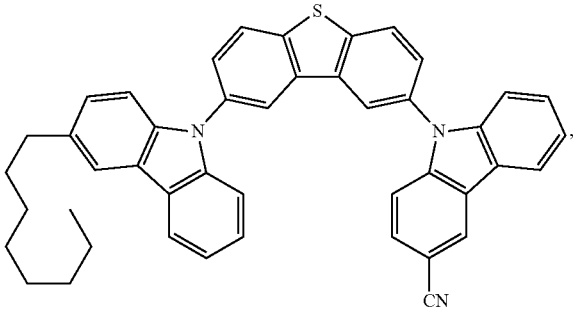
(A-65)
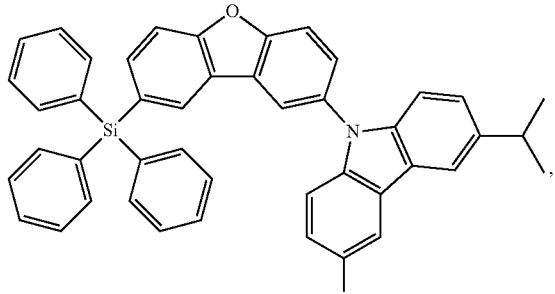

(A-66)
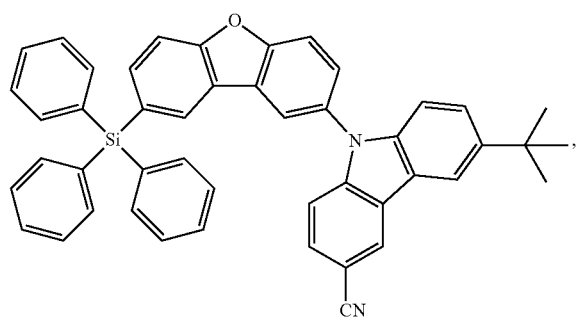
(A-67)
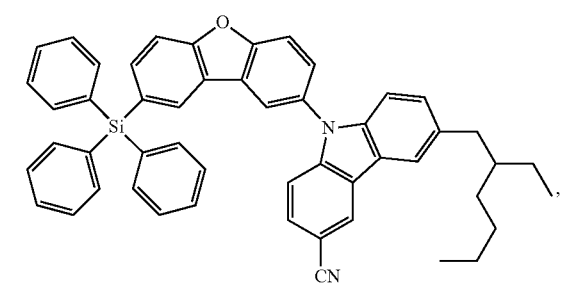
(A-68)
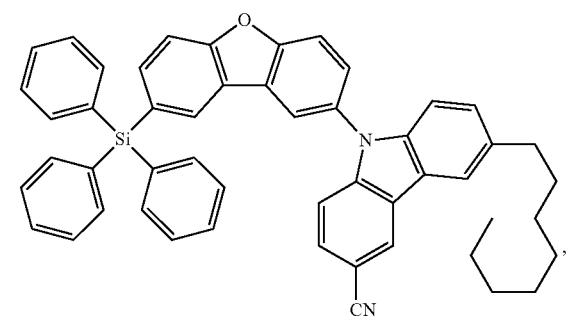
(A-69)
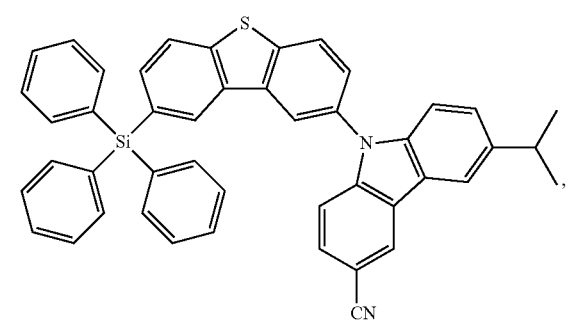
(A-70)
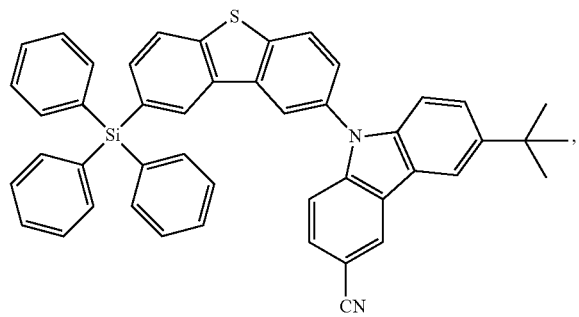
(A-71)
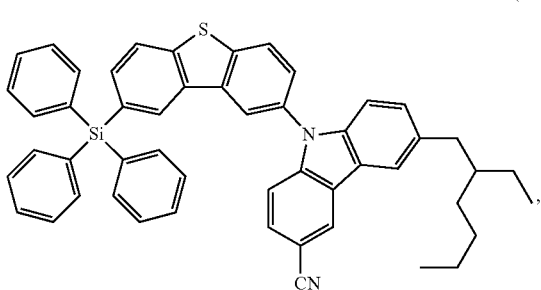
(A-72)
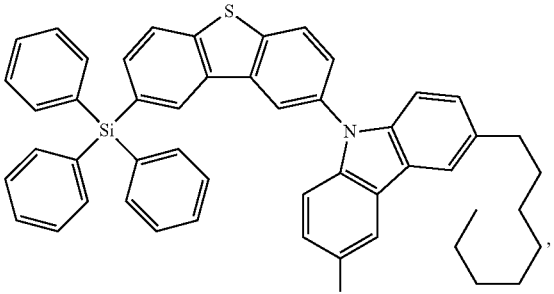
(A-73)
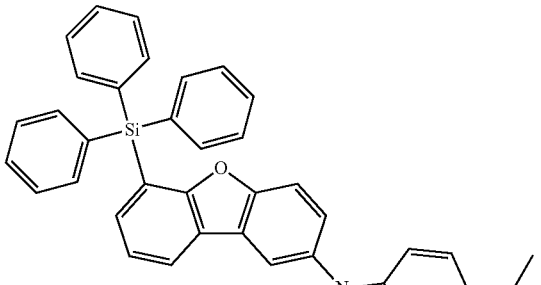
(A-74)
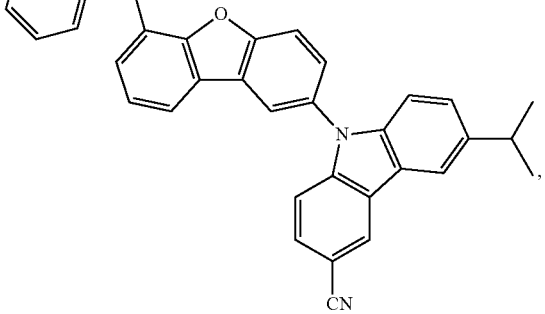

(A-75)
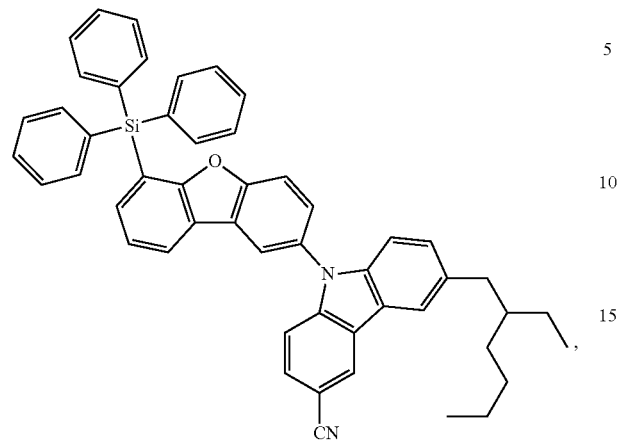
(A-76)
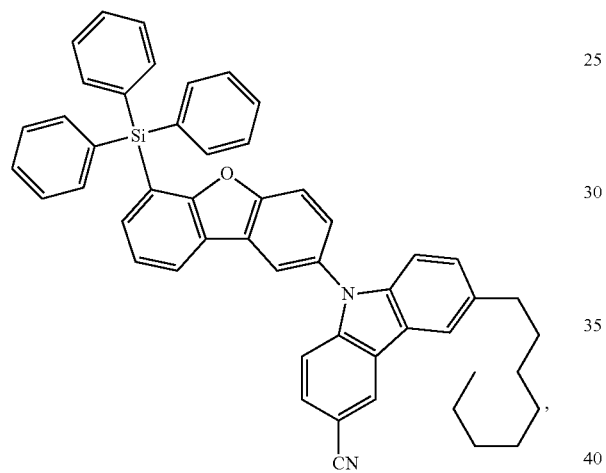
(B-1)
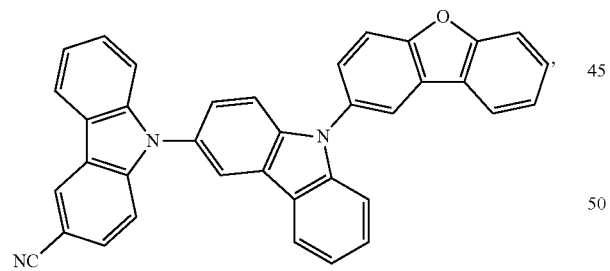
(B-2)
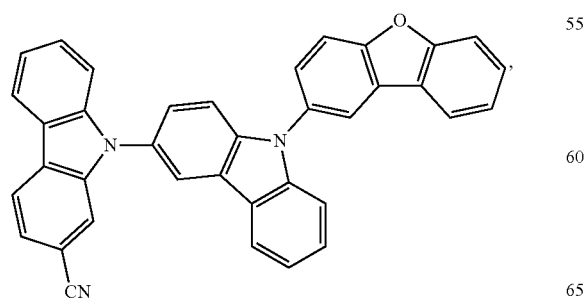
(B-3)
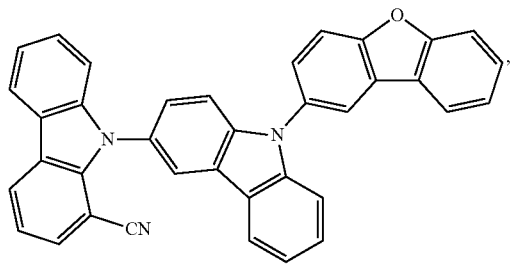
(B-4)
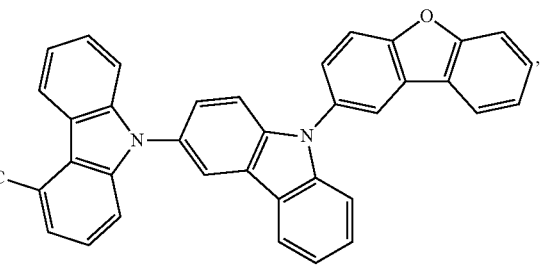
(B-5)
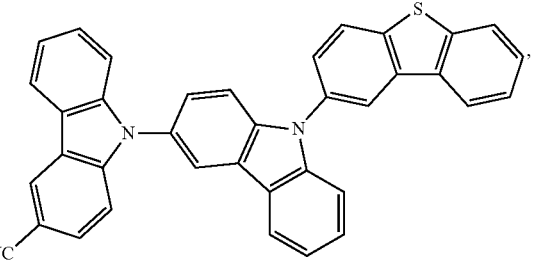
(B-6)
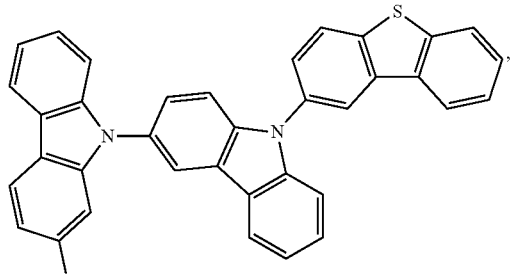
(B-7)
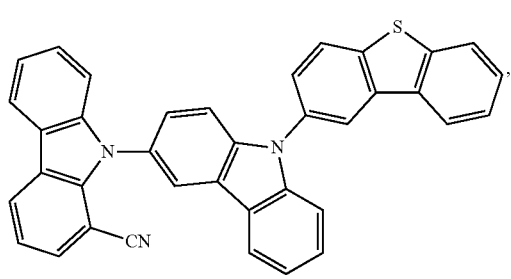

(B-8)
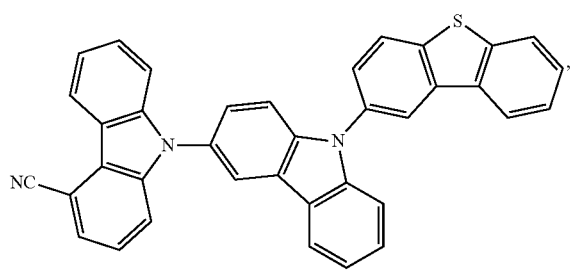
(B-9)
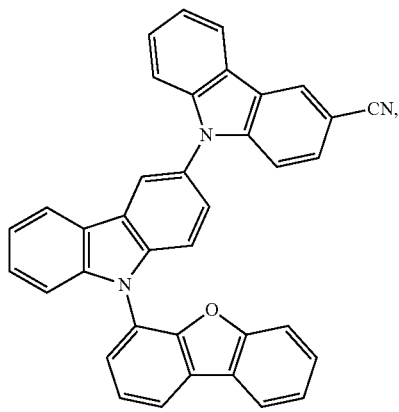
(B-10)
(B-11)
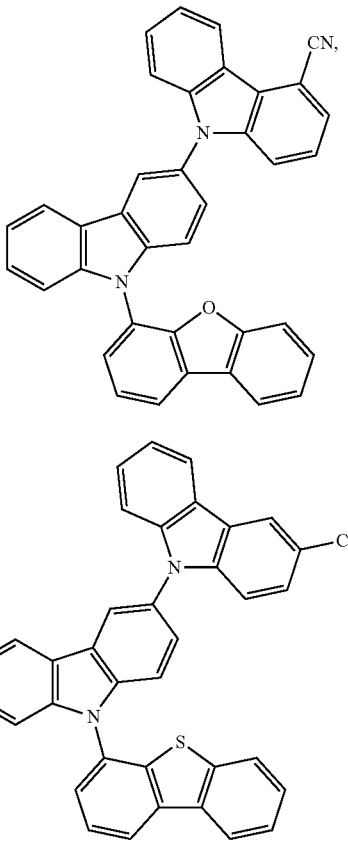
(B-12)
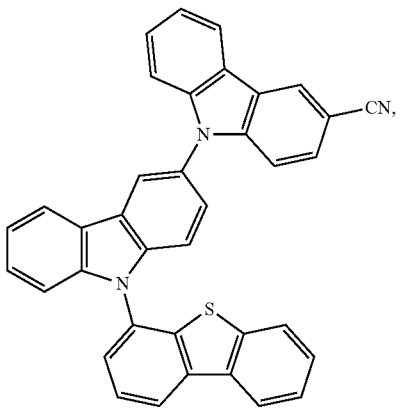
(B-13)
(B-14)
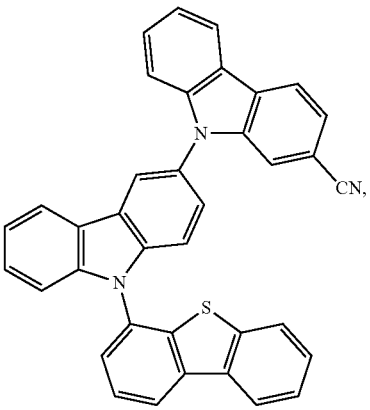
(B-15)
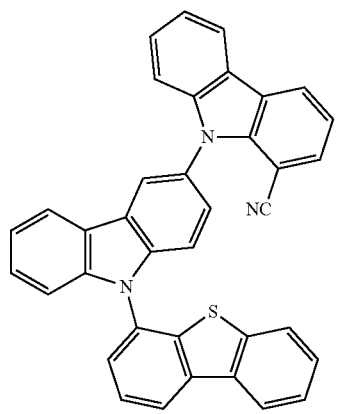

47
-continued
(B-16)
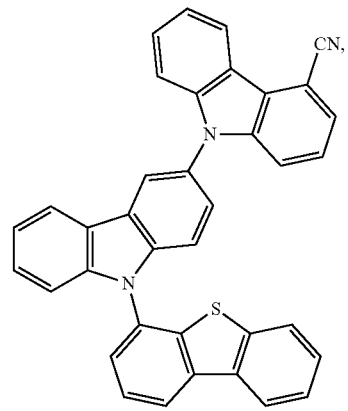
(B-17)
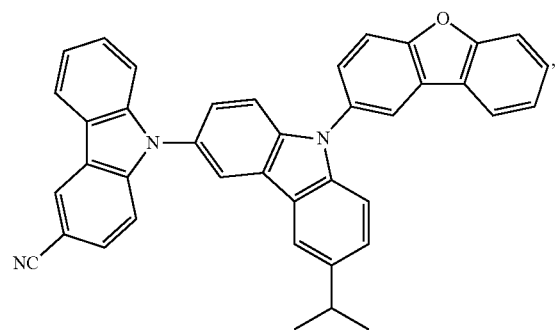
(B-18)
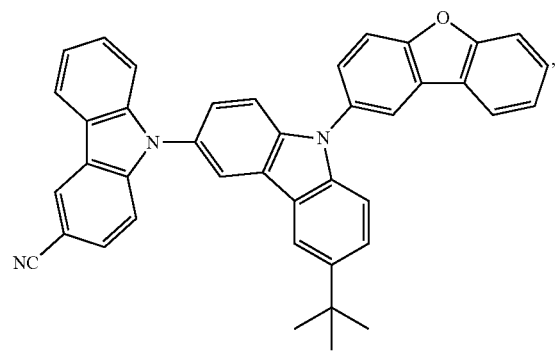
(B-19)
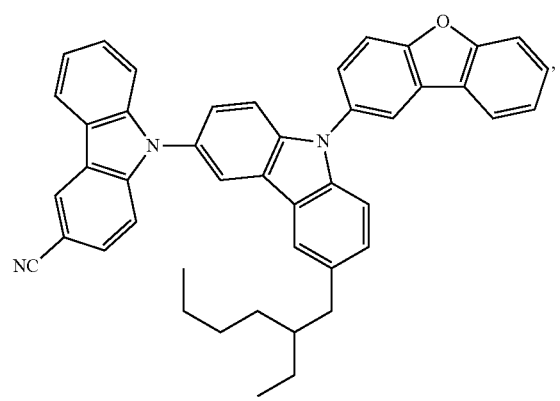
48
-continued
(B-20)
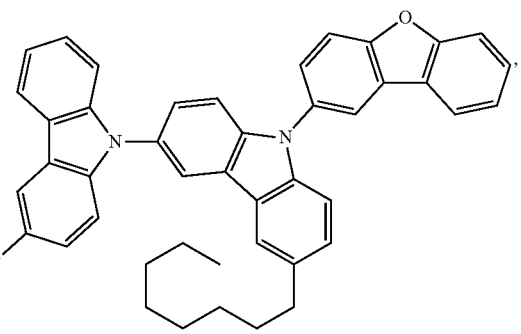
(B-21)
(B-22)
(B-23)
and
(B-24)
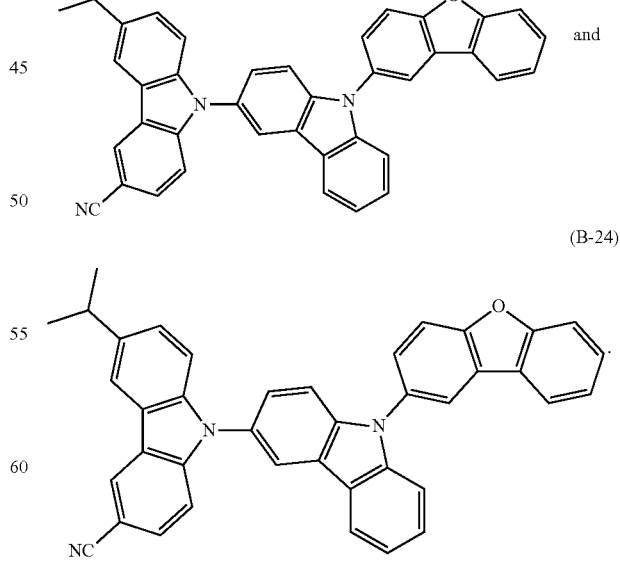
In another particularly preferred embodiment the present invention is directed to compounds of formula

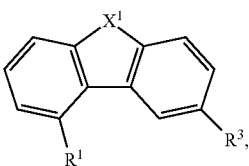

(Ic)

wherein
X¹ is O, or S;
R¹ is a group of formula

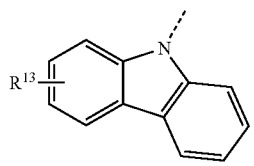

and R³ is a group of formula (XIIa), (XIIb), (XIIc), (XIId), (XIIf), (XIIg), or (XIIv); or
R¹ is a group of formula (XIIa), (XIIb), (XIIc), (XIId), (XIIf), (XIIg), or (XIIv) and R³ is a group of formula

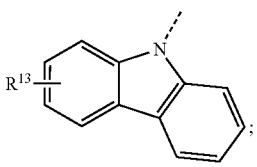

;

or
R¹ is a group of formula

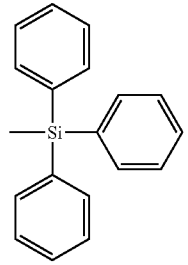 [SMILES: C[Si](c1ccccc1)(c1ccccc1)c1ccccc1]

and R³ is a group of formula (XIIa), (XIIb), (XIIc), (XIId), (XIIf), (XIIg), or (XIIv); or
R¹ is a group of formula (XIIa), (XIIb), (XIIc), (XIId), (XIIf), (XIIg), or (XIIv) and R³ is a group of formula

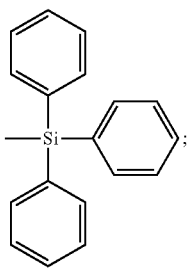 [SMILES: C[Si](c1ccccc1)(c1ccccc1)c1ccccc1]

;

or
R¹ and R³ are independently of each other a group of formula (XIIa), (XIIb), (XIIc), (XIId), (XIIf), (XIIg), or (XIIv); or R¹ is a group of formula (XIIIa), (XIIIb), (XIIIc), (XIIId), (XIIIf), (XIIIg), (XIIIs), or (XIIIt) and R³ is H. R¹³ is a $C_1$-$C_{25}$alkyl group, especially a $C_3$-$C_{12}$alkyl group, such as, for example, n-propyl, iso-propyl, n-butyl, isobutyl, tert-butyl, sec-butyl, hexyl, heptyl, octyl, or 2-ethylhexyl.

In another particularly preferred embodiment the present invention is directed to compounds of formula

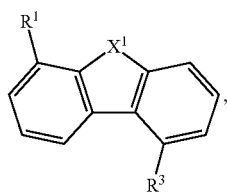

(Id)

wherein
X¹ is O, or S;
R¹ is a group of formula

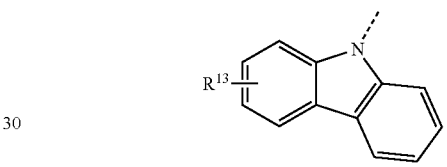

and R³ is a group of formula (XIIa), (XIIb), (XIIc), (XIId), (XIIf), (XIIg), or (XIIv); or
R¹ is a group of formula (XIIa), (XIIb), (XIIc), (XIId), (XIIf), (XIIg), or (XIIv) and R³ is a group of formula

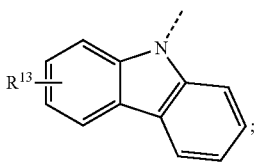

;

or
R¹ is a group of formula

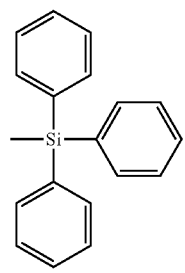 [SMILES: C[Si](c1ccccc1)(c1ccccc1)c1ccccc1]

and R³ is a group of formula (XIIa), (XIIb), (XIIc), (XIId), (XIIf), (XIIg), or (XIIv); or
R¹ is a group of formula (XIIa), (XIIb), (XIIc), (XIId), (XIIf), (XIIg), or (XIIv) and R³ is a group of formula

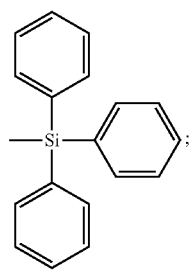 [SMILES: C[Si](c1ccccc1)(c1ccccc1)c1ccccc1]

or $R^1$ and $R^3$ are independently of each other a group of formula (XIIa), (XIIb), (XIIc), (XIId), (XIIf), (XIIg), or (XIIv); or $R^3$ is a group of formula (XIIIa), (XIIIb), (XIIIc), (XIIId), (XIIIf), (XIIIg), (XIIIs), or (XIIIt) and $R^1$ is H. $R^{13}$ is a $C_1$-$C_{25}$alkyl group, especially a $C_3$-$C_{12}$alkyl group, such as, for example, n-propyl, iso-propyl, n-butyl, isobutyl, tert-butyl, sec-butyl, hexyl, heptyl, octyl, or 2-ethylhexyl.

Examples of particularly preferred compounds of formula (Ic) and (Id) are shown below:

(A-77)
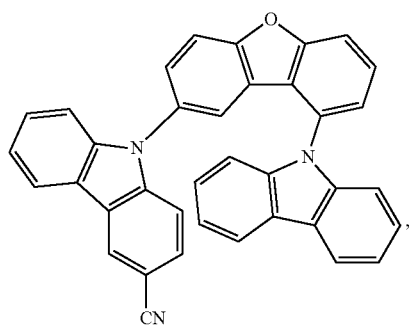

(A-78)
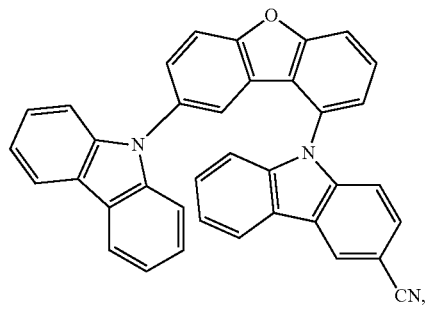

(A-79)
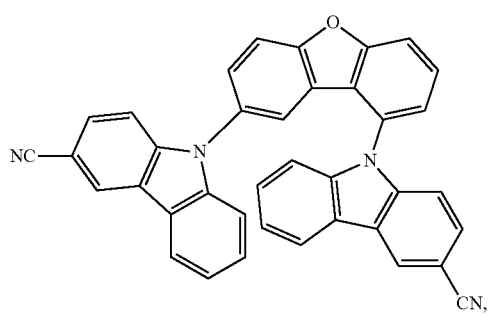

(A-80)
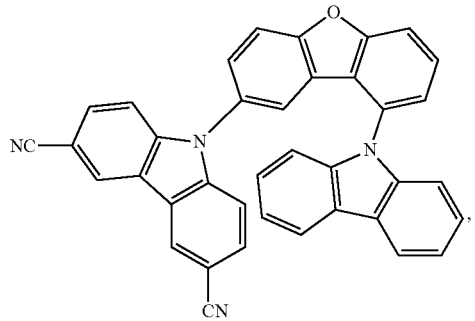

(A-81)
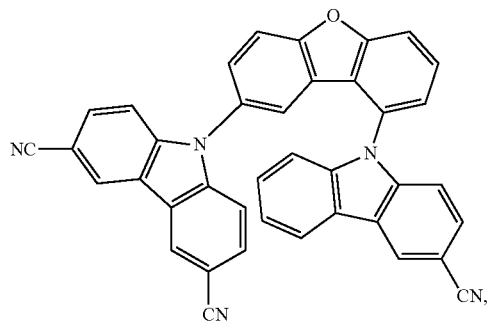

(A-82)
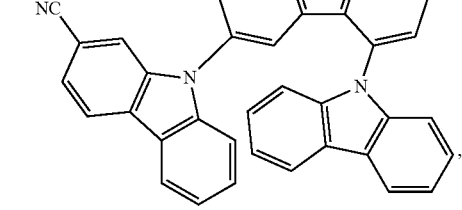

(A-83)
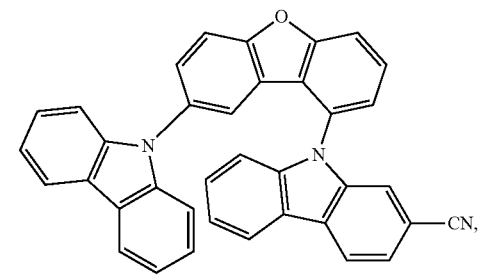

(A-84)
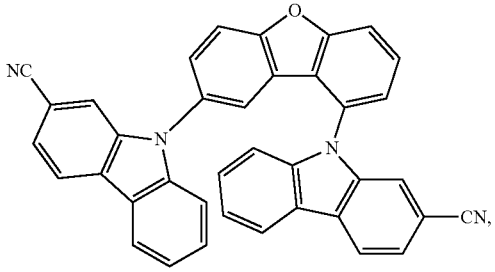

-continued
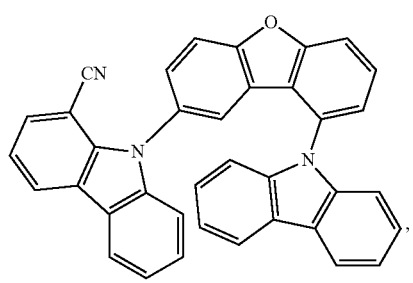
(A-85)
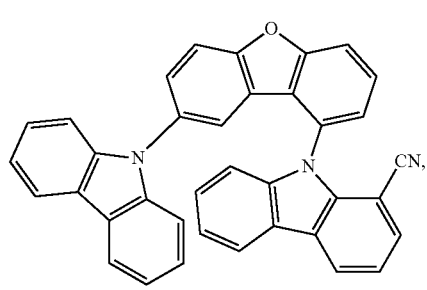
(A-86)
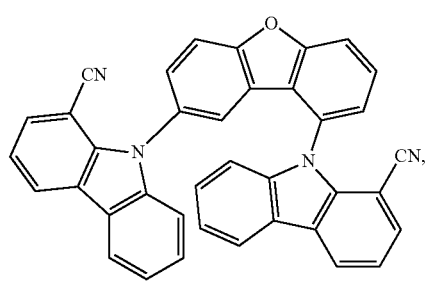
(A-87)
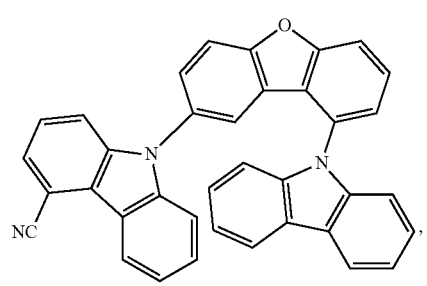
(A-88)
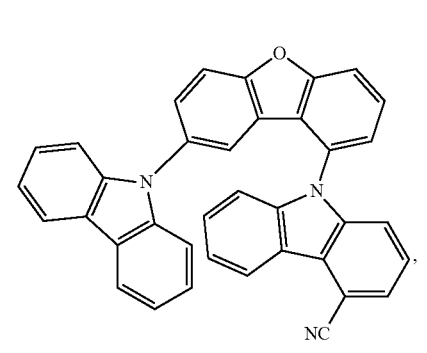
(A-89)
-continued
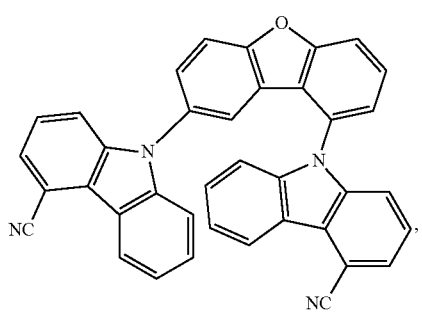
(A-90)
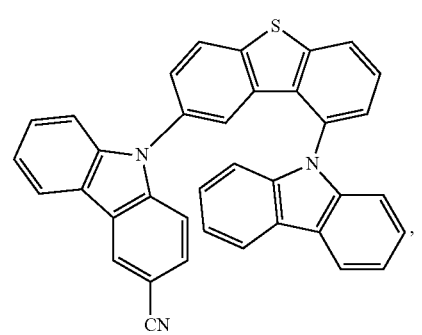
(A-91)
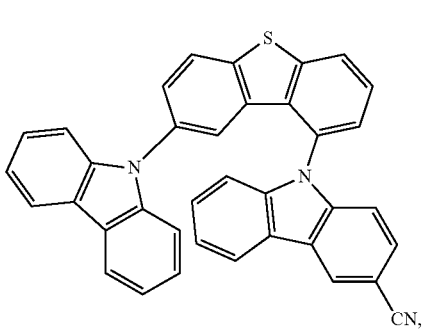
(A-92)
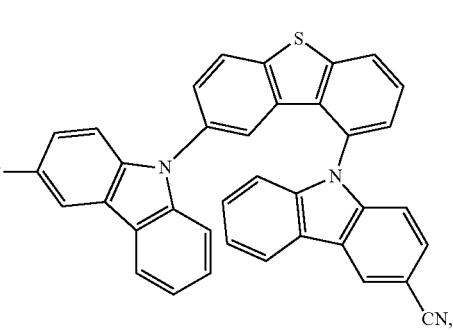
(A-93)
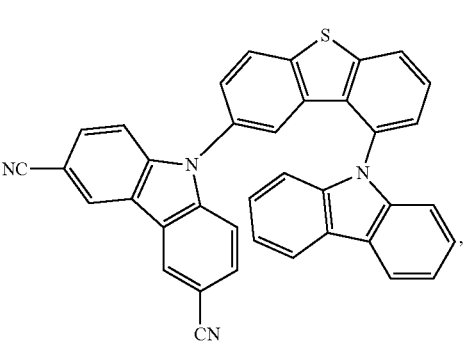
(A-94)

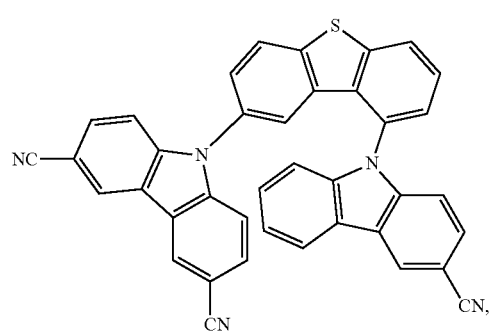
(A-95)
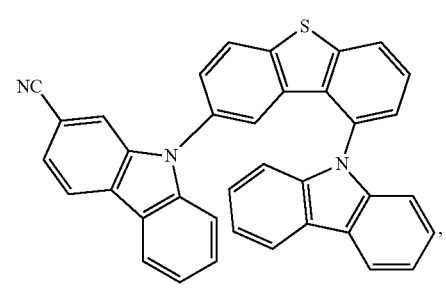
(A-96)
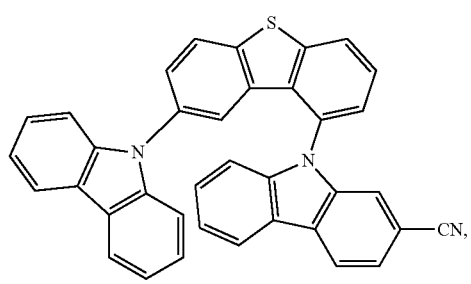
(A-97)
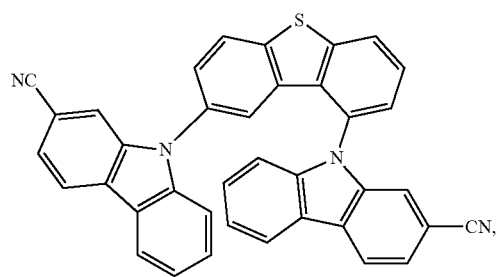
(A-98)
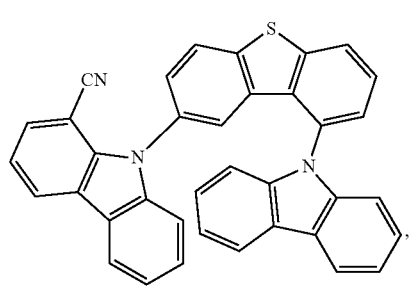
(A-99)
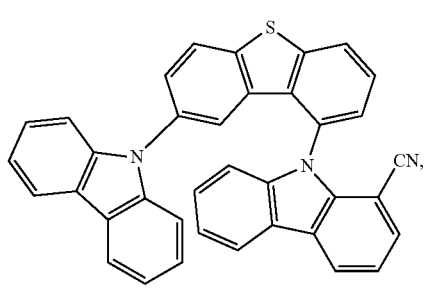
(A-100)
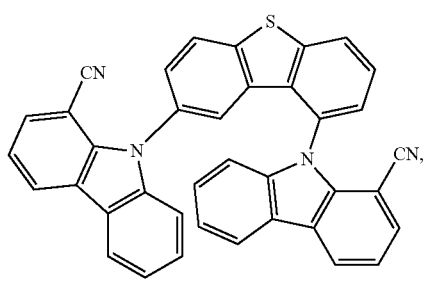
(A-101)
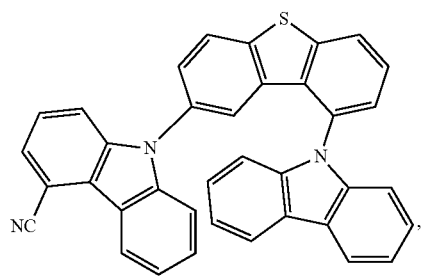
(A-102)
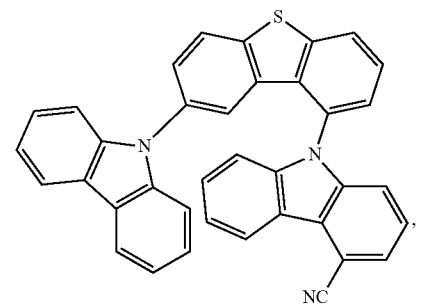
(A-103)
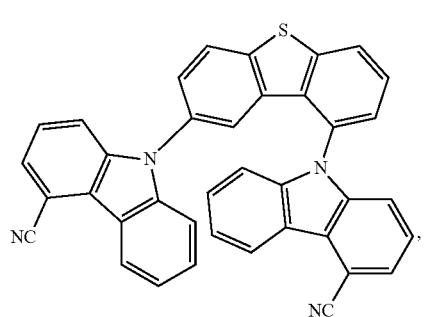
(A-104)

(A-105)
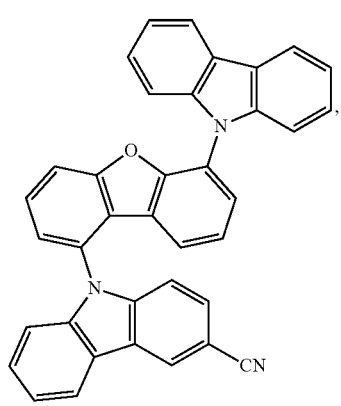
(A-106)
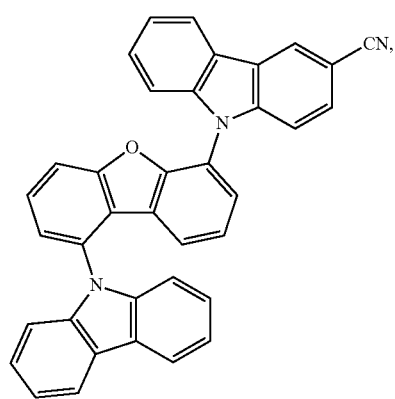
(A-107)
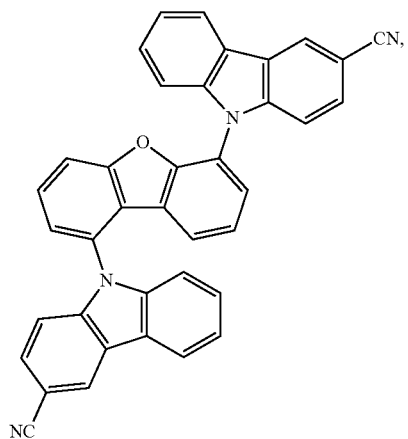
(A-108)
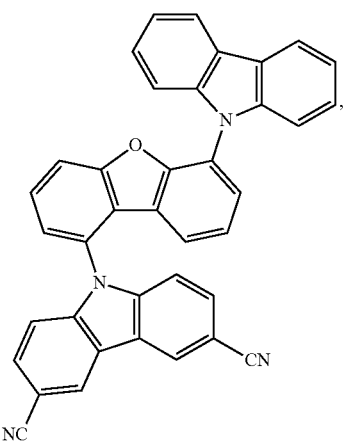
(A-109)
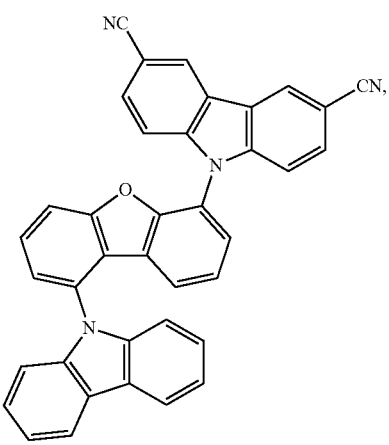
(A-110)
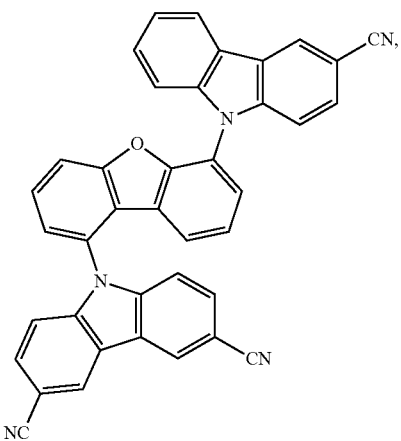

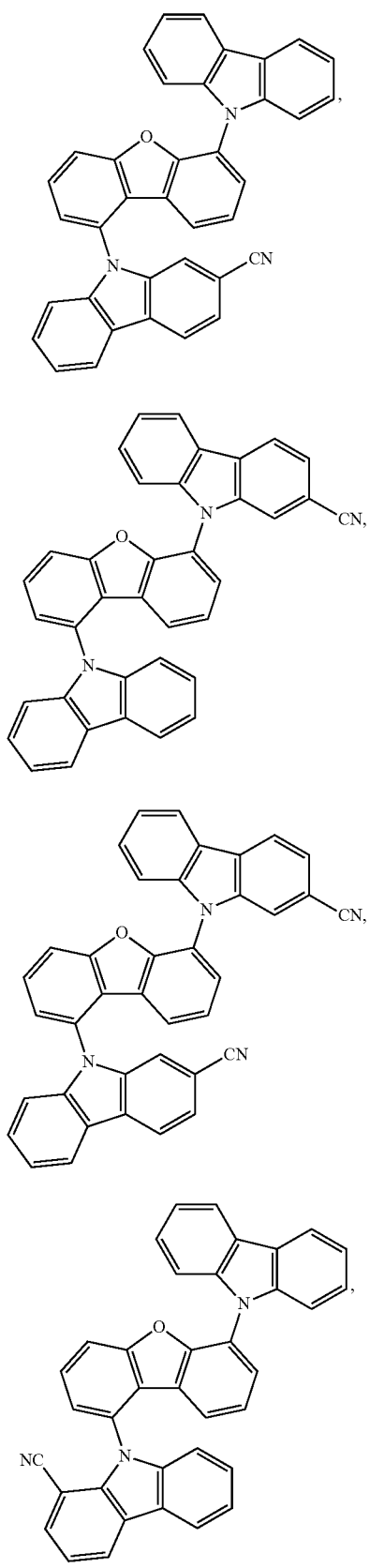
(A-111)
(A-112)
(A-113)
(A-114)
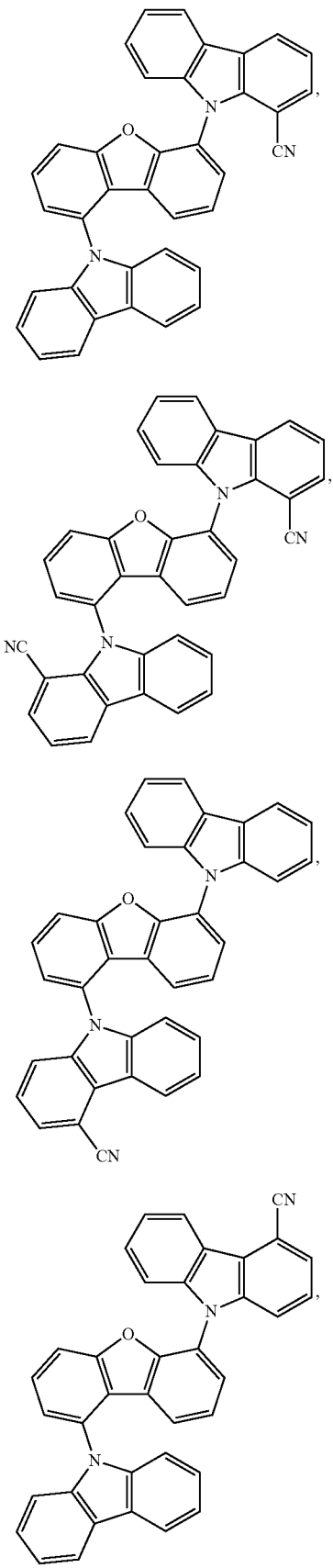
(A-115)
(A-116)
(A-117)
(A-118)

-continued
(A-119)
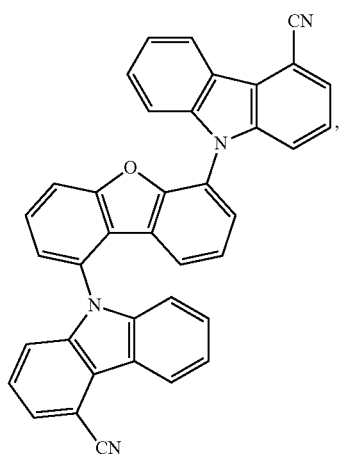
(A-122)
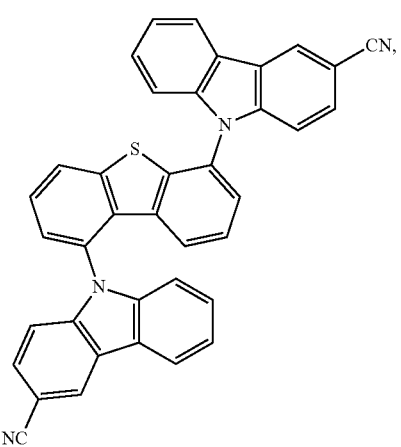
(A-120)
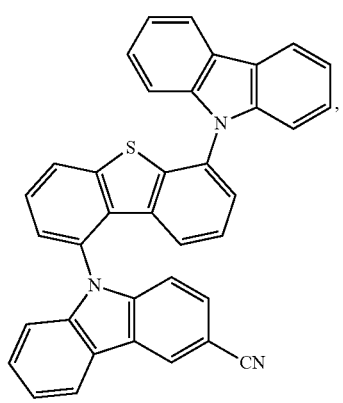
(A-123)
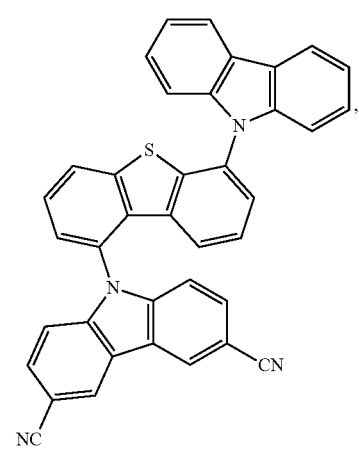
(A-121)
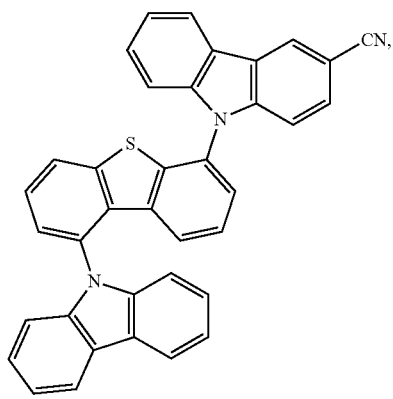
(A-124)
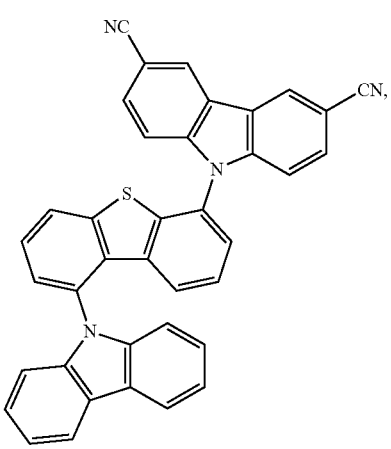

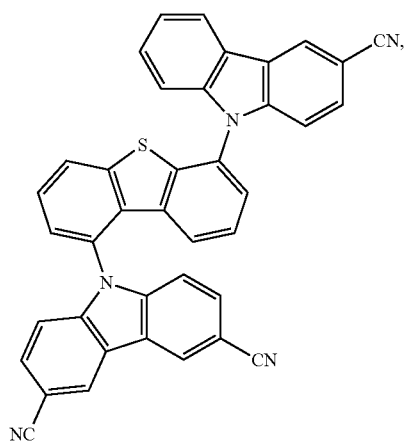
(A-125)
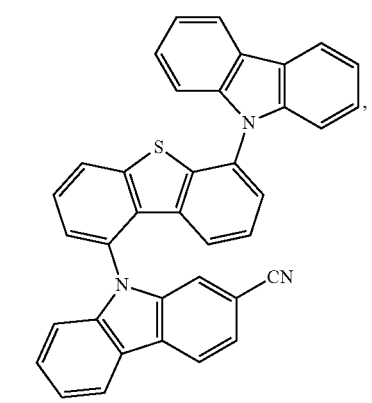
(A-126)
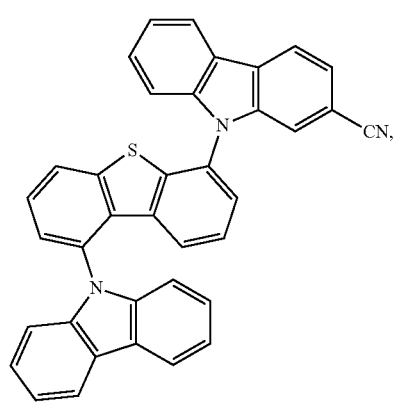
(A-127)
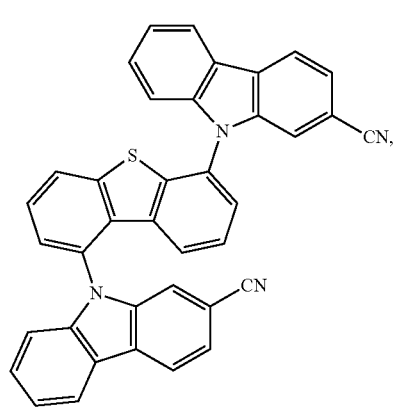
(A-128)
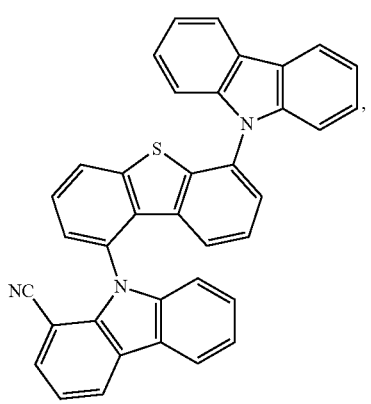
(A-129)
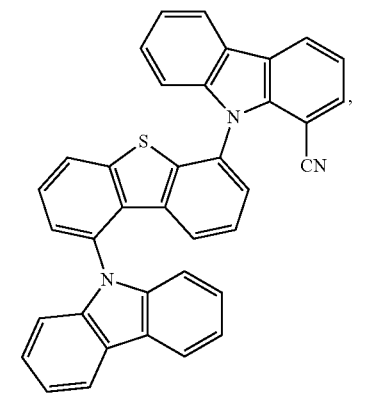
(A-130)
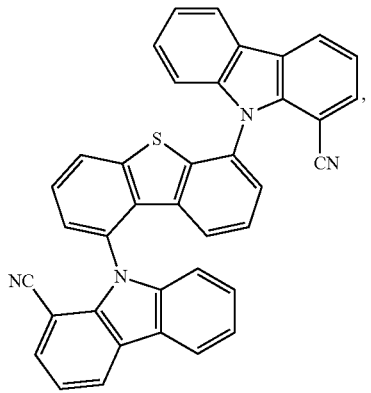
(A-131)
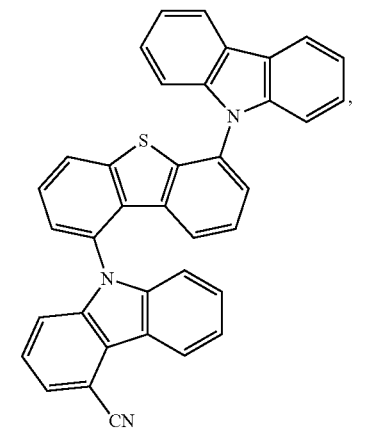
(A-132)

-continued

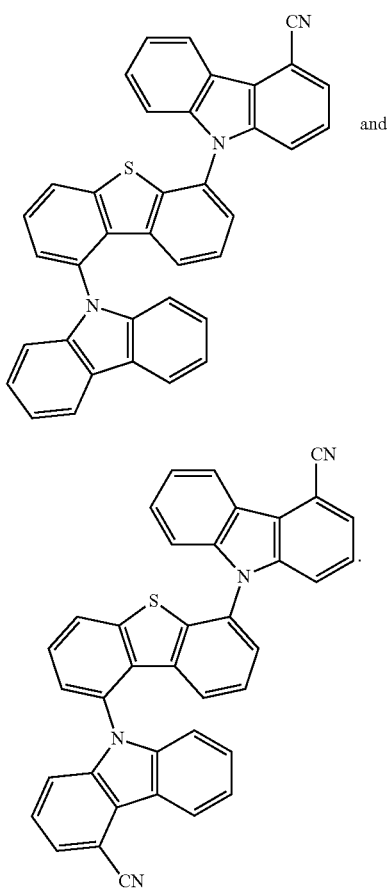

(A-133)

(A-134)

In another particularly preferred embodiment the present invention is directed to compounds of formula

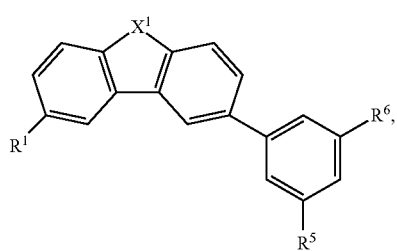

(IIa)

wherein
X¹ is O, or S; R⁵ is H, or a $C_1$-$C_{25}$alkyl group,
R¹ is a group of formula

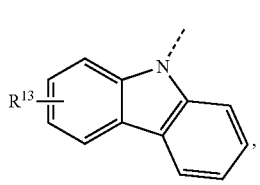

and R⁶ is a group of formula (XIIa), (XIIb), (XIIc), (XIId), (XIIf), (XIIg), or (XIIv); or R¹ is a group of formula (XIIa), (XIIb), (XIIc), (XIId), (XIIf), (XIIIg), or (XIIv) and R⁶ is a group of formula

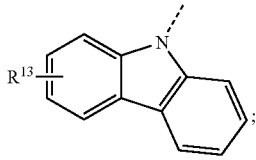

or R¹ and R⁶ are independently of each other a group of formula (XIIa), (XIIb), (XIIc), (XIId), (XIIf), (XIIg), or (XIIv). R¹³ is H, or a $C_1$-$C_{25}$alkyl group, especially a $C_3$-$C_{12}$alkyl group. Examples of particularly preferred compounds of formula (IIa) are shown below:

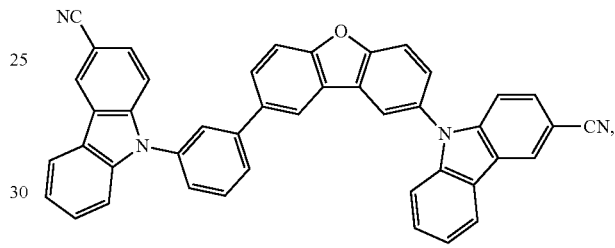

(C-1)

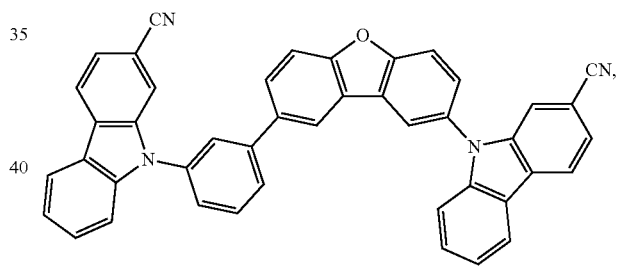

(C-2)

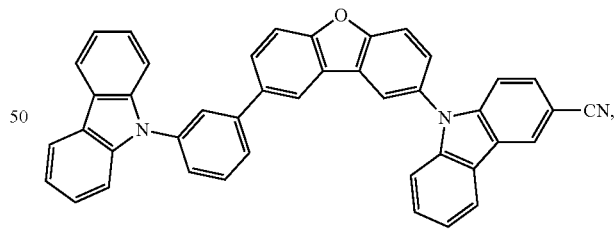

(C-3)

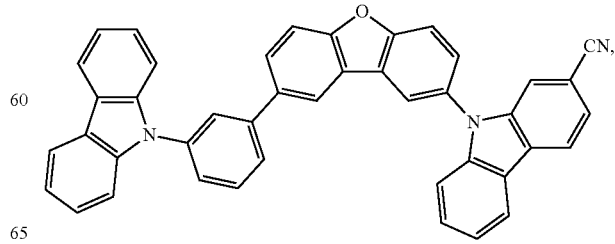

(C-4)

-continued
(C-5)
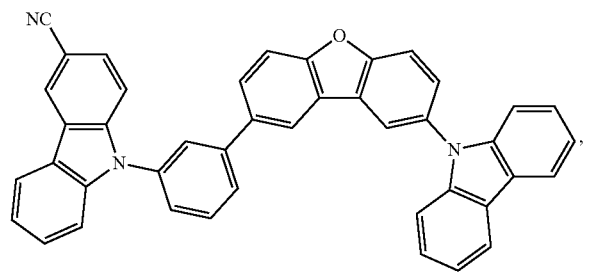
(C-6)
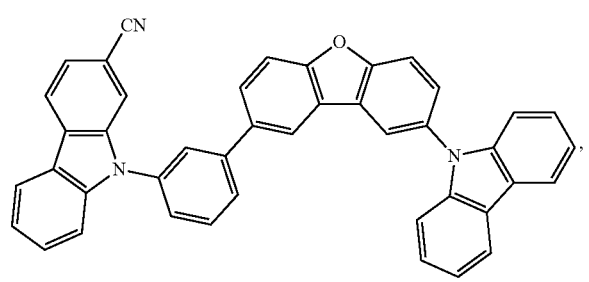
(C-7)
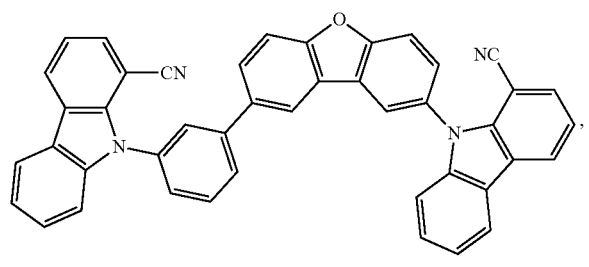
(C-8)
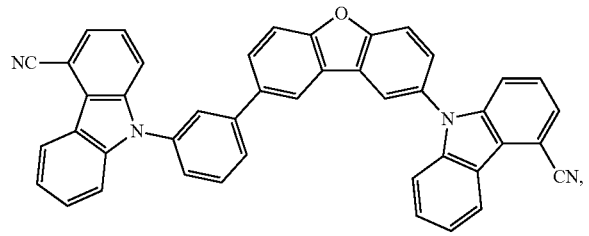
(C-9)
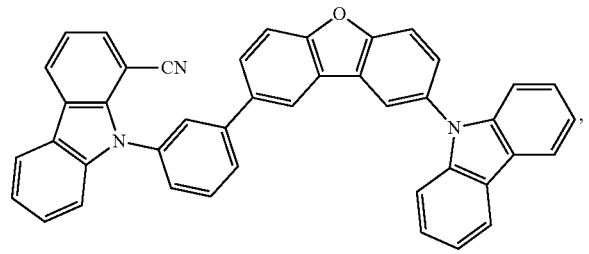
-continued
(C-10)
(C-11)
(C-12)
(C-13)
(C-14)
(C-15)
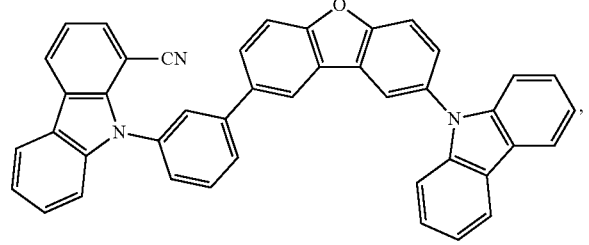

(C-16)
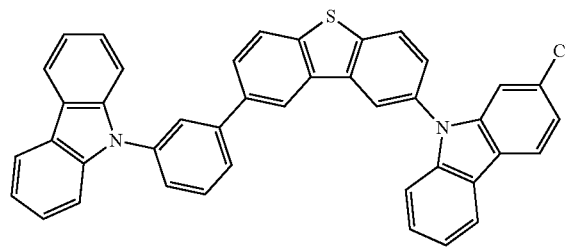
(C-17)
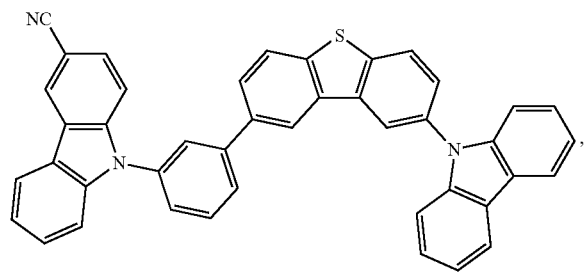
(C-18)
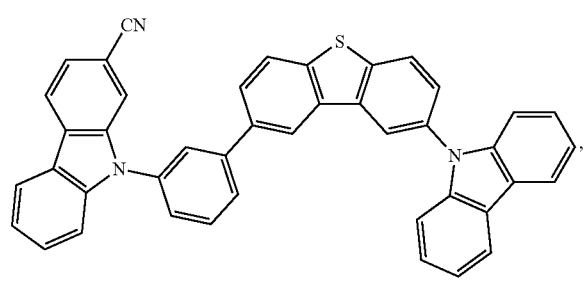
(C-19)
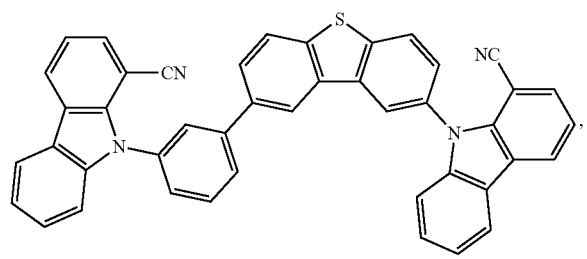
(C-20)
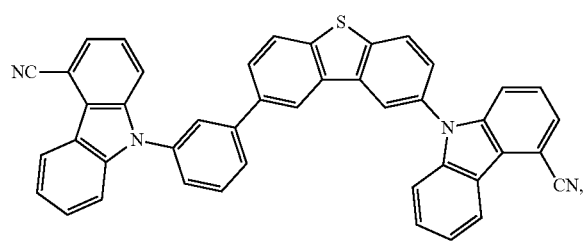
(C-21)
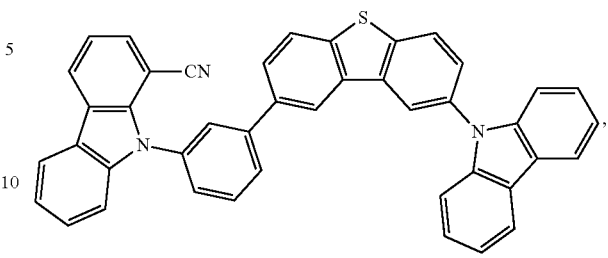
(C-22)
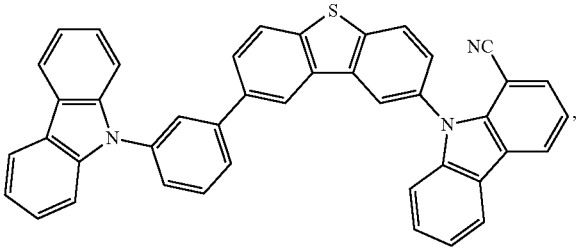
(C-23)
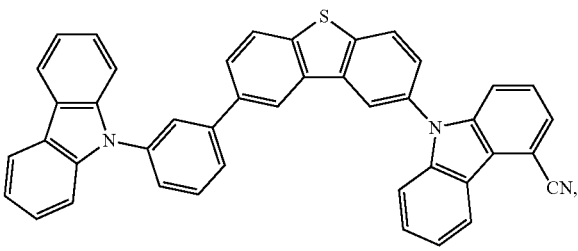
(C-24)
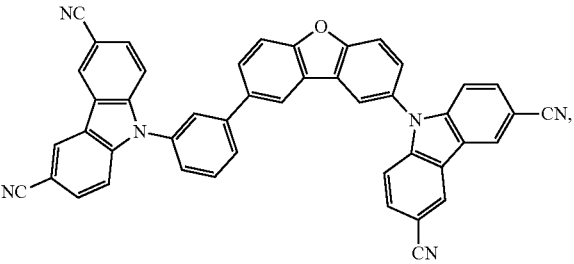
(C-25)

-continued
(C-26)
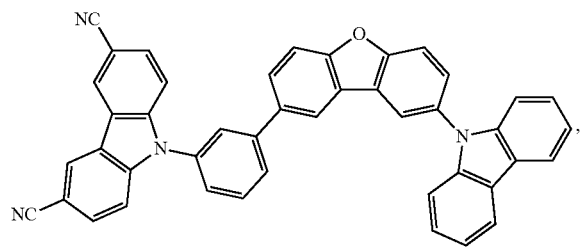
(C-27)
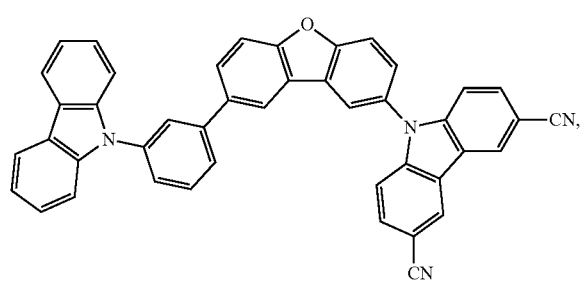
(C-28)
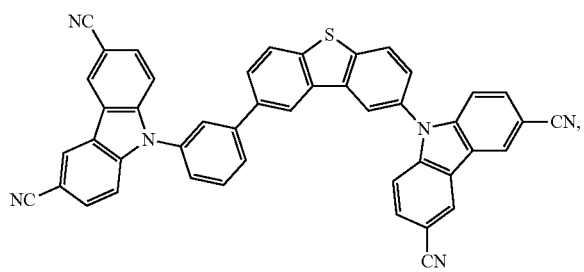
(C-29)
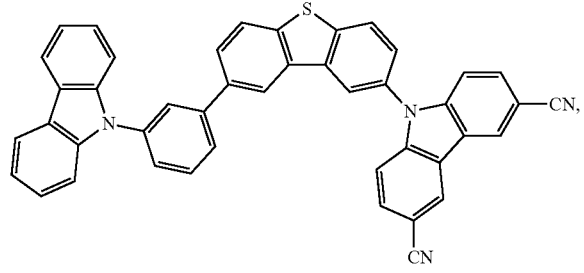
(C-30)
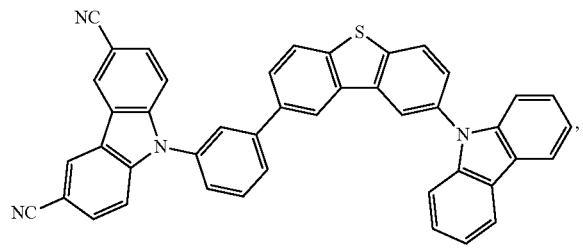
-continued
(C-31)
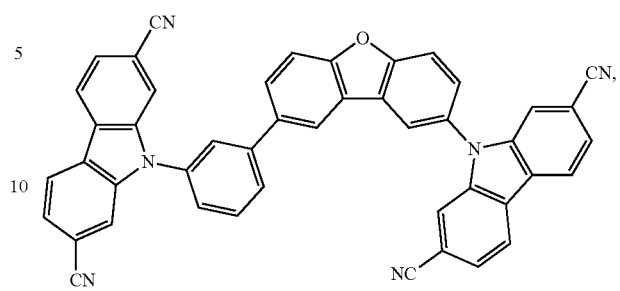
(C-32)
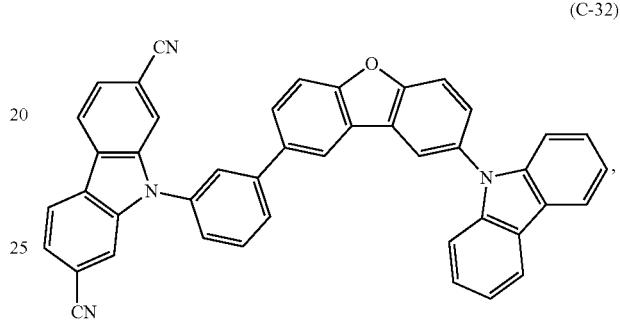
(C-33)
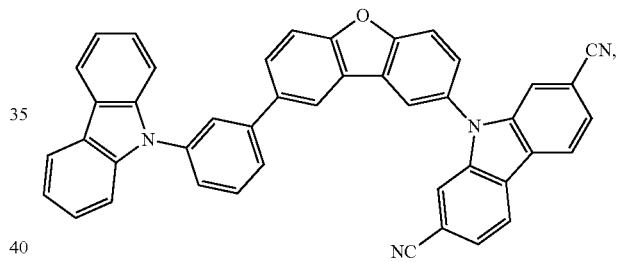
(C-34)
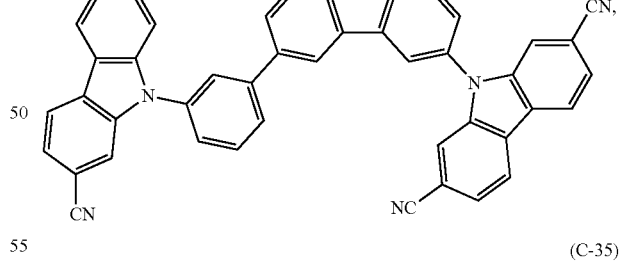
(C-35)
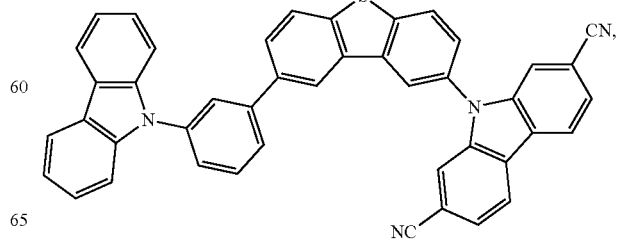

(C-36)
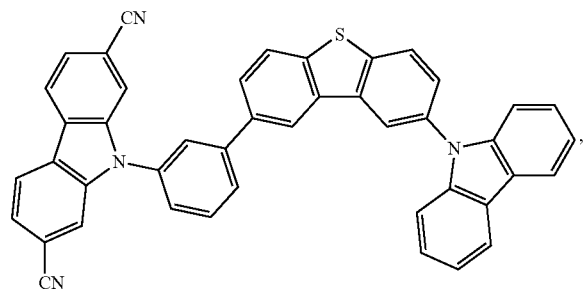
(C-37)
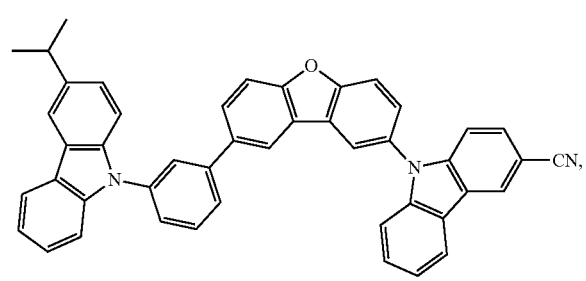
(C-38)
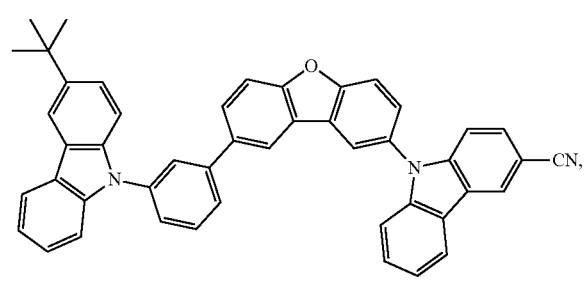
(C-39)
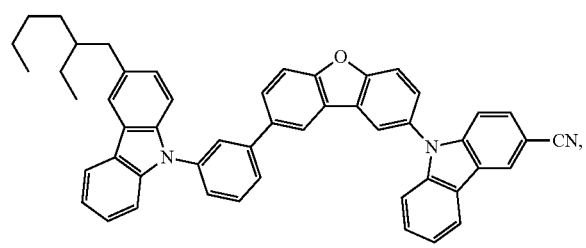
(C-40)
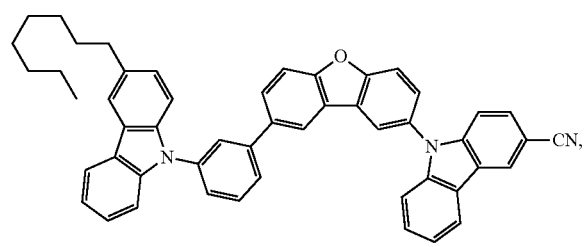
(C-41)
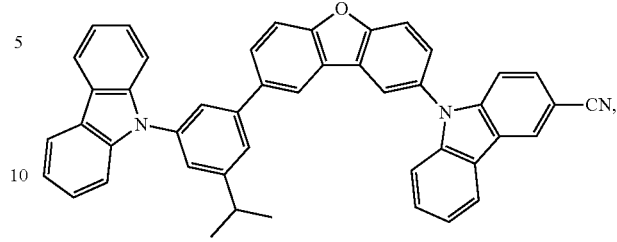
(C-42)
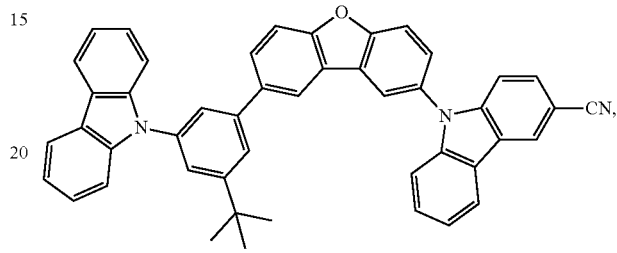
(C-43)
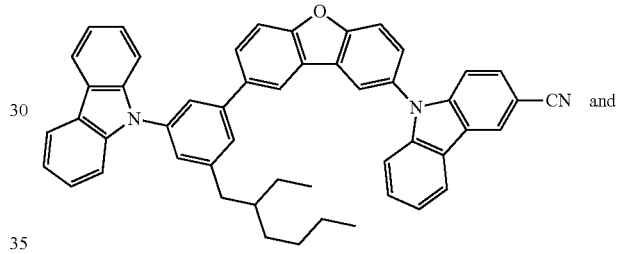
and
(C-44)
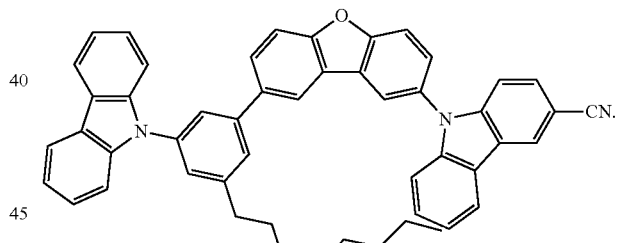
In another particularly preferred embodiment the present invention is directed to compounds of formula
(IIIa)
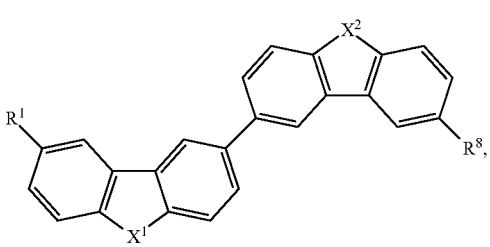
wherein
$X^1$ and $X^2$ are independently of each other O, or S;

R¹ is a group of formula

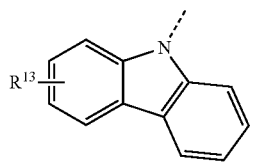

and R⁸ is a group of formula (XIIa), (XIIb), (XIIc), (XIId), (XIIf), (XIIg), or (XIIv); or R¹ is a group of formula (XIIa), (XIIb), (XIIc), (XIId), (XIIf), (XIIg), or (XIIv) and R⁸ is a group of formula

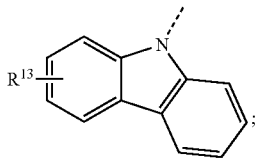

or R¹ and R⁸ are independently of each other a group of formula (XIIa), (XIIb), (XIIc), (XIId), (XIIf), (XIIg), or (XIIv) and R¹³ is H, or a $C_1$-$C_{25}$alkyl group, especially a $C_3$-$C_{12}$alkyl group. Examples of particularly preferred compounds of formula (IIIa) are shown below:

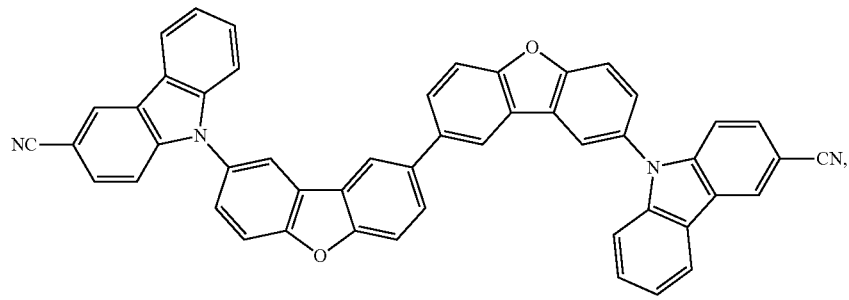

(D-1)

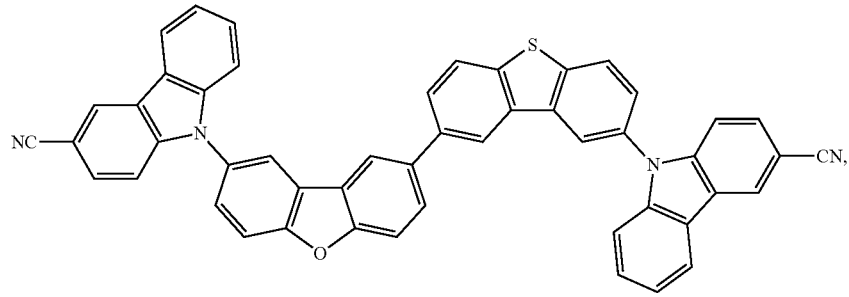

(D-2)

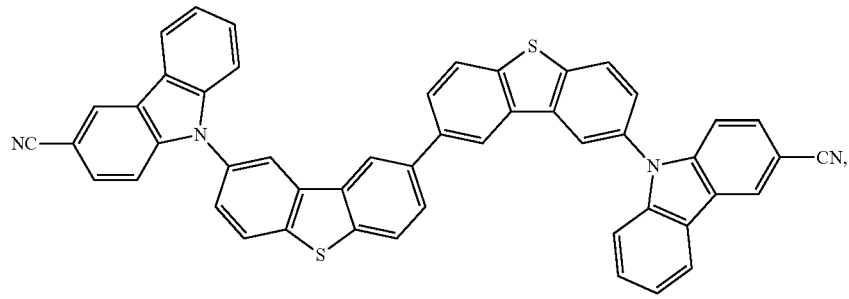

(D-3)

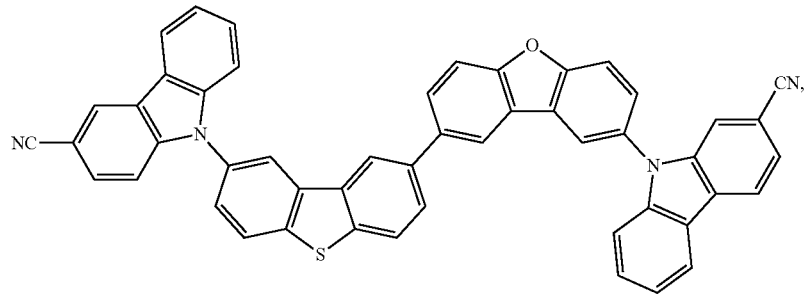

(D-4)

-continued
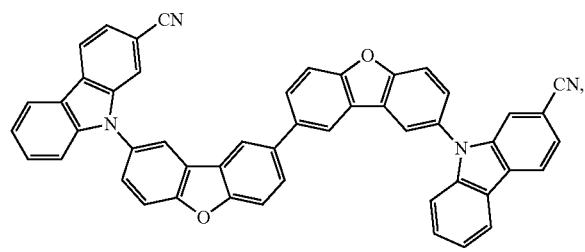
(D-5)
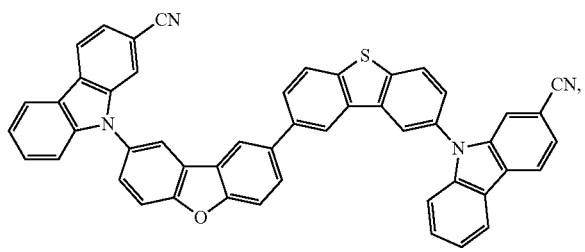
(D-6)
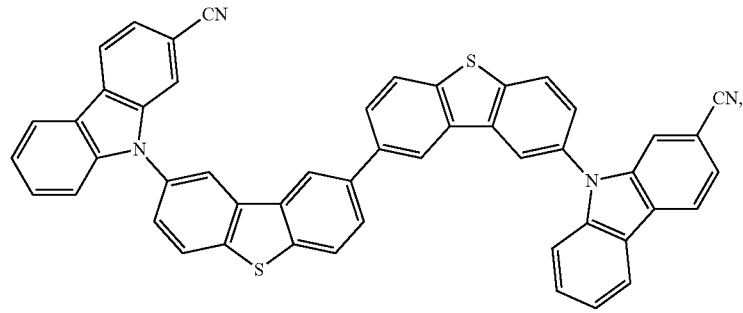
(D-7)
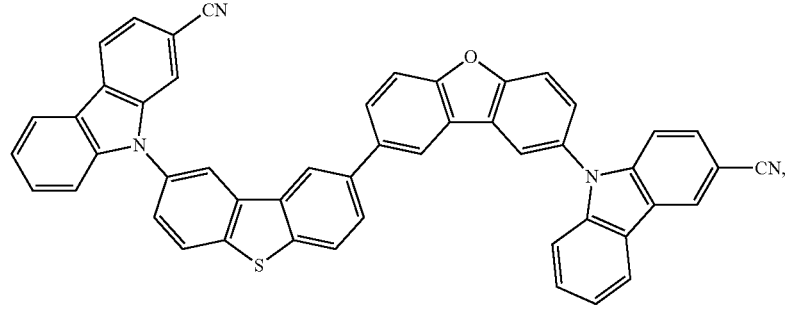
(D-8)
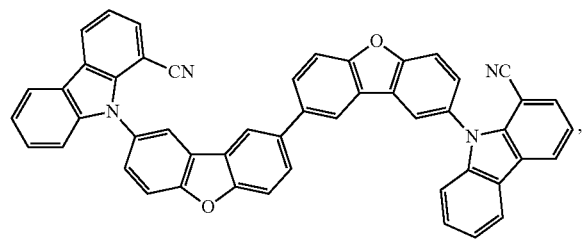
(D-9)
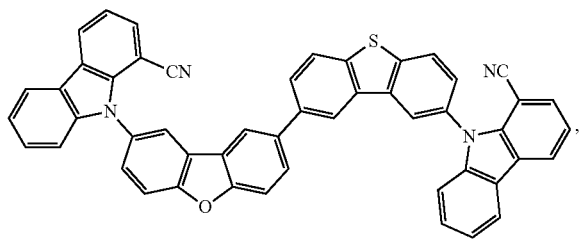
(D-10)
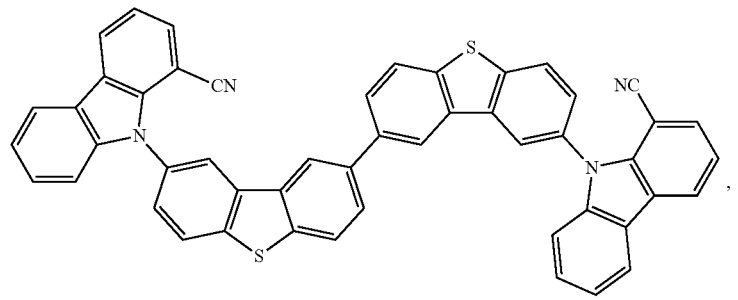
(D-11)

-continued
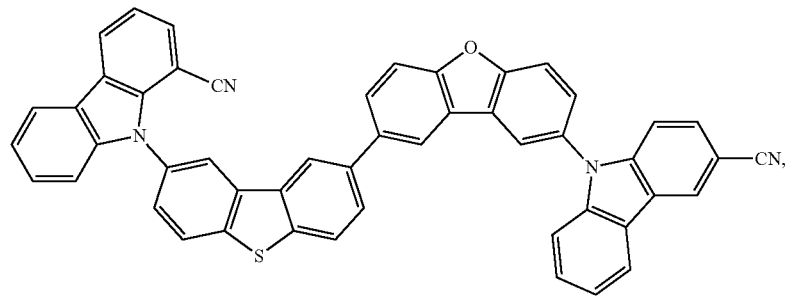
(D-12)
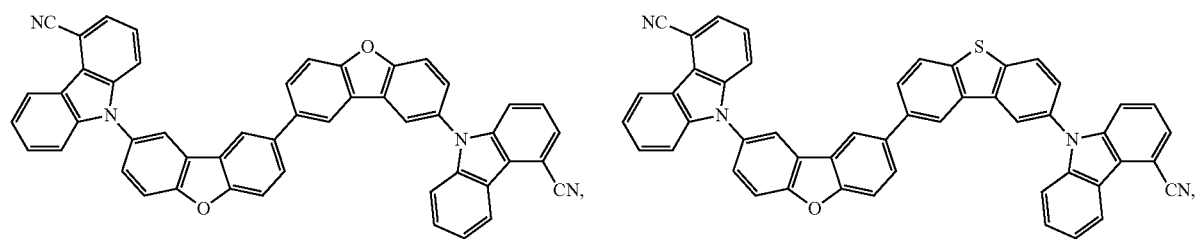
(D-13) (D-14)
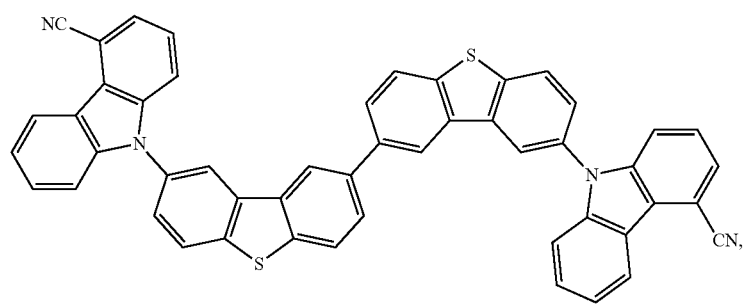
(D-15)
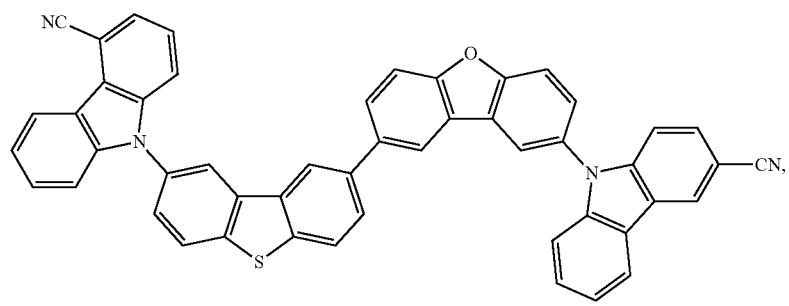
(D-16)
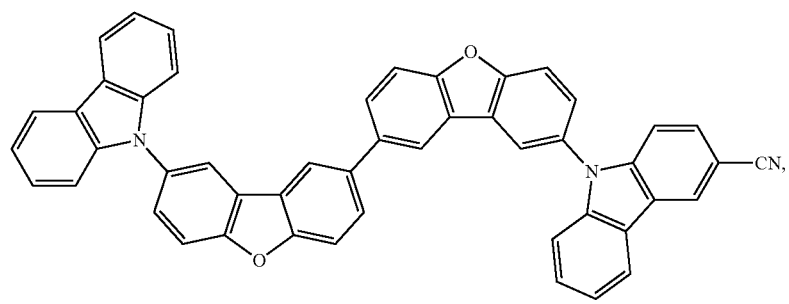
(D-17)

-continued
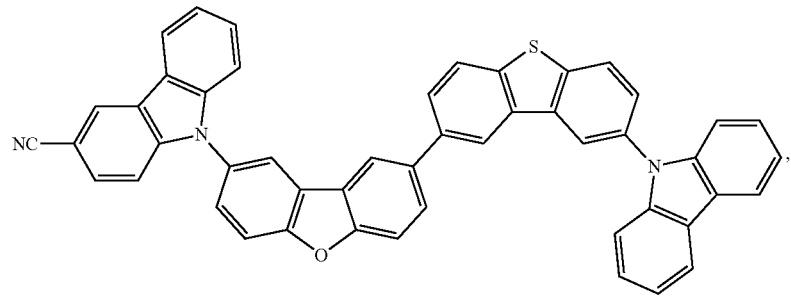
(D-18)
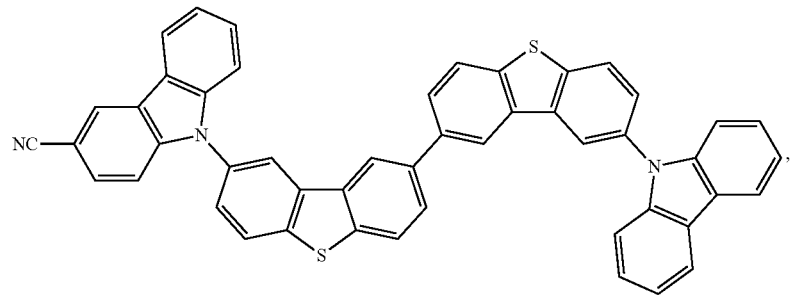
(D-19)
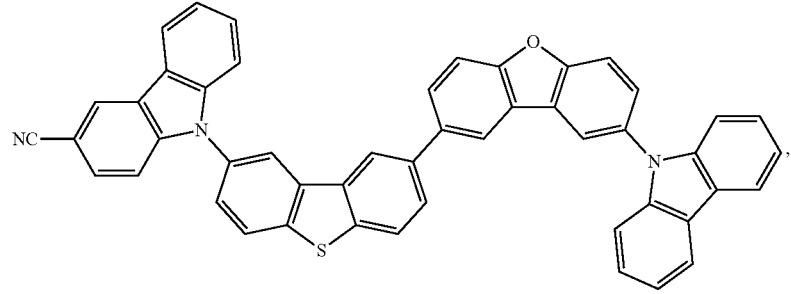
(D-20)
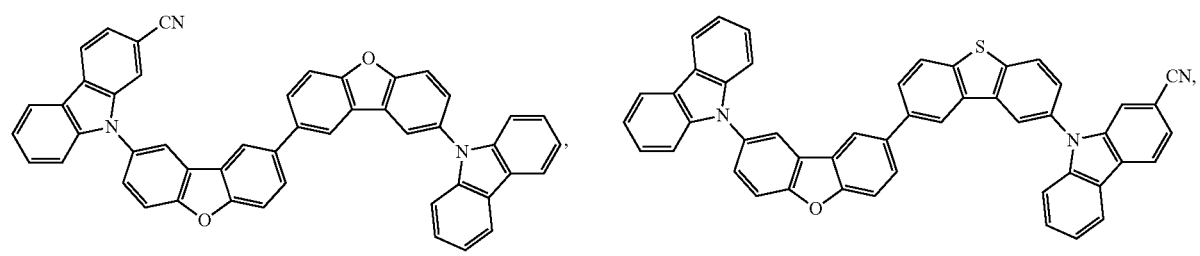
(D-21) (D-22)
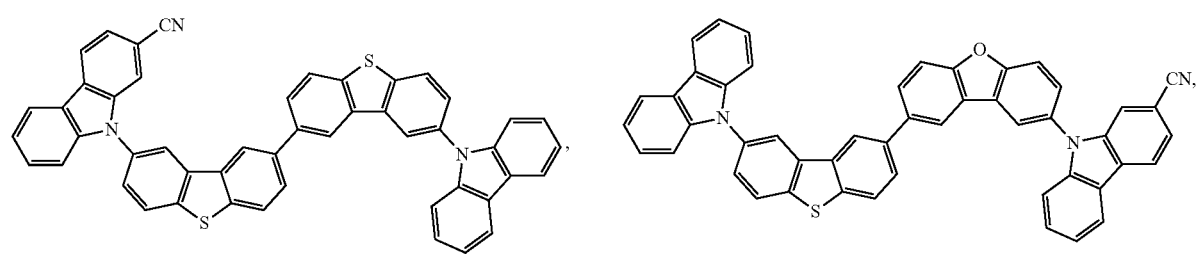
(D-23) (D-24)

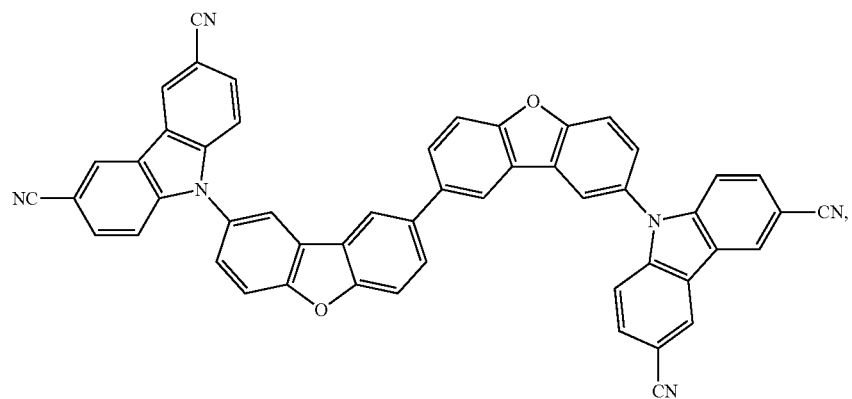
(D-25)
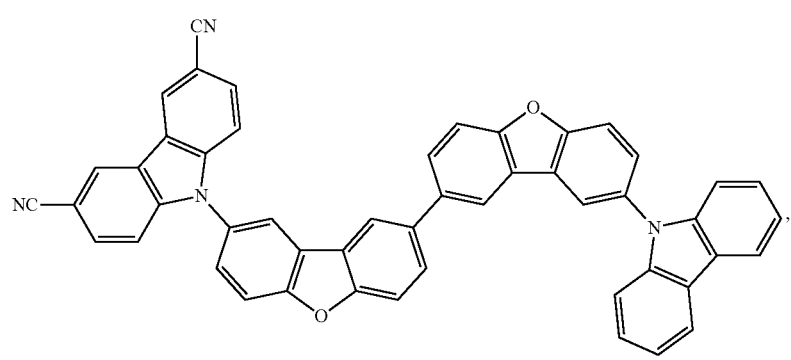
(D-26)
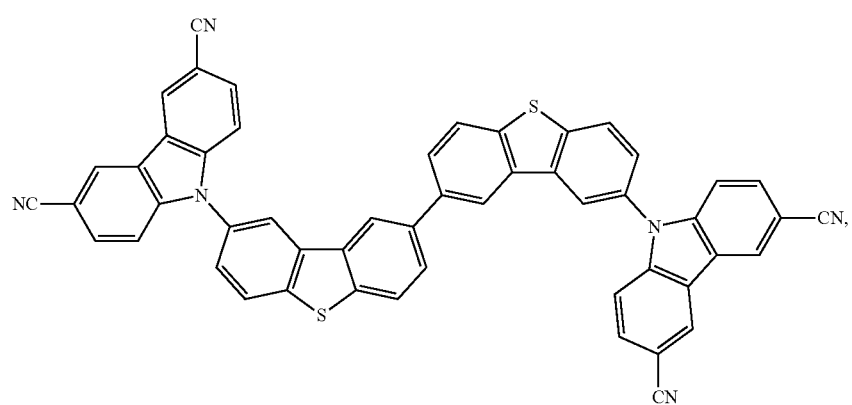
(D-27)
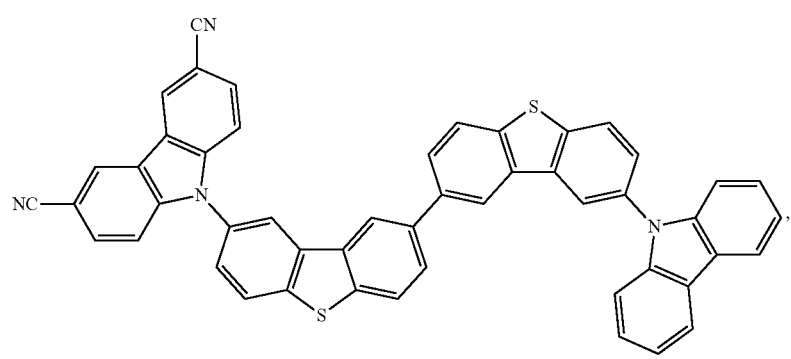
(D-28)

-continued
(D-29)
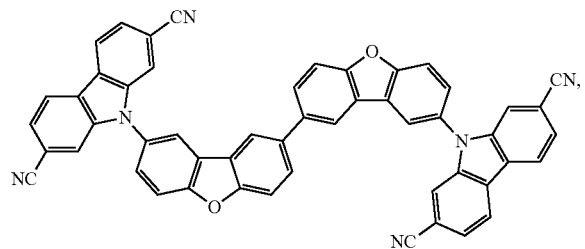
(D-30)
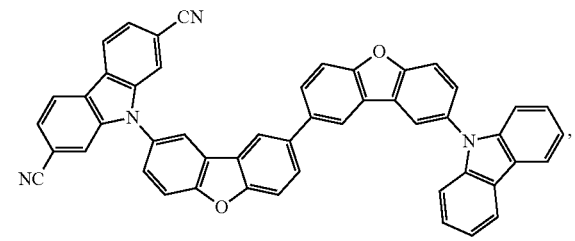
(D-31)
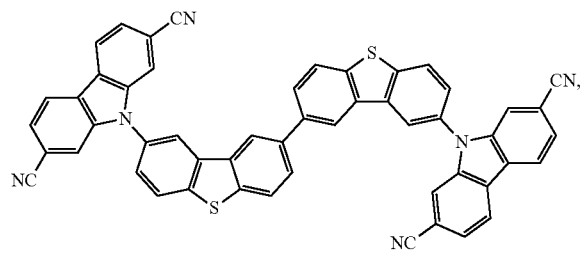
(D-32)
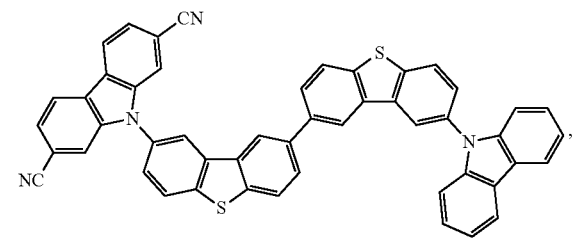
(D-33)
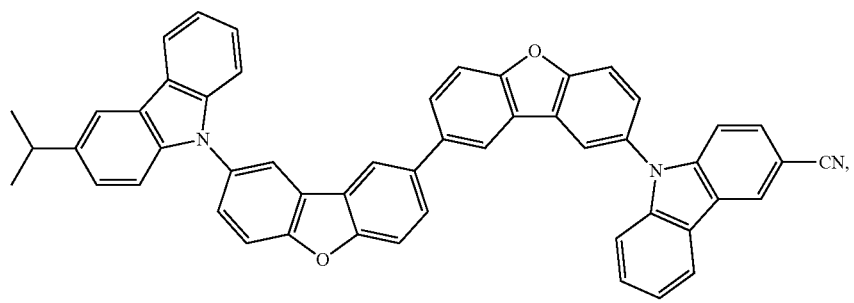
(D-34)
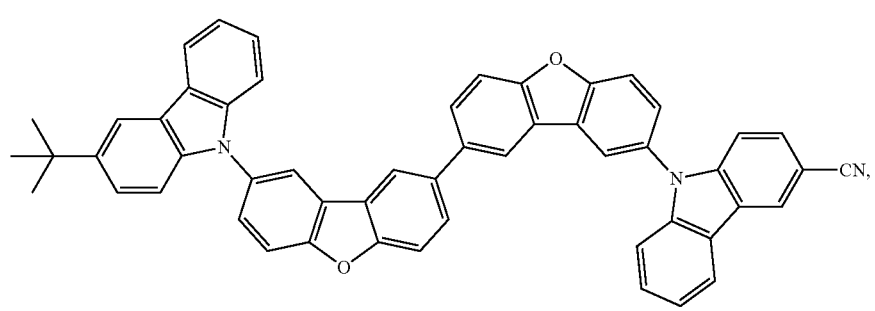
(D-35)
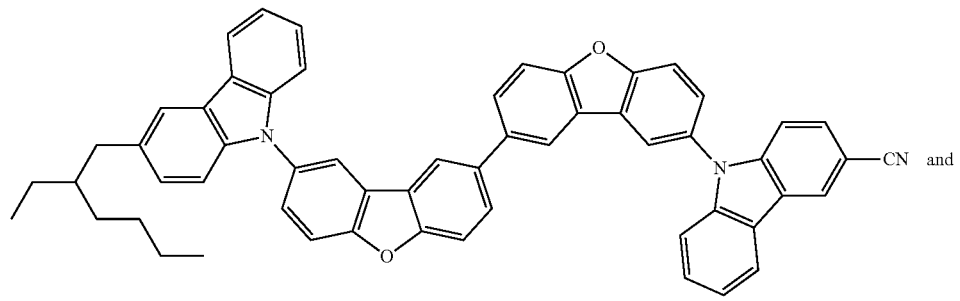
and

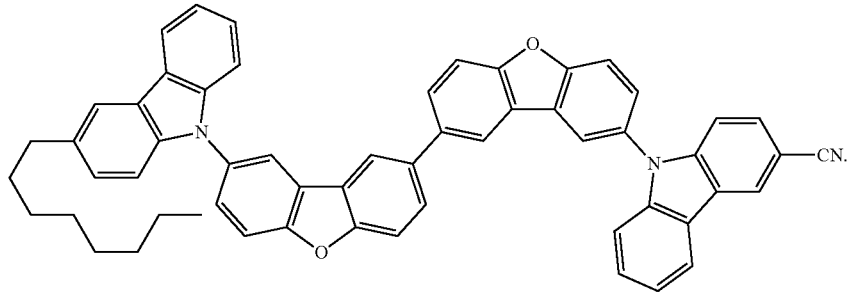

(D-36)

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted by G. Phenyl, 1-naphthyl and 2-naphthyl are examples of a $C_6$-$C_{10}$aryl group.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated n-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, carbazolyl, or phenoxazinyl, which can be unsubstituted or substituted by G. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

The term "cycloalkyl group" is typically $C_3$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted by G.

G is as defined above and is especially $C_1$-$C_{18}$alkyl, very especially $C_1$-$C_8$alkyl, such as methyl, ethyl, n-propyl, isopropyl, n-butyl, isobutyl, tert-butyl, sec-butyl, hexyl, octyl, or 2-ethyl-hexyl.

The wording "substituted by G" means that one, or more, especially one to three substituents G might be present. If a substituent occurs more than one time in a group, it can be different in each occurrence.

As described above, the aforementioned groups may be interrupted by D. Interruptions are of course possible only in the case of groups containing at least 2 carbon atoms connected to one another by single bonds. $C_1$-$C_{18}$alkyl interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—$CH(C_2H_5)C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR_z$, $CH(CH_3)COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—C($CH_3$)=$CH_2$.

Nitrile substituted carbazoles can be synthesized starting from the corresponding bromo or iodo substituted carbazoles using Rosenmund-von Braun reactions in DMF as described, for example, by D. A. Patrick, European Journal of Medicinal Chemistry (1997) 32. 781-793.

Alternatively nitrile substituted phenyl hydrazine can be reacted with cyclohexanone to yield nitrile substituted 2,3,4,9-tetrahydro-1H-carbazole that can be oxidized to nitrile substituted carbazoles by using chloranil as described, for example, by B. M. Barclay, Journal of the Chemical Society, 1945, 530.

Alternatively carbazole can be reacted to the corresponding aldehyde using VilsmeierHaack conditions followed by transforming the aldehyde to the nitrile as described by K. Moriyama, Tetrahedron, 201, 68, 4588.

The carbazole substituted dibenzofurans can be synthesized by reacting halogenated dibenzofuran derivatives with nitrile substituted carbazoles using copper catalyzed Ullmann conditions as described, for example, in EP2301921, H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151. The reaction can be performed in solvent or in a melt. Suitable solvents are, for example, (polar) aprotic solvents such as dimethyl sulfoxide, dimethylformamide, NMP, tridecane or alcohols.

Alternatively, the carbazole substituted dibenzofurans can be synthesized by reacting halogenated dibenzofuran derivatives with nitrile substituted carbazoles using palladium catalyzed Buchwald-Hartwig conditions as described, for example, in Björn Schlummer, Ulrich Scholz, Adv. Synth. Catal. 2004, 346, 1599-1626.

Suitable base skeletons of the formula

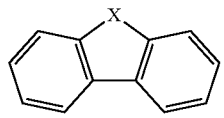

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula (II) 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with $Br_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzofuran, 2,8-dibromodibenzothiophene, 2-bromocarbazole, 3-bromodibenzothiophene, 3-bromodibenzofuran, 3-bromcarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles. The preparation is described, inter alia, in Tetrahedron. Lett. 47 (2006) 6957-6960, Eur. J. Inorg. Chem. 24 (2005) 4976-4984, J. Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957

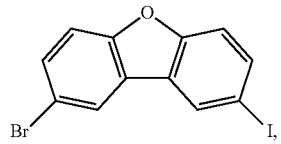

is described in EP1885818.

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as host material in a light-emitting layer and/or as hole and/or exciton blocker material and/or as electron transport material, especially in combination with a phosphorescence emitter, very especially blue, or green emitting phosphorescence emitters. In the case of use of the inventive compounds of the formula I in OLEDs, OLEDs which have good efficiencies and a long lifetime and which can be operated especially at a low use and operating voltage are obtained. Furthermore, the compounds of the formula I can be used as conductor/complementary materials in organic electronics applications selected from switching elements and organic solar cells.

In the emission layer or one of the emission layers of an OLED, it is also possible to combine an emitter material with a matrix material of the compound of the formula I and a further matrix material which has, for example, a good hole transport property. This achieves a high quantum efficiency of this emission layer.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The layer with electron transport capacity may comprise the compounds of formula I.

Structure of the Inventive OLED

The inventive organic light-emitting diode (OLED) generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different from the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the Light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used in accordance with the invention.

In a preferred embodiment the OLED according to the present invention comprises in this order:
(a) an anode,
(b) optionally a hole injection layer,
(c) optionally a hole transport layer,
(d) optionally an electron/exciton blocking layer
(e) an emitting layer,
(f) optionally a hole/exciton blocking layer
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an electron/exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the prior art and are described in more detail below on basis of preferred embodiments.

Anode (a):

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b):

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc, MTDATA, or dipyrazino[2,3-f:2',3'-h]quinoxaline-2,3,6,7,10,11-hexacarbonitrile (HAT-CN). Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly (4-styrenesulfonate) also called PEDOT/PSS.

Hole Transport Layer (c):

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophen/(di)benzofuran; Nan-Xing Hu et al. Synth. Met. 111 (2000) 421 (indolocarbazoles), WO2010002850 (substituted phenylamine compounds) and WO2012/16601 (in particular the hole transport materials mentioned on pages 16 and 17 of WO2012/16601). Combination of different hole transport material may be used. Reference is made, for example, to WO2013/022419, wherein

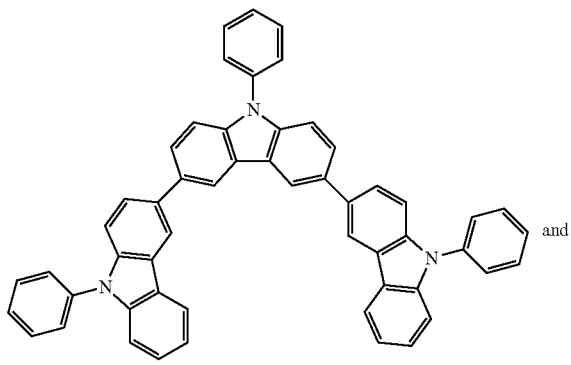
(HTL1-1)

and

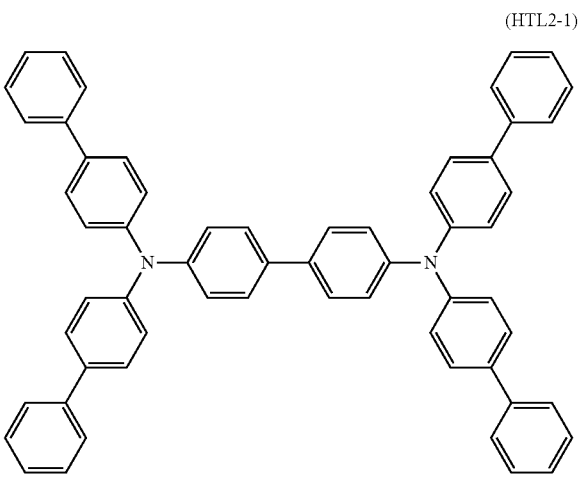
(HTL2-1)

constitute the hole transport layer.

Customarily used hole-transporting molecules are selected from the group consisting of

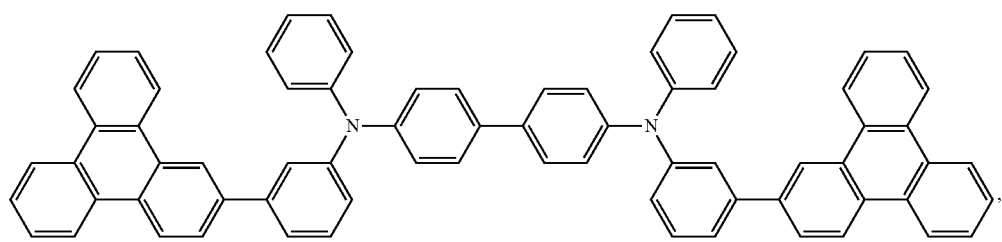

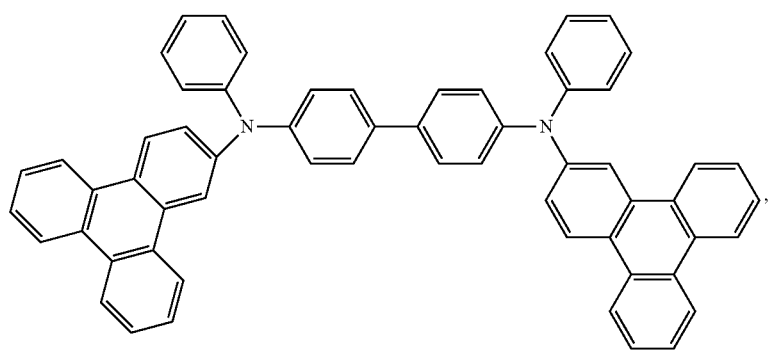

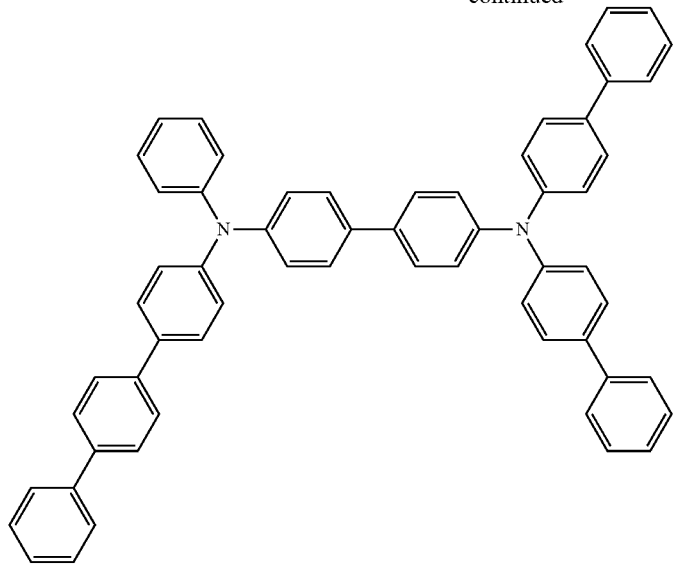

(4-phenyl-N-(4-phenylphenyl)-N-[4-[4-(N-[4-(4-phenyl-phenyl)phenyl]anilino)phenyl]phenyl]aniline),

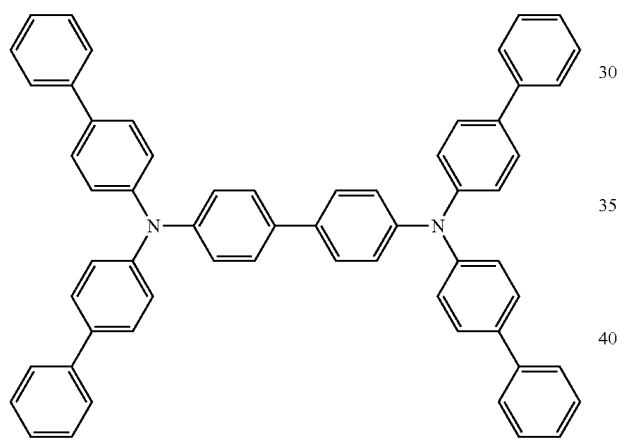

(4-phenyl-N-(4-phenylphenyl)-N-[4-[4-(4-phenylphenyl)anilino)phenyl]phenyl]aniline),

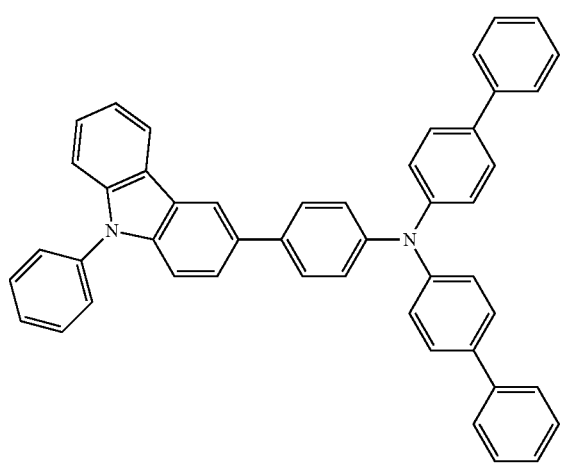 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

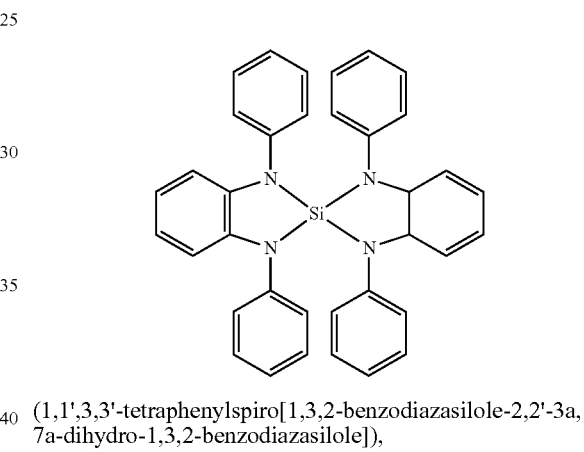

(1,1',3,3'-tetraphenylspiro[1,3,2-benzodiazasilole-2,2'-3a,7a-dihydro-1,3,2-benzodiazasilole]),

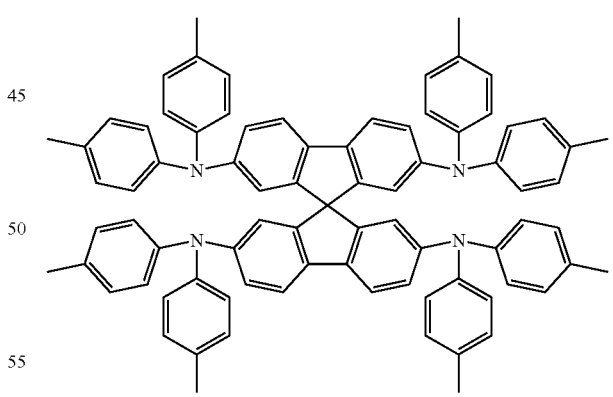

(N2,N2,N2,N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]-cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p(diethylamino)phenyl]pyrazoline (PPR or DEASP), 1,2-trans-bis(9H-carbazol9-yl)cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiroTTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl) benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Preferred examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT). In addition, dibenzofurane and dibenzothiophene compounds mentioned as host below, such as, for example,

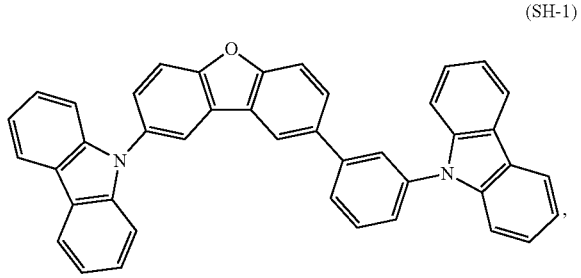 [SMILES: c1cc(-c2ccc3oc4ccc(-n5c6ccccc6c6ccccc65)cc4c3c2)cc(-n2c3ccccc3c3ccccc32)c1]

(SH-1)

may be used as hole transport material and exciton blocker material.

In a preferred embodiment it is possible to use metal carbene complexes as hole transport materials. Suitable carbene complexes are, for example, carbene complexes as described in WO2005/019373A2, WO2006/056418 A2, WO2005/113704, WO2007/115970, WO2007/115981, WO2008/000727 and WO2014147134. One example of a suitable carbene complex is Ir(DPBIC)₃ with the formula:

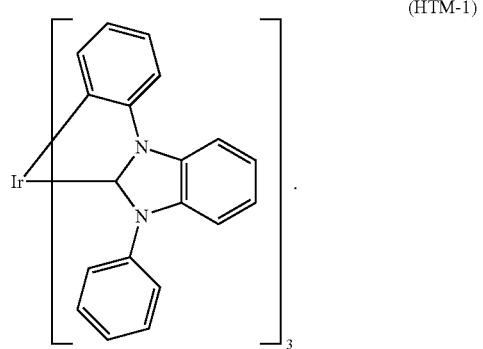

(HTM-1)

Another example of a suitable carbene complex is Ir(ABIC)₃ with the formula:

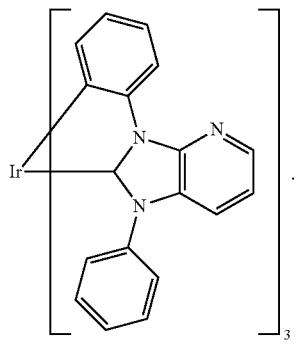

(HTM-2)

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, dicyanomethylene-1,3,4,5,7,8-hexafluoro-6Hnaphthalen-2-ylidene) malononitrile ($F_6$-TNAP), Mo(tfd)₃ (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254. Preferred mixtures comprise the aforementioned carbene complexes, such as, for example, the carbene complexes HTM-1 and HTM-2, and $MoO_3$ and/or $ReO_3$. In a particularly preferred embodiment the hole transport layer comprises from 0.1 to 10 wt % of $MoO_3$ and 90 to 99.9 wt % carbene complex, especially of a carbene complex HTM-1 and HTM-2, wherein the total amount of the $MoO_3$ and the carbene complex is 100 wt %. In another particularly preferred embodiment the hole transport layer comprises from 0.1 to 10 wt % of $MoO_3$ and 90 to 99.9 wt % dibenzofurane compound, especially compound (SH-1), wherein the total amount of the $MoO_3$ and the dibenzofurane compound is 100 wt %.

Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418A2, WO2005/113704, WO2007/115970, WO2007/115981, WO2008/000727 and WO2014147134. Explicit reference is made here to the disclosure of the WO applications cited, and these disclosures shall be considered to be incorporated into the content of the present application. One example of a suitable carbene complex is compound HTM-1. Another example of a suitable carbene complex is compound HTM-2. In addition, all hole transport materials having sufficient high triplet energy are suitable exciton blocking materials. Additional examples of hole transporting materials having sufficient high triplet energy are (SH-1) and (SH-11).

Emitting Layer (e)

The light-emitting layer (e) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266, WO2012/172482, WO2015000955 and PCT/EP2014/066272.

Further suitable metal complexes are the commercially available metal complexes tris(2-phenylpyridine)iridium (III), iridium(III) tris(2-(4-tolyl)pyridinato-N,$C^{2'}$), bis(2-phenylpyridine)(acetylacetonato)iridium(III), iridium(III) tris(1-phenylisoquinoline), iridium(III) bis(2,2'-benzothienyl)pyridinato-N,$C^{3'}$)(acetylacetonate), tris(2-phenylquinoline)iridium(III), iridium(III) bis(2-(4,6-difluorophenyl)pyridinato-N,$C^2$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-ylpyridine)(acetylacetonato) iridium(III).

In addition, the following commercially available materials are suitable: tris(dibenzoylacetonato)mono(phenanthroline)europium(III), tris(dibenzoylmethane)mono(phenanthroline)europium(III), tris(dibenzoylmethane)mono(5-aminophenanthroline)europium(III), tris(di-2-naphthoylmethane)mono(phenanthroline)europium(III), tris(4-bromobenzoylmethane)mono(phenanthroline)europium (III), tris(di(biphenyl)methane)mono(phenanthroline)europium(III), tris(dibenzoylmethane)mono(4,7-diphenylphenanthroline)europium(III), tris(dibenzoylmethane)mono(4,7-di-methylphenanthroline) europium(III), tris(dibenzoylmethane)mono(4,7-dimethylphenanthrolinedisulfonic acid)europium(III) disodium salt, tris[di(4-(2-(2-ethoxyethoxy)ethoxy)benzoylmethane)]mono(phenanthroline)europium(III) and tris[di[4-(2-(2-ethoxyethoxy)ethoxy)benzoylmethane)]mono(5-aminophenanthroline)europium(II), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Preferred phosphorescence emitters are carbene complexes. Suitable phosphorescent blue emitters are specified in the following publications: WO2006/056418A2, WO2005/113704, WO2007/115970, WO2007/115981, WO2008/000727, WO2009050281, WO2009050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266, WO2012/172482, WO2015000955 and PCT/EP2014/066272.

Preferably, the light emitting layer (e) comprises at least one carbine complex as phosphorescence emitter. Suitable carbine complexes are, for example, compounds of the formula

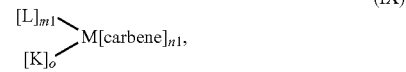

(IX)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with $M^1$;

n1 is the number of carbene ligands, where n1 is at least 1 and when n1>1 the carbene ligands in the complex of the formula I can be identical or different;

m1 is the number of ligands L, where m1 can be 0 or >1 and when m1>1 the ligands L can be identical or different;

o is the number of ligands K, where o can be 0 or >1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

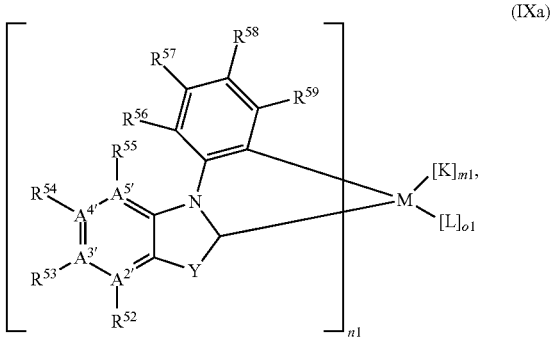

(IXa)

which are described in WO2011/073149, where M, n1, Y, $A^{2'}$, $A^{3'}$, $A^{4'}$, $A^{5'}$, $R^{51}$, $R^{52}$, $R^{53}$, $R^{54}$, $R^{55}$, $R^{56}$, $R^{57}$, $R^{58}$, $R^{59}$, K, L, m1 and o1 are each defined as follows:

M is Ir, or Pt, n1 is an integer selected from 1, 2 and 3,

Y is $NR^{51}$, O, S or $C(R^{25})_2$, $A^{2'}$, $A^{3'}$, $A^{4'}$, and $A^{5'}$ are each independently N or C, where 2 A'=nitrogen atoms and at least one carbon atom is present between two nitrogen atoms in the ring, $R^{51}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52}$, $R^{53}$, $R^{54}$ and $R^{55}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53}$ and $R^{54}$ together with $A^{3'}$ and $A^{4'}$ form an optionally substituted, unsaturated ring optionally interrupted by at least one further heteroatom and having a total of 5 to 18 carbon atoms and/or heteroatoms, $R^{56}$, $R^{57}$, $R^{58}$ and $R^{59}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56}$ and $R^{57}$, $R^{57}$ and $R^{58}$ or $R^{58}$ and $R^{59}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^{5'}$ is C, $R^{55}$ and $R^{56}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o1 is 0, 1 or 2, where, when o1 is 2, the L ligands may be the same or different.

The compound of formula IX is preferably a compound of the formula:

(BE-1)
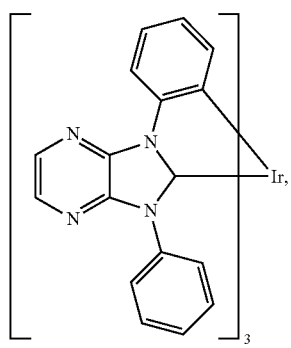
(BE-2)
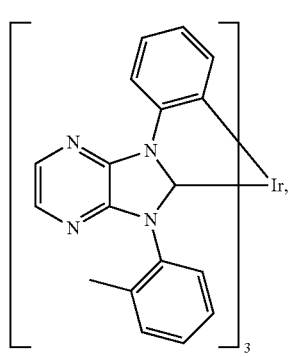
(BE-3)
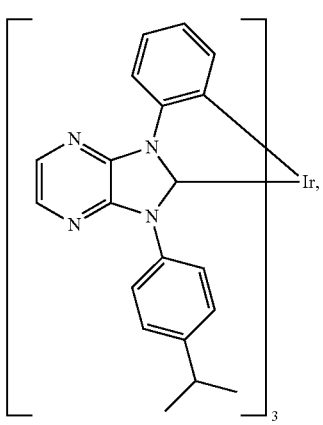
(BE-4)
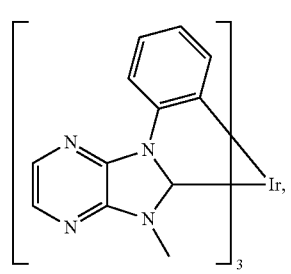
-continued
(BE-5)
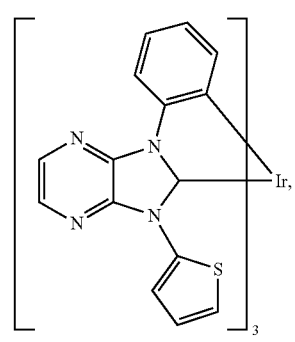
(BE-6)
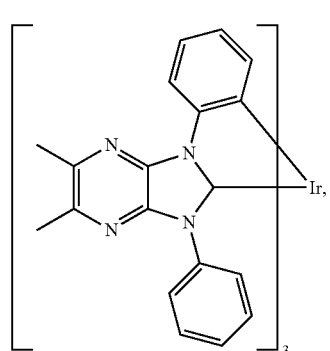
(BE-7)
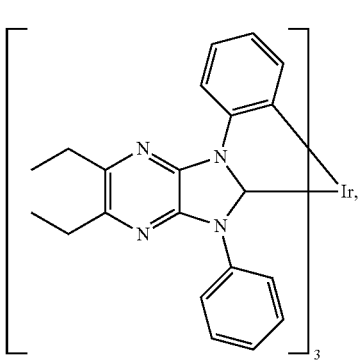
(BE-8)
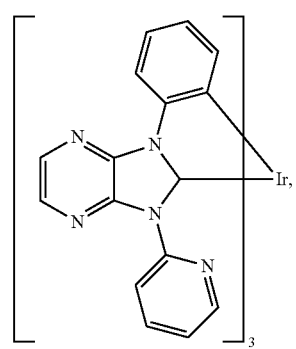

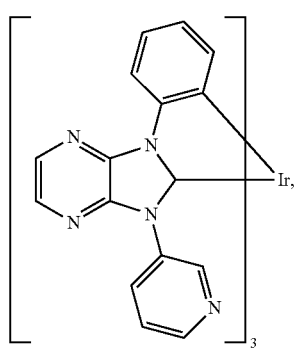
(BE-9)
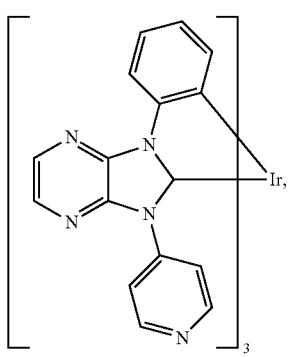
(BE-10)
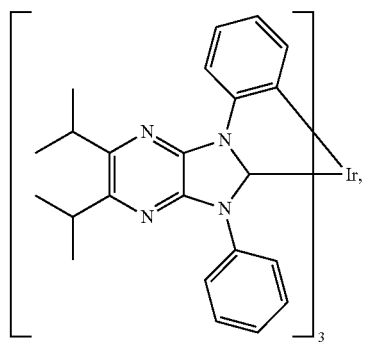
(BE-11)
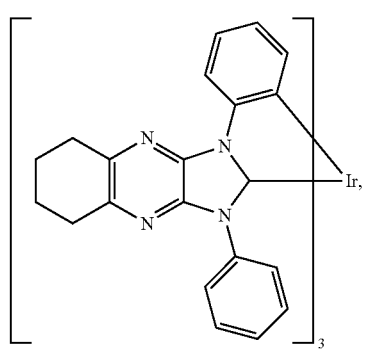
(BE-12)
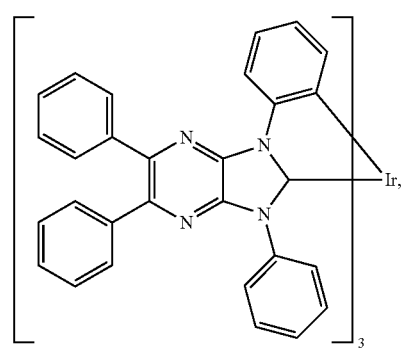
(BE-13)
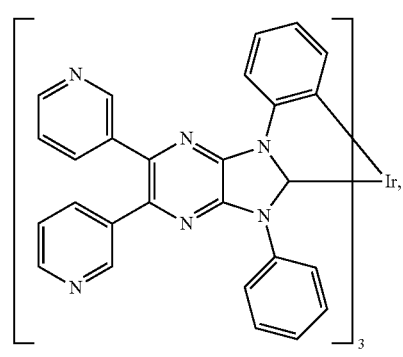
(BE-14)
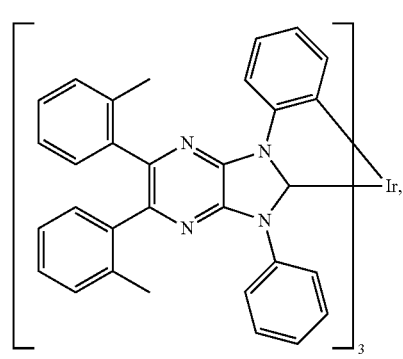
(BE-15)
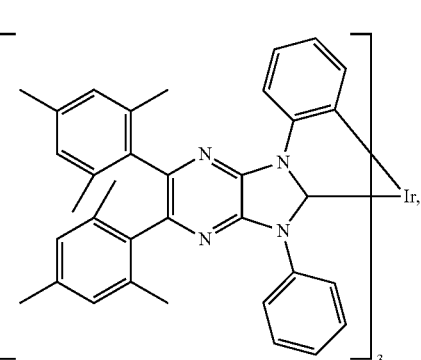
(BE-16)

107
-continued
(BE-17)
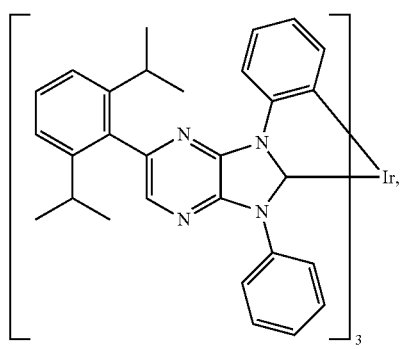
(BE-18)
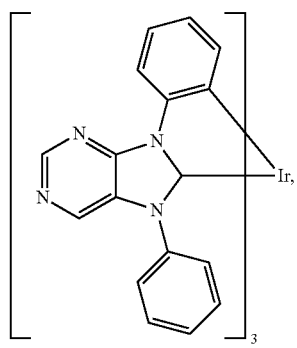
(BE-19)
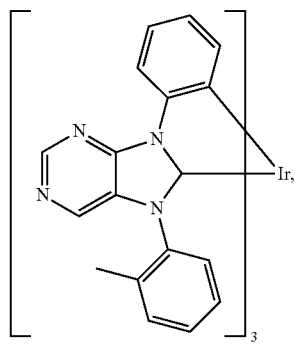
(BE-20)
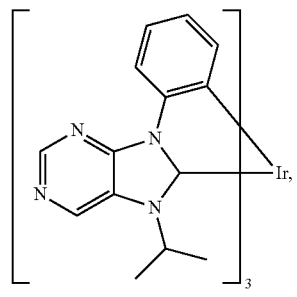
(BE-21)
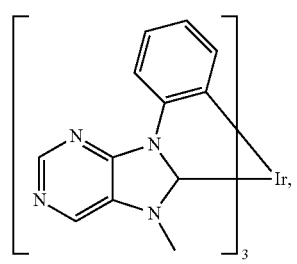
108
-continued
(BE-22)
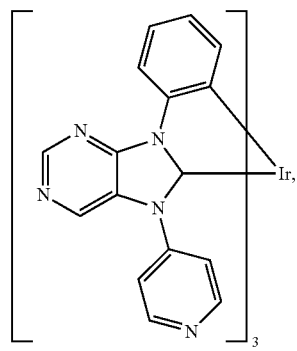
(BE-23)
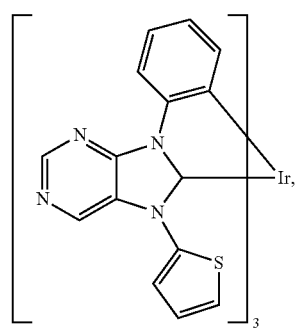
(BE-24)
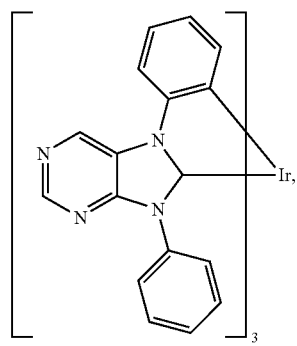
(BE-25)
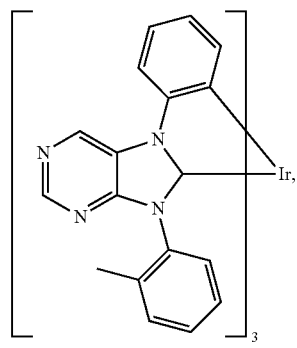

(BE-26) 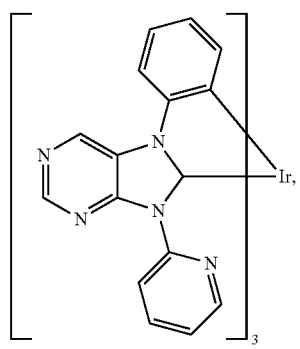
(BE-27) 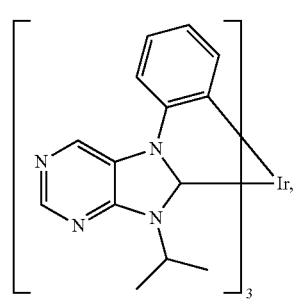
(BE-28) 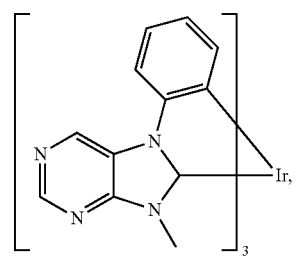
(BE-29) 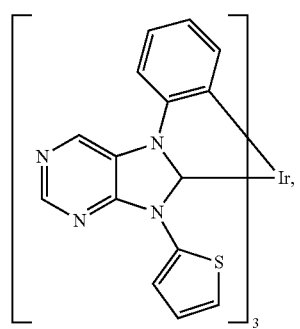
(BE-30) 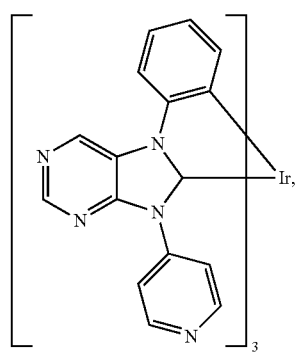
(BE-31) 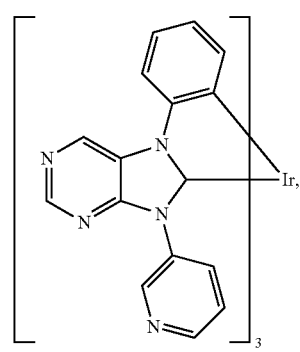
(BE-32) 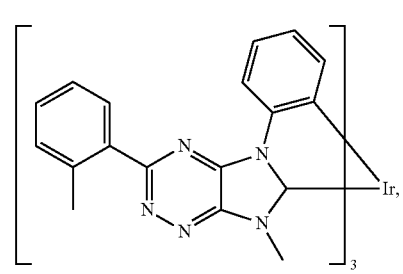
(BE-33) 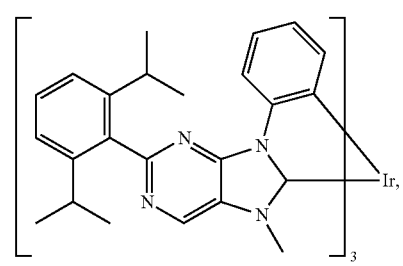
(BE-34) 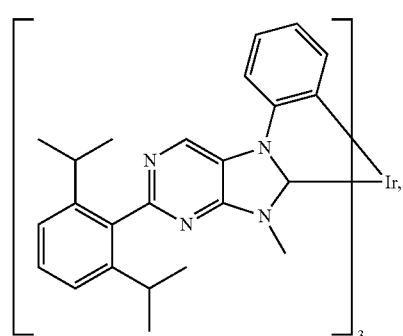
(BE-35) 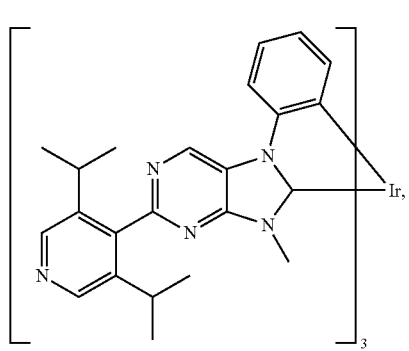

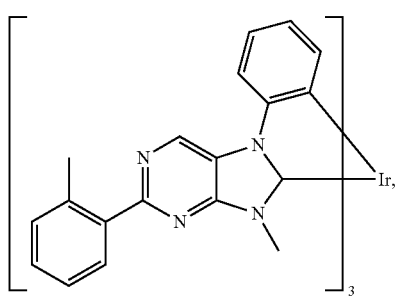
(BE-36)
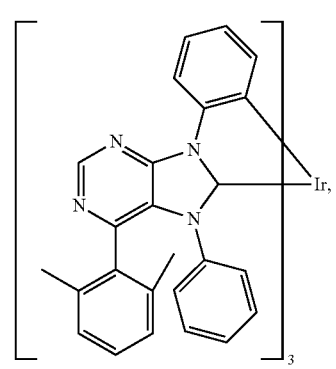
(BE-37)
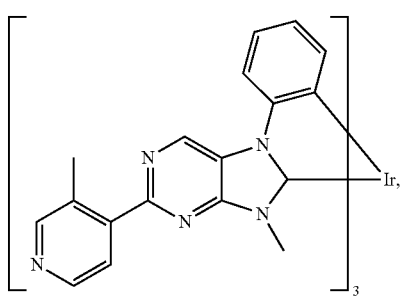
(BE-38)
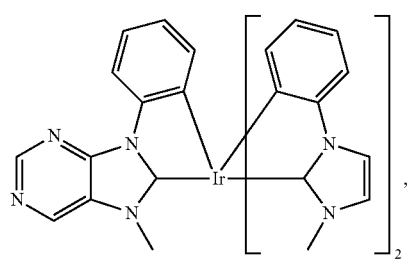
(BE-39)
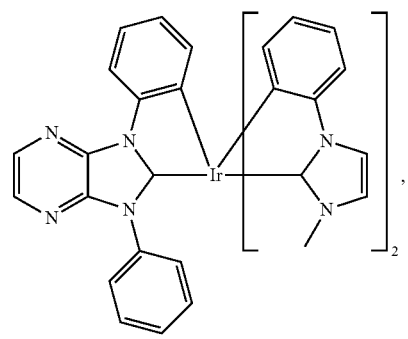
(BE-40)
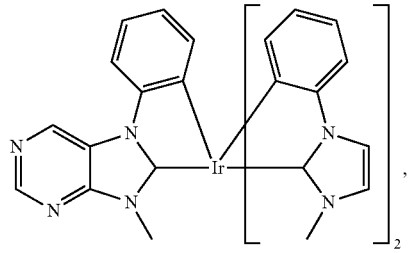
(BE-41)
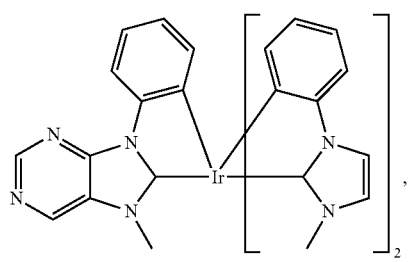
(BE-42)
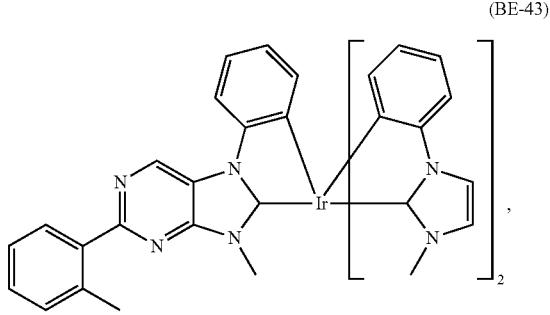
(BE-43)
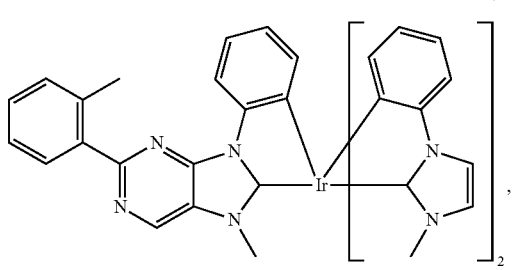
(BE-44)
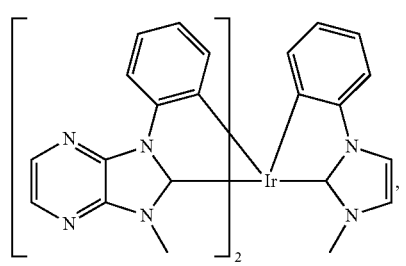
(BE-45)

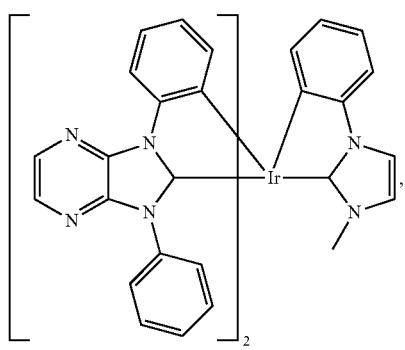
(BE-46)
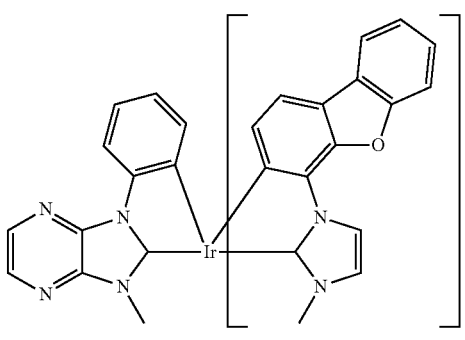
(BE-51)
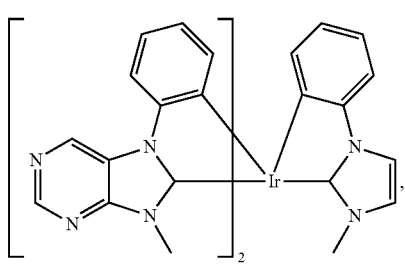
(BE-47)
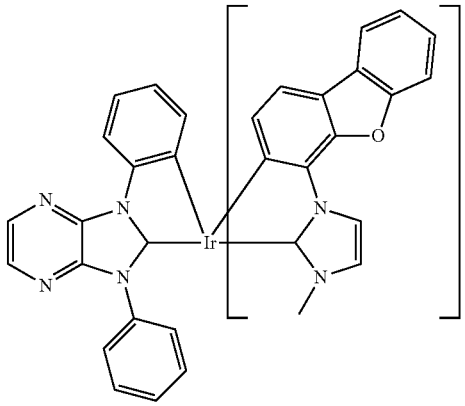
(BE-52)
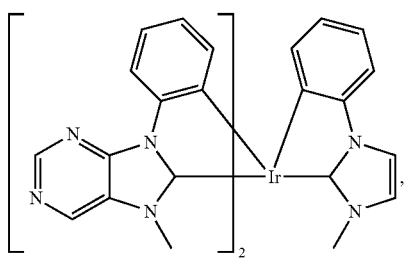
(BE-48)
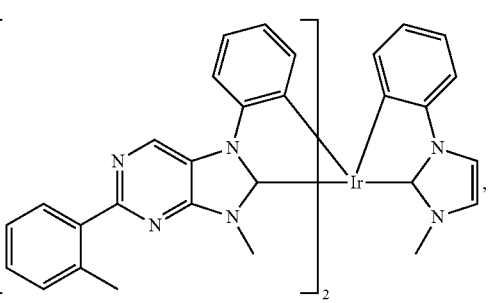
(BE-49)
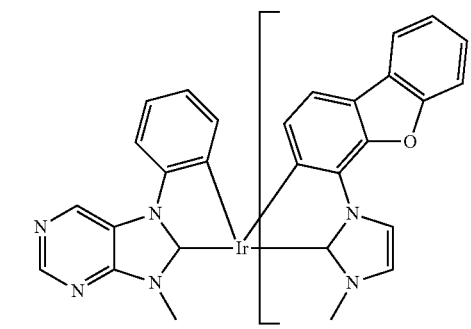
(BE-53)
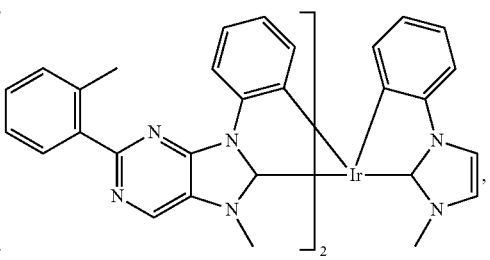
(BE-50)
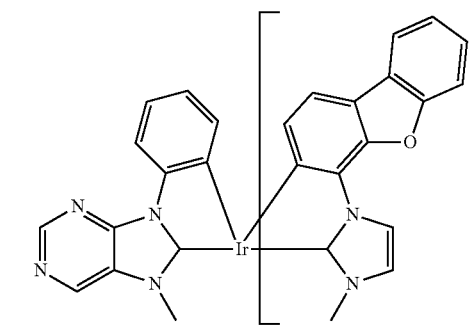
(BE-54)

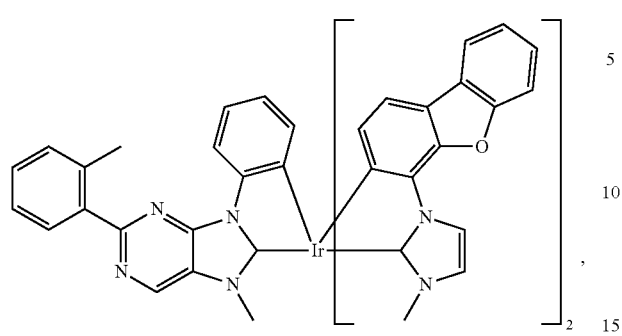
(BE-55)
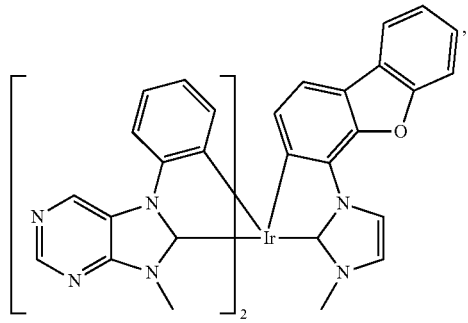
(BE-59)
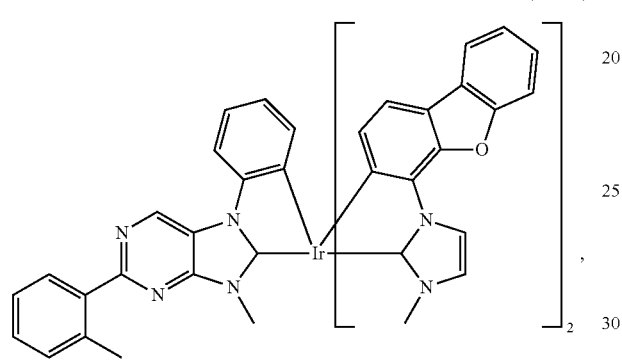
(BE-56)
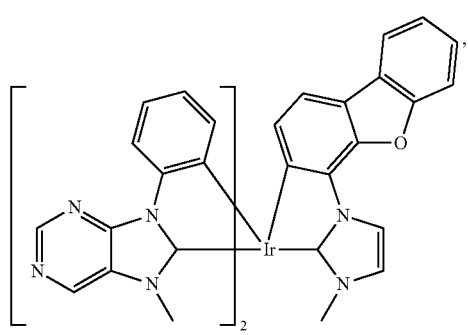
(BE-60)
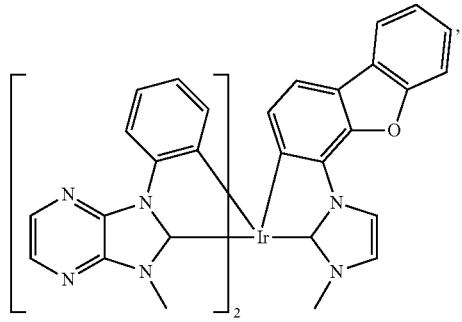
(BE-57)
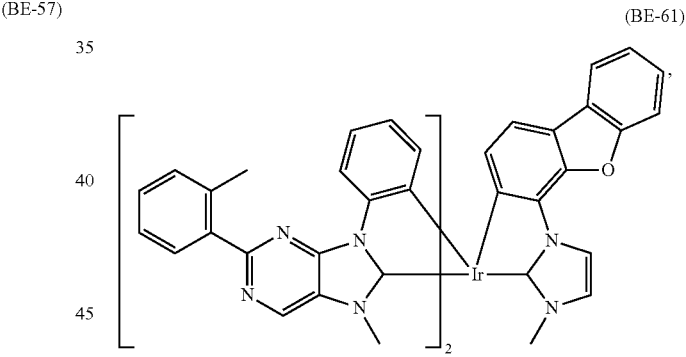
(BE-61)
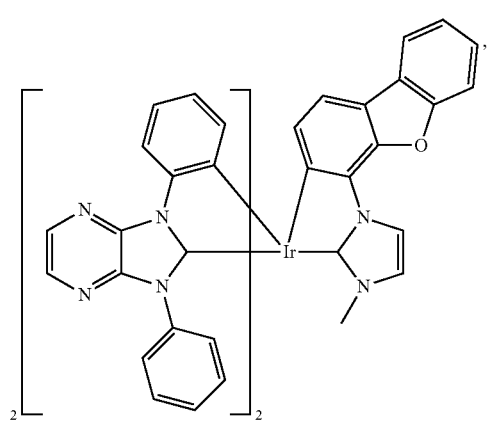
(BE-58)
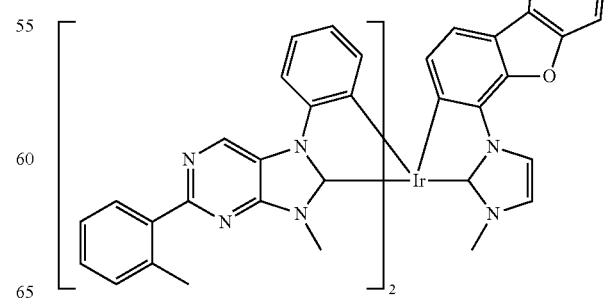
(BE-62)

(BE-63)
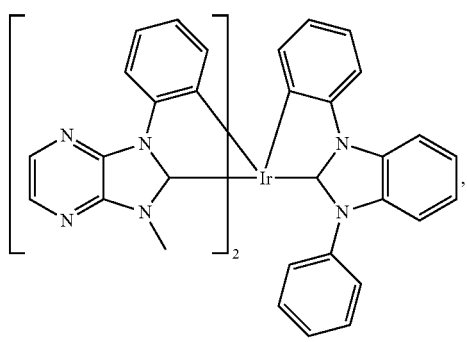
(BE-67)
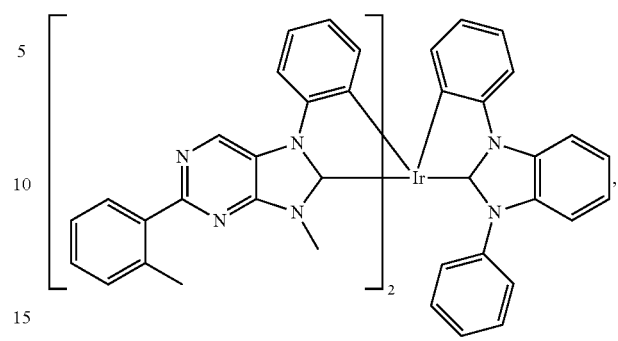
(BE-64)
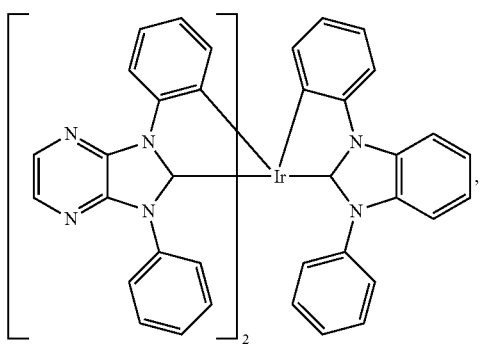
(BE-68)
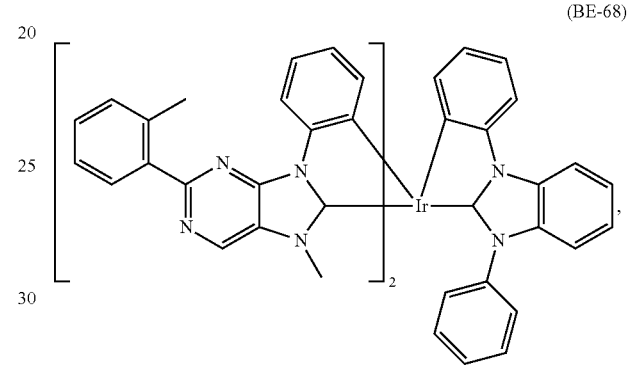
(BE-65)
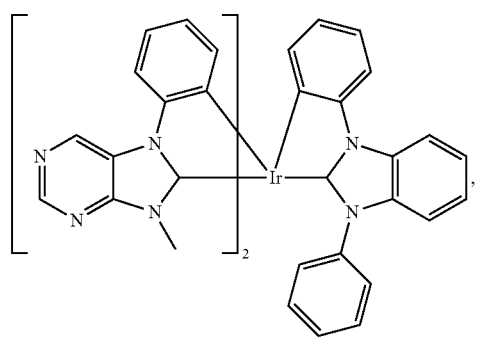
(BE-69)
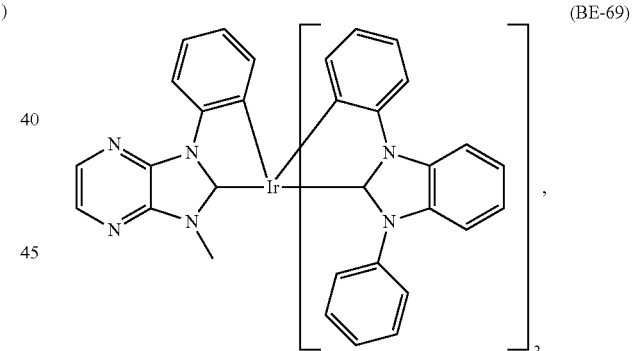
(BE-66)
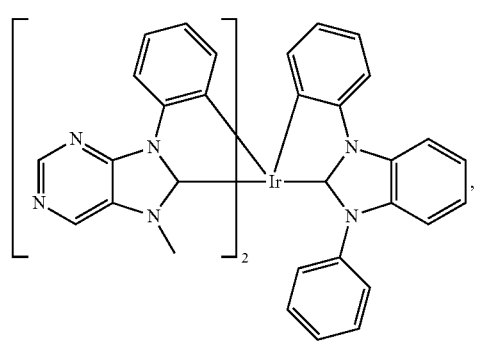
(BE-70)
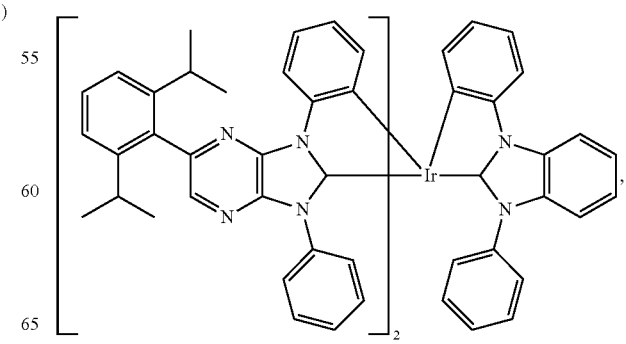

(BE-71)
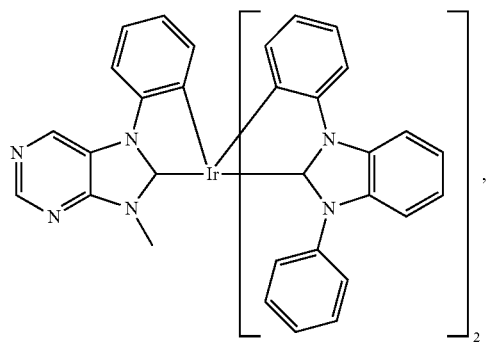
(BE-72)
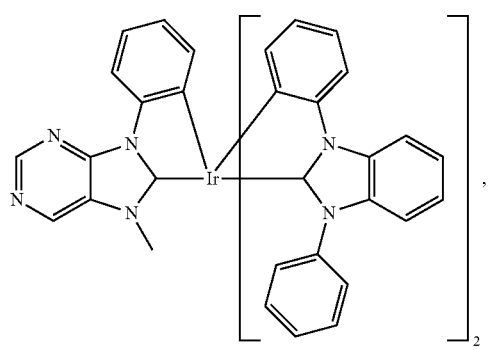
(BE-73)
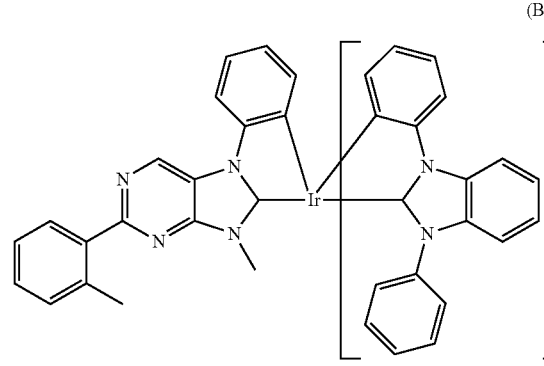
(BE-74)
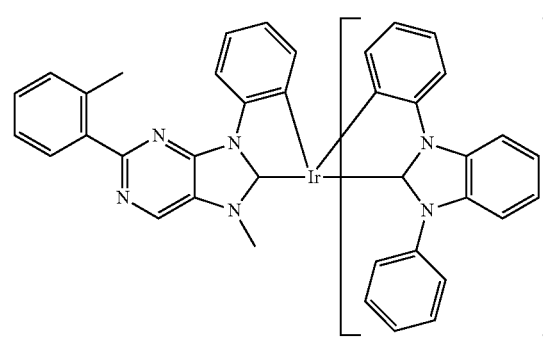
(BE-75)
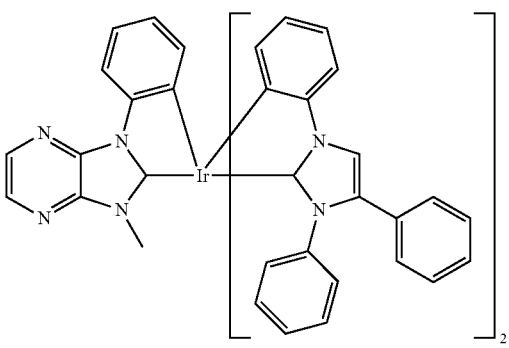
(BE-76)
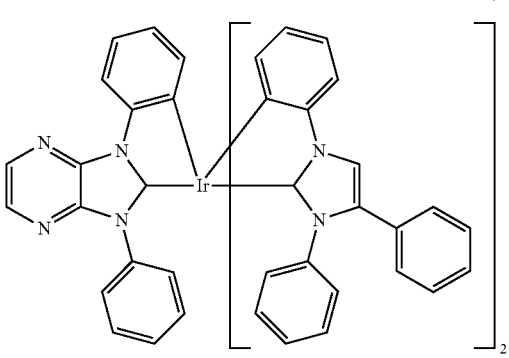
(BE-77)
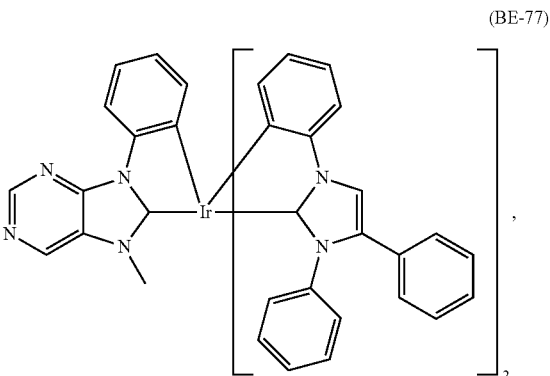
(BE-78)
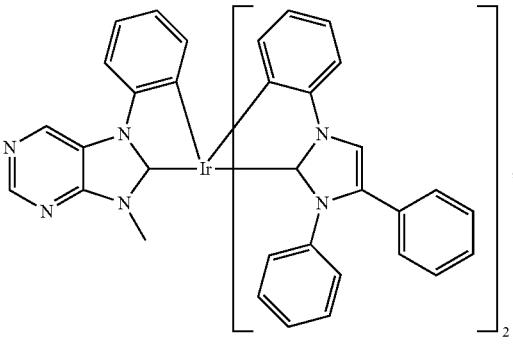

(BE-79)
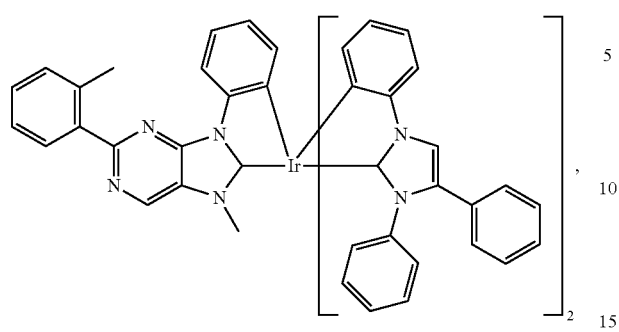
(BE-83)
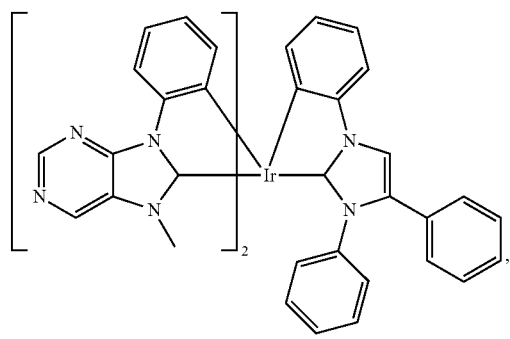
(BE-80)
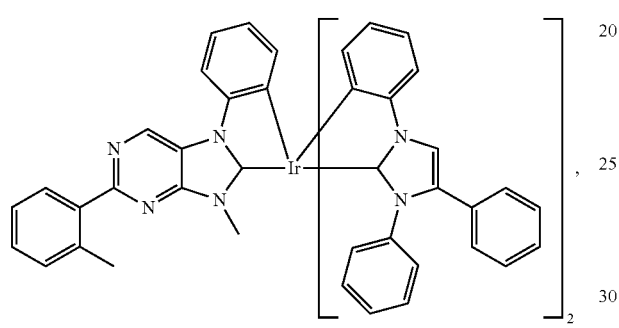
(BE-84)
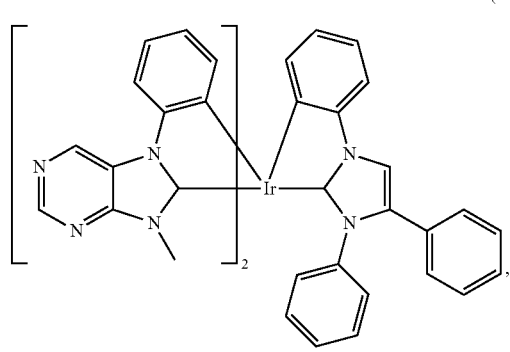
(BE-81)
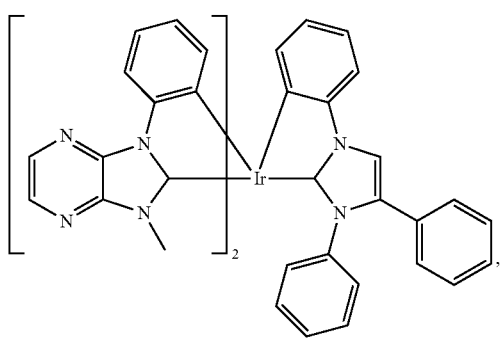
(BE-85)
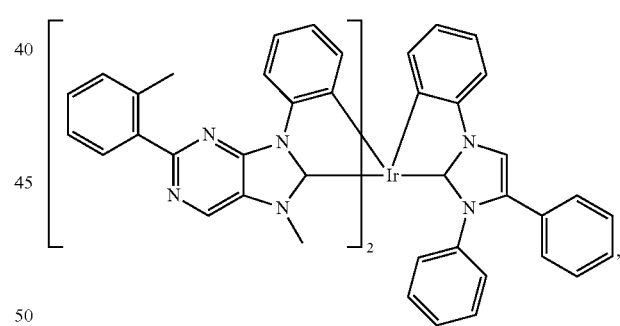
(BE-82)
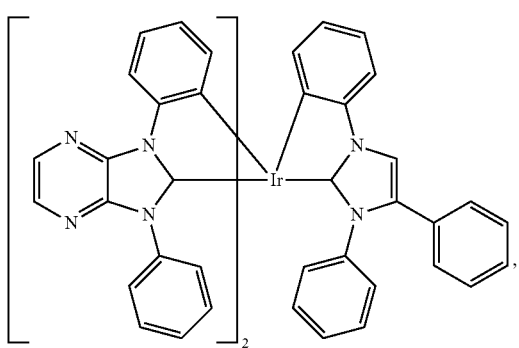
(BE-86)
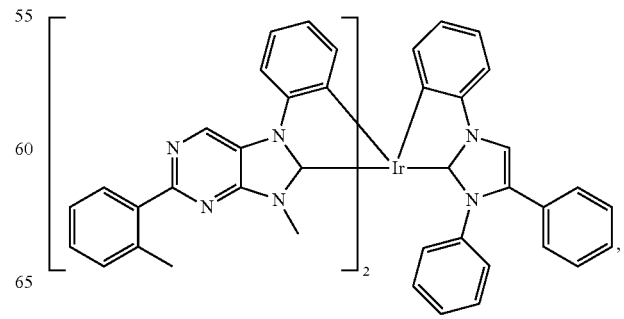

-continued
(BE-87)
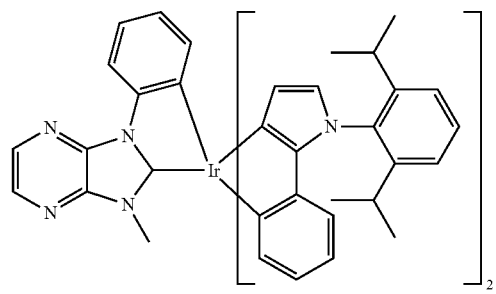
(BE-88)
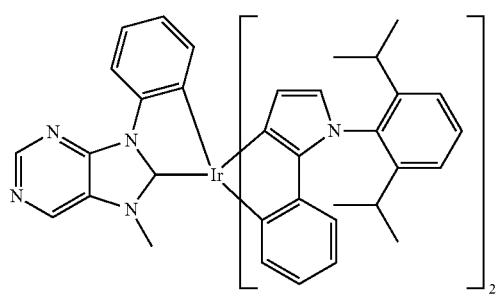
(BE-89)
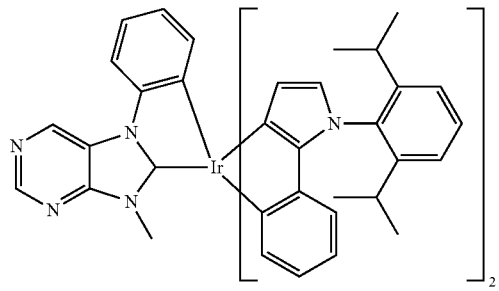
(BE-90)
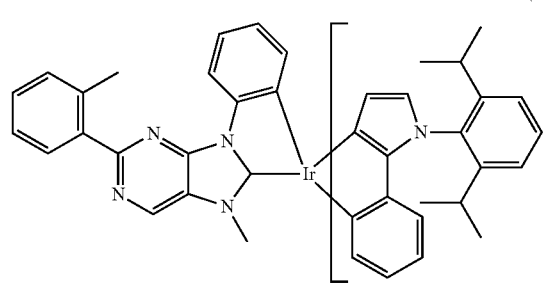
(BE-91)
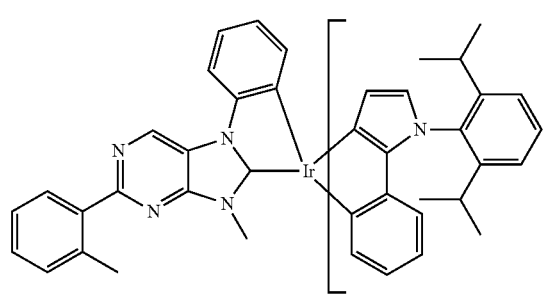
-continued
(BE-92)
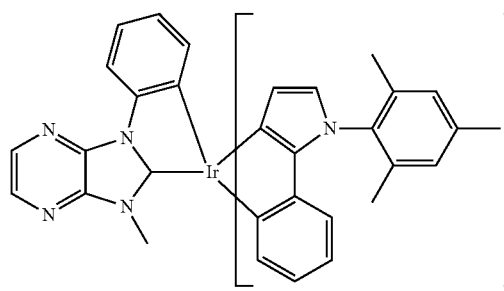
(BE-93)
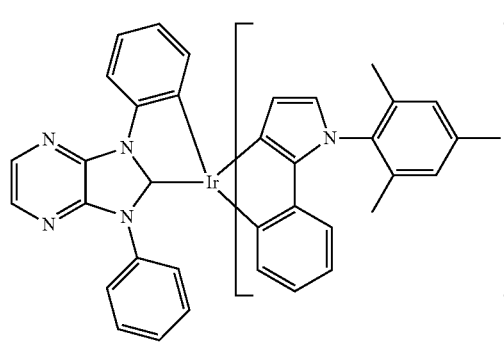
(BE-94)
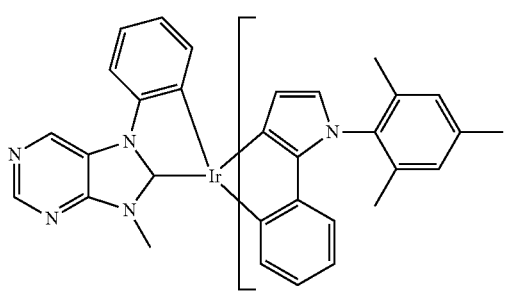
(BE-95)
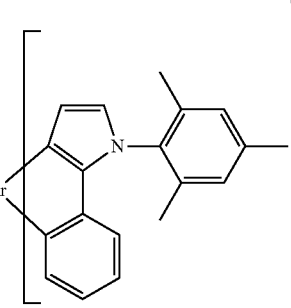
(BE-96)
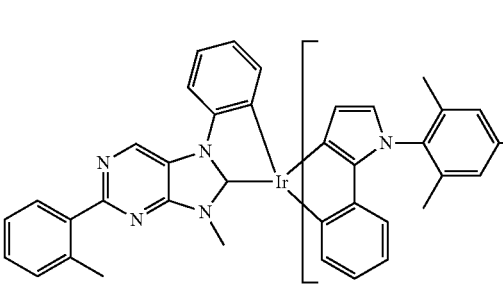

-continued
(BE-97)
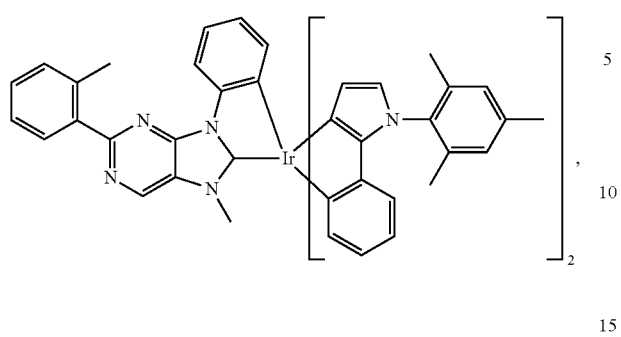
(BE-101)
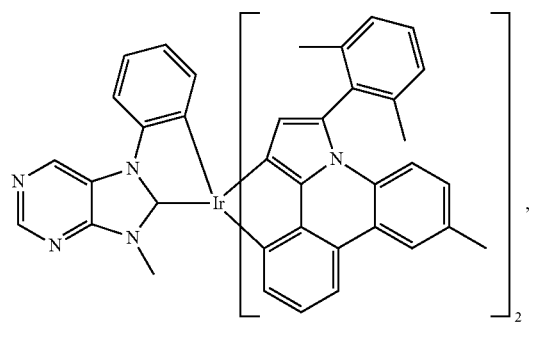
(BE-98)
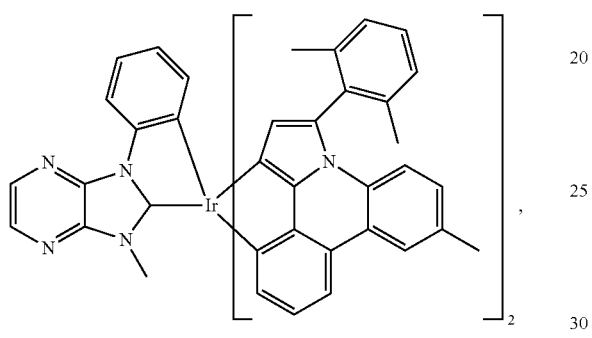
(BE-102)
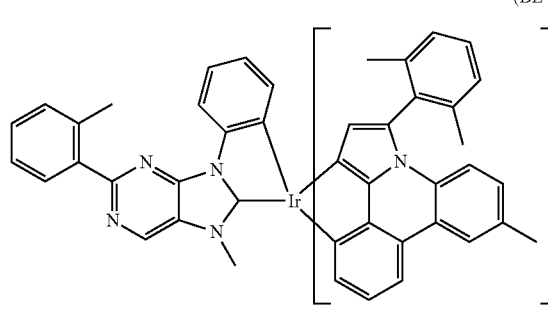
(BE-99)
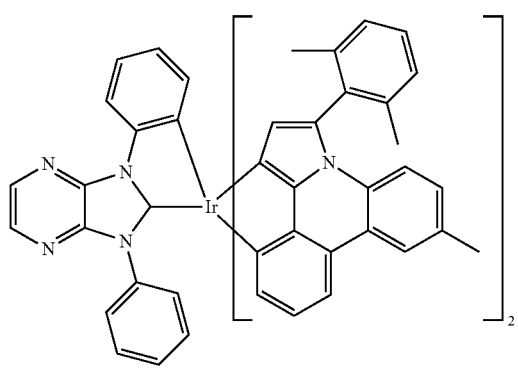
(BE-103)
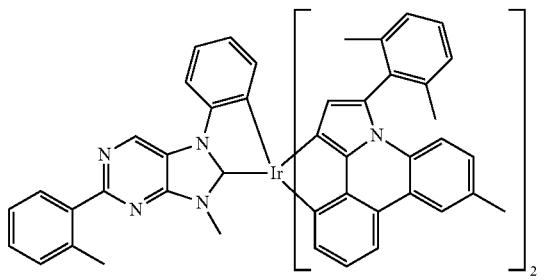
and
(BE-100)
(BE-104)
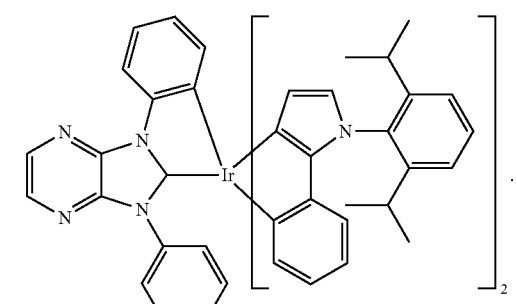
Further suitable non-carbene emitter materials are mentioned below:

(BE-105)
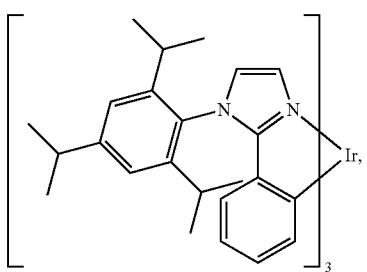
(BE-106)
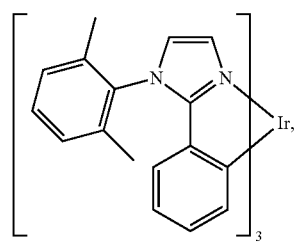
(BE-107)
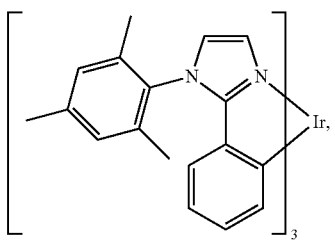
(BE-108)
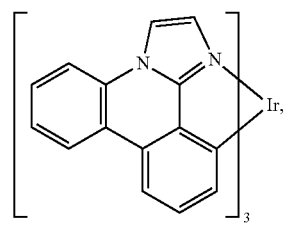
(BE-109)
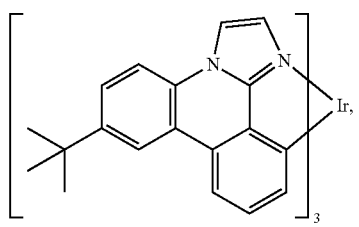
(BE-110)
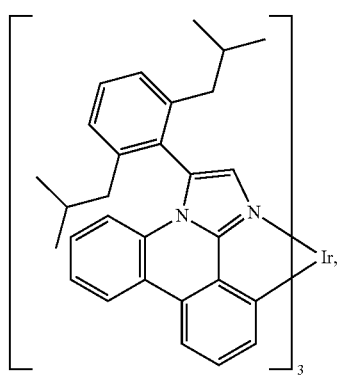
(BE-111)
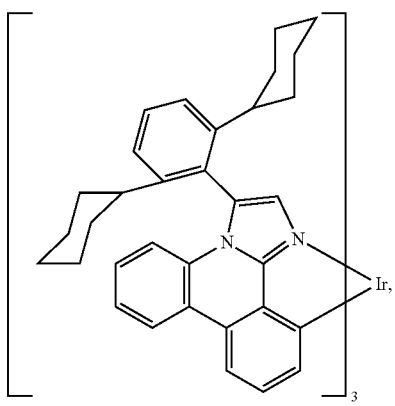
(BE-112)
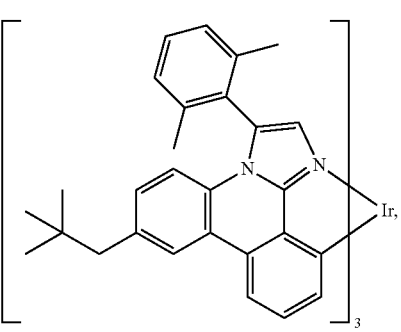
(BE-113)
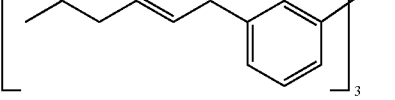
(BE-114)
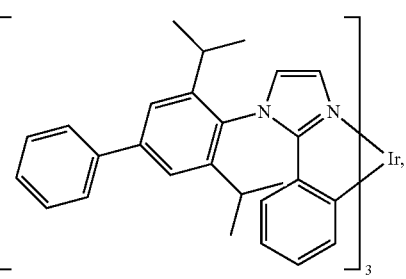
(BE-115)
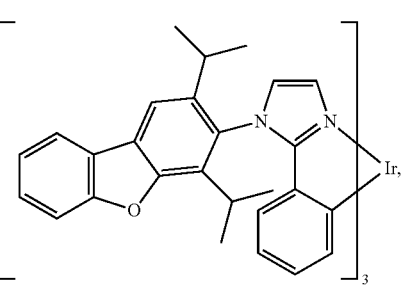

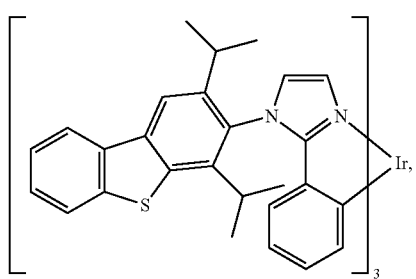
(BE-116)
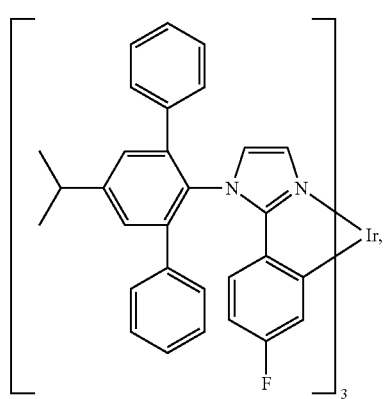
(BE-117)
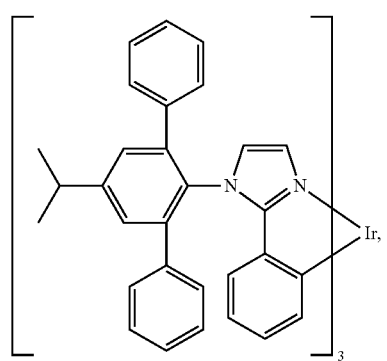
(BE-118)
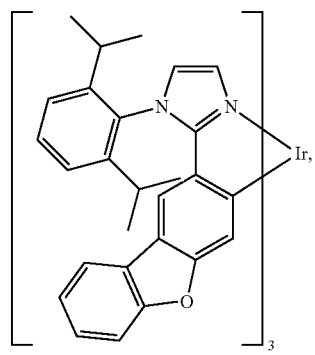
(BE-119)
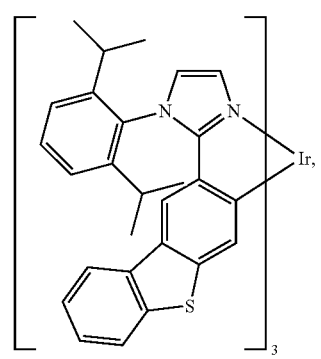
(BE-120)
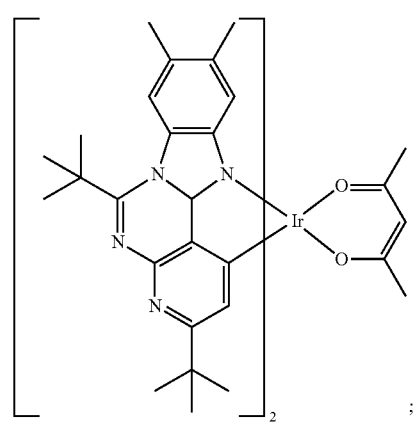
(BE-121)
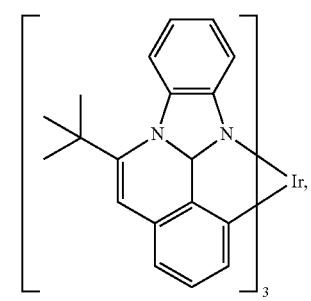
(BE-122)
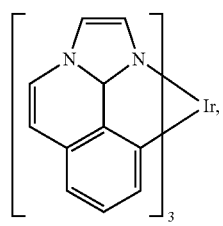
(BE-123)
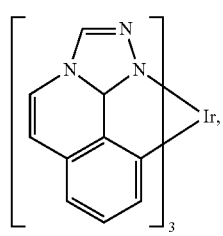
(BE-124)

-continued

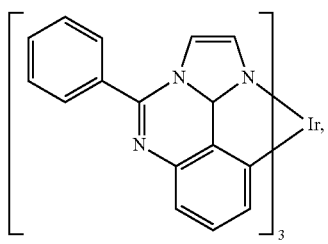
(BE-125)

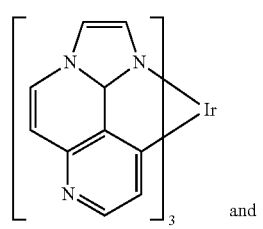
(BE-126)

and

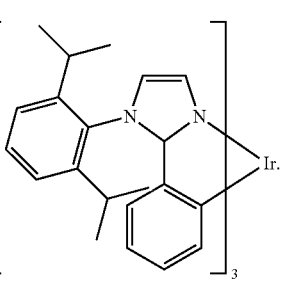
(BE-127)

The compound of formula IX is more preferably a compound (BE-1), (BE-2), (BE-7), (BE-12), (BE-16), (BE-64), or (BE-70). The most preferred phosphorescent blue emitters are compounds (BE-1) and (BE-12).

The homoleptic metal-carbene complexes may be present in the form of facial or meridional isomers, preference being given to the facial isomers.

Suitable carbene complexes of formula (IX) and their preparation process are, for example, described in WO2011/073149.

The compounds of the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; U.S. Pat. No. 6,687,266, US20070190359, US20070190359, US20060008670; WO2006098460, US20110210316, WO 2012053627; U.S. Pat. No. 6,921,915, US20090039776; JP2007123392 and European patent application no. 14180422.9.

Examples of suitable phosphorescent green emitters are shown below:

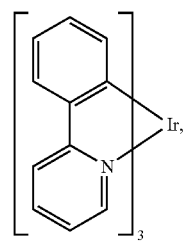
(GE-1)

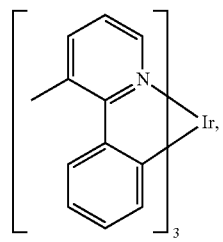
(GE-2)

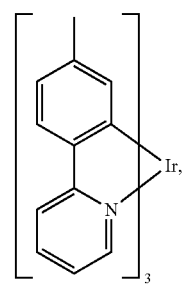
(GE-3)

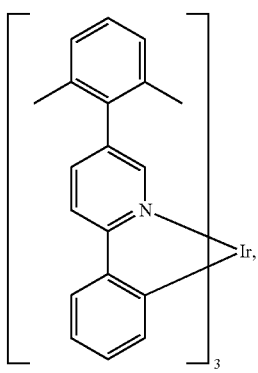
(GE-4)

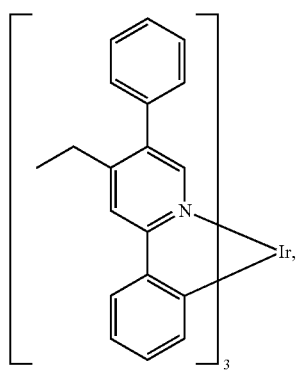
(GE-5)

(GE-6)
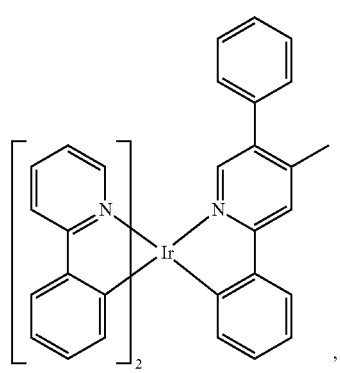
(GE-7)
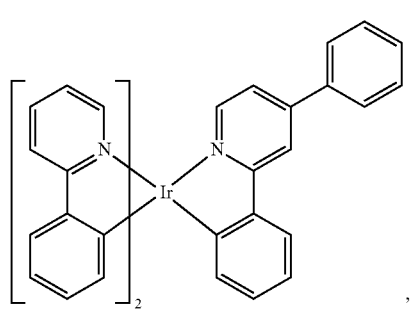
(GE-8)
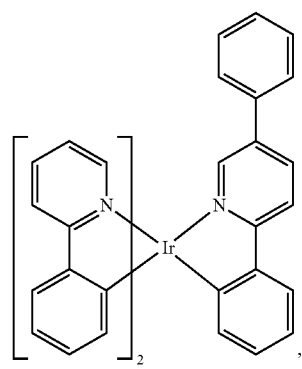
(GE-9)
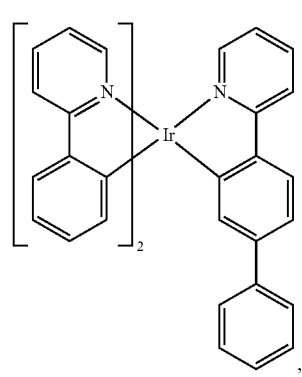
(GE-10)
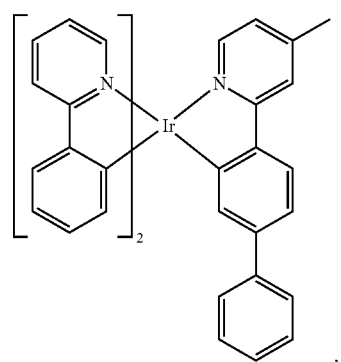
(GE-11)
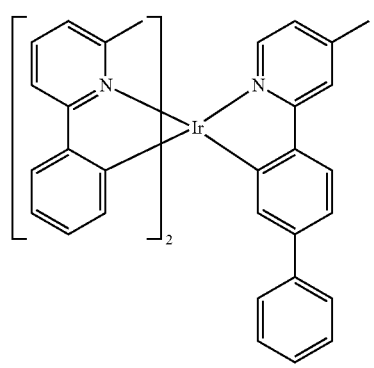
(GE-12)
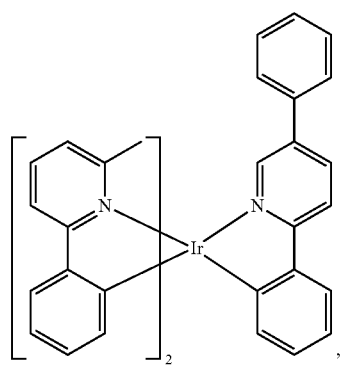
(GE-13)
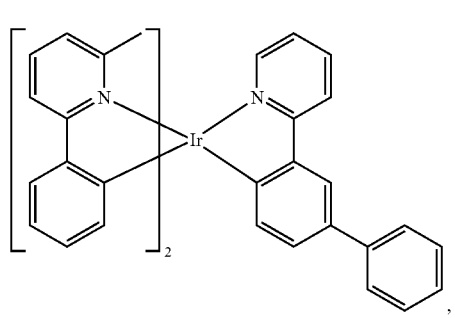

(GE-14)
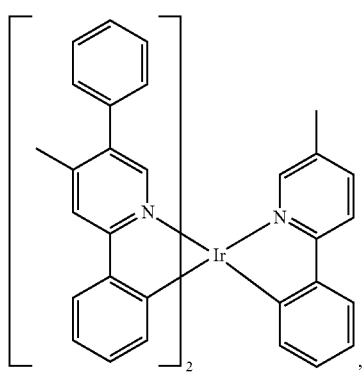
(GE-15)
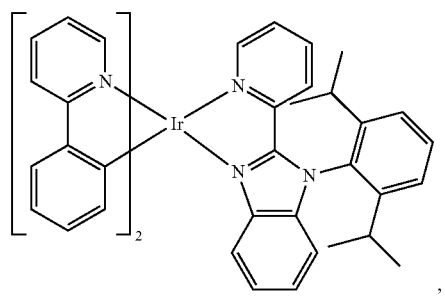
(GE-16)
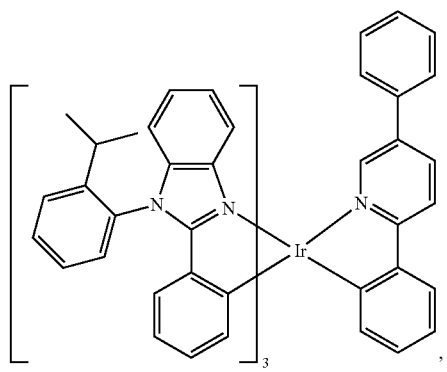
(GE-17)
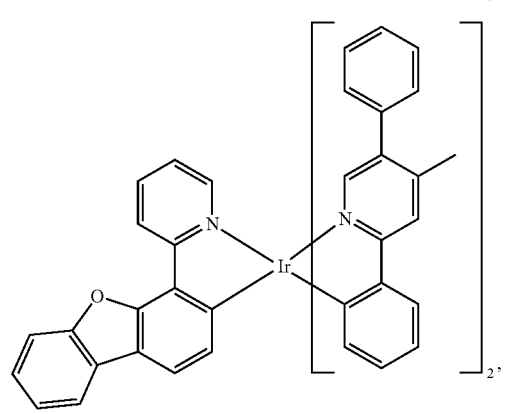
(GE-18)
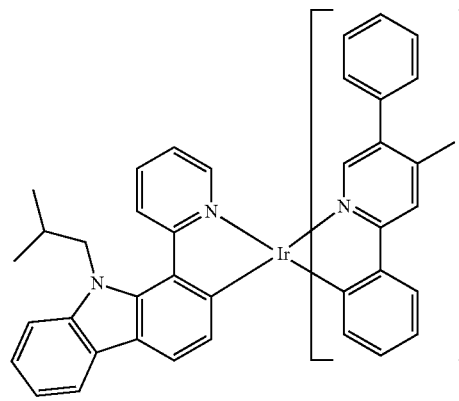
(GE-19)
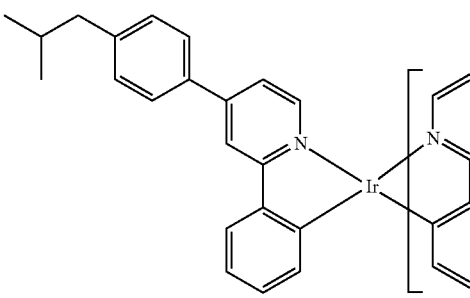
(GE-20)
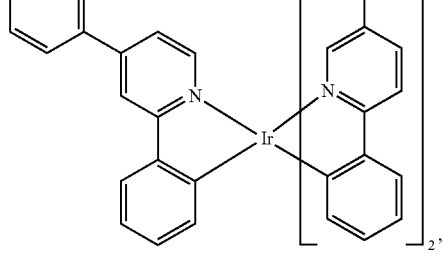
(GE-21)
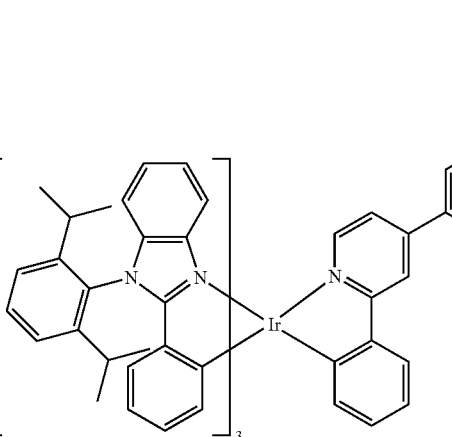

-continued
(GE-22)
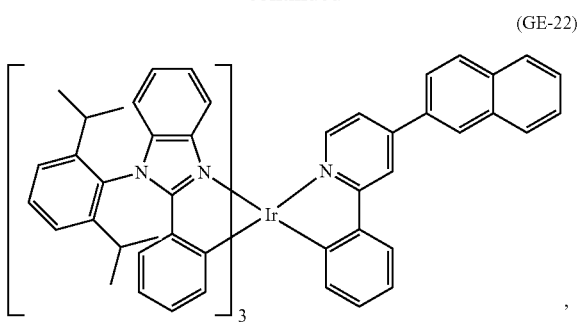
(GE-23)
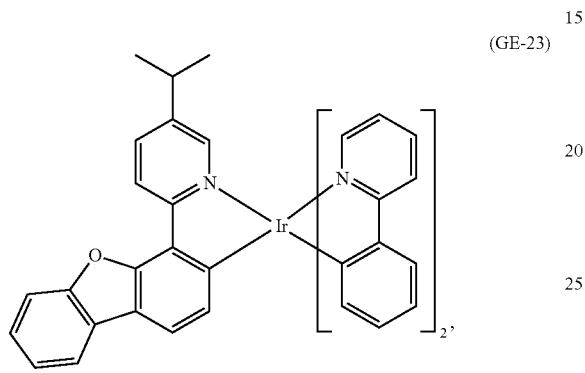
(GE-24)
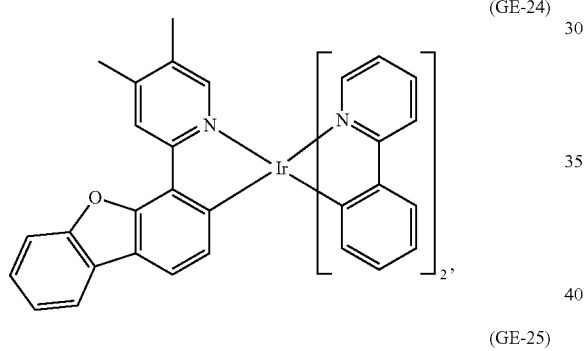
(GE-25)
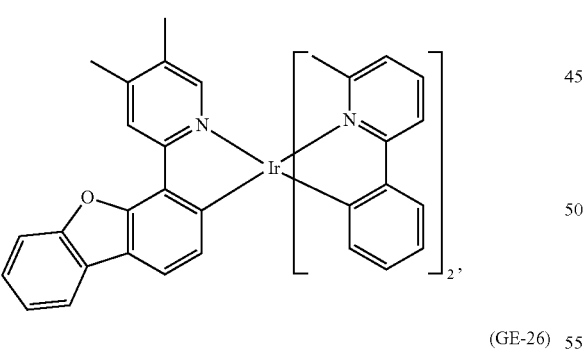
(GE-26)
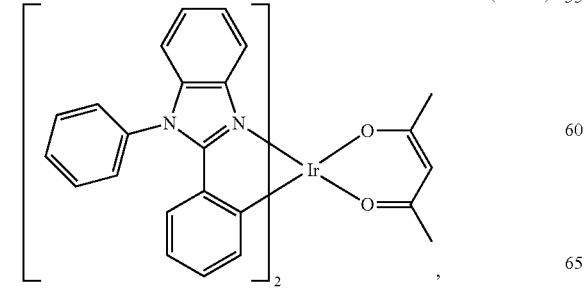
-continued
(GE-27)
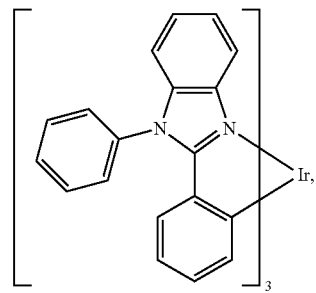
(GE-28)
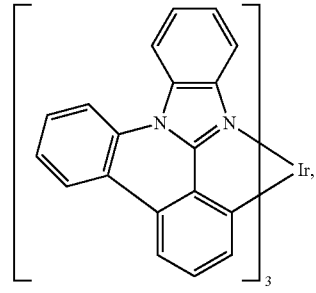
(GE-29)
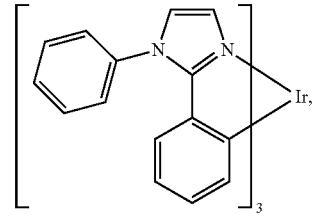
(GE-30)
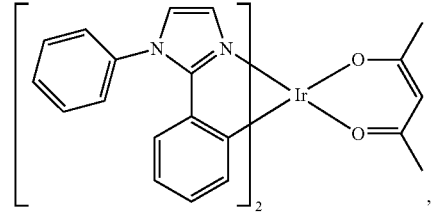
(GE-31)
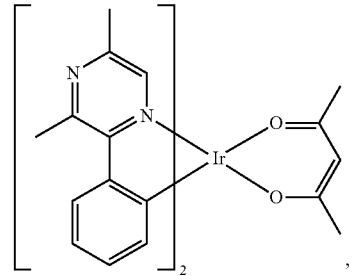
(GE-32)
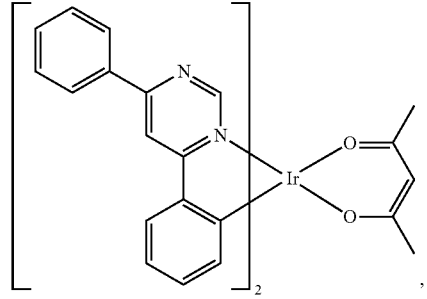

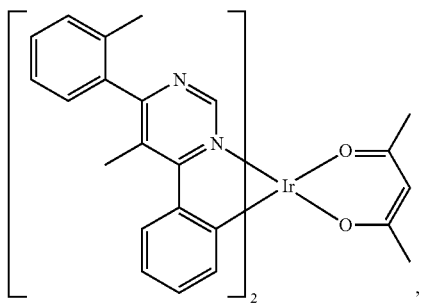
(GE-33)

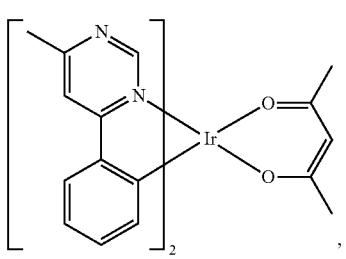
(GE-34)

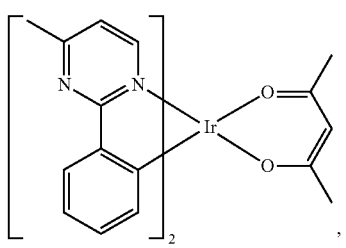
(GE-35)

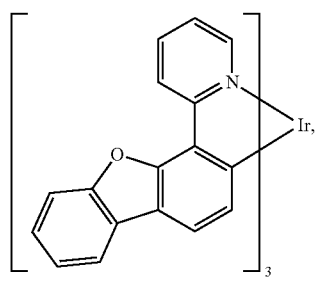
(GE-36)

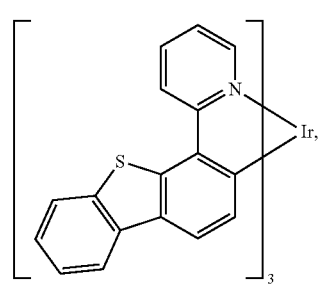
(GE-37)

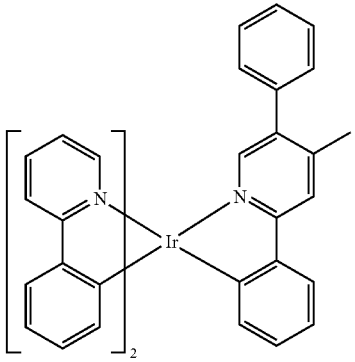
(GE-38)

and

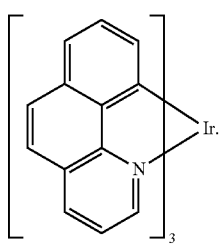
(GE-39)

Host (Matrix) Materials

The light-emitting layer may comprise further components in addition to the emitter material a1. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for exampie TCTA.

In a preferred embodiment of the present invention, at least one compound of the formula I, especially a compound of the formula Ia, IIa, or IIIa is used as matrix material. Examples of preferred compounds of formula I are compounds A-1 to A-134, B-1 to B-24, C-1 to C-44 as well as D-1 to D-36.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned, or belowmentioned matrix materials—in one embodiment at least one compound of the formula I—where the sum total of the emitter material and of the matrix material adds up to 100% by weight.

Suitable metal complexes for use together with the compounds of the formula I as matrix material in OLEDs are, for example, also carbene complexes as described in WO 2005/019373 A2, WO 2006/056418 A2, WO 2005/113704, WO 2007/115970, WO 2007/115981, WO 2008/000727 and WO2014147134.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No.

3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709, WO2014/009317 (in particular compound A-24), WO2014/044722 and WO2014/072320 (in particular page 25 to 29 of WO2014/072320).

The above-mentioned small molecules are more preferred than the above-mentioned (co)polymers of the small molecules.

Further suitable host materials, are described in WO2011137072 (for example,

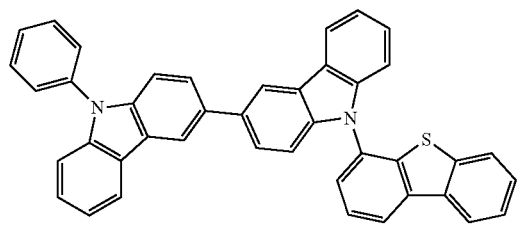

and

-continued

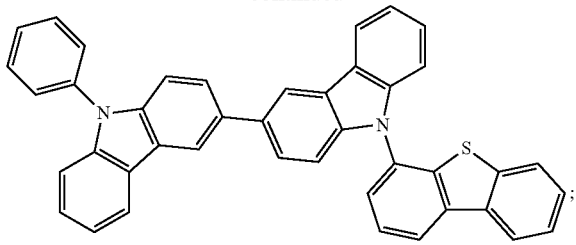

best results are achieved if said compounds are combined with

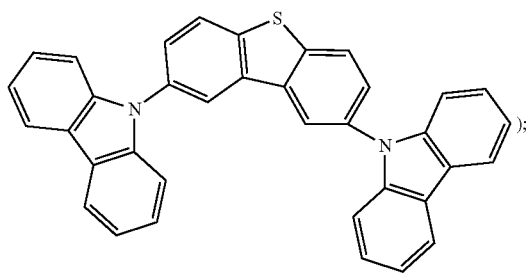 [SMILES: c1ccc2c(c1)c1ccccc1n2-c1ccc2sc3ccc(-n4c5ccccc5c5ccccc54)cc3c2c1]

WO2012048266 (for example,

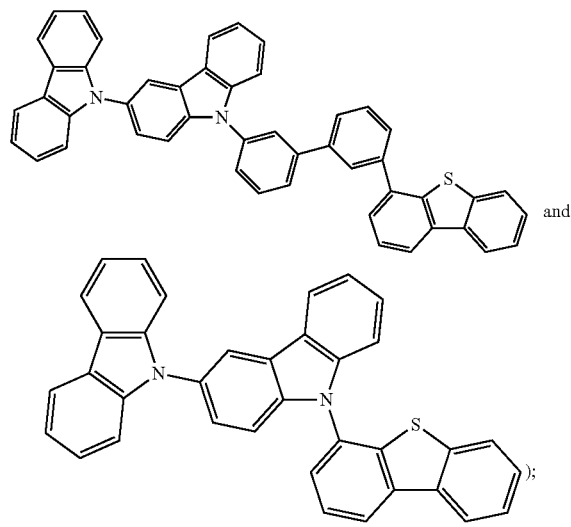

WO2012162325 (for example,

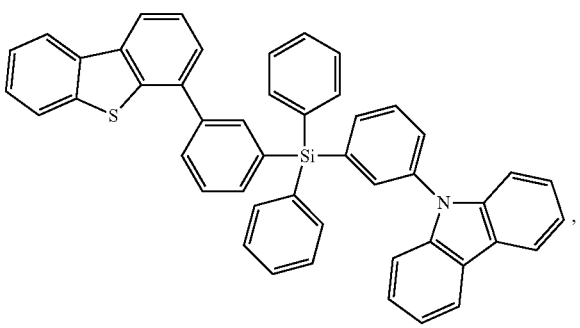

-continued

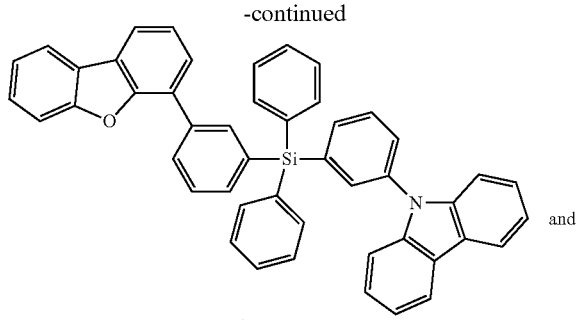

and

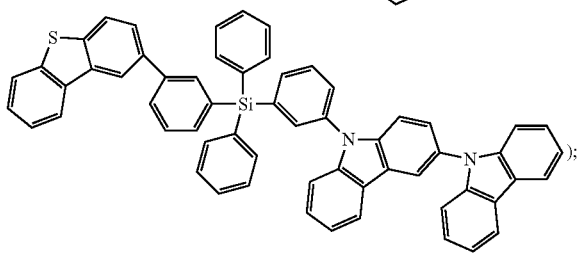

and EP2551932 (for example,

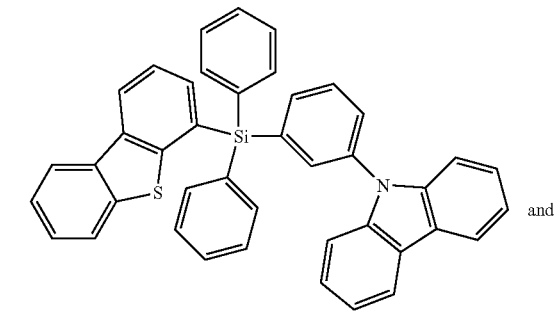

and

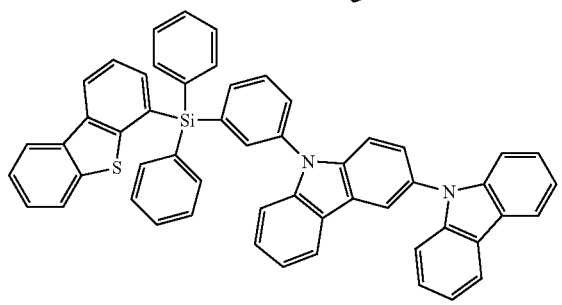

).

In a particularly preferred embodiment, one or more compounds of the general formula (X) specified hereinafter are used as second host material.

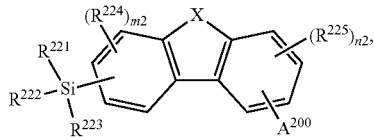

(X), wherein

X is NR, S, O or PR;

R is aryl, heteroaryl, alkyl, cycloalkyl, or heterocycloalkyl;

$A^{200}$ is —$NR^{206}R^{207}$, —$P(O)R^{208}R^{209}$, —$PR^{210}R^{211}$, —$S(O)_2R^{212}$, —$S(O)R^{213}$, —$SR^{214}$, or —$OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;

$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ und $R^{215}$ are independently of each other aryl, heteroaryl, alkyl, cycloalkyl, or heterocycloalkyl. Compounds of formula X, such as, for example,

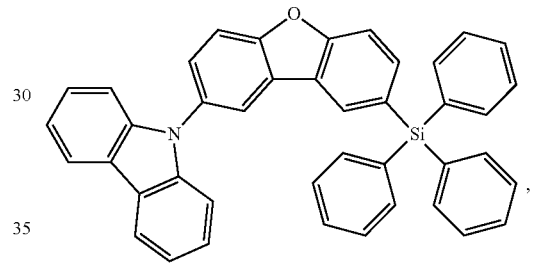
(SH-4)

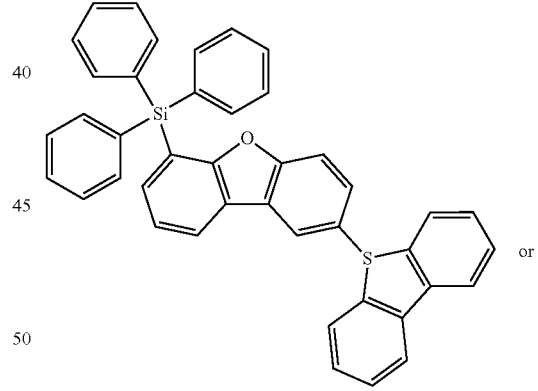
(SH-5)
or

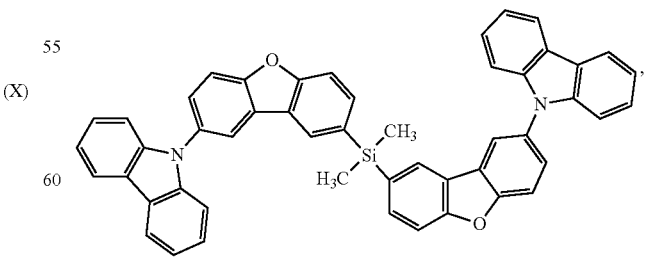
(SH-6)

are described in WO2010079051 (in particular pages on 19 to 26 and in tables on pages 27 to 34, pages 35 to 37 and pages 42 to 43).

Additional host materials on basis of dibenzofurane are, for example, described in US2009066226, EP1885818B1, EP1970976, EP1998388 and EP2034538. Examples of particularly preferred hostmaterials are shown below:
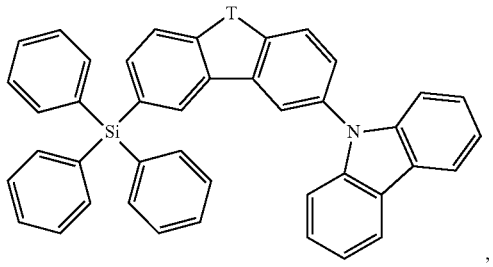
,
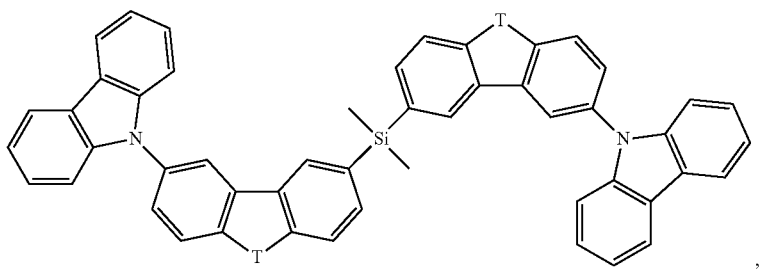
,
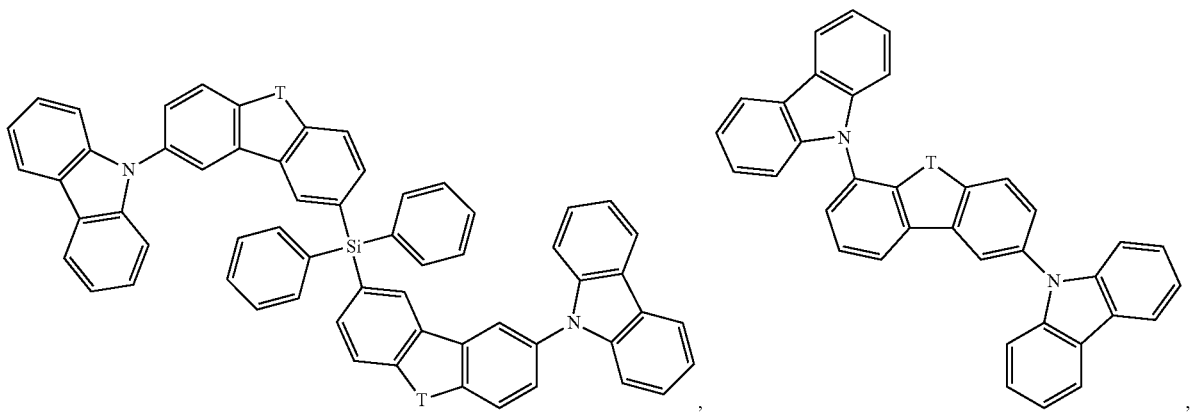
,
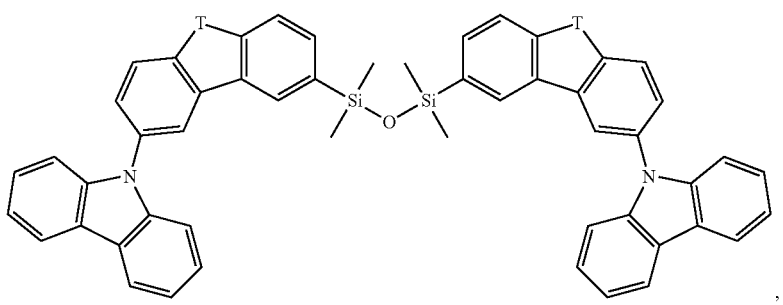
, -continued
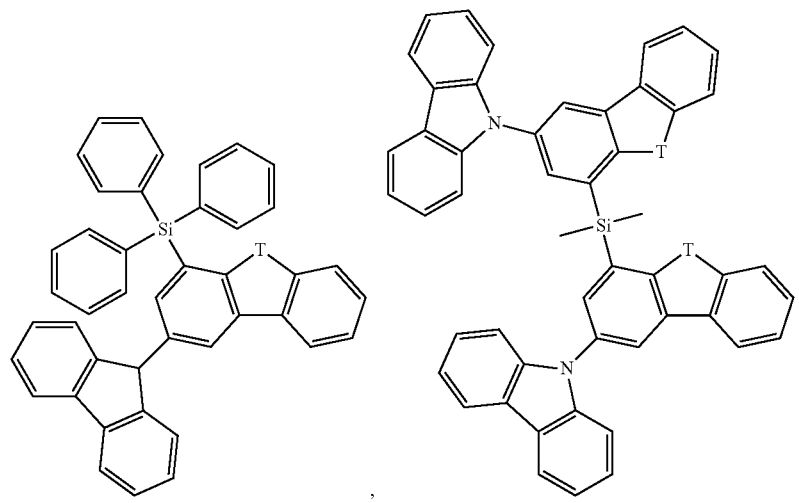
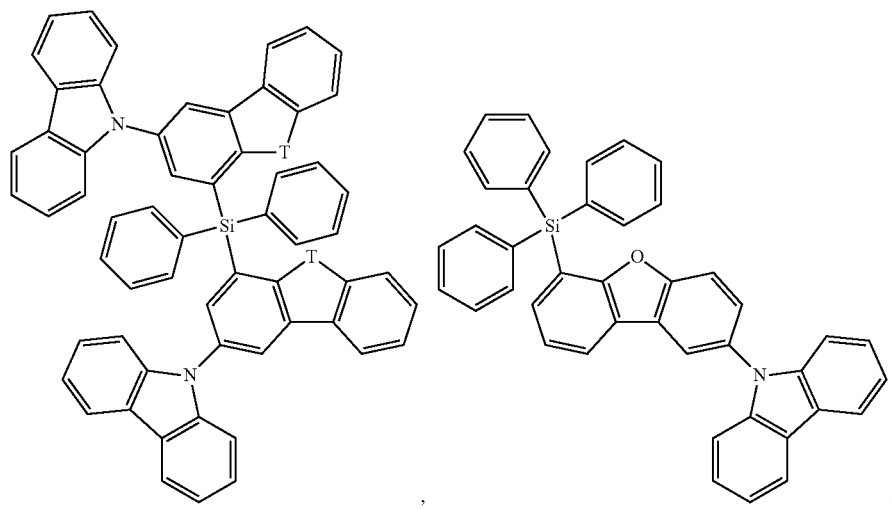
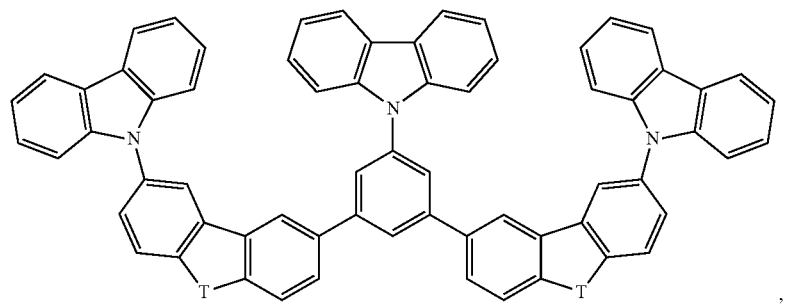
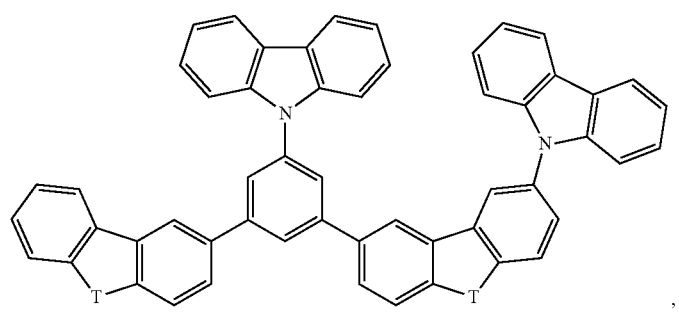

-continued
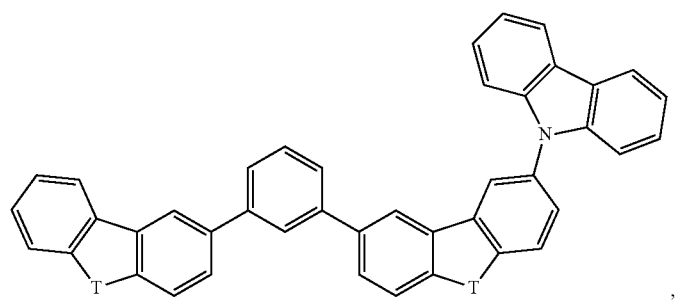,
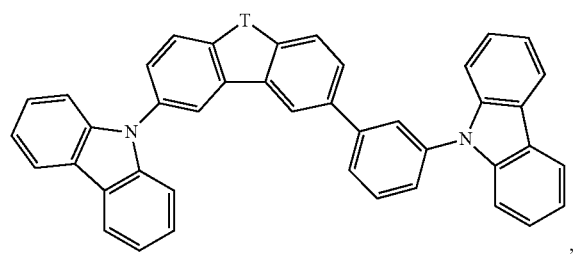,
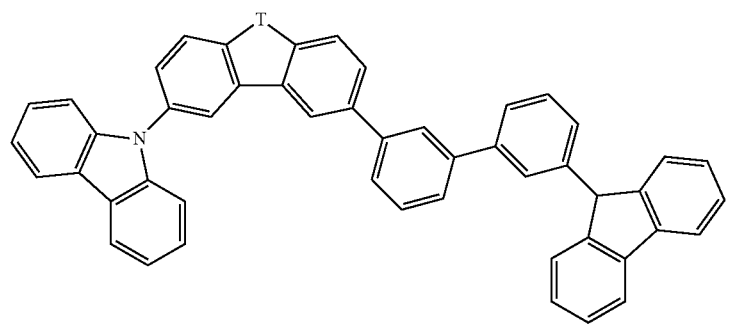,
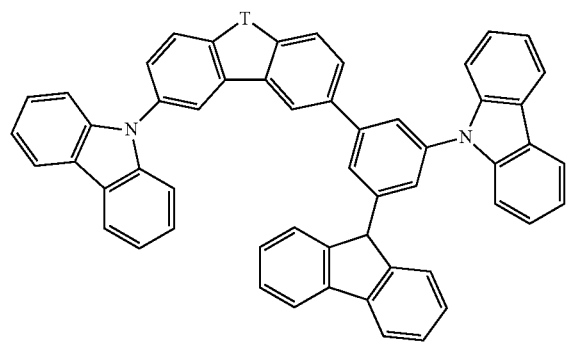,
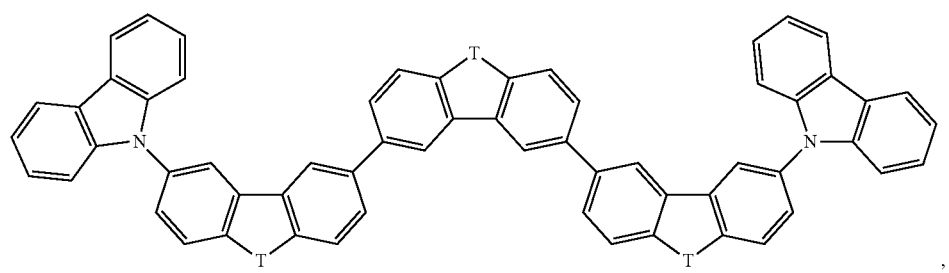,

-continued
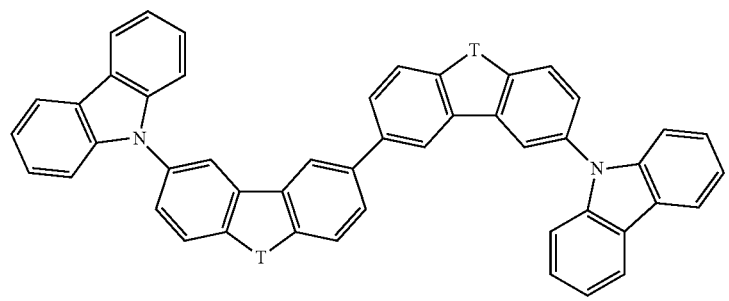
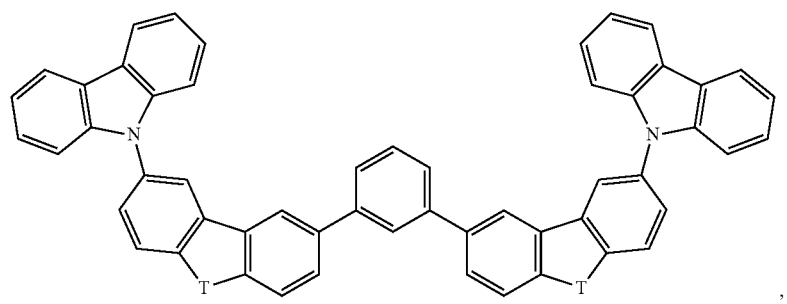
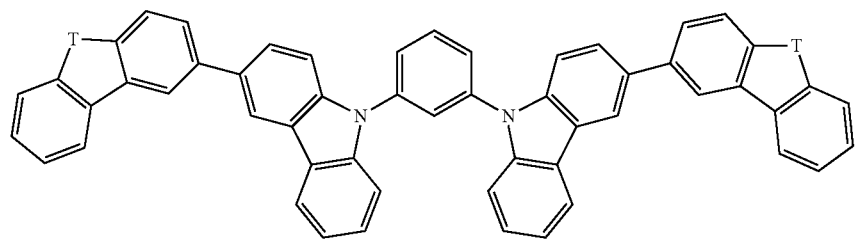
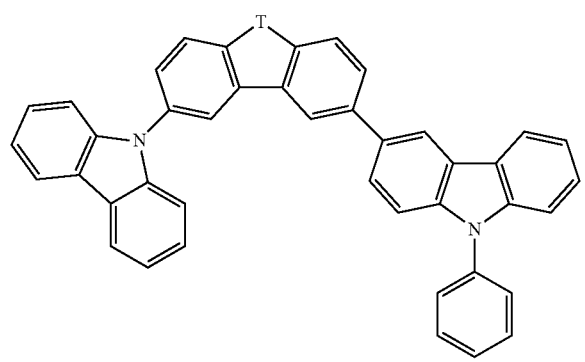
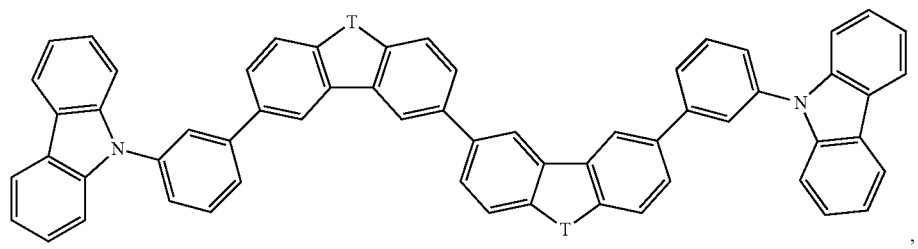

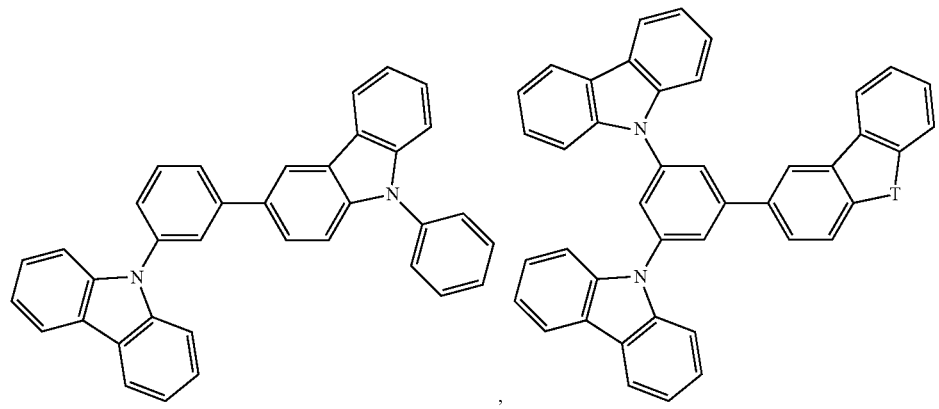
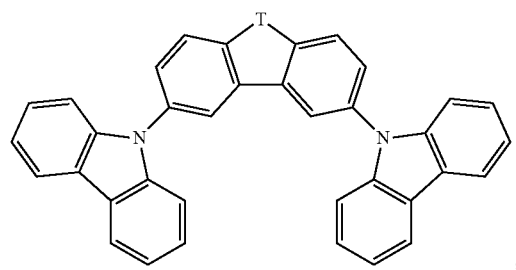
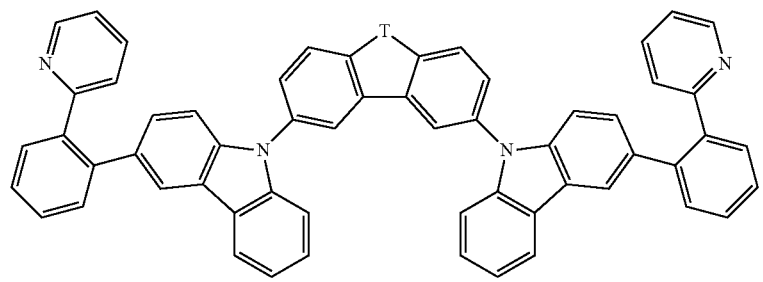
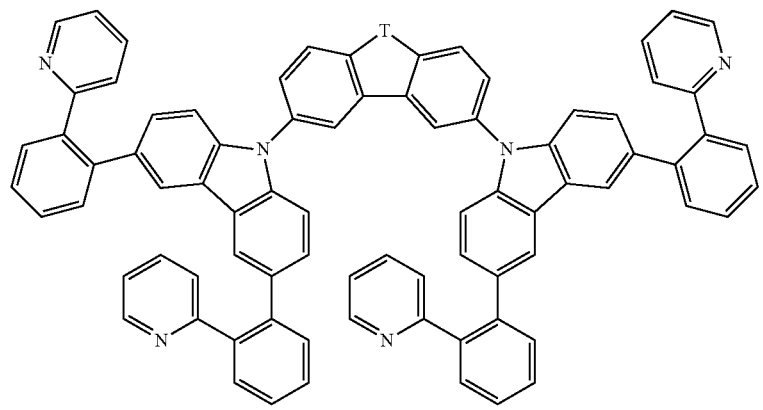
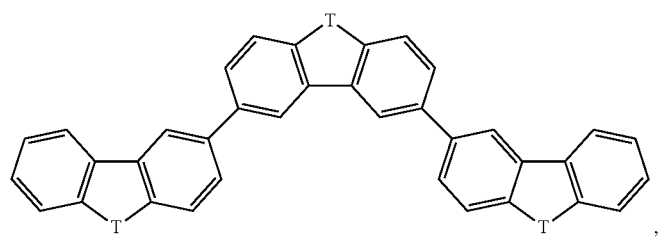

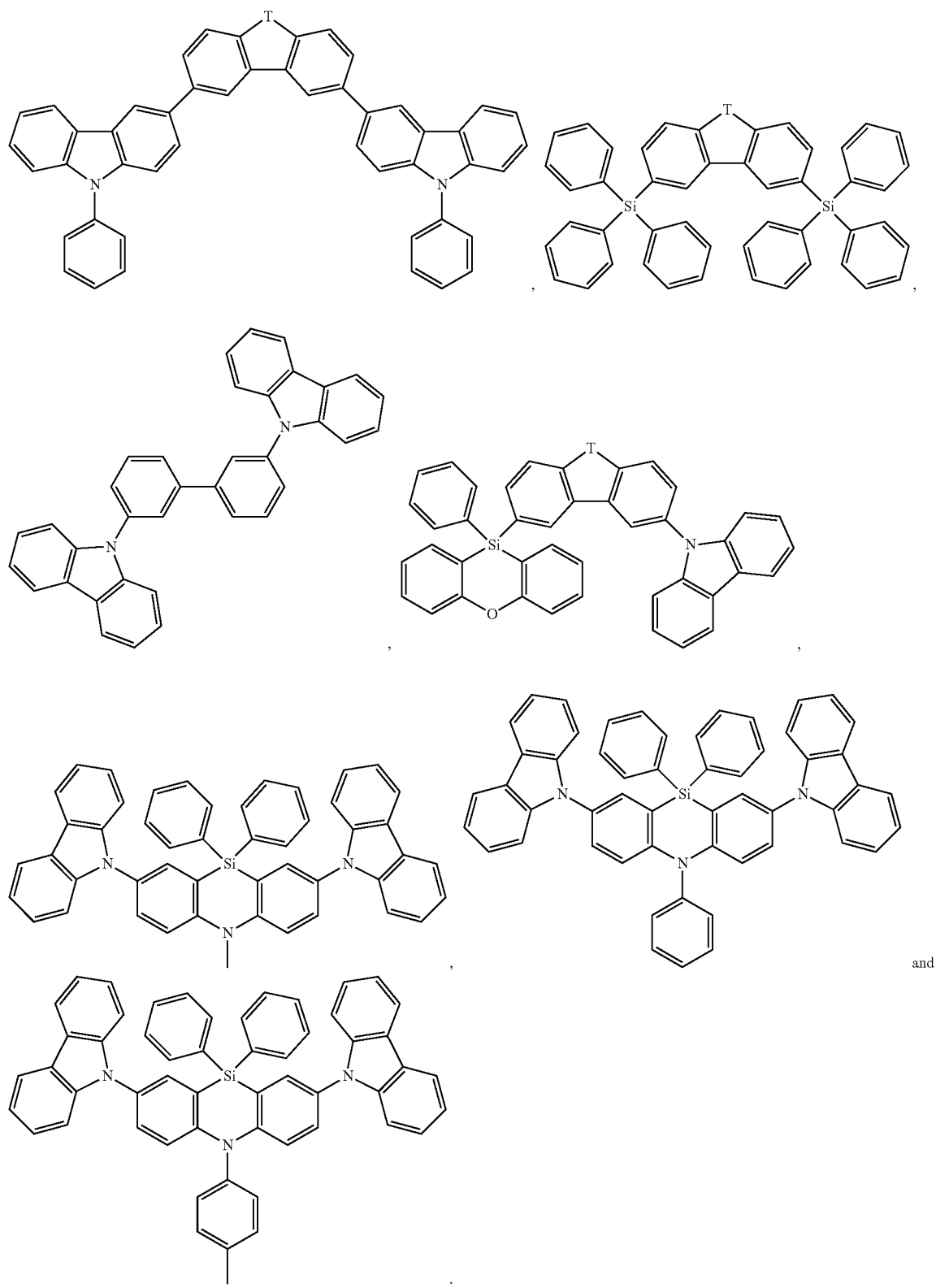
In the above-mentioned compounds T is O, or S, preferably O. If T occurs more than one time in a molecule, all groups T have the same meaning. Compounds (SH-1), (SH-2)
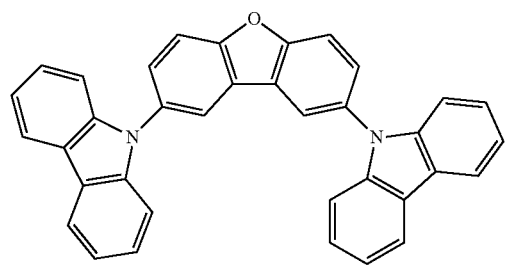
(SH-3) (SH-4) (SH-5) (SH-6)
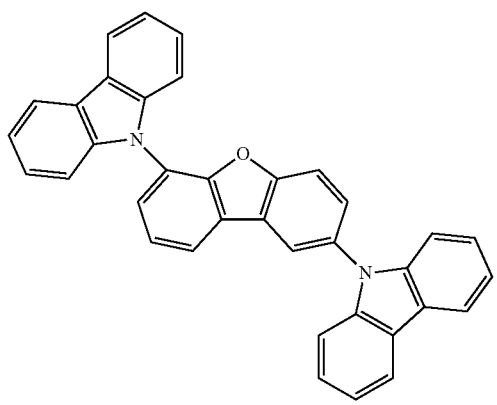
(SH-7)
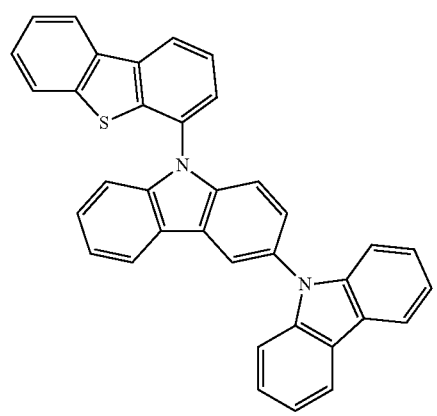
(SH-8)
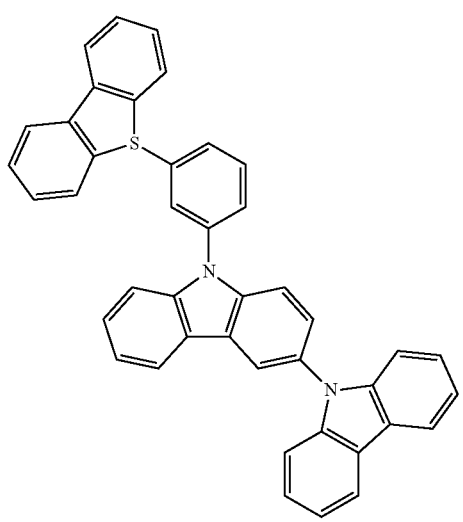
(SH-9)
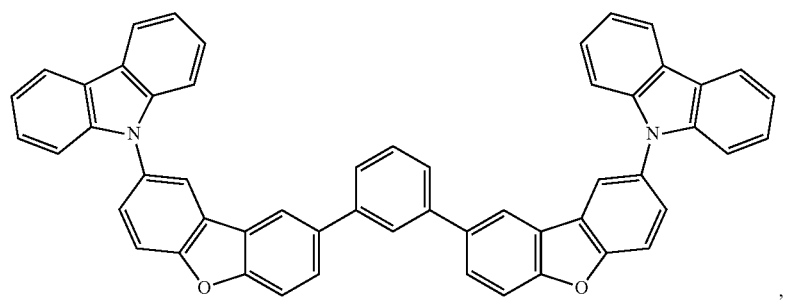
(SH-10)
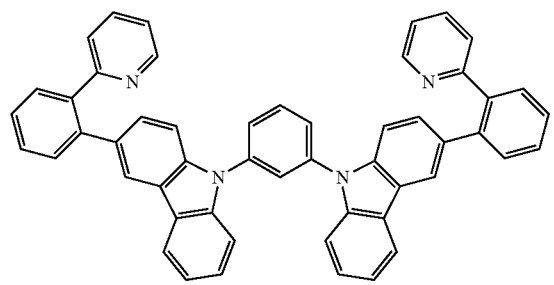
and
(SH-11)
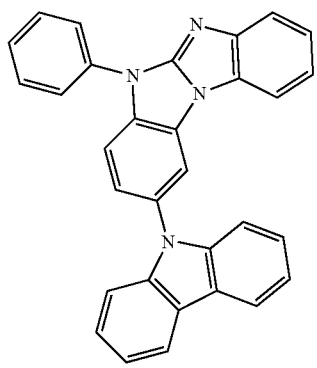

are most preferred.

Hole/Exciton Blocking Layer (f):

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer.

In a preferred embodiment of the present invention, at least one compound of the formula I, especially a compound of the formula Ia, IIa, or IIIa is used as hole/exciton blocking material. Examples of preferred compounds of formula I are compounds A-1 to A-134, B-1 to B-24, C-1 to C-44 as well as D-1 to D-36.

Additional hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009/003919 and WO2009003898 and disilyl compounds as disclosed in WO2008/034758, as a blocking layer for holes/excitons (f).

In another preferred embodiment compounds (SH-1), (SH-2), (SH-3), (SH-4), (SH-5), (SH-6), (SH-7), (SH-8), (SH-9) and (SH-10) may be used as hole/exciton blocking materials.

Electron Transport Layer (g):

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum (Alq₃), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

In a preferred embodiment of the present invention, at least one compound of the formula I, especially a compound of the formula Ia, IIa, or IIIa is used as electron transport material. Examples of preferred compounds of formula I are compounds A-1 to A-134, B-1 to B-24, C-1 to C-44 as well as D-1 to D-36.

It is likewise possible to use mixtures of at least two materials in the electron-transporting layer, in which case at least one material is electron-conducting. Preferably, in such mixed electron-transport layers, at least one phenanthroline compound is used, preferably BCP, or at least one pyridine compound according to the formula (VIII) below, preferably a compound of the formula (VIIIaa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes and with Y, Ce, Sm, Gd, Tb, Er, Tm, Yb, $Li_3N$, $Rb_2CO_3$, dipotassium phthalate, W(hpp)₄ from EP1786050, or with compounds described in EP1837926B1, EP1837927, EP2246862 and WO2010132236.

In a preferred embodiment, the electron-transport layer comprises at least one compound of the general formula (VII)

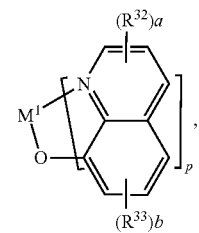

in which $R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;

a and b are each independently 0, or 1, 2 or 3,
$M^1$ is an alkaline metal atom or alkaline earth metal atom,
p is 1 when $M^1$ is an alkali metal atom, p is 2 when $M^1$ is an earth alkali metal atom.

A very particularly preferred compound of the formula (VII) is

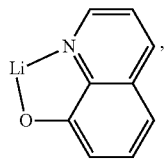
(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (VIII),

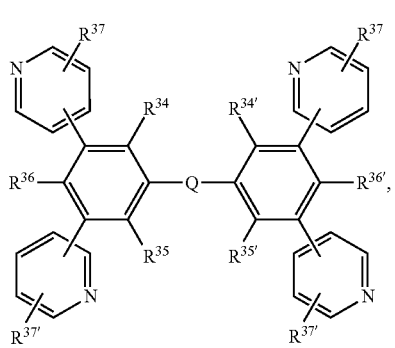
(VIII)

in which
$R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;
D is —CO—; —COO—; —S—; —SO—; —SO$_2$—; —O—; —NR$^{40}$—; —SiR$^{45}$R$^{46}$—; —POR$^{47}$—; —CR$^{38}$=CR$^{39}$—; or —C≡C—; E is —OR$^{44}$; —SR$^{44}$; —NR$^{40}$R$^{41}$; —COR$^{43}$; —COOR$^{42}$; —CONR$^{40}$R$^{41}$; —CN; or F;
G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;
$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or
$R^{40}$ and $R^{41}$ together form a 6-membered ring;
$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—,
$R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl,
$R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa) in which Q is:

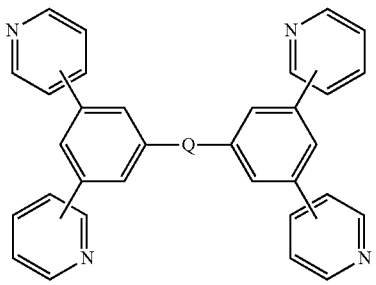
(VIIIa)

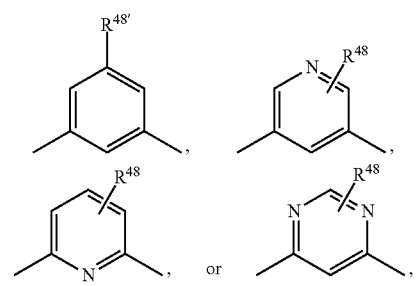

$R^{48}$ is H or $C_1$-$C_{18}$-alkyl and
$R^{48'}$ is H, $C_1$-$C_{18}$-alkyl or

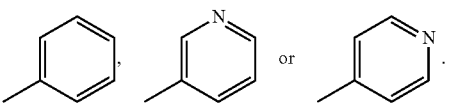

Particular preference is given to a compound of the formula

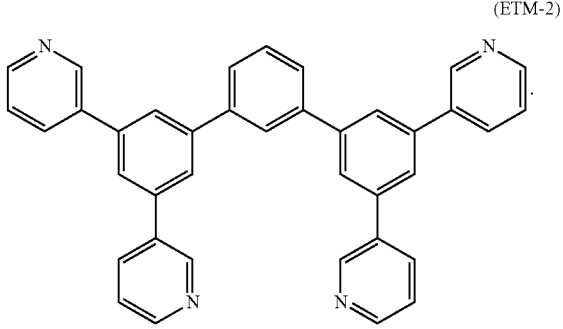 [SMILES: c1cncc(-c2cc(-c3cccnc3)cc(-c3cccc(-c4cc(-c5cccnc5)cc(-c5cccnc5)c4)c3)c2)c1]
(ETM-2)

In a further, very particularly preferred embodiment, the electron-transport layer comprises a compound Liq and a compound ETM-2.

In a preferred embodiment, the electron-transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

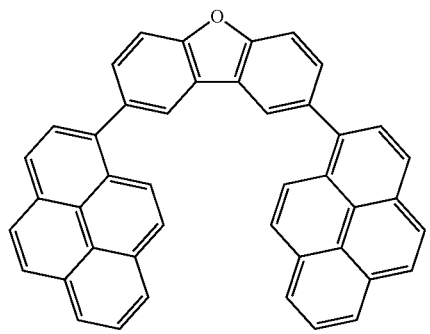

(A-10; = ETM-1) is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron-transport layer comprises at least one phenanthroline derivative and/or pyridine derivative.

In a further preferred embodiment, the electron-transport layer comprises at least one phenanthroline derivative and/or pyridine derivative and at least one alkali metal hydroxyquinolate complex.

In a further preferred embodiment, the electron-transport layer comprises at least one of the dibenzofuran compounds A-1 to A-36 and B-1 to B-22 described in WO2011/157790, especially ETM-1.

In a further preferred embodiment, the electron-transport layer comprises a compound described in WO2012/111462, WO2012/147397, WO2012014621, such as, for example, a compound of formula (ETM-3)

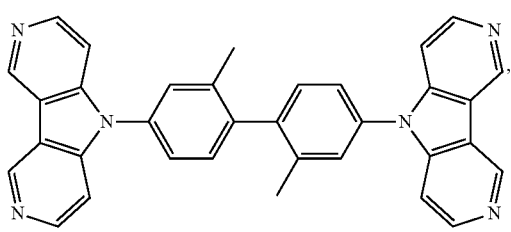

US2012/0261654, such as, for example, a compound of formula (ETM-4)

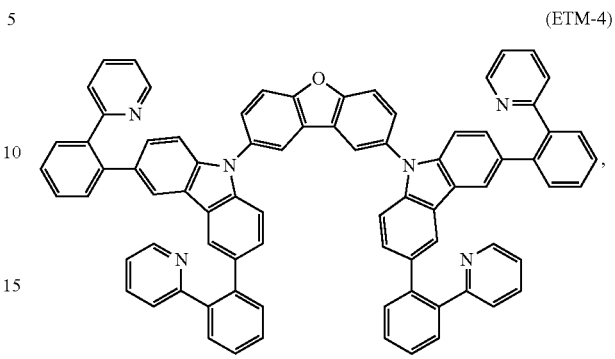

and WO2012/115034, such as for example, such as, for example, a compound of formula (ETM-5)

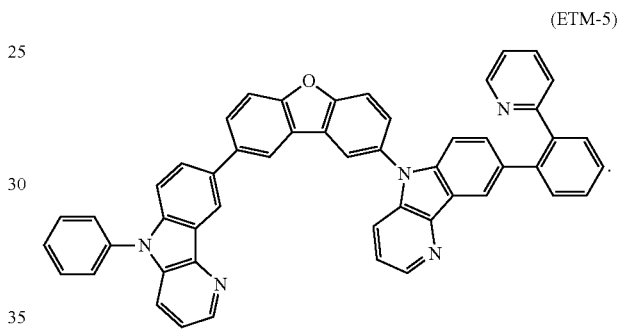

Electron Injection Layer (h):

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

anode (a): 500 to 5000 Å (angström), preferably 1000 to 2000 Å;

hole injection layer (b): 50 to 1000 Å, preferably 200 to 800 Å, hole-transport layer (c): 50 to 1000 Å, preferably 100 to 800 Å, electron/exciton blocking layer (d): 10 to 500 Å, preferably 50 to 100 Å, light-emitting layer (e): 10 to 1000 Å, preferably 50 to 600 Å,
hole/exciton blocking layer (f): 10 to 500 Å, preferably 50 to 100 Å,
electron-transport layer (g): 50 to 1000 Å, preferably 200 to 800 Å,
electron injection layer (h): 10 to 500 Å, preferably 20 to 100 Å,
cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

Use of the compounds of the formula I in at least one layer of the OLED, preferably in the light-emitting layer (preferably as a matrix material), charge transport layer and/or in the charge/exciton blocking layer makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Example 1

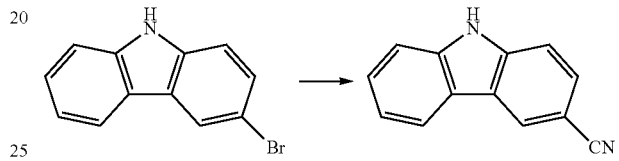

a) 100 g (0.406 mol) 3-Bromo-9H-carbazole and 58.2 g (0.650 mol) CuCN are added to 800 ml of DMF and the suspension is heated to reflux for 20 h under nitrogen. The resulting solution is cooled to room temperature and then poured on 4 l of water. The suspension is filtered and the residue is washed three times with water (1 l each). The white solid is suspended in 1.5 l of 10% Ammonia in water, stirred for three hours, filtered, washed three times with water (1 l each) and dried at 80° C./125 mbar overnight. The resulting solid is dissolved in 1 l of boiling tetrahydrofurane (THF), 100 g of silica is added, stirred for 1 h and then filtered hot. The filtrate is evaporated to 400 ml, cooled to room temperature, filtered, washed three times with cold THF (50 ml each) and dried at 80° C./125 mbar overnight to yield 43.3 g (55.6% of theory) 9H-Carbazole-3-carbonitrile as a white solid.

$^1$H-NMR (400 MHz, CDCl$_3$): δ 8.39 (br s, 2H), 8.10 (d, J=8.0 Hz, 1H), 7.67 (d×d, J$_1$=8.4 Hz, J$_2$=1.6 Hz, 1H), 7.54-7.47 (m, 3H), 7.35-7.31 (m, 1H).

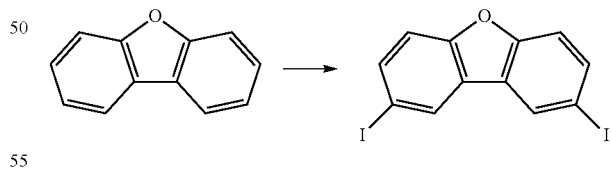

b) 100 g (0.594 mol) Dibenzofuran are dissolved in 1.2 l of acetic acid. 116.1 g (0.457 mol) I$_2$, 44.2 g (0.252 mol) HIO$_3$, 40 ml of water, 12 ml of H$_2$SO$_4$ 97% and 60 ml of CCl$_4$ are added and the mixture is stirred at reflux for 22 h under nitrogen. The resulting suspension is cooled to room temperature, filtered, washed four times with water (1 l each) and dried at 60° C./125 mbar overnight. The crude product is crystallized twice from toluene to yield 113.5 g (59.1% of theory) 2,8-Diiododibenzofuran as a white solid.

$^1$H-NMR (300 MHz, CDCl$_3$): δ 8.22 (s, 2H), 7.76 (d, J=6.9 Hz, 2H), 7.35 (d, J=6.9 Hz, 2H).

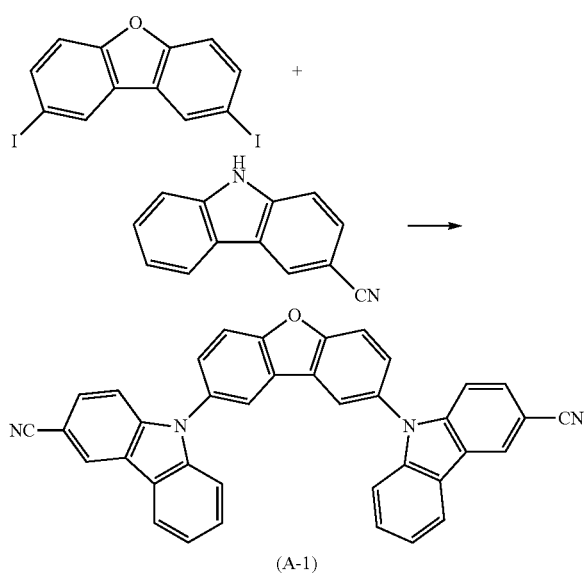

(A-1)

c) 20 g (47.4 mmol) 2,8-Diiododibenzofuran, 20.19 g (104.4 mmol) 9H-Carbazole-3-carbonitrile, 1.36 g (7.1 mmol) CuI, 2.84 g (14.2 mmol) 1,10-Phenanthroline, 32.2 g (151.9 mmol) $K_3PO_4$ and 500 ml Mesitylene are mixed and heated to reflux for 72 h under nitrogen. The brown suspension is cooled to 0° C., filtered and the residue is washed three times with heptane (100 ml each) and twice with methanol (100 ml each). The filter cake is suspended in 1 l of water, stirred for 30 min, filtered, washed three times with water (200 ml each) and dried at 80° C./125 mbar overnight. The crude product is suspended in 1.2 l of THF and heated to reflux. 60 g of silica are added, stirred for 15 min, filtered hot and the residue is washed three times with hot THF (250 ml each). The filtrate is evaporated and the residue is decocted with 200 ml of methanol for 1 h, filtered hot and washed three times with methanol (50 ml each). The product is purified by Soxhlet extraction with toluene, followed by Soxhlet extraction with MEK then by decocting with 150 ml of 1,4-dioxane, filtered hot and washed three times with 1,4-dioxane (20 ml each) to yield 12.3 g (47.1% of theory) 9-[8-(3-Cyanocarbazol-9-yl)dibenzofuran-2-yl]carbazole-3-carbonitrile as a white solid.

$^1$H-NMR (400 MHz, DMSO): δ 8.89 (d, J=1.2 Hz, 2H), 8.60 (d, J=2.0 Hz, 2H), 8.41 (d, J=7.6 Hz., 2H), 8.14 (d, J=8.8 Hz, 2H), 7.86 (dxd, J$_1$=8.8 Hz, J$_2$=2.0 Hz, 2H), 7.82 (dxd, J$_1$=8.8 Hz, J$_2$=1.2 Hz, 2H), 758-7.50 (m, 4H), 7.45-7.41 (m, 4H).

Example 2

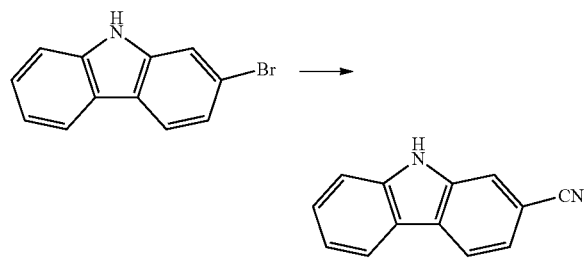

a) 20 g (81.3 mmol) 2-Bromo-9H-carbazole and 11.6 g (130 mmol) CuCN are added to 160 ml of DMF and the suspension is heated to reflux for 22 h under nitrogen. The resulting solution is cooled to room temperature and then poured on 1 l of water. The suspension is filtered and the residue is washed three times with water (200 ml each). The white solid is suspended in 1 l of 10% Ammonia in water, stirred for one hour, filtered, washed three times with water (200 ml each) and dried at 60° C./125 mbar overnight. The crude product is dissolved in 300 ml of boiling THF, 20 g of silica are added, stirred for 1 h, filtered hot and the filtrate is evaporated. The crude product is decocted in 40 ml of boiling heptane for 3 h, cooled to 0° C., filtered, washed twice with cold heptane (10 ml each) and then crystallized from 250 ml heptane/toluene=2:3 to yield 14.6 g (75.1% of theory) 9H-Carbazole-2-carbonitrile as a white solid.

$^1$H-NMR (400 MHz, CDCl$_3$): δ 8.45 (br s, 1H), 8.12 (d, J=8.0 Hz, 1H), 8.11 (d, J=7.6 Hz, 1H), 7.75 (s, 1H), 7.55-7.47 (m, 3H), 7.33-7.29 (m, 1H).

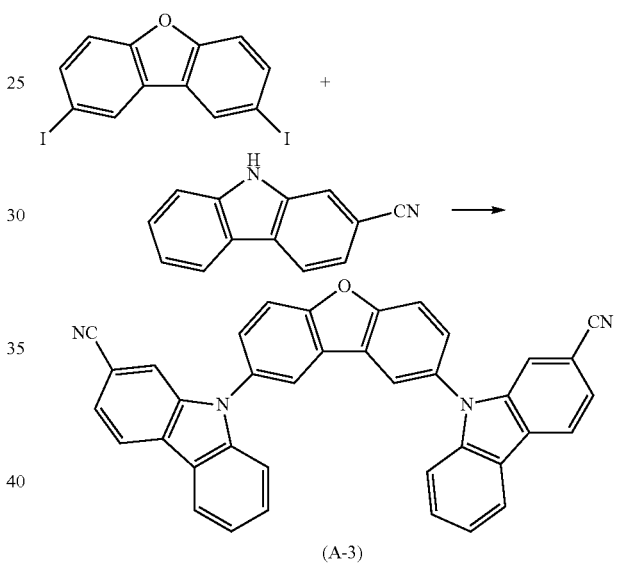

(A-3)

b) 9.0 g (21.4 mmol) 2,8-Diiododibenzofuran, 9.03 g (47.0 mmol) 9H-Carbazole-2-carbonitrile, 0.61 g (3.2 mmol) CuI, 1.27 g (6.4 mmol) 1,10-Phenanthroline, 14.5 g (68.3 mmol) $K_3PO_4$ and 270 ml Mesitylene are mixed and heated to reflux for 48 h under nitrogen. The resulting brown suspension is filtered hot, the residue washed three times with hot toluene (150 ml each) and then dried at 80° C./125 mbar overnight. The residue is subjected to a Soxhlet extraction using 200 ml of toluene and the resulting suspension is combined with the toluene filtrate of above, heated to reflux and then 30 g of silica are added. The mixture is stirred for 30 min., filtered hot and the residue is washed twice with hot toluene (200 ml each). The yellow solution is evaporated to 100 g and then cooled to room temperature. The resulting suspension is filtered; the residue is washed twice with toluene (10 ml each) and dried at 80° C./125 mbar overnight. The product is decocted in toluene/Cyclohexane=2:1 for 4 h, filtered hot, washed three times with Cyclohexane and dried at 80° C./125 mbar overnight, followed by Soxhlet extraction using MEK as a solvent to yield 3.04 g (25.9% of theory) 9-[8-(2-Cyanocarbazol-9-yl)dibenzofuran-2-yl]carbazole-2-carbonitrile as a white solid.

¹H-NMR (400 MHz, CDCl₃): δ 8.22 (d, J=8.0 Hz, 2H), 8.20 (d, J=8.8 Hz, 2H), 8.12 (d, J=2.0 Hz, 2H), 7.94 (d, J=8.8 Hz, 2H), 7.69 (dxd, J₁=8.8 Hz, J₂=2.2 Hz, 2H), 7.66 (s, 2H), 7.57-7.50 (m, 4H), 7.43-7.35 (m, 4H).

Example 3

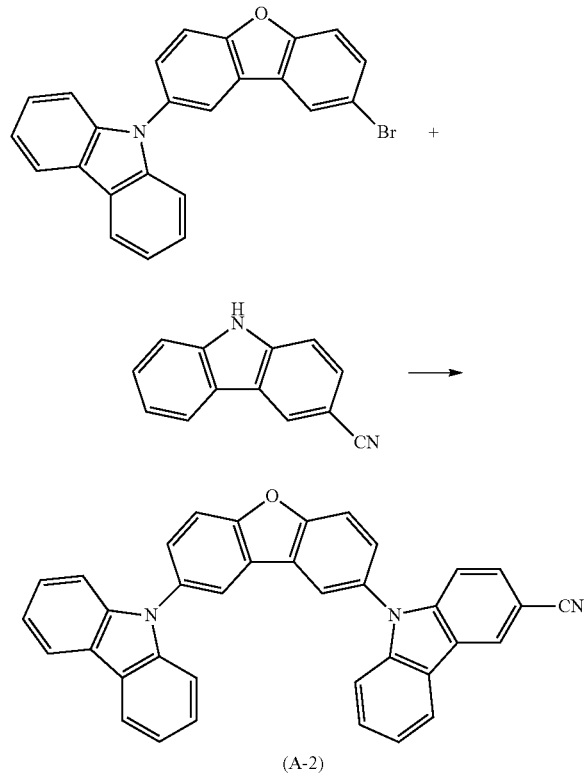

(A-2)

8.65 g (20.8 mmol) 9-(8-Bromodibenzofuran-2-yl)carbazole (prepared according to WO2010079051, example 13), 4.79 g (24.9 mmol) 9H-Carbazole-3-carbonitrile, 1.19 g (6.2 mmol) CuI, 2.47 g (12.5 mmol) 1,10-Phenanthroline, 14.1 g (66.5 mmol) K₃PO₄ and 200 ml Mesitylene are mixed and heated to reflux for 72 h under nitrogen. The resulting brown suspension is diluted with 200 ml toluene, heated to reflux, filtered through Hyflo and washed three times with hot toluene (200 ml each). The filtrate is mixed with 25 g of silica, refluxed for 1 h, filtered hot and washed three times with hot toluene (100 ml each). The filtrate is evaporated on the rotavap, the residue is triturated with 200 ml of methanol, stirred for 1 h and the resulting suspension is filtered and the filter cake is dried in the hood for 24 h. Purification using CombiFlash and heptane/CH₂Cl₂ as eluent yielded 4.40 g (40.4% of theory) 9-(8-Carbazol-9-yldibenzofuran-2-yl) carbazole-3-carbonitrile as a white solid.

¹H-NMR (400 MHz, CDCl₃): δ 8.47 (d, J=1.2 Hz, 1H), 8.19-8.17 (m, 3H), 8.11 (dxd, J₁=13.6 Hz, J₂=2 Hz, 2H), 7.91 (d, J=8.8 Hz, 1H), 7.89 (d, J=8.8 Hz, 1H), 7.72 (dxd, J₁=8.8 Hz, J₂=2.4 Hz, 1H), 7.67-7.64 (m, 2H), 7.53-7.48 (m, 1H), 7.44-7.28 (m 9H).

Example 4

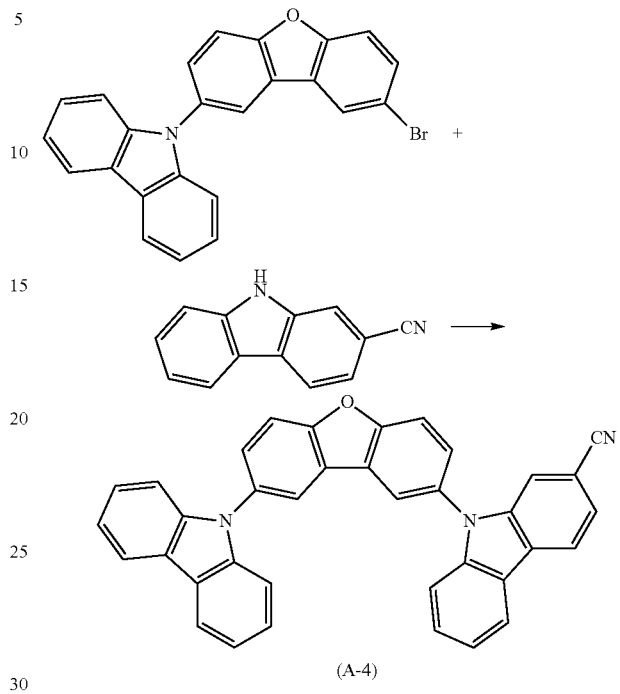

(A-4)

8.0 g (19.4 mmol) 9-(8-Bromodibenzofuran-2-yl) carbazole (prepared according to WO2010079051, example 13), 4.1 g (21.3 mmol) 9H-Carbazole-2-carbonitrile, 0.55 g (2.91 mmol) CuI, 1.15 g (5.82 mmol) 1,10-Phenanthroline, 13.18 g (62.1 mmol) K₃PO₄ and 240 ml Mesitylene are mixed and heated to reflux for 48 h under nitrogen. The resulting brown suspension is diluted with 200 ml of toluene, heated to reflux, filtered through Hyflo and washed three times with hot toluene (250 ml each). The filtrate is mixed with 25 g of silica, refluxed for 1 h, filtered hot and washed three times with hot toluene (100 ml each). The filtrate is evaporated on the rotavap, the residue is triturated with 200 ml of methanol, stirred for 1 h and the resulting suspension is filtered and the filter cake is dried in the hood for 24 h. Purification using CombiFlash and heptane/CH₂Cl₂ as eluent followed by crystallization from 1,4-dioxane/methanol yielded 3.52 g (34.7% of theory) 9-(8-carbazol-9-yldibenzofuran-2-yl) carbazole-2-carbonitrile as a white solid.

¹H-NMR (400 MHz, CDCl₃): δ 8.22-8.13 (m, 5H), 8.09 (d, J=2.0 Hz, 1H), 7.90 (t, J=8.4 Hz, 2H), 7.72 (dxd, J₁=8.8 Hz, J₂=2.0 Hz, 1H), 7.67-7.63 (m, 2H), 7.57-7.50 (m, 2H), 7.45-7.28 (m, 8H).

Example 5

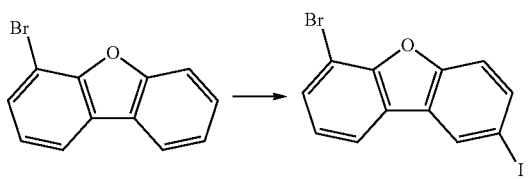 [SMILES: Brc1cccc2c1oc1ccccc12 ; Brc1cccc2c1oc1ccc(I)cc12]

a) 50 g (0.202 mol) 4-Bromo-dibenzofuran are added to 500 ml acetic acid under nitrogen. At room temperature 32.5 g (0.101 mol) (Diacetoxy-iodo)benzene, 25.7 g (0.101 mol) $I_2$ and 16 drops of $H_2SO_4$ 97% are added in four portions each within 2 h. The resulting suspension is stirred overnight, filtered, the residue is washed three times with cold methanol (50 ml each) and dried at 80° C./125 mbar overnight. The product is crystallized from Cyclohexane to yield 36.9 g (49.0% of theory) 6-Bromo-2-iodo-dibenzofuran as a white solid.

$^1$H-NMR (400 MHz, $CDCl_3$): δ 8.25 (s, 1H), 7.82 (d, J=7.6 Hz, 1H), 7.76 (d, J=8.4 Hz, 1H), 7.64 (d, J=7.6 Hz, 1H), 7.42 (d, J=8.4 Hz, 1H), 7.26-7.21 (m, 1H).

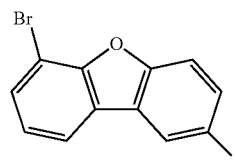

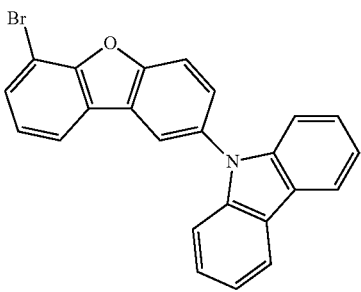

b) 33.56 g (89.98 mmol) 6-Bromo-2-iodo-dibenzofuran, 15.05 g (89.98 mmol) Carbazole 51.47 g (809.84 mmol) Cu and 37.31 g (269.95 mmol) $K_2CO_3$ are added to 450 ml of DMA and the suspension is stirred at 145° C. for 24 h under nitrogen. The reaction mixture is filtered hot through Hyflo and the filtrate is added drop by drop to 4 l of water. The residue is washed three times with water (500 ml each) and dried at 80° C./125 mbar overnight. Purification using CombiFlash and heptane/$CH_2Cl_2$ as eluent yielded 20.4 g (55.1% of theory) 9-(6-Bromodibenzofuran-2-yl) carbazole as a white solid.

$^1$H-NMR (400 MHz, $CDCl_3$): δ 8.19 (d, J=7.6 Hz, 2H), 8.11 (d, J=2.0 Hz, 1H), 7.89-7.86 (m, 2H), 7.71-7.66 (m, 2H), 7.45-7.26 (m, 7H).

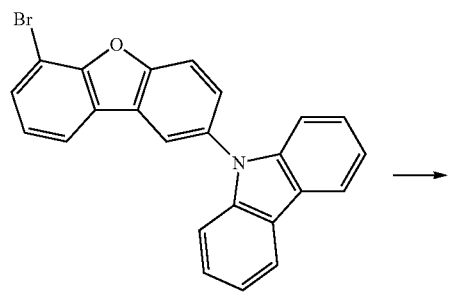

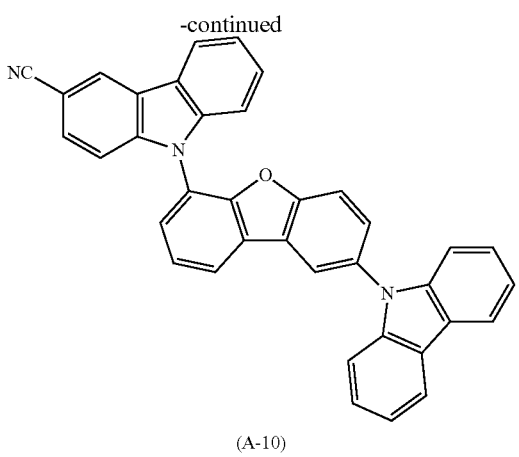

(A-10)

c) 11.97 g (29.03 mmol) 9-(6-Bromodibenzofuran-2-yl) carbazole, 6.14 g (31.94 mmol) 9H-Carbazole-3-carbonitrile, 1.66 g (8.71 mmol) CuI, 3.45 g (17.42 mmol) 1,10-Phenanthroline, 19.7 g (92.9 mmol) $K_3PO_4$ and 350 ml Mesitylene are mixed and heated to reflux for 24 h under nitrogen. Further 1.66 g (8.71 mmol) CuI, 3.45 g (17.42 mmol) 1,10-Phenanthroline and 19.7 g (92.9 mmol) $K_3PO_4$ are added and the suspension is refluxed for another 48 h. The resulting brown suspension is diluted with 200 ml of toluene, heated to reflux, filtered through Hyflo and washed three times with hot toluene (200 ml each). The filtrate is mixed with 30 g of silica, refluxed for 30 min, filtered hot, washed three times with hot toluene (200 ml each). The filtrate is evaporated on the rotavap, the residue is triturated with 100 ml of Cyclohexane, the solvent is decanted and the residue is dried on the rotavap. The residue is triturated with 200 ml of methanol, stirred for 1 h and the resulting suspension is filtered and the filter cake is dried in the hood for 24 h. Purification using CombiFlash and heptane $CH_2Cl_2$ as eluent followed by decocting in methanol yielded 2.89 g (19.0% of theory) 9-(8-Carbazol-9-yldibenzofuran-4-yl)carbazole-3-carbonitrile as a white solid.

$^1$H-NMR (400 MHz, $CDCl_3$): δ 8.54 (d, J=1.6 Hz, 1H), 8.26-8.13 (m, 5H), 7.74-7.61 (m, 5H), 7.56-7.51 (m, 1H), 7.51-7.33 (m, 9H).

Example 6

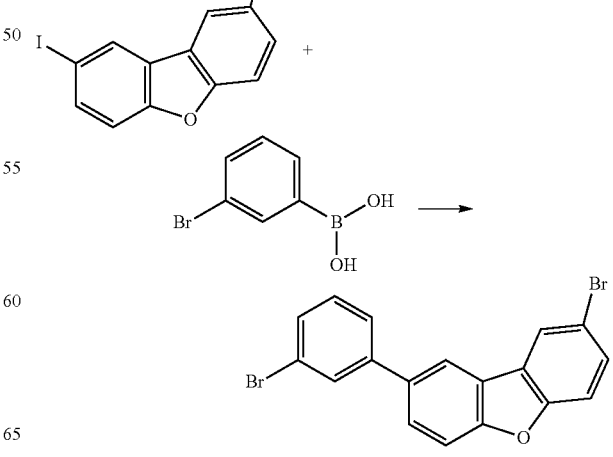

a) 10.0 g (26.8 mmol) 2-Bromo-8-iododibenzofuran, 5.92 g (29.5 mmol) 3-Bromobenzene boronic acid, 0.620 g (0.536 mmol) Tetrakis(triphenylphosphine)palladium(0) and 44 ml 2M $Na_2CO_3$ aq. in 88 ml dimethoxyethane (DME) are stirred for 6h at 105° C. under argon. Then the reaction mixture is cooled to room temperature. Dichloromethane and water are added, and the organic phase is separated. The organic phase is washed with water and dried with magnesium sulfate. Column chromatography on silica gel with heptane/$CH_2Cl_2$ (19/1) results in the crude product, which is crystalized from hexane/toluene to yield 6.72 g (62% of theory) 2-Bromo-8-(3-bromophenyl)dibenzofuran as a white solid.

$^1$H NMR (300 MHz, $CDCl_3$): δ 8.15 (d, J=1.8 Hz, 1H), 8.09 (d, J=1.8 Hz, 1H), 7.82 (d×d, $J_1$=1.8 Hz, $J_2$=1.8 Hz, 1H), 7.47-7.71 (m, 6H), 7.37 (d×d, $J_1$=7.8 Hz, $J_2$=8.1 Hz, 1H).

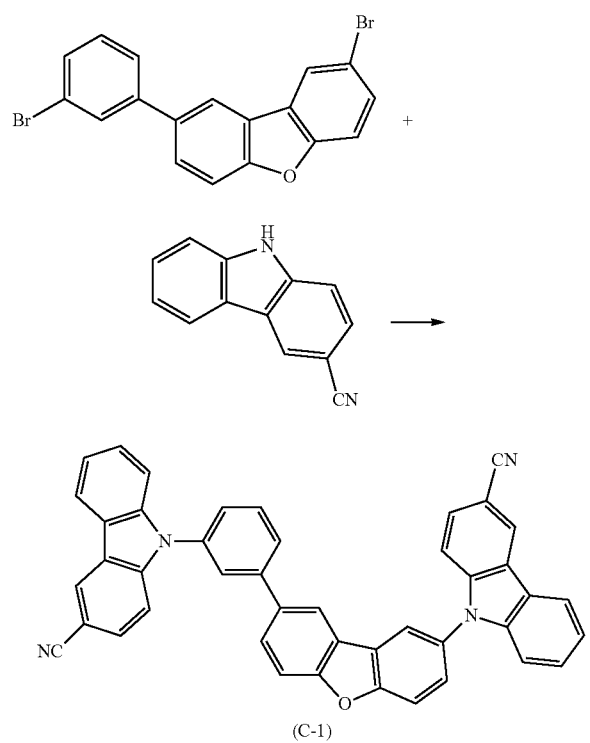

(C-1)

b) 3.00 g (7.46 mmol) 2-Bromo-8-(3-bromophenyl)-dibenzofuran, 3.21 g (17.9 mmol) 9H-Carbazole-3-carbonitrile, 1.42 g (7.46 mmol) Copper(I) iodide, 7.60 g (35.8 mmol) Potassium phosphate tribasic, and 4.35 ml trans-1,2-Diaminocyclohexane in 60 ml 1,4-dioxane are stirred for 24 h at 115° C. under nitrogen. The product is filtered off and washed with water and dried with magnesium sulfate. The solvent is distilled off. The product is washed two times with ethyl acetate under sonication and crystalized from hexane/1,4-dioxane to yield 2.00 g (43% of theory) 9-[3-[8-(3-cyanocarbazol-9-yl)dibenzofuran-2-yl]phenyl]carbazole-3-carbonitrile as a white solid. $^1$H NMR (300 MHz, DMSO-d6): δ 8.88 (d, J=0.9 Hz, 1H), 8.87 (d, J=0.9 Hz, 1H), 8.75 (d, J=1.5 Hz, 1H), 8.53 (d, J=2.1 Hz, 1H), 8.40 (d, J=7.8 Hz, 1H), 8.39 (d, J=7.8 Hz, 1H), 8.00-8.10 (m, 3H), 7.92 (d, J=8.7 Hz, 1H), 7.76-7.88 (m, 4H), 7.66 (d, J=8.1 Hz, 1H), 7.35-7.59 (m, 7H), 7.15-7.28 (m, 2H).

Example 7

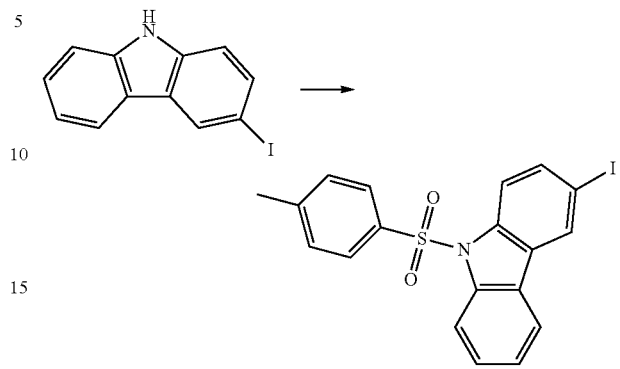

a) 20 g (68.2 mmol) 3-Iodo-9H-carbazole are added to 400 ml toluene under nitrogen, followed by 1.67 g (4.48 mmol) $Bu_4N^+HSO_4^-$ and 15.6 g (81.9 mmol) Tosyl chloride. 100 g of a 50% solution of KOH in $H_2O$ are added drop by drop within 30 min. while keeping the temperature at about 20° C. using a water bath. After further 2h stirring at room temperature the reaction is diluted with 200 ml $H_2O$ and 200 ml ethyl acetate. The organic phase is washed three times with $H_2O$ (250 ml each), dried over $MgSO_4$, filtered and evaporated on the rotavap. The crude product is decocted in 100 ml Isopropanol under reflux for 1 h, cooled to room temperature, filtered and dried at 80° C./125 mbar overnight to yield 29.0 g (95.1% of theory) 3-Iodo-9-(p-tolylsulfonyl)carbazole as a white solid. $^1$H-NMR (400 MHz, $CDCl_3$): δ 8.31 (d, J=8.4 Hz, 1H), 8.20 (d, J=1.6 Hz, 1H), 8.10 (d, J=8.4 Hz, 1H), 7.82 (d, J=8.0 Hz, 1H), 7.75 (d×d, $J_1$=8.8 Hz, $J_2$=2.0 Hz, 1H), 7.67 (d, J=8.4 Hz, 2H), 7.54-7.49 (m, 1H), 7.38-7.33 (m, 1H), 7.10 (d, J=8.4 Hz, 2H), 2.25 (s, 3H).

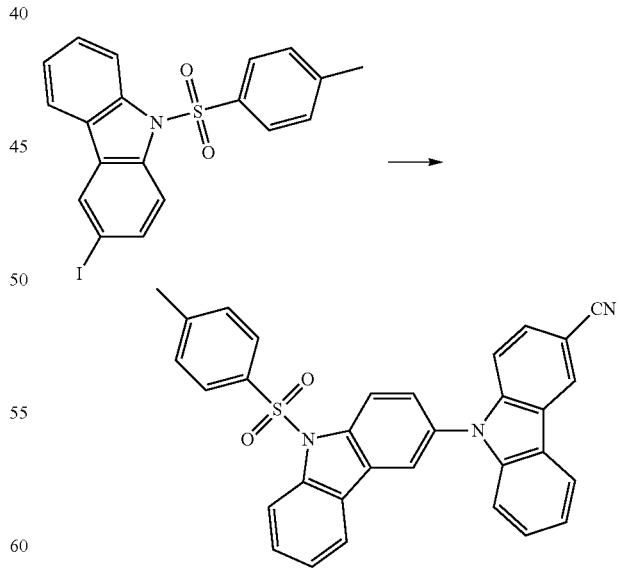

b) 20 g (4.7 mmol) 3-Iodo-9-(p-tolylsulfonyl)carbazole, 10.3 g (53.6 mmol) 9H-Carbazole-3-carbonitrile, 4.77 g (25.0 mmol) CuI, 3.06 g (26.8 mmol) trans-1,2-Diaminocyclohexane, 59.8 g (281.7 mmol) $K_3PO_4$ and 300 ml 1,4-dioxane are mixed and heated to reflux under nitrogen for 18 h. The reaction mixture is filtered hot through Hyflow, washed with hot 1,4-dioxane and evaporated on the rotavap. The residue is heated to reflux in 200 ml methanol, cooled to room temperature, filtered, washed twice with methanol (20 ml each) and dried at 80° C./125 mbar to yield 9.62 g (42.1% of theory) of 9-[9-(p-Tolylsulfonyl)carbazol-3-yl]carbazole-3-carbonitrile as a white solid. $^1$H-NMR (300 MHz, CDCl$_3$): δ 8.58 (d, J=9.0 Hz, 1H), 8.47 (d, J=1.6 Hz, 1H), 8.40 (d, J=8.7 Hz, 1H), 8.18 (d, J=7.8 Hz, 1H), 8.06 (d, J=1.6 Hz, 1H), 7.90 (d, J=7.2 Hz, 1H), 7.83 (d, J=8.4 Hz, 2H), 7.66-7.55 (m, 3H), 7.53-7.47 (m, 1H), 7.43-7.38 (m, 4H), 7.22 (d, J=8.4 Hz, 2H), 2.35 (s, 3H).

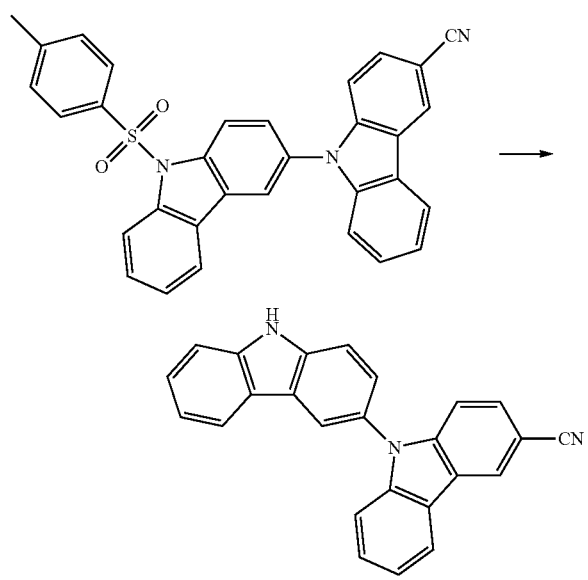

c) 2.45 g (37.1 mmol) KOH 85% are dissolved in 100 ml EtOH. A solution of 9.6 g (18.8 mmol) 9-[9-(p-Tolylsulfonyl)carbazol-3-yl]carbazole-3-carbonitrile in 150 ml THF is added drop by drop under nitrogen. The reaction mixture is heated to reflux for 4 h and then cooled to room temperature. The reaction mixture is diluted with 500 ml H$_2$O and extracted three times with ethyl acetate (500 ml each). The organic phase is washed with H$_2$O to pH=6, dried over MgSO$_4$, filtered and evaporated on the rotavap. Purification using CombiFlash and heptane/THF as eluent yields 4.68 g (69.7% of theory) of 9-(9H-Carbazol-3-yl)carbazole-3-carbonitrile as a white solid. $^1$H-NMR (400 MHz, DMSO): δ 8.48 (d, J=1.6 Hz, 1H), 8.47 (br s, 1H), 8.20-8.15 (m, 2H), 8.04 (d, J=7.6 Hz, 1H), 7.65-7.61 (m, 2H), 7.55-7.46 (m, 4H), 7.41-7.35 (m, 3H), 7.31-7.27 (m, 1H).

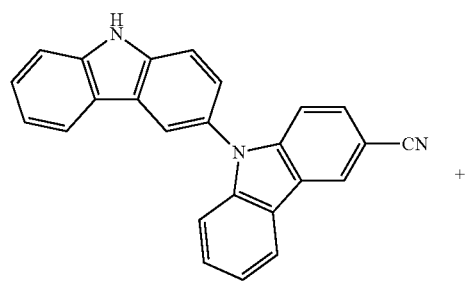

+

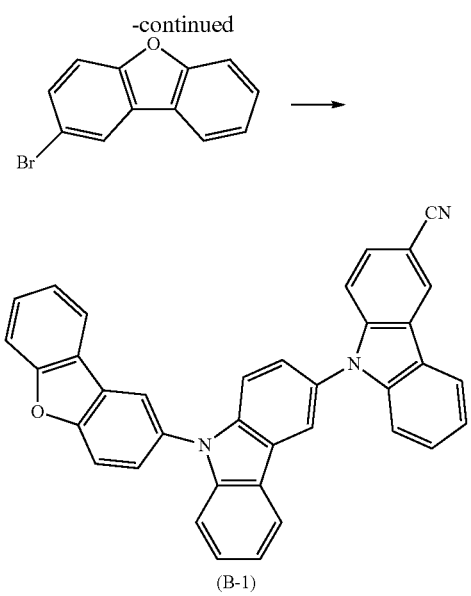

(B-1)

d) 3.17 g (8.87 mmol) 9-(9H-Carbazol-3-yl)carbazole-3-carbonitrile, 2.63 g (10.64 mmol) 2-Bromo-dibenzofuran, 0.51 g (2.66 mmol) CuI, 1.05 g (5.32 mmol) 1,10-Phenanthroline, 6.02 g (28.36 mmol) K$_3$PO$_4$ and 150 ml Mesitylene are mixed and heated to reflux under nitrogen for 48 h. The resulting brown suspension is diluted with 100 ml toluene, heated to reflux, filtered through Hyflo and washed three times with hot toluene (100 ml each). The filtrate is mixed with 15 g of silica, refluxed for 1 h, filtered hot and washed three times with hot toluene (100 ml each). The filtrate is washed three times with 1M 3-Amino-1-propanol in water (100 ml each), washed neutral with water, dried over MgSO$_4$, filtered and evaporated on the rotavap. The residue is triturated with 50 ml of methanol, stirred at reflux for 1 h, then cooled to 0° C. with an ice bath and the resulting suspension is filtered and the filter cake is dried in the hood for 24 h. Purification using CombiFlash and heptane/CH$_2$Cl$_2$ as eluent followed by crystallization from 2-Butanone yields 1.05 g (22.6% of theory) 9-(9-Dibenzofuran-2-ylcarbazol-3-yl)carbazole-3-carbonitrile as a white solid. 1H-NMR (300 MHz, CDCl$_3$): δ 8.50 (s, 1H), 8.29 (d, J=1.5 Hz, 1H), 8.21-8.19 (m, 2H), 8.15 (d, J=7.8 Hz, 1H), 7.99 (d, J=7.8 Hz, 1H), 7.85 (d, J=8.4 Hz, 1H), 7.71-7.63 (m, 3H), 7.60-7.33 (m, 11H).

Comparative Application Example 1

The ITO substrate used as the anode is first cleaned with an acetone/isopropanol mixture in an ultrasonic bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm). Thereafter, the organic materials specified below are applied by vapor deposition to the clean substrate at a rate of approx. 0.5-5 nm/min at about 10$^{-7}$-10$^{-9}$ mbar. As a hole transport and exciton blocker, (HTM-1)

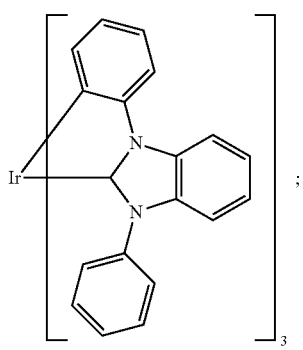

for preparation, see Ir complex (7) in the application WO2005/019373), is applied to the substrate with a thickness of 20 nm, wherein the first 10 nm are doped with MoO$_3$ (~10%) to improve the conductivity.

Subsequently, a mixture of 10% by weight of emitter compound, (BE-1)

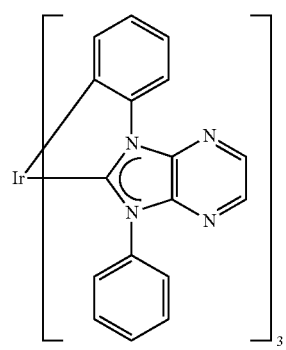

5% by weight of compound (HTM-1) and 85% by weight of compound (SH-1)

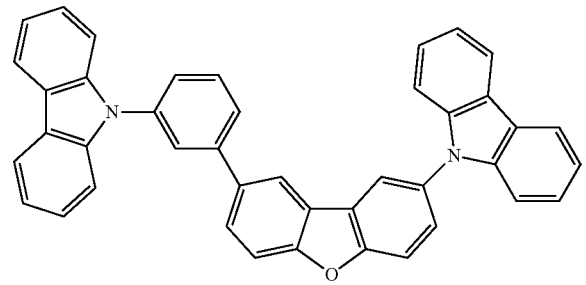

is applied by vapor deposition in a thickness of 40 nm.

Subsequently, material (SH-1) is applied by vapour deposition with a thickness of 5 nm as blocker. Thereafter, a 20 nm thick electron transport layer is deposited consisting of 50% by weight of (ETM-1)

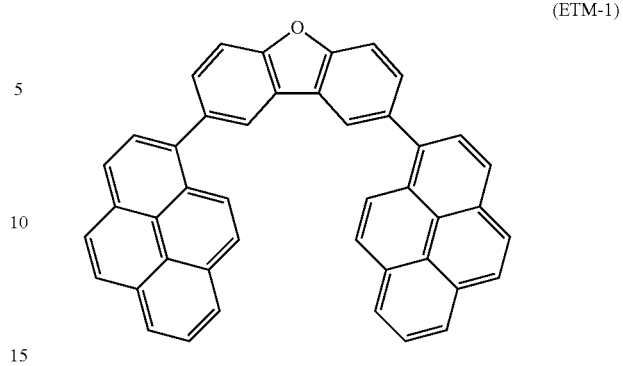

and of 50% of (Liq)

Finally a 2 nm KF layer serves as an electron injection layer and a 100 nm-thick Al electrode completes the device.

All fabricated parts are sealed with a glass lid and a getter in an inert nitrogen atmosphere.

Application Example 1 and 2

Comparative Application Example 1 is repeated, except that compound (SH-1) (host and hole blocking material) is replaced by compound (A-1)

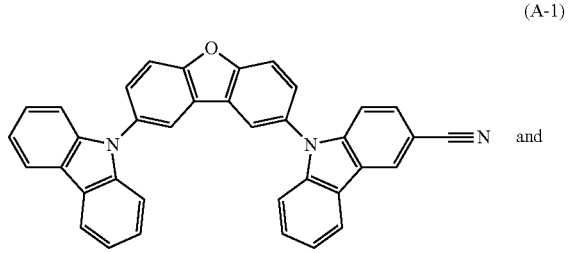

and (A-2)

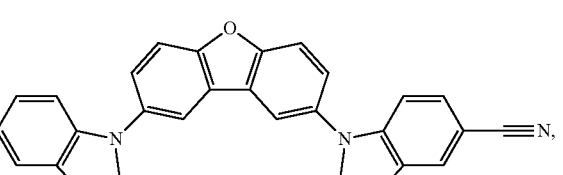

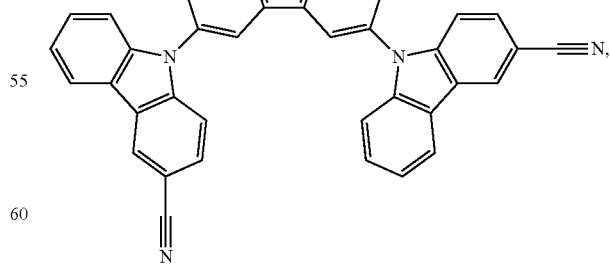

respectively.

OLED Characterization

To characterize the OLED, electroluminescence spectra are recorded at various currents and voltages. In addition, the current-voltage characteristic is measured in combination with the light output emitted. The light output is converted to photometric parameters by calibration with a photometer. The results are shown in Table 1. Data are given at luminance (L)=1000 Cd/m² except otherwise stated.

TABLE 1

| Appl. Ex. | Host/ HBL | U [V] |
|---|---|---|
| 1 | A-1 | 5.8 |
| 2 | A-2 | 5.1 |
| Comp. Appl. Ex. 1 | SH-1 | 7.7 |

[1])External quantum efficiency (EQE) is # of generated photons escaped from a substance or a device/# of electrons flowing through it.
It is evident that the voltage is reduced by replacing the host/hole blocking material SH-1 by compounds A-1 and A-2, respectively.

Comparative Application Example 2

The ITO substrate used as the anode is first cleaned with an acetone/isopropanol mixture in an ultrasonic bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm). Thereafter, the organic materials specified below are applied by vapor deposition to the clean substrate at a rate of approx. 0.5-5 nm/min at about $10^{-7}$-$10^{-9}$ mbar. As a hole transport and exciton blocker compound (SH-1) is applied to the substrate with a thickness of 20 nm, wherein the first 10 nm are doped with $MoO_3$ (~10%) to improve the conductivity. Subsequently, a mixture of 10% by weight of emitter compound (BE-1) and 90% by weight of compound (SH-1) is applied by vapor deposition in a thickness of 40 nm. Subsequently, material (SH-1) is applied by vapour deposition with a thickness of 5 nm as blocker. Thereafter, a 20 nm thick electron transport layer is deposited consisting of 50% by weight of compound (ETM-1) and of 50% of Liq. Finally a 2 nm KF layer serves as an electron injection layer and a 100 nm-thick Al electrode completes the device.

Application Example 3 and 4

Comparative Application Example 2 is repeated, except that the host and hole blocking material (SH-1) is replaced by compound (A-1) and (A-2), respectively. The device results are shown in Table 2. Data are given at luminance (L)=1000 Cd/m² except otherwise stated.

TABLE 2

| Appl. Ex. | Host/ HBL | U [V] | [Cd/A] | [lm/W] | EQE[1]) [%] |
|---|---|---|---|---|---|
| 3 | A-1 | 4.6 | 23.5 | 16.0 | 11.2 |
| 4 | A-2 | 4.2 | 24.8 | 18.7 | 12.8 |
| Comp. Appl. Ex. 2 | SH-1 | 5.1 | 6.4 | 3.9 | 3.5 |

[1])External quantum efficiency (EQE) is # of generated photons escaped from a substance or a device/# of electrons flowing through it.
It is evident that the voltage is reduced and the efficiency is increased by replacing the host/hole blocking material SH-1 by compounds A-1 and A-2, respectively.

Example 8

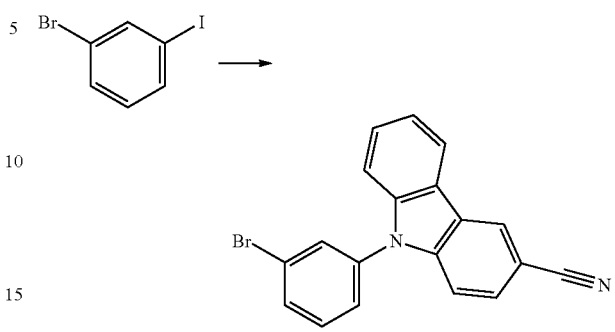

a) 12.4 g (0.044 mol) 1-bromo-3-iodobenzene, 7.00 g (0.036 mol) 9H-carbazole-3-carbonitrile, 0.347 g (1.82 mmol) CuI, 11.3 g (0.093 mol) $K_3PO_4$, and 0.656 g (3.64 mmol) 1,10-phenanthroline are added to 140 ml of mesitylene and the suspension is heated to 170° C. for 36 h under nitrogen. The resulting solution is cooled to room temperature. And then, dichloromethane and water are added and the organic phase is separated. The organic phase is washed with water, dried with magnesium sulfate, and evaporated under reduced pressure to give a crude material as a black solid. The crude material is purified by chromatography on silica gel using hexane/$CH_2Cl_2$ (9/1-1/2) as eluent and then is recrystallized from toluene/hexane to yield 6.00 g (47.5% of theory) 9-(3-bromophenyl) carbazole-3-carbonitrile.

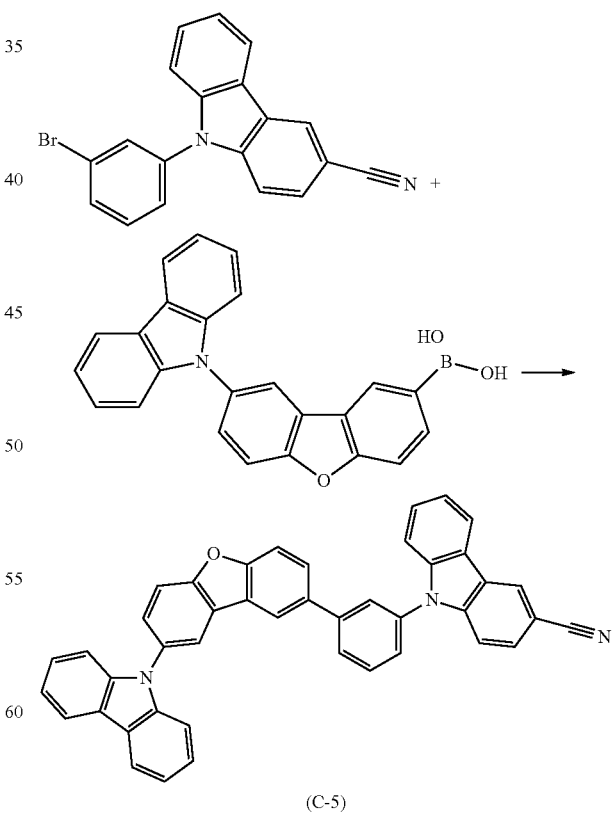

(C-5)

b) 5.50 g (0.016 mol) 9-(3-bromophenyl)carbazole-3-carbonitrile, 6.57 g (0.017 mol) 8-(carbazol-9-yl)dibenzofuran-2-boronic acid, 0.366 g (0.317 mmol) Pd(PPh₃)4, and 26 ml 2M Na₂CO₃aq. are added to 80 ml of toluene and 28 ml of DME. The suspension is heated to 110° C. for 2 h under nitrogen. The resulting solution is cooled to room temperature. And then, toluene and water are added, and the organic phase is separated. The organic phase is washed with water, dried with magnesium sulfate, and evaporated under reduced pressure to give a crude material as a brown solid. The crude material is washed three times with hot methanol and hot ethyl acetate and then recrystallized from toluene to yield 3.63 g (45.9% of theory) 9-[3-(8-carbazol-9-yldibenzofuran-2-yl)phenyl]carbazole-3-carbonitrile as a white solid. Product confirmed by LCMS m/z=600 (M+1).

¹H-NMR (400 MHz, CDCl₃): δ 8.46 (s, 1H), 8.19-8.15 (m, 5H), 7.85-7.64 (m, 8H), 7.54-7.29 (m, 11H).

Example 9

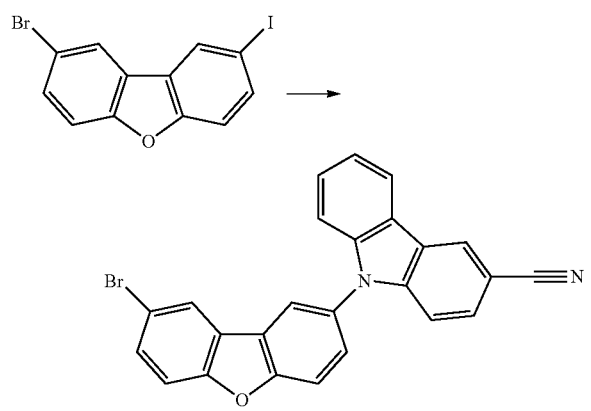

a) 23.3 g (0.062 mol) 2-bromo-8-iodo-dibenzofuran, 10.0 g (0.052 mol) 9H-carbazole-3-carbonitrile, 0.495 g (2.60 mmol) CuI, 12.6 g (0.104 mol) K₃PO₄, and 0.938 g (5.20 mmol) 1,10-phenanthroline are added to 200 ml of mesitylene and the suspension is heated to 170° C. for 30 h under nitrogen. The resulting solution is cooled to room temperature. And then, the crude material is purified by chromatography on silica gel using hexane/CH₂Cl₂ (9/1-1/1) as eluent to yield 14.8 g (65.1% of theory) 9-(8-bromodibenzofuran-2-yl)carbazole-3-carbonitrile as a white solid.

Product confirmed by LCMS m/z=437 (M+1).

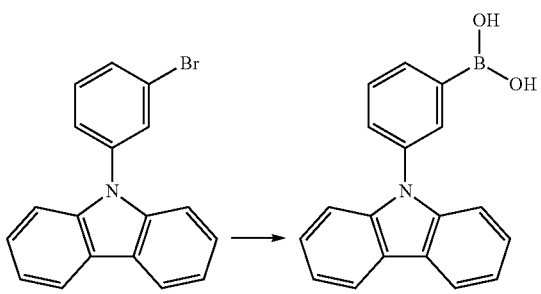 [SMILES: Brc1cccc(-n2c3ccccc3c3ccccc32)c1 ; OB(O)c1cccc(-n2c3ccccc3c3ccccc32)c1]

b) 22 ml of 1.55M n-butyl lithium in heptane is added to 10.0 g (0.031 mol) 9-(3-bromophenyl) carbazole in 100 ml of THF at −78° C. under nitrogen. The resulting solution is stirred for 1h at −78° C. Then, 10.7 ml of triisopropyl borate is added to the reaction at −78° C.

The reaction mixture is stirred at −78° C. for 1 h, then warmed to 0° C., and stirred for 3 h. 100 ml of 1M HCl aq. and 100 ml of dichloromethane are added and the organic phase is separated. The organic phase is washed with water and dried with magnesium sulfate and evaporated under reduced pressure to give a crude material. The crude material is recrystallized from toluene/hexane to yield 5.30 g (59.5% of theory) 3-(carbazol-9-yl)phenylboronic acid as a white solid.

¹H-NMR (400 MHz, CDCl₃): δ 8.26-8.25 (m, 4H), 8.05-7.93 (m, 2H), 7.67-7.64 (m, 2H), 7.47-7.26 (m, 6H).

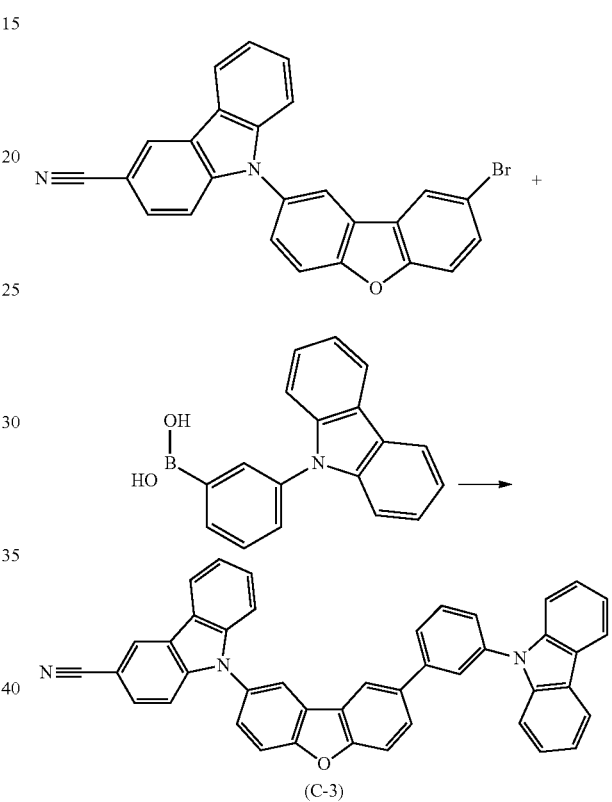

(C-3)

c) 6.90 g (0.016 mol) 9-[3-(8-carbazol-9-yldibenzofuran-2-yl)phenyl]carbazole-3-carbonitrile, 5.00 g 3-(carbazol-9-yl)phenylboronic acid, 0.366 g (0.317 mmol) Pd(PPh₃)₄, and 26.0 ml 2M Na₂CO₃aq. are added to 85 ml of toluene and 15 ml of DME. The suspension is heated to 110° C. for 12 h under nitrogen. The resulting solution is cooled to room temperature. And then, toluene and water are added, and the organic phase is separated. The organic phase is washed with water and dried with magnesium sulfate and evaporated under reduced pressure to give a crude material as a black solid. The crude material is purified by chromatography on silica gel using hexane/CH₂Cl₂ (7/3-1/1) as eluent and then washed with hot toluene to yield 6.99 g (73.6% of theory) 9-[8-(3-carbazol-9-ylphenyl)dibenzofuran-2-yl]carbazole-3-carbonitrile as a white solid. Product confirmed by LCMS m/z=600 (M+1).

¹H-NMR (400 MHz, CDCl₃): δ 8.48 (d, J=1.6 Hz, 1H), 8.20-8.14 (m, 4H), 8.12 (d, J=2.4 Hz, 1H), 7.87-7.82 (m, 3H), 7.73-7.69 (m, 3H), 7.66-7.57 (m, 3H), 7.51-7.47 (m, 3H), 7.43-7.36 (m, 5H), 7.31-7.27 (m, 2H).

Example 10

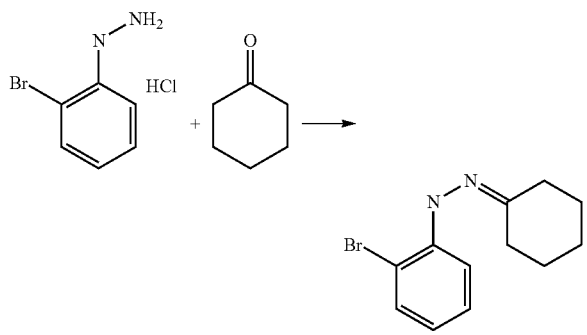

a) 51 g (0.22 mol) (2-bromophenyl)hydrazine hydrochloride are added to 500 ml EtOH. 3 g HCl 37% are added followed by the dropwise addition at room temperature of 21.95 g (0.22 mol) cyclohexanone dissolved in 50 ml EtOH within 20 minutes. The reaction mixture is stirred for additional 30 minutes and then evaporated on the rotavap to yield 67.8 g (113.4% of theory) 2-bromo-N-(cyclohexylideneamino)aniline as a brown oil that is used as crude product in the next step.

$^1$H-NMR (400 MHz, CDCl$_3$): δ 7.89 (br s, 1H), 7.39 (d, J=8.0 Hz, 1H), 7.26-7.24 (m, 2H), 6.95 (t, J=7.6 Hz, 1H), 2.78-2.69 (m, 4H), 1.96-1.84 (m, 4H), 1.65-1.50 (m, 2H).

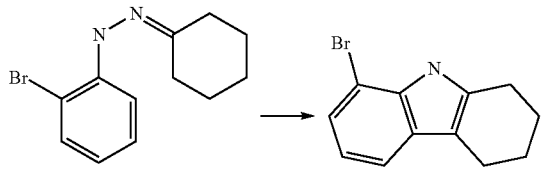 [SMILES: Brc1ccccc1NN=C1CCCCC1 ; Brc1cccc2c3c([nH]c12)CCCC3]

b) 67.8 g (0.22 mol) 2-bromo-N-(cyclohexylideneamino) aniline is dissolved in 250 ml acetic acid. 40 ml of H$_2$SO$_4$ conc. are added drop by drop within 20 minutes. The reaction mixture is then heated to 85° C. for 2 h, then cooled to room temperature and poured on 250 g of ice with stirring. The mixture is brought to pH 11 by the addition of NaOH 50%. The product is extracted with 700 ml ethyl acetate and the organic phase is washed three times with H$_2$O (400 ml each), dried with Na$_2$SO$_4$, filtered and evaporated on the rotavap to yield 35.7 g (56.3% of theory) 8-bromo-2,3,4,9-tetrahydro-1H-carbazole as a yellow oil that is used as crude product in the next step.

$^1$H-NMR (400 MHz, CDCl$_3$): δ 7.87 (br s, 1H), 7.39 (d, J=7.6 Hz, 1H), 7.25 (d, J=7.6 Hz, 1H), 6.95 (t, J=7.6 Hz, 1H), 2.78-2.68 (m, 4H), 1.96-1.84 (m, 4H).

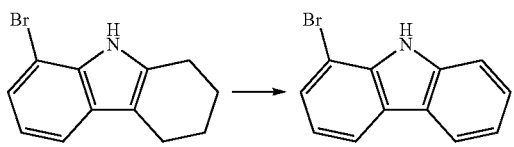 [SMILES: Brc1cccc2c3c([nH]c12)CCCC3 ; Brc1cccc2c1[nH]c1ccccc12]

c) 35.7 g (0.14 mol) 8-bromo-2,3,4,9-tetrahydro-1H-carbazole is dissolved in 200 ml Xylene. 70.2 g (0.29 mol) chloranil are added and the reaction mixture is heated to reflux for 4 h and then filtered hot over Hyflo. The residue is washed with 400 ml ethyl acetate and the filtrate is washed 80 ml NaOH solution (10%) and three times with hot H$_2$O (250 ml each). The organic phase is dried with Na$_2$SO$_4$, filtered and evaporated on the rotavap to yield 58.4 g (166% of theory) of a crude product. The crude product is dissolved again 500 ml ethyl acetate and washed three times with NaOH solution (20%, 300 ml each) and then five times with hot H$_2$O (300 ml each)). The organic phase is dried with Na$_2$SO$_4$, filtered and evaporated on the rotavap to yield 23.4 g (66.6% of theory) product which is further purified by CombiFlash using heptane/ethyl acetate as eluent yielding 15.3 g (43.6% of theory) 1-bromo-9H-carbazole as a white solid.

$^1$H-NMR (300 MHz, CDCl$_3$): δ 8.18 (br s, 1 H), 7.99 (q, J=8.0 Hz, 2H), 7.53 (d, J=8.0 Hz, 1H), 7.40-7.46 (m, 2H), 7.19-7.28 (m, 1H), 7.09 (t, J=8.0 Hz, 1H).

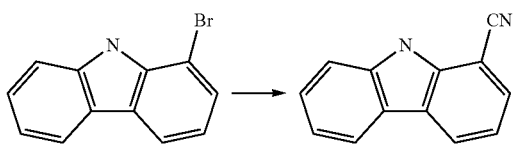 [SMILES: Brc1cccc2c1[nH]c1ccccc12 ; N#Cc1cccc2c1[nH]c1ccccc12]

d) 11.3 g (45.9 mmol) 1-bromo-9H-carbazole and 6.46 g (72.9 mmol) CuCN are added to 100 ml DMF and the suspension is heated to reflux for 18 h. The reaction mixture is filtered hot through Hyflo and the filtrate is added dropwise to 1.6 l H$_2$O while stirring. The suspension is filtered and the residue is washed three times with H$_2$O (200 ml each). The residue is added to 200 ml THF, 50 g of silica is added and the suspension is heated to reflux for 2h, then filtered hot through Hyflow and evaporated to yield 6.72 g of a greyish solid. The crude product is purified by CombiFlash using heptane/THF 85:15 as eluent. The suitable fractions are collected and the solvents are evaporated on the rotavap until a suspension begins to form. The suspension is cooled to room temperature and then filtered, washed twice with cold heptane (20 ml each) and dried at 80° C./125 mbar overnight yielding 6.3 g (72.9% of theory) 9H-carbazole-1-carbonitrile as a white solid.

$^1$H-NMR (400 MHz, CDCl$_3$): δ 8.72 (br s, 1H), 8.27 (d, J=7.6 Hz, 1H), 8.09 (d, J=7.6 Hz, 1H), 7.70 (d, J=7.6 Hz, 1H), 7.56-7.50 (m, 2H), 7.27-7.26 (m, 2H).

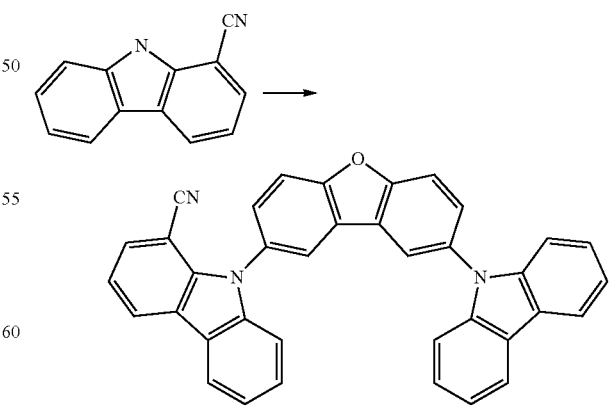

(A-6)

e) 6.27 g (32.6 mmol) 9H-carbazole-1-carbonitrile and 11.20 g (27.2 mmol) 2-bromo-8-carbazolyl-dibenzofuran are dissolved in 300 ml dioxane. 3.1 g (16.3 mmol) CuI, 1.86 g (16.3 mmol) trans-1,2-diamino-cyclohexane and 18.45 g (86.9 mol) $K_3PO_4$ are added and the suspension is heated to reflux for 10 d. The suspension is filtered hot through Hyflo and the residue is washed three times with THF (50 ml each). To the filtrate is added 5 g silica and then heated to reflux for 1 h. The suspension is filtered hot and evaporated on the rotavap to yield 14.9 g of crude product. The crude product is purified by CombiFlash using heptane/$CH_2Cl_2$ 0 to 80% as eluent to yield 2.5 g (17.6% of theory) 9-(8-carbazol-9-yldibenzofuran-2-yl)carbazole-1-carbonitrile as a white solid.

$^1$H-NMR (400 MHz, $CDCl_3$): δ 8.38 (d×d, $J_1$=7.6 Hz, $J_2$=0.8 Hz, 1H), 8.18-8.14 (m, 3H), 8.11 (d, J=2.0 Hz, 1H), 8.90 (d, J=2.0 Hz, 1H), 7.90 (d, J=8.8 Hz, 1H), 7.87 (d, J=8.8 Hz, 1H), 7.74-7.56 (m, 3H), 7.49-7.27 (m, 9H), 7.20 (d, J=8.8 Hz, 1H).

Example 11

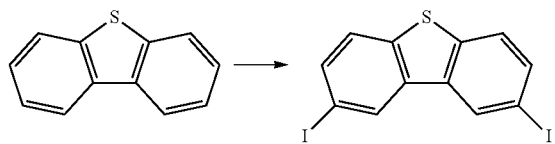 [SMILES: c1ccc2c(c1)sc1ccccc12 ; Ic1ccc2sc3ccc(I)cc3c2c1]

a) 50 g (0.27 mol) dibenzothiophene is dissolved in 500 ml acetic acid. 51.9 g (0.21 mol) $I_2$, 19.8 g (0.11 mol) $HIO_3$, 30 ml $H_2SO_4$ conc and 6 ml $CCl_4$ are added and the red suspension is heated to 78° C. for 18 h. The orange suspension is cooled to room temperature, filtered and the residue is washed three times with $H_2O$ (500 ml each), once with methanol (100 ml) and then dried at 80° C./125 mbar overnight yielding 106.3 g of an orange solid. The crude product is purified twice by Soxhlet extraction using methyl ethyl ketone (MEK)/toluene 9:1 yielding 61.3 g (68.7% of theory) 2,8-diiododibenzothiophene as a white solid.

$^1$H-NMR (400 MHz, THF-$D_8$): δ 8.71 (d, J=1.6 Hz, 2H), 7.81 (d×d, $J_1$=8.4 Hz, $J_2$=1.6 Hz, 2H), 7.73 (d, J=8.4 Hz, 2H).

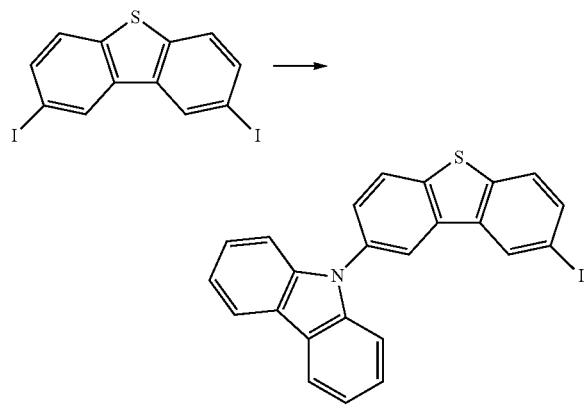

b) 50 g (0.11 mmol) 2,8-diiododibenzothiophene, 19.2 g (0.11 mmol) 9H-carbazole, are dissolved in a mixture of 450 ml dioxane and 50 ml of $H_2O$. 4.4 g (22.9 mmol) CuI, 8.64 g (75.7 mmol) trans-1,2-diamino-cyclohexane and 49.4 g (232.8 mol) $K_3PO_4$ are added and the suspension is heated to reflux for 20 h. The reaction mixture is filtered hot through Hyflo and the residue is washed with 500 ml ethyl acetate. 100 g of silica is added to the filtrate and the suspension is heated to reflux for 2 h, filtered hot through Hyflow and evaporated on the rotavap to yield 62.5 g of crude product as brown oil. The crude product is purified twice by CombiFlash using heptane/toluene+$CH_2Cl_2$ (2:1) 0 to 50% as eluent to yield 5.45 g (9.9% of theory) 9-(8-iododibenzothiophen-2-yl)carbazole as a white solid.

$^1$H-NMR (400 MHz, $CDCl_3$): δ 8.45 (d, J=1.6 Hz, 1H), 8.28 (d, J=1.6 Hz, 1H), 8.19 (d, J=7.6 Hz, 2H), 8.06 (d, J=8.4 Hz, 1H), 7.78 (d×d, $J_1$=8.4 Hz, $J_2$=1.6 Hz, 1H), 7.69-7.65 (m, 2H), 7.46-7.41 (m. 4H), 7.35-7.31 (m, 2H).

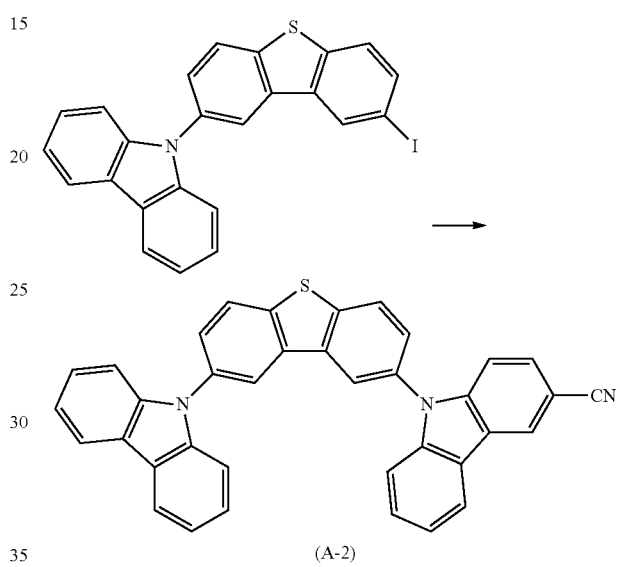

(A-2)

c) 5.42 g (11.4 mmol) 9-(8-iododibenzothiophen-2-yl)carbazole, 2.63 g (13.7 mmol) 9H-carbazole-3-carbonitrile, 0.65 g (3.4 mmol) CuI, 1.36 g (6.8 mmol) 1,10-phenanthroline and 15.7 g (74.1 mmol) $K_3PO_4$ are added to 200 ml mesitylene and the suspension is heated ro reflux for 24 h. The reaction mixture is filtered hot through Hyflo and the residue is washed twice with toluene (200 ml each). To the filtrate 20 g silica is added and stirred at reflux for 1 h. The suspension is filtered hot through Hyflo and evaporated on the rotavap to yield 6.24 g of a yellow crude product that is purified by Soxhlet extraction using ethoxyethanol as solvent to yield 4.58 g of a white solid. This product is purified by CombiFlash using heptane/$CH_2Cl_2$ (4:6) as eluent to yield 3.50 g (56.9% of theory) 9-(8-carbazol-9-yldibenzothiophen-2-yl)carbazole-3-carbonitrile as a white solid.

$^1$H-NMR (400 MHz, $CDCl_3$): δ 8.45 (d, J=1.2 Hz, 1H), 8.31 (d, J=2.0 Hz, 1H), 8.27 (d, J=2.0 Hz, 1H), 8.19-8.14 (m, 5H), 7.74 (d×d, $J_1$=8.4 Hz, $J_2$=2.0 Hz, 1H), 7.68-7.62 (m, 2H), 7.51-7.46 (m, 1H), 7.42-7.35 (m, 7H), 7.33-7.27 (m, 2H).

Example 12

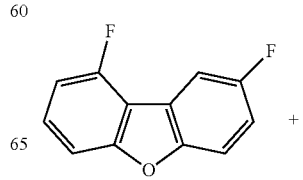

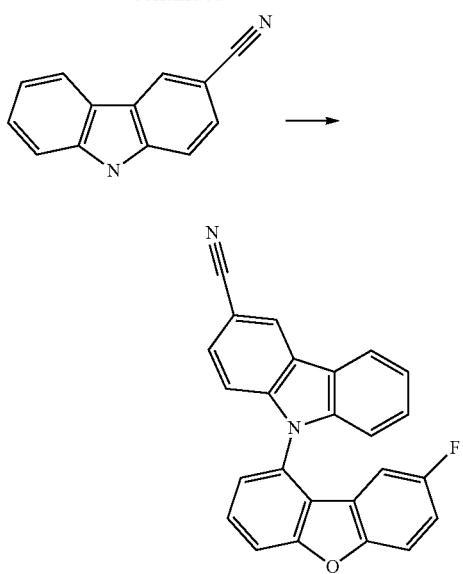

a) 1,8-difluorobenzonitrile (3.00 g, 14.69 mmol) and 9H-carbazole-3-carbonitrile (2.82 g, 14.69 mmol) are dissolved in N-methyl-2-pyrrolidone (NMP, 73 ml). To this solution potassium phosphate (6.24 g, 29.39 mmol) is added, the mixture is stirred at 100° C. for 3 d. After the reaction mixture is cooled to room temperature, it is diluted with 146 ml of water to give a solid. The solid is collected by filtration and dried in vacuum oven at 50° C. The crude product is purified by column chromatography on silica gel eluting with a mixed solvent of heptane and toluene (1:1) to yield 5.17 g (94%) of 9-(8-fluorodibenzofuran-1-yl)carbazole-3-carbonitrile as a white solid.

$^1$H-NMR (300 MHz, CDCl$_3$): δ 8.59 (dd, J=0.6, 1.6 Hz, 1H), 8.31-8.26 (m, 1H), 7.85-7.72 (m, 2H), 7.63 (dd, J=1.6, 8.6 Hz, 1H), 7.58-7.44 (m, 4H), 7.20-7.09 (m, 3H), 5.99 (dd, J=2.6, 8.3 Hz, 1H)

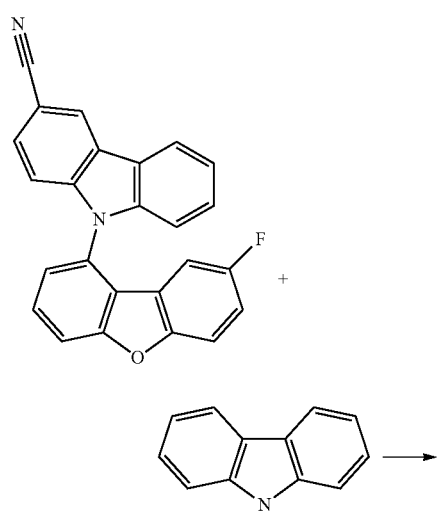

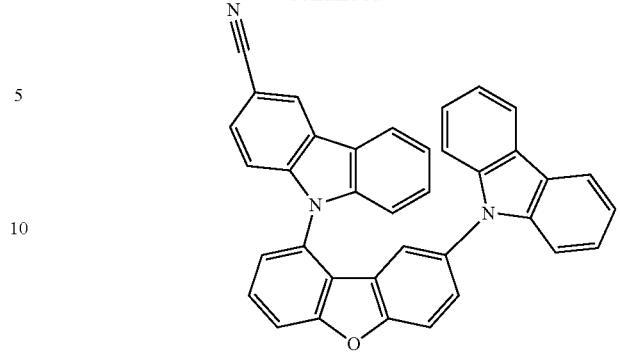

b) 9-(8-fluorodibenzofuran-1-yl)carbazole-3-carbonitrile (4.95 g, 13.15 mmol) and carbazole (2.31 g, 13.81 mmol) are dissolved in NMP (66 ml). To this solution potassium phosphate (5.86 g, 27.62 mmol) is added, the mixture is stirred at 190° C. for 9 d. After the reaction mixture is cooled to room temperature, it is diluted with 165 ml of water to give a solid. The solid is collected by filtration and dried in vacuum oven at 50° C. The crude product is purified by column chromatography on silica gel eluting with a mixed solvent of heptane and CHCl$_3$ (2:1) to yield 4.11 g (60%) of 9-(8-carbazol-9-yldibenzofuran-1-yl)carbazole-3-carbonitrile as a pale yellow solid.

$^1$H-NMR (300 MHz, CDCl$_3$): δ 8.39 (d, J=1.2 Hz, 1H), 8.10-8.03 (m, 3H), 7.93 (dd, J=0.8, 8.3 Hz, 1H), 7.84-7.79 (m, 2H), 7.70 (dd, J=1.6, 8.3 Hz, 1H), 7.62-7.50 (m, 3H), 7.43-7.38 (m, 1H), 7.32-7.21 (m, 6H), 6.90-6.87 (m, 2H), 6.56 (d, J=2.0 Hz, 1H).

Example 13

1,6-difluorobenzonitrile (2.50 g, 12.0 mmol) and 9H-carbazole-3-carbonitrile (4.80 g, 25.0 mmol) are dissolved in NMP (60 ml). To this solution potassium phosphate (10.8 g, 50.0 mmol) is added, the mixture is stirred at 150° C. for 15 h. After the reaction mixture is cooled at room temperature, it is diluted with 120 ml of water to give a solid. The solid is collected by filtration and dried in vacuum oven at 50° C. The crude product is purified by column chromatography on silica gel eluting with a mixed solvent of $CH_2Cl_2$ and toluene (10:1), followed by recrystallization with toluene to yield 3.3 g (50%) of 9-[6-(3-cyanocarbazol-9-yl)dibenzofuran-1-yl]carbazole-3-carbonitrile as a white solid.

$^1$H-NMR (300 MHz, DMSO-$d_6$): δ 9.04 (d, J=1.2 Hz, 1H), 8.94 (d, J=1.2 Hz, 1H), 8.56-8.53 (m, 1H), 8.47-8.43 (m, 1H), 7.95-7.72 (m, 6H), 7.57-7.26 (m, 9H), 6.39 (dd, J=1.2, 7.8 Hz, 1H).

LC-MS (m/z) 548

Comparative Application Example 3

A glass substrate with 120 nm-thick indium-tin-oxide (ITO) transparent electrode used as an anode is first cleaned with isopropanol in an ultrasonic bath for 10 min. To eliminate any possible organic residues, the substrate is exposed to an ultraviolet light and ozone for further 30 min. This treatment also improves the hole injection properties of the ITO. The cleaned substrate is mounted on a substrate holder and loaded into a vacuum chamber. Thereafter, the organic materials specified below are applied by vapor deposition to the ITO substrate at a rate of approx. 0.2-1 Å/sec at about $10^{-6}$-$10^{-8}$ mbar. As a hole injection layer, compound

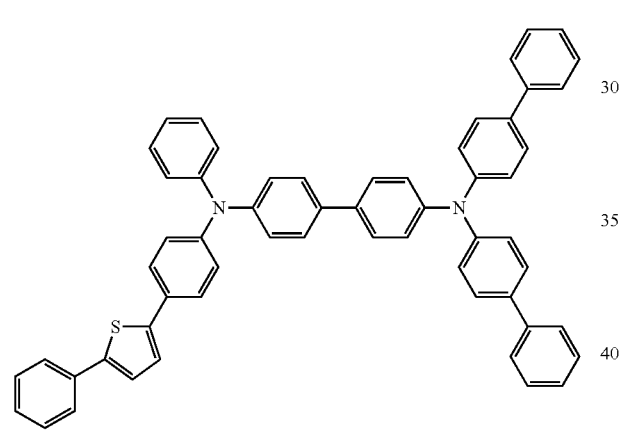

with 30 nm thickness is applied is applied. Then compound with 60 nm thickness is applied as a hole transporting layer. As an exciton and electron blocker, compound

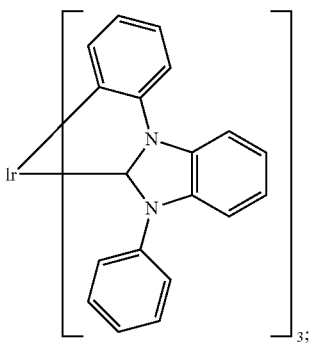

(HTM-1)

for preparation, see Ir complex (7) in the application WO2005/019373) is then applied with a thickness of 10 nm. Subsequently, a mixture of 20% by weight of emitter compound,

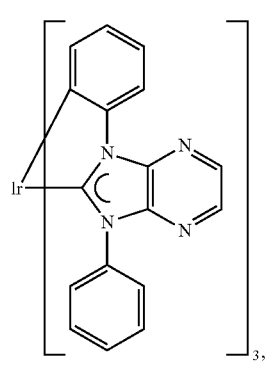

(BE-1)

15% by weight of compound (HTM-1) and 65% by weight of host

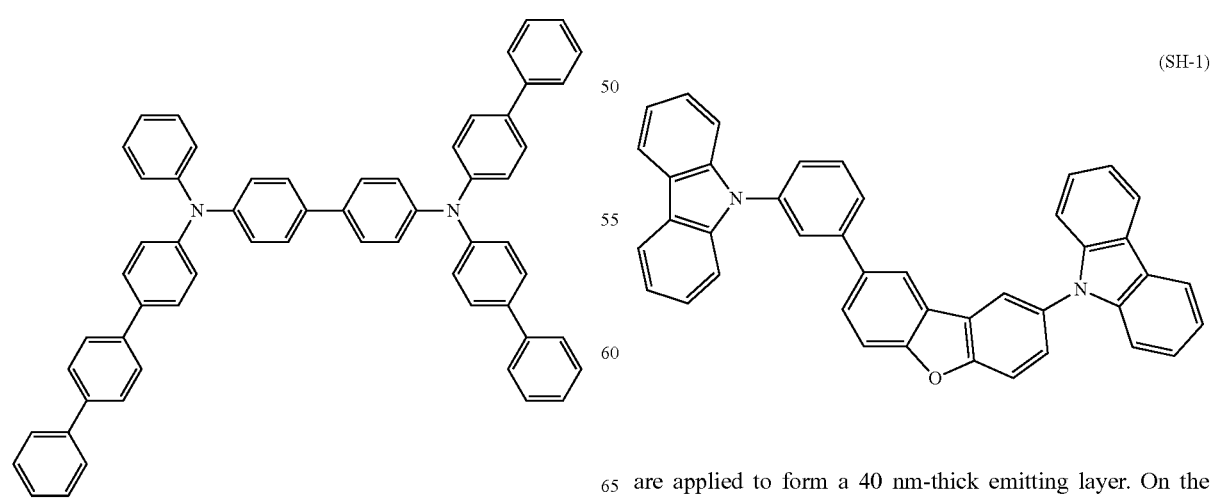

(SH-1)

are applied to form a 40 nm-thick emitting layer. On the emitting layer, 5 nm-thick material (SH-1) is applied as an exciton blocker.

Thereafter, compound

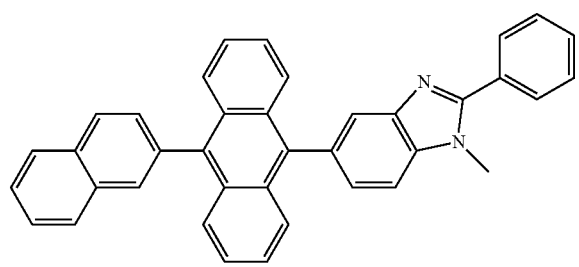 [SMILES: Cn1c(-c2ccccc2)nc2cc(-c3c4ccccc4c(-c4ccc5ccccc5c4)c4ccccc34)ccc21]

with 20 nm thickness is deposited as an electron transport layer. Finally, 1 nm-thick LiF is deposited as an electron injection layer and 80 nm-thick Al is then deposited as a cathode to complete the device. The device is sealed with a glass lid and a getter in an inert nitrogen atmosphere with less than 1 ppm of water and oxygen.

OLED Characterization

To characterize the OLED, electroluminescence spectra are recorded at various currents and voltages. In addition, the current-voltage characteristic is measured in combination with the luminance to determine luminous efficiency and external quantum efficiency (EQE). Driving voltage U and EQE are given at luminance (L)=1000 cd/m² except otherwise stated.

Application Example 5

Comparative Application Example 3 is repeated except that both the host (SH-1) and exciton blocker (SH-1) is replaced by compound

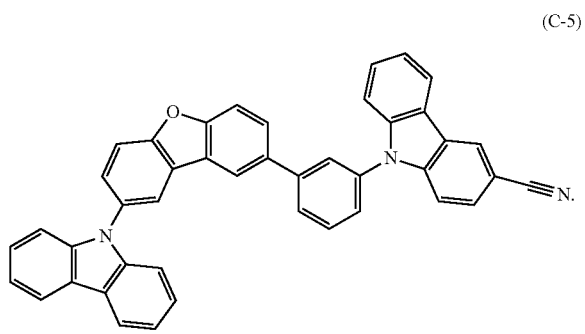 [SMILES: N#Cc1ccc2c(c1)c1ccccc1n2-c1cccc(-c2ccc3oc4ccc(-n5c6ccccc6c6ccccc65)cc4c3c2)c1]
(C-5)

The device results are shown in Table 3.

Application Example 6

Comparative Application Example 3 is repeated except that both the host (SH-1) and exciton blocker (SH-1) is replaced by compound

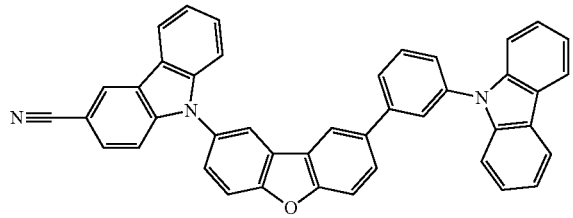
(C-3)

The device results are shown in Table 3.

Application Example 7

Comparative Application Example 3 is repeated except that both the host (SH-1) and exciton blocker (SH-1) is replaced by compound

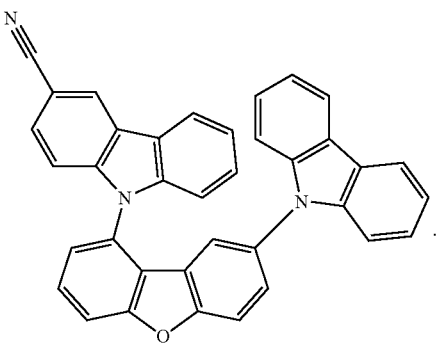
(A-78)

The device results are shown in Table 3.

Application Example 8

Comparative Application Example 3 is repeated except that both the host (SH-1) and exciton blocker (SH-1) is replaced by compound

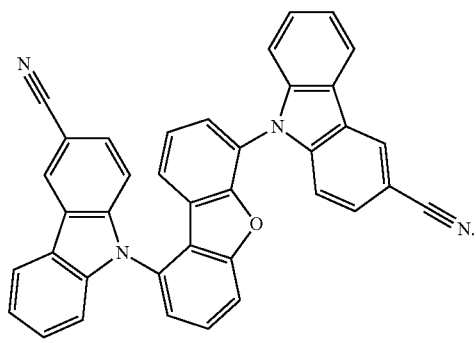
(A-107)

The device results are shown in Table 3.

TABLE 3

| Appl. Ex. | Host | Exciton blocker | U [V] | EQE [%] |
|---|---|---|---|---|
| Comp. Appl. Ex. 3 | (SH-1) | (SH-1) | 5.42 | 17.1 |
| Appl. Ex. 5 | (C-5) | (C-5) | 4.92 | 16.7 |
| Appl. Ex. 6 | (C-3) | (C-3) | 4.71 | 16.9 |

TABLE 3-continued

| Appl. Ex. | Host | Exciton blocker | U [V] | EQE [%] |
|---|---|---|---|---|
| Appl. Ex. 7 | (A-78) | (A-78) | 4.79 | 18.1 |
| Appl. Ex. 8 | (A-107) | (A-107) | 4.05 | 16.7 |

The results shown in Table 1 demonstrate that the driving voltage U are significantly reduced with keeping EQE high enough when compounds (C-5), (C-3), (A-78) and (A-107) are used as host and exciton blocker instead of reference compound (SH-1).

Comparative Application Example 4

A glass substrate with 120 nm-thick ITO is cleaned and treated in the same manner as comparative application example 1. As a hole injection layer, compound

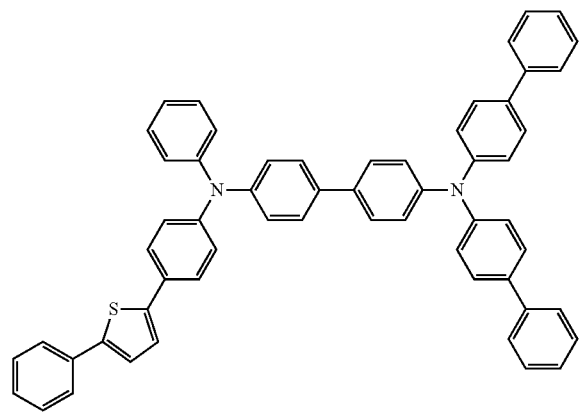 [SMILES: c1ccc(-c2ccc(N(c3ccc(-c4ccccc4)cc3)c3ccc(-c4ccc(N(c5ccccc5)c5ccc(-c6ccc(-c7ccccc7)s6)cc5)cc4)cc3)cc2)cc1]

with 30 nm thickness is applied by vapor deposition. Then 60 nm of compound (SH-1) doped with MoOx (~10%) is deposited as hole transporting layer. MoOx is used to improve the hole conductivity of SH-1. As an exciton and electron blocker, compound (SH-1) is applied with a thickness of 10 nm. Subsequently, a mixture of 20% by weight of emitter compound (BE-1) and 80% by weight of host (SH-1) are applied to form a 40 nm of emitting layer. On the emitting layer, 5 nm of material (SH-1) is applied as an exciton blocker. Thereafter, compound

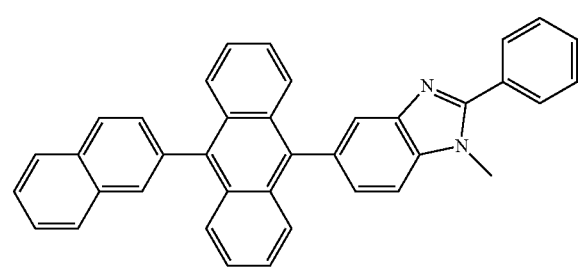 [SMILES: Cn1c(-c2ccccc2)nc2cc(-c3c4ccccc4c(-c4ccc5ccccc5c4)c4ccccc34)ccc21]

with 20 nm thickness is deposited as an electron transport layer. Finally, 1 nm of LiF is deposited as an electron injection layer and 80 nm of Al is then deposited as a cathode to complete the device. The device is sealed with a glass lid and a getter in an inert nitrogen atmosphere with less than 1 ppm of water and oxygen.

Application Example 9

Comparative Application Example 4 is repeated except that both the host (SH-1) and exciton blocker (SH-1) is replaced by compound

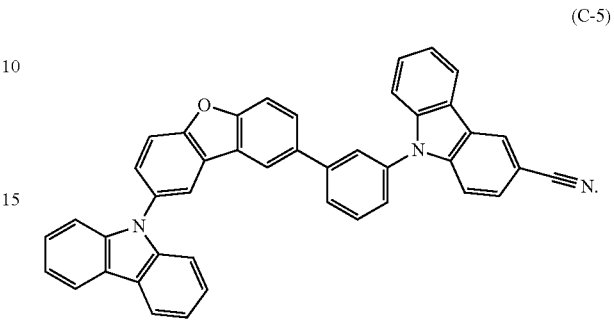

(C-5)

The device results are shown in Table 4.

Application Example 10

Comparative Application Example 4 is repeated except that both the host (SH-1) and exciton blocker (SH-1) is replaced by compound

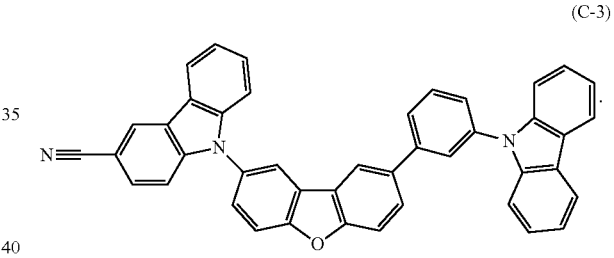

(C-3)

The device results are shown in Table 4.

Application Examples 11

Comparative Application Example 4 is repeated except that both the host (SH-1) and exciton blocker (SH-1) is replaced by compound

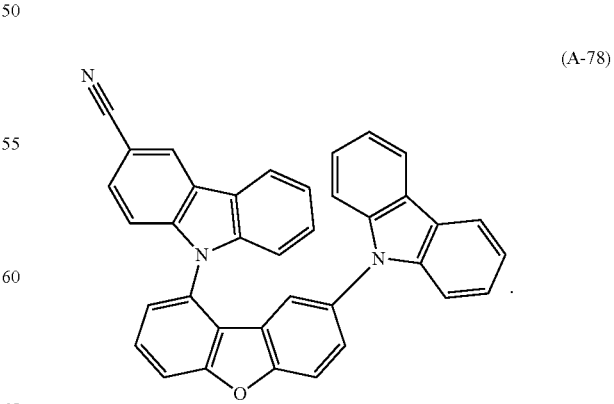

(A-78)

The device results are shown in Table 4.

Application Example 12

Comparative Application Example 4 is repeated except that both the host (SH-1) and exciton blocker (SH-1) is replaced by compound

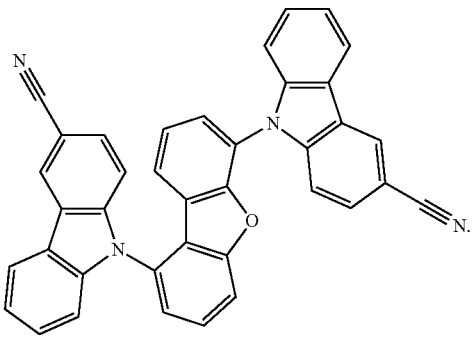

(A-107)

The device results are shown in Table 4.

TABLE 4

| Appl. Ex. | Host | Exciton blocker | U [V] | EQE [%] |
|---|---|---|---|---|
| Comp. Appl. Ex. 4 | (SH-1) | (SH-1) | 5.54 | 2.0 |
| Appl. Ex. 9 | (C-5) | (C-5) | 4.21 | 12.7 |
| Appl. Ex. 10 | (C-3) | (C-3) | 4.06 | 15.6 |
| Appl. Ex. 11 | (A-78) | (A-78) | 4.06 | 16.9 |
| Appl. Ex. 12 | (A-107) | (A-107) | 3.84 | 18.2 |

The results shown in Table 4 demonstrate that the driving voltage and EQE are improved when compounds (C-5), (C-3), (A-78) and (A-107) are used as host and exciton blocker instead of reference compound (SH-1).

The invention claimed is:

1. A compound of formula (Ia):

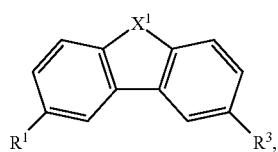

(Ia)

wherein:
$X^1$ is O or S;
$R^1$ is a group of formula

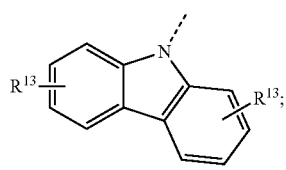

and
$R^3$ is a group of formula (Xa):

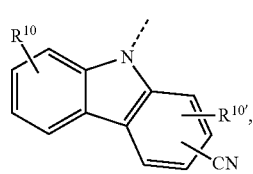

(Xa)

or
$R^1$ and $R^3$ are independently of each other a group of formula (Xa); or
a compound of formula (Ib):

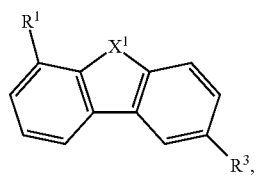

(Ib)

wherein:
$X^1$ is O or S;
$R^1$ is a group of formula

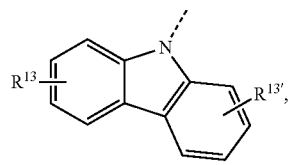

and
$R^3$ is a group of formula (Xa); or
$R^1$ is a group of formula (Xa), and
$R^3$ is a group of formula

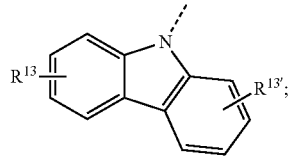

or
$R^1$ and $R^3$ are independently of each other a group of formula (Xa);
$R^{13}$ and $R^{13'}$ are independently of each other H, or a $C_1$-$C_{25}$alkyl group; and
$R^{10}$ is H, or a $C_1$-$C_{25}$alkyl group and $R^{10'}$ is H, or a $C_1$-$C_{25}$alkyl group; or $R^{10}$ is H, or a $C_1$-$C_{25}$alkyl group and $R^{10'}$ is CN; or $R^{10}$ is CN and $R^{10'}$ is H, or a $C_1$-$C_{25}$alkyl group.

2. A compound of formula (IIa):

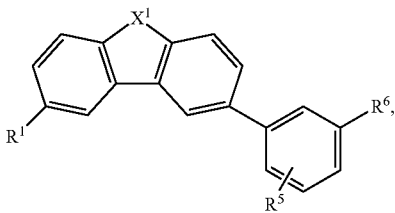

(IIa)

wherein:
$X^1$ is O or S;

$R^1$ is a group of formula

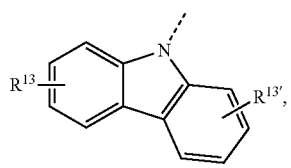

and $R^6$ is a group of formula (Xa):

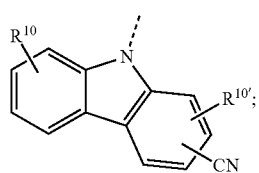
(Xa)

or $R^1$ is a group of formula(Xa), and $R^6$ is a group of formula

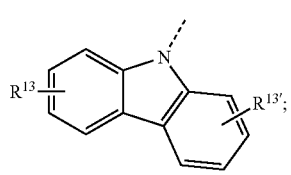

or $R^1$ and $R^6$ are independently of each other a group of formula (Xa);

$R^5$ is H, or a $C_1$-$C_{25}$alkyl group;

$R^{13}$ and $R^{13'}$ are independently of each other H, or a $C_1$-$C_{25}$alkyl group; and $R^{10}$ is H, or a $C_1$-$C_{25}$alkyl group and $R^{10'}$ is H, or a $C_1$-$C_{25}$alkyl group; or $R^{10}$ is H, or a $C_1$-$C_{25}$alkyl group and $R^{10'}$ is CN; or $R^{10}$ is CN and $R^{10'}$ is H, or a $C_1$-$C_{25}$alkyl group.

3. The compound according to claim 1, wherein the group of formula (Xa) is a group of formula:

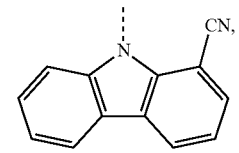
(XIIa)

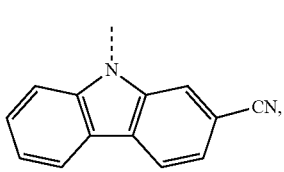
(XIIb)

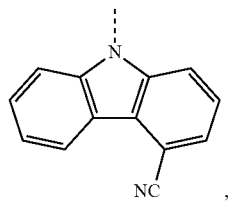
(XIIc)

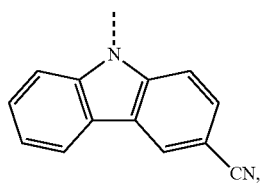
(XIId)

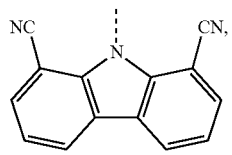
(XIIe)

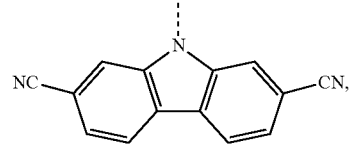
(XIIf)

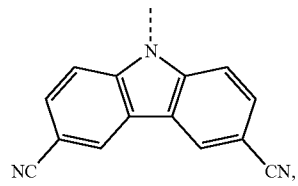
(XIIg)

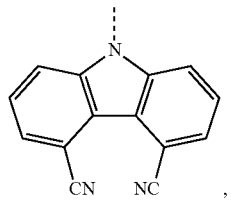
(XIIh)

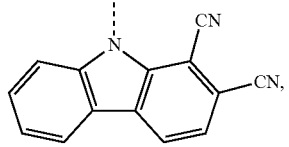
(XIIi)

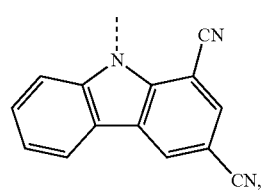
(XIIj)

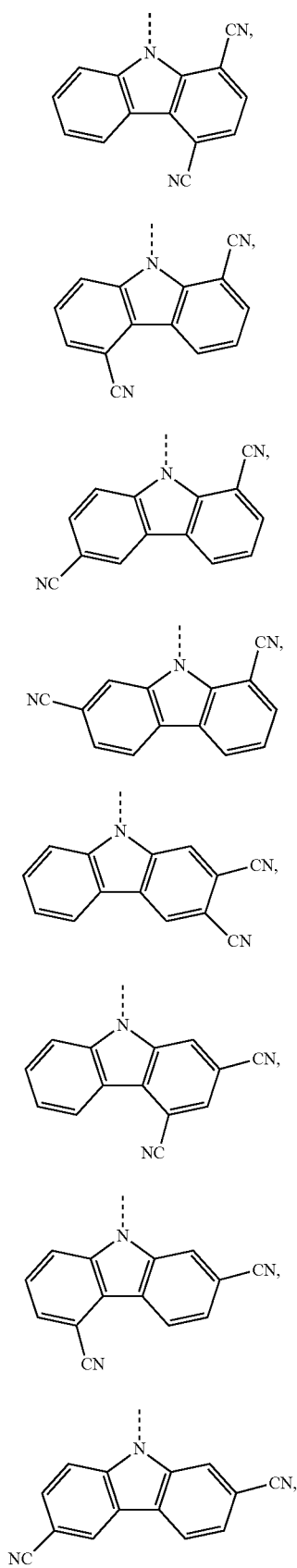
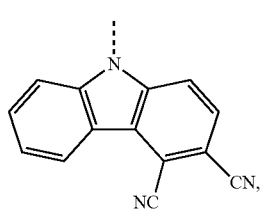
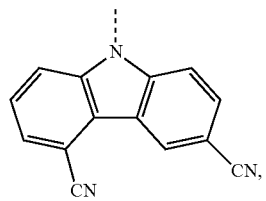
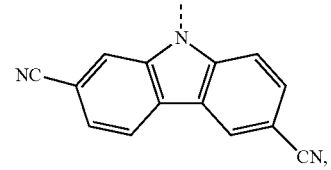
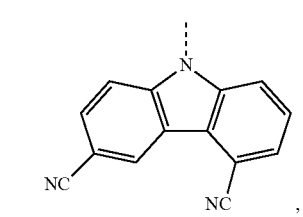
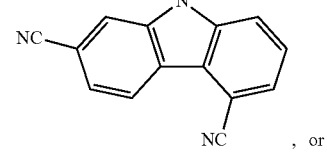
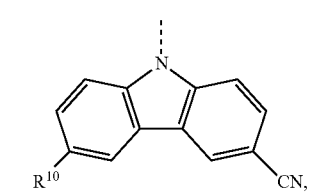
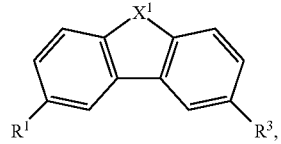
wherein R$^{10}$ is a C$_1$-C$_{25}$alkyl group.
4. The compound according to claim 1, which is a compound of formula:
(Ia)
wherein:
X$^1$ is O or S;

$R^1$ is a group of formula

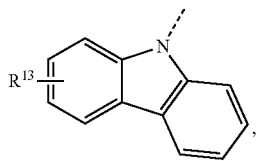

and
$R^3$ is a group of formula (XIIa), (XIIb), (XIIc), (XIId), (XIIg), or (XIIv):

(XIIa)

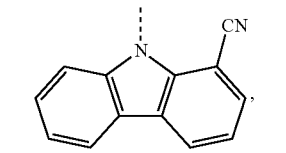

(XIIb)

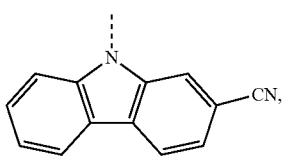

(XIIc)

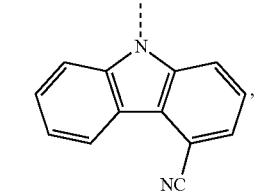

(XIId)

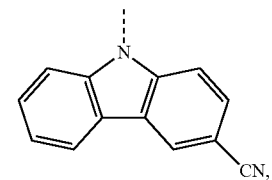

(XIIf)

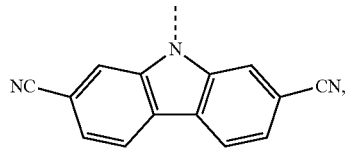

(XIIg)

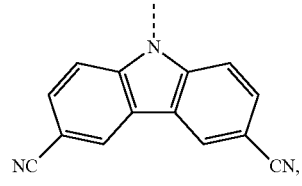

(XIIv)

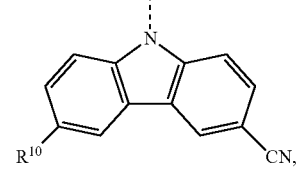

and
$R^{10}$ is a $C_1$-$C_{25}$alkyl group; or
$R^1$ and $R^3$ are independently of each other a group of formula (XIIa), (XIIb), (XIIc), (XIId), (XIIf), (XIIg), or (XIIv); or
a compound of formula (Ib):

(Ib)

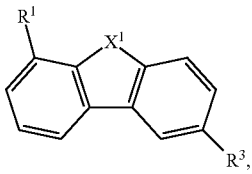

wherein:
$X^1$ is O or S;
$R^1$ is a group of formula

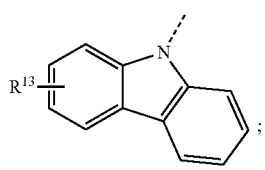

and
$R^3$ is a group of formula (XIIa), (XIIb), (XIIc), (XIId), (XIIf), (XIIg), (XIIv); or
$R^1$ is a group of formula (XIIa), (XIIb), (XIIc), (XIId), (XIIf), (XIIg), or (XIIv), and
$R^3$ is a group of formula

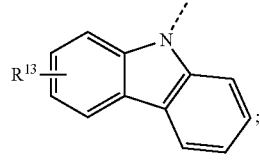

or
$R^1$ and $R^3$ are independently of each other a group of formula (XIIa), (XIIb), (XIIc), (XIId), (XIIf), (XIIg), or (XIIv); and
$R^{13}$ is H, or a $C_1$-$C_{25}$alkyl group.

5. The compound according to claim 2, which is a compound of formula:

(IIa)

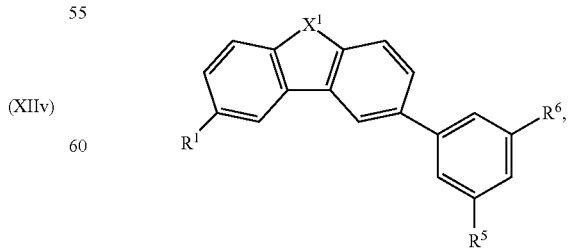

wherein:
$X^1$ is O or S;

$R^5$ is H, or a $C_1$-$C_{25}$alkyl group,
$R^1$ is a group of formula

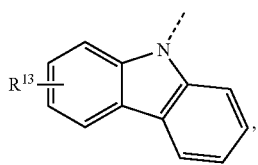

and
$R^6$ is a group of formula (XIIa), (XIIb), (XIIc), (XIId), (XIIf), (XIIg), or (XIIv,):

(XIIa)
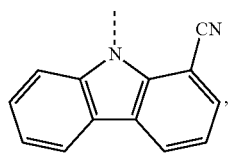

(XIIb)
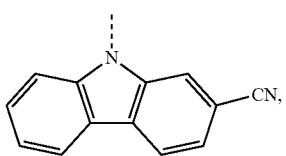

(XIIc)
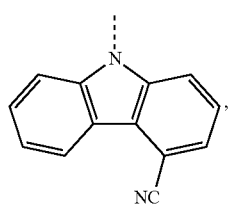

(XIId)
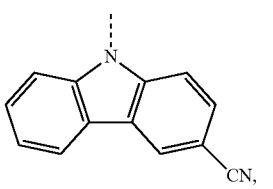

(XIIf)
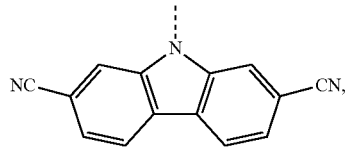

(XIIg)
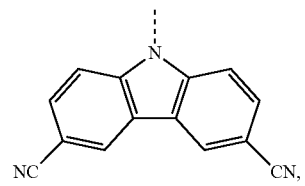

(XIIv)
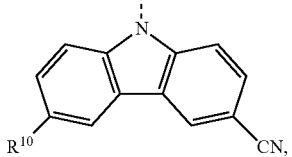

and
$R^{10}$ is a $C_1$-$C_{25}$alkyl group; or
$R^1$ is a group of formula (XIIa), (XIIb), (XIIc), (XIId), (XIIf), (XIIg), or XIIv) and
$R^6$ is a group of formula

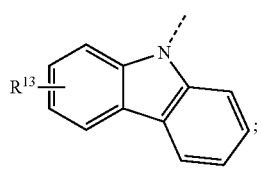

or
$R^1$ and $R^6$ are independently of each other a group of formula (XIIa), (XIIb), (XIIc), (XIId), (XIIf), (XIIg), or (XIIv); and
$R^{13}$ is H, or a $C_1$-$C_{25}$alkyl group.

6. A compound of formula (Ic):

(Ic)
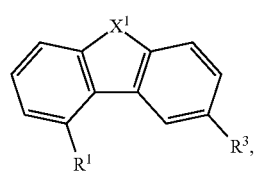

wherein:
$X^1$ is O or S;
$R^1$ is a group of formula

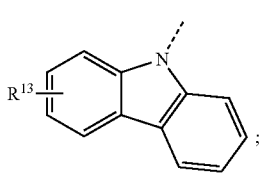

and
$R^3$ is a group of formula (XIIa), (XIIb), (XIIc), (XIId), (XIIf), (XIIg), or (XIIv):

(XIIa)
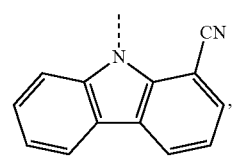

-continued (XIIb)
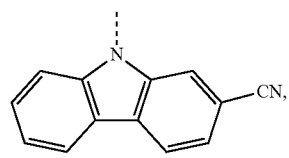

(XIIc)
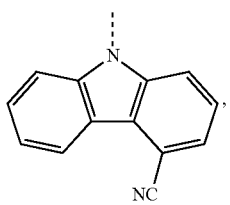

(XIId)
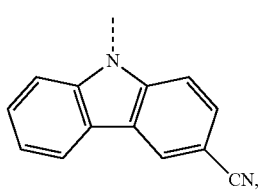

(XIIf)
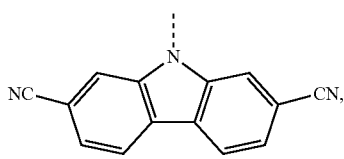

(XIIg)
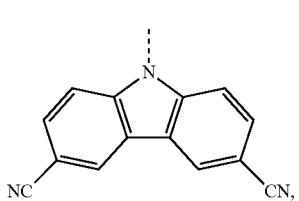

(XIIv)
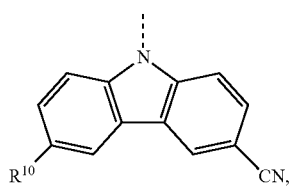

and
$R^{10}$ is a $C_1$-$C_{25}$alkyl group; or
$R^1$ is a group of formula (XIIa), (XIIb), (XIIc), (XIId), (XIIf), (XIIg), or (XIIv) and
$R^3$ is a group of formula

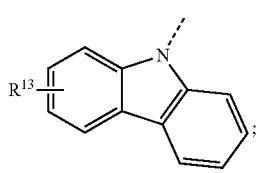

or
$R^1$ and $R^3$ are independently of each other a group of formula (XIIa), (XIIb), (XIIc), (XIId), (XIIf), (XIIg), or (XIIv); or a compound of formula (Id):

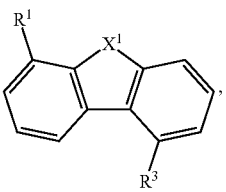
(Id)

wherein:
$X^1$ is O or S;
$R^1$ is a group of formula

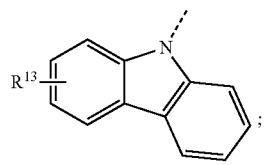

and
$R^3$ is a group of formula (XIIa), (XIIb), (XIIc), (XIId), (XIIf), (XIIg), or (XIIv), or
$R^1$ is a group of formula (XIIa), (XIIb), (XIIc), (XIId), (XIIf), (XIIg), or (XIIv); and $R^3$ is a group of formula

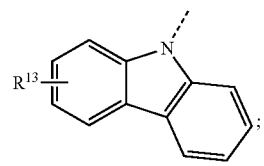

or
$R^1$ and $R^3$ are independently of each other a group of formula (XIIa), (XIIb), (XIIc), (XIId), (XIIf), (XIIg), or (XIIv); and
$R^{13}$ is a $C_1$-$C_{25}$alkyl group.

7. An electronic device, comprising a compound according to claim 1.

8. The electronic device according to claim 7, which is an electroluminescent device.

9. An electron transport layer, hole blocking layer, or an emitting layer comprising a compound according to claim 1.

10. The emitting layer according to claim 9, comprising the compound as a host material in combination with a phosphorescent emitter.

11. An apparatus selected from the group consisting of stationary visual display units; mobile visual display units; illumination units; keyboards; items of clothing; furniture; and wallpaper, comprising the organic electronic device according to claim 7.

12. An electrophotographic photoreceptor, a photoelectric converter, an organic solar cell, a switching element, an organic light emitting field effect transistor, an image sensor, a dye laser, or an electroluminescent device, comprising the compound of claim 1 as a transport material in a hole blocking layer and/or an emissive layer and/or as an electron blocking layer.

13. An apparatus selected from the group consisting of stationary visual display units; mobile visual display units; illumination units; keyboards; items of clothing; furniture;

and wallpaper, comprising the electron transport layer, the hole blocking layer and/or the emitting layer according to claim 9.
14. The compound according to claim 2, wherein the group of formula (Xa) is a group of formula:
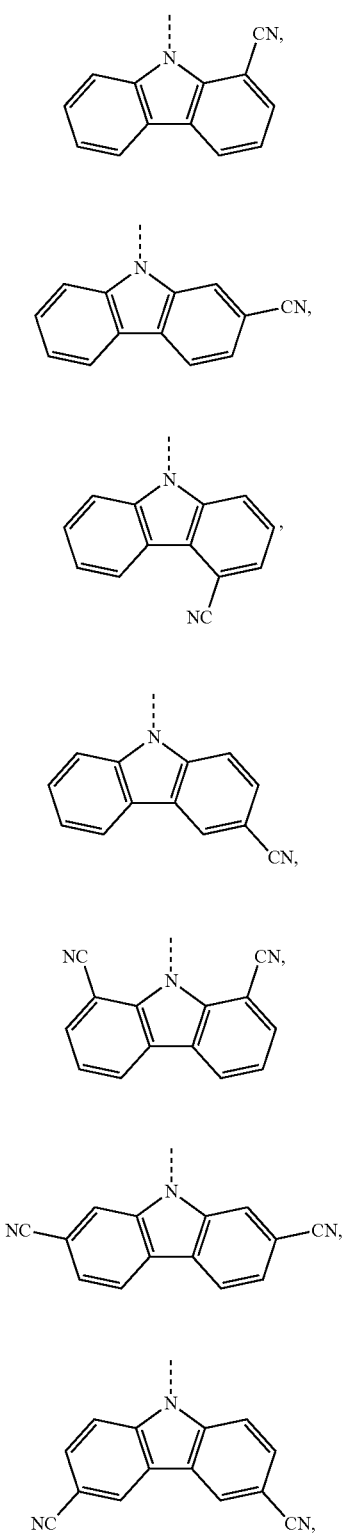
(XIIa)
(XIIb)
(XIIc)
(XIId)
(XIIe)
(XIIf)
(XIIg)
-continued
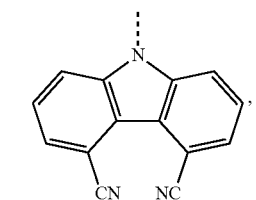
(XIIh)
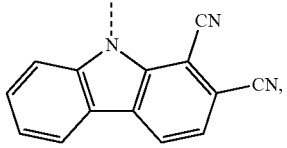
(XIIi)
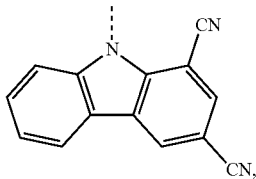
(XIIj)
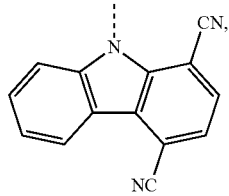
(XIIk)
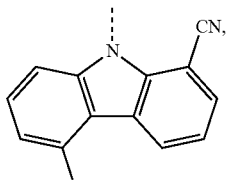
(XIIi)
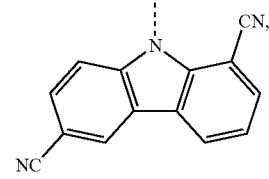
(XIIk)
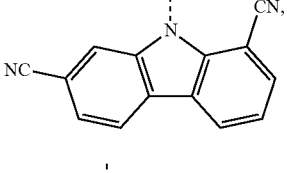
(XIIl)
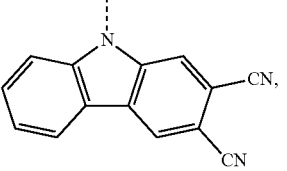
(XIIm)

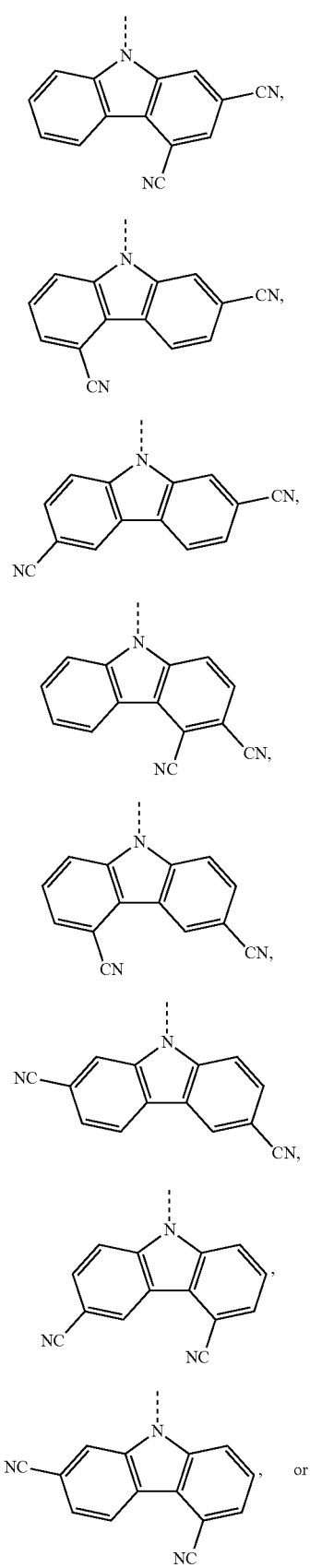

(XIIn)
(XIIo)
(XIIp)
(XIIq)
(XIIr)
(XIIs)
(XIIt)
(XIIu)

(XIIv)

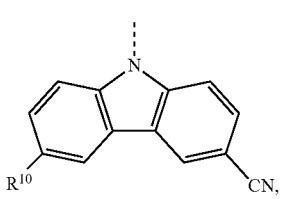

wherein $R^{10}$ is a $C_1$-$C_{25}$alkyl group.

15. An electronic device, comprising a compound according to claim 2.

16. The electronic device according to claim 15, which is an electroluminescent device.

17. An electron transport layer, hole blocking layer, or an emitting layer comprising a compound according to claim 2.

18. The emitting layer according to claim 17, comprising the compound as a host material in combination with a phosphorescent emitter.

19. An apparatus selected from the group consisting of stationary visual display units; mobile visual display units; illumination units; keyboards; items of clothing; furniture; and wallpaper, comprising the organic electronic device according to claim 15.

20. An electrophotographic photoreceptor, a photoelectric converter, an organic solar cell, a switching element, an organic light emitting field effect transistor, an image sensor, a dye laser, or an electroluminescent device, comprising the compound of claim 2 as a transport material in a hole blocking layer and/or an emissive layer and/or as an electron blocking layer.

21. An apparatus selected from the group consisting of stationary visual display units; mobile visual display s; illumination units; keyboards; items of clothing; furniture; and wallpaper, comprising the electron sport layer, the hole blocking layer and/or the emitting layer according to claim 17.

22. An electronic device, comprising a compound according to claim 6.

23. The electronic device according to claim 22, which is an electroluminescent device.

24. An electron transport layer, hole blocking layer, or an emitting layer comprising a compound according to claim 6.

25. The emitting layer according to claim 24, comprising the compound as a host material in combination with a phosphorescent emitter.

26. An apparatus selected from the group consisting of stationary visual display units; mobile visual display units; illumination units; keyboards; items of clothing; furniture; and wallpaper, comprising the organic electronic device according to claim 22.

27. An electrophotographic photoreceptor, a photoelectric converter, an organic solar cell, a switching element, an organic light emitting field effect transistor, an image sensor, a dye laser, or an electroluminescent device, comprising the compound of claim 6 as a transport material in a hole blocking layer and/or an emissive layer and/or as an electron blocking layer.

28. An apparatus selected from the group consisting of stationary visual display units; mobile visual display units; illumination units; keyboards; items of clothing; furniture; and wallpaper, comprising the electron transport layer, the hole blocking layer and/or the emitting layer according to claim 24.

* * * * *